US008163792B2

(12) United States Patent
Laurent et al.

(10) Patent No.: US 8,163,792 B2
(45) Date of Patent: Apr. 24, 2012

(54) IAP BIR DOMAIN BINDING COMPOUNDS

(75) Inventors: Alain Laurent, Montreal (CA); Scott Jarvis, Longueil (CA); Patrick Bureau, Kirkland (CA); Alain Boudreault, Dorval (CA); James Jaquith, Pincourt (CA)

(73) Assignee: Pharmascience Inc., Montréal QC (CA)

( * ) Notice: Subject to any disclaimer, the term of this patent is extended or adjusted under 35 U.S.C. 154(b) by 404 days.

(21) Appl. No.: 12/301,213

(22) PCT Filed: May 16, 2007

(86) PCT No.: PCT/CA2007/000887
§ 371 (c)(1),
(2), (4) Date: Nov. 26, 2008

(87) PCT Pub. No.: WO2007/131366
PCT Pub. Date: Nov. 22, 2007

(65) Prior Publication Data
US 2009/0192140 A1 Jul. 30, 2009

Related U.S. Application Data

(60) Provisional application No. 60/800,414, filed on May 16, 2006, provisional application No. 60/833,773, filed on Jul. 28, 2006, provisional application No. 60/879,352, filed on Jan. 9, 2007.

(51) Int. Cl.
*C07D 207/09* (2006.01)
*A61K 31/4025* (2006.01)

(52) U.S. Cl. ...................................... 514/422; 548/540

(58) Field of Classification Search ................... 548/518; 514/422
See application file for complete search history.

(56) References Cited

U.S. PATENT DOCUMENTS

| | | | |
|---|---|---|---|
| 6,110,691 A | 8/2000 | Wang et al. | |
| 6,608,026 B1 | 8/2003 | Wang et al. | |
| 6,992,063 B2 | 1/2006 | Shi | |
| 7,041,784 B2 | 5/2006 | Wang et al. | |
| 7,094,758 B2 | 8/2006 | Wang et al. | |
| 7,229,617 B2 | 6/2007 | Nasoff et al. | |
| 7,244,851 B2 | 7/2007 | Cohen et al. | |
| 7,309,792 B2 | 12/2007 | Harran et al. | |
| 2004/0180828 A1 | 9/2004 | Shi et al. | |
| 2006/0025347 A1 | 2/2006 | Condon et al. | |
| 2006/0194741 A1 | 8/2006 | Condon et al. | |
| 2006/0211627 A1 | 9/2006 | Reed et al. | |
| 2006/0258581 A1 | 11/2006 | Reed et al. | |
| 2007/0032437 A1 | 2/2007 | Shi et al. | |
| 2007/0093428 A1 | 4/2007 | Laurent | |
| 2007/0093429 A1 | 4/2007 | Laurent et al. | |
| 2007/0219140 A1 | 9/2007 | Laurent et al. | |
| 2008/0069812 A1 | 3/2008 | Boudreault et al. | |
| 2008/0089896 A1 | 4/2008 | Wang et al. | |
| 2008/0207525 A1 | 8/2008 | Boudreault et al. | |

FOREIGN PATENT DOCUMENTS

| | | | |
|---|---|---|---|
| CA | 2 560 162 A1 | 10/2005 | |
| CA | 2 574 040 A1 | 2/2006 | |
| JP | 61183297 A | 8/1986 | |
| JP | 04208299 A | 7/1992 | |
| WO | WO 02/30959 A2 | 4/2002 | |
| WO | WO 2004/005248 A1 | 1/2004 | |
| WO | WO 2004072641 A1 * | 8/2004 | |
| WO | WO 2005/069888 A2 | 8/2005 | |
| WO | WO 2005/084317 A2 | 9/2005 | |
| WO | WO 2005/094818 A1 | 10/2005 | |
| WO | WO 2005/097791 A1 | 10/2005 | |
| WO | WO 2006/010118 A2 | 1/2006 | |
| WO | WO 2006/017295 A2 | 2/2006 | |
| WO | WO 2006/069063 A1 | 6/2006 | |
| WO | WO 2006/113376 A1 | 10/2006 | |
| WO | WO 2006/122408 A1 | 11/2006 | |
| WO | WO 2006/128455 A2 | 12/2006 | |
| WO | WO 2006/133147 A2 | 12/2006 | |
| WO | WO 2007/048224 A1 | 5/2007 | |
| WO | WO 2007/075525 A2 | 7/2007 | |
| WO | WO 2007/101347 A1 | 9/2007 | |
| WO | WO 2007/104162 A1 | 9/2007 | |
| WO | WO 2007/106192 A2 | 9/2007 | |
| WO | WO 2007/131366 A1 | 11/2007 | |

(Continued)

OTHER PUBLICATIONS

RN 172333-99-2; Accession No. 1996:12194 (1995).* Abstract Only:Samson et al. Let. in Pep. Sci. 2:217 (1995).*
Arnt et al., *J. Biol. Chem.*, "Synthetic Smac/DIABLO peptides enhance the effects of chemotherapeutic agents by binding XIAP and cIAP1 in Situ," 277(46): 44236-44243 (2002).
Bertrand et al., *Mol. Cell*, "cIAP1 and cIAP2 facilitate cancer cell survival by functioning as E3 ligases that promote RIP1 ubiquitination," 30: 689-700 (2008).
Bucher et al., *Helv. Chim. Acta.*, 78(4):935-46 (1995).
Chai et al., *Nature*, "Structural and biochemical basis of apoptotic activation by Smac/DIABLO," 406: 855-62 (2000).
Chauhan et al., *Blood*, "Targeting mitochondrial factor Smac/DIABLO as therapy for multiple myeloma (MM)," 109(3): 1220-7 (2007).

(Continued)

*Primary Examiner* — Kamal Saeed
*Assistant Examiner* — Michael Barker
(74) *Attorney, Agent, or Firm* — Leydig, Voit & Mayer, Ltd.

(57) ABSTRACT

Disclosed herein is an isomer, enantiomer, diastereoisomer or tautomer of a compound represented by Formula I:

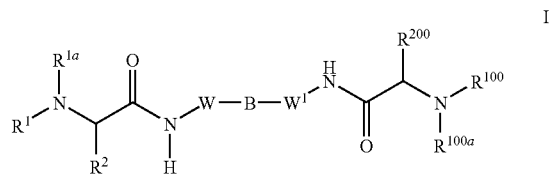

or a prodrug, or a pharmaceutically acceptable salt, or labeled with a detectable label or an affinity tag thereof; wherein $R^1$, $R^{1a}$, $R^{100}$, $R^{100a}$, $R^2$, $R^{200}$, W, B, and $W^1$ are defined herein. Also disclosed are methods of using compounds of Formula I to treat proliferative disorders such as cancer.

28 Claims, No Drawings

FOREIGN PATENT DOCUMENTS

| | | |
|---|---|---|
| WO | WO 2007/136921 A2 | 11/2007 |
| WO | WO 2008/014229 A2 | 1/2008 |
| WO | WO 2008/014236 A1 | 1/2008 |
| WO | WO 2008/014238 A2 | 1/2008 |
| WO | WO 2008/014240 A2 | 1/2008 |
| WO | WO 2008/014252 A2 | 1/2008 |
| WO | WO 2008/014263 A2 | 1/2008 |
| WO | WO 2008/016893 A1 | 2/2008 |
| WO | WO 2008/045905 A1 | 4/2008 |
| WO | WO 2008/057172 A2 | 5/2008 |
| WO | WO 2008/067280 A2 | 6/2008 |
| WO | WO 2008/073306 A1 | 6/2008 |
| WO | WO 2008/079735 A1 | 7/2008 |
| WO | WO 2008/085610 A1 | 7/2008 |

OTHER PUBLICATIONS

Chen et al., *Bioorg. Med. Chem. Lett.*, "Design, synthesis, and characterization of new embelin derivatives as potent inhibitors of X-linked inhibitor of apoptosis protein," 16(22): 5805-5808 (2006).

Eckelman et al., *Cell Death Differ.*, "The mechanism of peptide-binding specificity of IAP BIR domains," 15(5): 920-8 (2008).

Elmore et al., *Annual Rep. Med. Chem.*, "Inhibitors of Anti-apoptotic Proteins for Cancer Therapy," 40: 245-62 (2006).

Franklin et al., *Biochemistry*, "Structure and function analysis of peptide antagonists of melanoma inhibitor of apoptosis (ML-IAP)," 42: 8223-31 (2003).

Fulda et al., *Nature Medicine*, "Smac agonists sensitize for Apo2L/TRAIL- or anticancer drug-induced apoptosis and induce regression of malignant glioma in vivo," 8: 808-15 (2002).

Gao et al., *J. Biol. Chem.*, "A dimeric Smac/Diablo peptide directly relieves caspase-3 inhibition by XIAP. Dynamic and cooperative regulation of XIAP by Smac/Diablo," 282(42): 30718-27 (2007).

Haining et al., *Proc. Natl. Acad. Sci. USA*, "The proapoptotic function of Drosophila HID is conserved in mammalian cells," 96(9): 4936-41 (1999).

Kipp et al., *Biochemistry*, "Molecular targeting of inhibitor of apoptosis proteins based on small molecule mimics of natural binding partners," 41: 7344-9 (2002).

Li et al., *Science*, "A small molecule Smac mimic potentiates TRAIL- and TNFalpha-mediated cell death," 305(5689): 1471-4 (2004).

Liu et al., *Nature*, "Structural basis for binding of Smac/DIABLO to the XIAP BIR3 domain," 408: 1004-8 (2000).

Marik et al., *J. Peptide. Res.*, "Synthesis and effect of shortened oostatic decapeptide (TMOF) analogs with isosteric structures on reproduction of Neobellieria bullata," 57(5): 401-8 (2001).

McCarthy et al., *J. Biol. Chem.*, "Apoptosis induced by Drosophila reaper and grim in a human system. Attenuation by inhibitor of apoptosis proteins (cIAPs)," 273(37): 24009-15 (1998).

Nikolovska-Coleska et al., *Anal. Biochem.*, "Development and optimization of a binding assay for the XIAP BIR3 domain using fluorescence polarization," 332: 261-273 (2004).

Nikolovska-Coleska et al., *J. Med. Chem.*, "Discovery of embelin as a cell-permeable, small-molecular weight inhibitor of XIAP through structure-based computational screening of a traditional herbal medicine three-dimensional structure database," 47(10): 2430-40 (2004).

Nikolovska-Coleska et al., *Anal. Biochem.*, "Design and characterization of bivalent Smac-based peptides as antagonists of XIAP and development and validation of a fluorescence polarization assay for XIAP containing both BIR2 and BIR3 domains," 374(1): 87-98 (2008).

Oost et al., *J. Med. Chem.*, "Discovery of potent antagonists of the antiapoptotic protein XIAP for the treatment of cancer," 47(18): 4417-26 (2004).

Park et al., *Bioorg. Med. Chem. Lett.*, "Non-peptidic small molecule inhibitors of XIAP," 15(3): 771-5 (2005).

Petersen et al., *Cancer Cell*, "Autocrine TNFalpha signaling renders human cancer cells susceptible to Smac-mimetic-induced apoptosis," 12(5): 445-56 (2007).

Srinivasula et al., *J. Biol. Chem.*, "Molecular determinants of the caspase-promoting activity of Smac/DIABLO and its role in the death receptor pathway," 275(46): 36152-7 (2000).

Sun et al., *J. Am. Chem. Soc.*, "Structure-Based Design of Potent, Conformationally Constrained Smac Mimetics," 126(51): 16686-87 (2004).

Sun et al., *J. Med. Chem.*, "Structure-based design, synthesis, and evaluation of conformationally constrained mimetics of the second mitochondria-derived activator of caspase that target the X-linked inhibitor of apoptosis protein/caspase-9 interaction site," 47(17): 4147-50 (2004).

Sun et al., *Biorg. Med. Chem. Lett.*, "Structure-based design, synthesis and biochemical testing of novel and potent Smac peptido-mimetics," 15(3): 793-97 (2005).

Sun et al., *Tetrahedron Letters*, "Design and synthesis of a potent biotinylated Smac mimetic," 46: 7015-18 (2005).

Sun et al., *J. Med. Chem.*, "Design, synthesis, and evaluation of a potent, cell-permeable, conformationally constrained second mitochondria derived activator of caspase (Smac) mimetic," 49(26): 7916-20 (2006).

Sun et al., *J. Am. Chem. Soc.*, "Design, synthesis, and characterization of a potent, nonpeptide, cell-permeable, bivalent Smac mimetic that concurrently targets both the BIR2 and BIR3 domains in XIAP," 129(49): 15279-94 (2007).

Sweeney et al., *Biochemistry*, "Determination of the sequence specificity of XIAP BIR domains by screening a combinatorial peptide library," 45(49): 14740-8 (2006).

Terui et al., *Cancer Res.*, "NH2-terminal pentapeptide of endothelial interleukin 8 is responsible for the induction of apoptosis in leukemic cells and has an antitumor effect in vivo," *Cancer Res* 59(22): 5651-5 (1999).

Varfolomeev et al., *Cell*, "IAP antagonists induce autoubiquitination of c-IAPs, NF-kappaB activation, and TNFalpha-dependent apoptosis," 131(4): 669-81 (2007).

Vince et al., *Cell*, "IAP antagonists target cIAP1 to induce TNFalpha-dependent apoptosis," 131(4): 682-93 (2007).

Voskoglou-Nomikos et al., *Clin. Cancer Res.*, "Clinical Predictive Value of the in vitro Cell Line, Human Xenograft, and Mouse Allograft Preclinical Cancer Models," 9:4227-4239 (2003).

Vucic et al., *Mol. Cell. Biol.*, "Inhibitor of apoptosis proteins physically interact with and block apoptosis induced by Drosophila proteins HID and GRIM," 18(6): 3300-9 (1998).

Wist et al., *Bioorg. Med. Chem.*, "Structure-activity based study of the Smac-binding pocket within the BIR3 domain of XIAP," 15(8): 2935-43 (2007).

Wu et al., *Nature*, "Structural basis of IAP recognition by Smac/DIABLO," 408: 1008-12 (2000).

Wu et al., *Chem. Biol.*, "Development and characterization of nonpeptidic small molecule inhibitors of the XIAP/caspase-3 interaction," 10(8): 759-67 (2003).

Zobel et al., *ACS Chem. Biol.*, "Design, Synthesis, and Biological Activity of a Potent Smac Mimetic That Sensitizes Cancer Cells to Apoptosis by Antagonizing IAPs," 1(8): 525-33 (2006).

\* cited by examiner

IAP BIR DOMAIN BINDING COMPOUNDS

FIELD OF THE INVENTION

The present invention concerns bridged compounds that bind to IAP BIR domains, and which are useful for treating proliferative disorders and disorders of dysregulated apoptosis, such as cancer.

BACKGROUND OF THE INVENTION

Apoptosis, or programmed cell death, typically occurs in the normal development and maintenance of healthy tissues in multicellular organisms. It is a complex process which results in the removal of damaged, diseased or developmentally redundant cells, in the absence of signs of inflammation or necrosis.

Intrinsic apoptotic pathways are known to be dysregulated, most particularly in cancer and lymphoproliferative syndromes, as well as autoimmune disorders such as multiple sclerosis, in neurodegenerative diseases and in inflammation. As well, alterations in a host apoptotic response have been described in the development or maintenance of viral and bacterial infections.

The caspases are a family of proteolytic enzymes from the class of cysteine proteases which are known to initiate and execute apoptosis. In normal cells, the caspases are present as inactive zymogens, which are catalytically activated following external signals, for example those resulting from ligand driven Death Receptor activation, such as cytokines or immunological agents, or by release of mitochondrial factors, such as cytochrome C following genotoxic, chemotoxic, or radiation-induced cellular injury. The Inhibitors of Apoptosis Proteins (IAPs) constitute a family of proteins which are capable of binding to and inhibiting the caspases, thereby suppressing cellular apoptosis. Because of their central role in regulating caspase activity, the IAPs are capable of inhibiting programmed cell death from a wide variety of triggers, which include loss of homeostatic, or endogenous cellular growth control mechanisms, as well as chemotherapeutic drugs and irradiation.

The IAPs contain one to three homologous structural domains known as baculovirus IAP repeat (BIR) domains. They may also contain a RING zinc finger domain at the C-terminus, with a capability of inducing ubiquitinylation of IAP-binding molecules via its E3 ligase function. The human IAPs, XIAP, HIAP1 (also referred to as cIAP2), and HIAP2 (cIAP1) each have three BIR domains, and a carboxy terminal RING zinc finger. Another IAP, NAIP, has three BIR domains (BIR1, BIR2 and BIR3), but no RING domain, whereas Livin, TsIAP and MLIAP have a single BIR domain and a RING domain. The X chromosome-linked inhibitor of apoptosis (XIAP) is an example of an IAP which can inhibit the initiator caspase, known as caspase-9, and the effector caspases, Caspase-3 and Caspase-7, by direct binding. XIAP can also induce the removal of caspases through the ubiquitylation-mediated proteasome pathway via the E3 ligase activity of a RING zinc finger domain. Additionally, the BIR3 domain of XIAP binds to and inhibits caspase-9. The linker-BIR2 domain of XIAP inhibits the activity of caspases-3 and -7. The BIR domains have also been associated with the interactions of IAPs with tumor necrosis factor-receptor associated factor (TRAFs)-1 and -2, and to TAB1, as adaptor proteins effecting survival signaling through NFkB activation. The IAPs thus function as a direct brake on the apoptosis cascade, by preventing the action of, or inhibiting active caspases and by re-directing cellular signaling to a pro-survival mode.

Progress in the cancer field has led to a new paradigm in cancer biology wherein neoplasia may be viewed as a failure of cancer cells to execute normal pathways of apoptosis. Normal cells receive continuous feedback from their environment through various intracellular and extracellular factors, and "commit suicide" if removed from this context. This induction of apoptosis is achieved by activation of the caspase cascade. Cancer cells, however, gain the ability to overcome or bypass this apoptosis regulation and continue with inappropriate proliferation. The majority of treatments for cancer induce at least a partial apoptotic response in the cancer target cell, resulting in remission or initiation of tumor regression. In many cases, however, residual cells which are apoptosis-resistant are capable of escaping therapy and continuing the process of oncogenic/genetic change, resulting in the emergence of highly drug-resistant, metastatic disease which overcomes our ability to effectively treat the disease. Furthermore, most cancer therapies, including radiation therapy and traditional chemotherapy do induce apoptosis in cancer cells, but cause additional cellular injury, due to their lack of specificity in inducing apoptosis solely in cancer cells. The need to improve the specificity/potency of pro-apoptosis agents used to treat cancer, and indeed other proliferative disorders, is important because of the benefits in decreasing the side effects associated with administration of these agents. Therefore, finding novel means of inducing apoptosis in cancer cells is a highly desired medical need and its solution offers the possibility of entirely new treatments for cancer.

A growing body of data indicates that cancer cells may avoid apoptosis by the sustained over-expression of one or more members of the IAP family of proteins, as documented in many primary tumor biopsy samples, as well as most established cancer cell lines. Epidemiological studies have demonstrated that over-expression of the various IAPs is associated with poor clinical prognosis and survival. For XIAP this is shown in cancers as diverse as leukemia and ovarian cancer. Over expression of HIAP1 and HIAP2 resulting from the frequent chromosome amplification of the 11q21-q23 region, which encompasses both, has been observed in a variety of malignancies, including medulloblastomas, renal cell carcinomas, glioblastomas, and gastric carcinomas. (X) IAP negative regulatory molecules such as XAF, appear to be tumor suppressors, which are very frequently lost in clinical cancers. Thus, by their ability to suppress the activation and execution of the intrinsic mediators of apoptosis, the caspases, the IAPs may directly contribute to tumor progression and resistance to pharmaceutical intervention. Induction of apoptosis in cancer cells by the use of potent small molecules which bind to specific IAP domains is the subject of this invention.

We and others have demonstrated the critical importance of the individual BIR domains for affecting the antiapoptotic function of the IAPs. We have proposed that antagonists of the IAPs, which may bind to the individual BIR domains, would disrupt the antiapoptotic function of the IAPs. Indeed, individual BIRs serve as critical binding sites for the N-terminal Ser-Gly-Val-Asp, Ser-Gly-Pro-Ile and Ala-Thr-Pro-Ile residues of the Caspases 3, 7, and 9, respectively, and such binding is imperative for the caspase-inhibitory function of the IAPs. The binding of N-terminal AxPy tetra-peptide residues to XIAP results in the release of the active caspases 3, 7 and 9. In the case of the other IAPs, such as c-IAP1 and c-IAP2, the functions of the BIRs, when ligand-bound, appear to direct the activation of the ubiquitin ligase RING function of the IAPs to a bound target, or individual IAPs themselves, to cause proteosomal loss. In either case, small molecule antagonists of the IAPs should be excellent pro-apoptotic agents, with potential uses in cancer, various proliferative disorders and inflammation.

A mammalian mitochondrial protein, namely Second Mitochondria-derived Activator of Caspases (SMAC) which antagonizes IAP function, binds mainly to the BIR 3 or 2 sites on respective IAPs via an AxPy amino-terminal tetrapeptide. Four *Drosophila* death-inducing proteins, Reaper, HID, Grim, and Sickle, which antagonize the ability of the *Drosophila* IAPs to inhibit caspases, also bind the BIR domains of the analogous *Drosophila* IAPs via a short AxPy amino-terminal tetrapeptide, a sequence that fits into the BIR binding pocket and disrupts IAP-caspase interactions.

The overall topology of individual BIR domains is highly conserved between the human IAPs and between individual BIR domains of the human IAPs, each BIR being a zinc finger polypeptide domain, locked into a coordinated Zn atom by three cysteines and a histidine residue. The X-ray crystallographic structures of XIAP BIR2 and BIR3 reveal a critical binding pocket for an AxPy motif on the surface of each BIR domain. There are alterations in the intervening amino acid sequences that form the binding pocket and groove in both BIR2 and BIR3. Likewise, we have described homologous domains in the BIRs of other IAPs cIAP1 and cIAP2. This opens the possibility of obtaining various classes of natural and synthetic binding compounds which will have different specificity and binding affinities between each of the BIR domains for each of the IAPs. Discerning the way in which such compounds will affect the biological function of the IAPs in cancer cells as compared to normal cells is a major new challenge in the discovery of novel mechanism agents to treat cancer and other proliferative disorders where dysregulated IAP function is observed. It is our finding that certain classes of BIR binding compounds may bind to IAP BIRs, with unexpected selectivity and potency, resulting in distinct therapeutic advantages for certain structural classes, potentially resulting from either IAP loss of function or loss of cellular IAP protein, or both.

A number of peptidic AxPy-like and heterocyclic modified AxPy peptidic compounds have been described which activate cellular caspase 3 by reportedly binding to XIAP BIR3. For a recent reviews, see Elmore et al., Annual Reports in Medicinal Chemistry, 40 (2006) 245-262; Sun et al., Bioorg. Med. Chem. Let. 15 (2005) 793-797; Oost et al., J. Med. Chem., 2004, 47(18), 4417-4426; Park et al., Bioorg. Med. Chem. Lett. 15 (2005) 771-775; Franklin et al., Biochemistry, Vol. 42, No. 27, 2003, 8223-8231; Kip et al., Biochemistry 2002, 41, 7344-7349; Wu et al., Chemistry and Biology, Vol. 10, 759-767 (2003); Glover et al., Analytical Biochemistry, 320 (2003) 157-169; United States published patent application number 20020177557; and United States published patent application number 20040180828; United States published patent application number US2006/0025347A1; United States published patent application number US2005/0197403A1; and United States published patent application number US2006/0194741 A1.

The aforesaid compounds have been shown to target an isolated BIR3 domain of XIAP via displacement of a fluorescently-labeled probe and they appear to induce an apoptotic event in a select set of cancer cell lines with potency in the low micromolar-nanomolar range. These compounds displayed poor in-vivo activity, likely due to limited bioavailability and may therefore have limited therapeutic application.

Thus, IAP BIR domains represent an attractive target for the discovery and development of novel therapeutic agents, especially for the treatment of proliferative disorders such as cancer.

SUMMARY OF THE INVENTION

The inventors have previously disclosed a series of compounds which bind to the BIR units of the IAPs and induce apoptosis in various cancer cell lines (US published patent application number 20060264379). We herein disclose that the linkage of two BIR binding units, with preference for the site, orientation and chemical nature of the linkage, provides novel and distinctly advantageous classes of compounds with up to 1000 fold increase in potency against various cancer cell lines, over their corresponding non-bridged BIR binding compounds. These compounds display the requisite potency, stability and pharmaceutical properties for the treatment of human cancers. Advantageously, the chemical nature of the bridging group can be chosen to cause the translation of the high intrinsic cellular potency to microgram/kg potency in inhibiting and/or suppressing IAPs in tumour samples. Furthermore, the compounds described have pharmaceutically acceptable stability in a range of mammalian tissues and fluids and have pharmaceutical properties that ensure adequate solubility and bioavailability using various routes of administration, suitable for clinical use. Such administration results in sustained in vivo effects in mammals as measured in normal and tumor tissues.

In one embodiment of the present invention, there is provided an isomer, enantiomer, diastereoisomer or tautomer of a compound represented by Formula I:

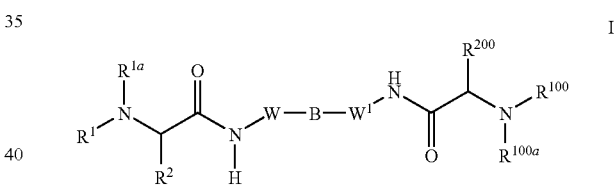

wherein:
n is 0 or 1;
m is 0, 1 or 2;
Y is NH, O or S;
W is

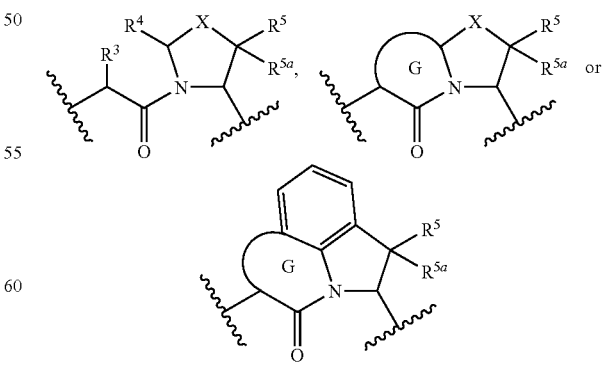

wherein X is $C_1$-$C_3$ alkyl which forms part of a ring system, the ring system being optionally substituted with one or more $R^{11}$ substituents; or X is part of a 5, 6, or 7 membered heterocyclic ring system optionally including one, two or three heteroatoms selected from O, N or S, the ring system being optionally substituted with one or more $R^{11}$; or X is —C(O)—; and G is a 5, 6, or 7 membered ring system optionally including one or more heteroatoms selected from O, N or S, the ring system being optionally substituted with one or more $R^{11}$; and
$W^1$ is

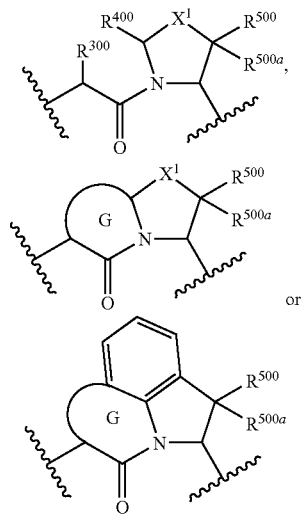

wherein $R^{300}$, $R^{400}$, $R^{500}$, $R^{500a}$, $X^1$, $G^1$ are as defined as $R^3$, $R^4$, $R^5$, X and G respectively; or
W and $W^1$ is independently selected from

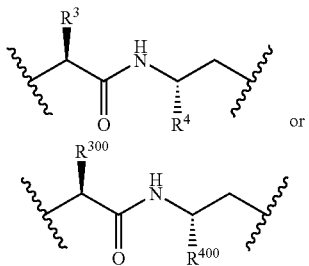

wherein $R^3$, $R^4$ are defined as $R^{300}$, $R^{400}$ respectively;
B is

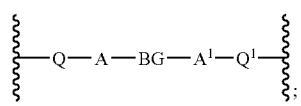

Q and $Q^1$ are independently selected from
1) —CH$_2$—,
2) —CH$_2$CH$_2$—,
3) —CH(C$_1$-C$_6$ alkyl)-,
4) —CH(C$_3$-C$_7$ cycloalkyl)-,
5) —C$_3$-C$_7$ cycloalkyl-,
6) —CH(C$_1$-C$_6$ alkyl-C$_3$-C$_7$ cycloalkyl)-; or
7) —C(O)—;
A and $A^1$ are independently selected from
1) NR$^6$ or
2) NR$^{600}$;

BG is
1) —$Y^1$-L-$Y^{100}$—; or
2) -L-; or
BG is —$Y^1$-$L^1$-Z-$L^{100}$-$Y^{100}$—, wherein $L^1$ and $L^{100}$ are equal or $L^1$ and $L^{100}$ are different;
$Y^1$ and $Y^{100}$ are independently selected from
1) —C(O)—,
2) —S(O)$_2$—, or
3) —C(O)N(R$^8$)—;
L, $L^1$ and $L^{100}$ are selected from:
1) —C$_1$-C$_{12}$ alkyl-,
2) —C$_2$-C$_{12}$ alkenyl-,
3) —C$_2$-C$_{12}$ alkynyl-,
4) —C$_3$-C$_7$ cycloalkyl-,
5) —C$_3$-C$_7$ cycloalkenyl-,
5) -aryl-,
6) -biphenyl-,
7) -heteroaryl-,
8) -heterocycyl-,
9) —C$_1$-C$_6$ alkyl-(C$_2$-C$_6$ alkenyl)-C$_1$-C$_6$ alkyl-,
10) —C$_1$-C$_6$ alkyl-(C$_2$-C$_4$ alkynyl)-C$_1$-C$_6$ alkyl,
11) —C$_1$-C$_6$ alkyl-(C$_3$-C$_7$ cycloalkyl)-C$_1$-C$_6$ alkyl,
12) —C$_1$-C$_6$ alkyl-aryl-C$_1$-C$_6$ alkyl,
13) —C$_1$-C$_6$ alkyl-biphenyl-C$_1$-C$_6$ alkyl,
14) —C$_1$-C$_6$ alkyl-heteroaryl-C$_1$-C$_6$ alkyl,
15) —C$_1$-C$_6$ alkyl heterocycyl-C$_1$-C$_6$ alkyl, or
16) —C$_1$-C$_6$ alkyl-O—C$_1$-C$_6$ alkyl; or
L, $L^1$ and $L^{100}$ are selected from:
1) -N(R$^8$)C(O)N(R$^8$)—, or
2) —C$_1$-C$_6$ alkyl-Z—C$_1$-C$_6$ alkyl-;
wherein the alkyl, the alkenyl, the alkynyl, the cycloalkyenyl and the cycloalkyl are optionally substituted with one or more $R^7$ substituents; and the aryl, the heteroaryl, the biphenyl and the heterocyclyl are optionally substituted with one or more $R^{11}$ substituents;
Z is selected from:
1) —N(R$^8$)CON(R$^8$)
2) —N(R$^8$)C(O)-aryl-C(O)N(R$^8$)—,
3) —N(R$^8$)C(O)-heteroaryl-C(O)N(R$^8$)—,
4) —C(O)—,
5) —S(O)$_2$—,
6) —N(R$^8$)C(O)—,
7) —C(O)N(R$^8$)—,
8) —OC(O)N(R$^8$)—,
9) —S(O)$_2$N(R$^8$)—,
10) —N(R$^8$)—C$_1$-C$_{12}$-alkyl-N(R$^8$)—,
11) —N(R$^8$)—C(O)C(O)—N(R$^8$)—,
12) —N(R$^8$)—C(O)—C$_1$-C$_{12}$-alkyl-C(O)—N(R$^8$)—,
13) —N(R$^8$)—C(O)-aryl-C(O)—N(R$^8$)—,
14) —N(R$^8$)—C(O)-aryl-O-aryl-C(O)—N(R$^8$)—,
15) —N(R$^8$)—C(O)-heteroaryl-C(O)—N(R$^8$)—,
16) —N(R$^8$)—C(O)-biphenyl-C(O)—N(R$^8$)—,
17) —N(R$^8$)—S(O)$_2$—C$_1$-C$_{12}$-alkyl-S(O)$_2$—N(R$^8$)—,
18) —N(R$^8$)—S(O)$_2$-aryl-S(O)$_2$—N(R$^8$)—,
19) —N(R$^8$)—S(O)$_2$-heteroaryl-S(O)$_2$—N(R$^8$)—,
20) —N(R$^8$)—S(O)$_2$-biphenyl-S(O)$_2$—N(R$^8$)—,
21) —N(R$^8$)—C$_1$-C$_{12}$-alkyl-N(R$^8$)—,
22) —N(R$^8$)-aryl-N(R$^8$)—,
23) —N(R$^8$)-heteroaryl-N(R$^8$)—, or
24) —N(R$^8$)-biphenyl-N(R$^8$)—;
wherein the alkyl and the cycloalkyl are optionally substituted with one or more $R^7$ substituents, and the aryl, the heteroaryl and the heterocyclyl are optionally substituted with one or more $R^{11}$ substituents;
$R^1$ and $R^{100}$ are independently selected from
1) H, or
2) C$_1$-C$_6$ alkyl optionally substituted with one or more $R^7$ substituents;

$R^2$, $R^3$, $R^4$, $R^5$, $R^{5a}$, $R^{200}$, $R^{300}$, $R^{400}$, $R^{500}$ and $R^{500a}$ are each independently H or $C_1$-$C_6$ alkyl optionally substituted with one or more $R^7$ substituents;

$R^6$ and $R^{600}$ are each independently
1) H,
2) haloalkyl,
3) ←$C_1$-$C_6$ alkyl,
4) ←$C_2$-$C_6$ alkenyl,
5) ←$C_2$-$C_4$ alkynyl,
6) ←$C_3$-$C_7$ cycloalkyl,
7) ←$C_3$-$C_7$ cycloalkenyl,
8) ←aryl,
9) ←heteroaryl,
10) ←heterocyclyl,
11) ←heterobicyclyl,
12) ←$C(O)(O)_n$—$R^{12}$,
13) ←$C(=Y)NR^9R^{10}$, or
14) ←$S(O)_2$—$R^{12}$, wherein the alkyl, alkenyl, alkynyl, cycloalkyl, cycloalkenyl is optionally substituted with one or more $R^7$ substituents; and wherein the aryl, heteroaryl, heterocyclyl, and heterobicyclyl is optionally substituted with one or more $R^{11}$ substituents;

$R^7$ is
1) halogen,
2) $NO_2$,
3) CN,
4) haloalkyl,
5) $C_1$-$C_6$ alkyl,
6) $C_2$-$C_6$ alkenyl,
7) $C_2$-$C_4$ alkynyl,
8) $C_3$-$C_7$ cycloalkyl,
9) $C_3$-$C_7$ cycloalkenyl,
10) aryl,
11) heteroaryl,
12) heterocyclyl,
13) heterobicyclyl,
14) $OR^8$,
15) $S(O)_mR^8$,
16) $NR^9R^{10}$,
17) $NR^9S(O)_2R^{12}$,
18) $COR^8$,
19) $C(O)OR^8$,
20) $CONR^9R^{10}$,
21) $S(O)_2NR^9R^{10}$,
22) $OC(O)R^8$,
23) $OC(O)Y$—$R^{12}$,
24) $SC(O)R^8$, or
25) $NC(Y)R^9R^{10}$, wherein the aryl, heteroaryl, heterocyclyl, and heterobicyclyl is optionally substituted with one or more $R^{11}$ substituents;

$R^8$ is
1) H,
2) haloalkyl,
3) $C_1$-$C_6$ alkyl,
4) $C_2$-$C_6$ alkenyl,
5) $C_2$-$C_4$ alkynyl,
6) $C_3$-$C_7$ cycloalkyl,
7) $C_3$-$C_7$ cycloalkenyl,
8) aryl,
9) heteroaryl,
10) heterocyclyl,
11) heterobicyclyl,
12) $R^9R^{10}NC(=Y)$, or
13) $C_1$-$C_6$ alkyl-$C_2$-$C_4$ alkenyl, or
14) $C_1$-$C_6$ alkyl-$C_2$-$C_4$ alkynyl, wherein the alkyl, alkenyl, alkynyl, cycloalkyl, cycloalkenyl is optionally substituted with one or more $R^7$ substituents; and wherein the aryl, heteroaryl, heterocyclyl, and heterobicyclyl is optionally substituted with one or more $R^{11}$ substituents;

$R^9$ and $R^{10}$ are each independently
1) H,
2) haloalkyl,
3) $C_1$-$C_6$ alkyl,
4) $C_2$-$C_6$ alkenyl,
5) $C_2$-$C_4$ alkynyl,
6) $C_3$-$C_7$ cycloalkyl,
7) $C_3$-$C_7$ cycloalkenyl,
8) aryl,
9) heteroaryl,
10) heterocyclyl,
11) heterobicyclyl,
12) $C(O)R^{12}$,
13) $C(O)Y$—$R^{12}$, or
14) $S(O)_2$—$R^{12}$, wherein the alkyl, alkenyl, alkynyl, cycloalkyl, cycloalkenyl is optionally substituted with one or more $R^7$ substituents; and wherein the aryl, heteroaryl, heterocyclyl, and heterobicyclyl is optionally substituted with one or more $R^{11}$ substituents; or $R^9$ and $R^{10}$ together with the nitrogen atom to which they are bonded form a five, six or seven membered heterocyclic ring optionally substituted with one or more $R^7$ substituents;

$R^{11}$ is
1) halogen,
2) $NO_2$,
3) CN,
4) $B(OR^{13})(OR^{14})$,
5) $C_1$-$C_6$ alkyl,
6) $C_2$-$C_6$ alkenyl,
7) $C_2$-$C_4$ alkynyl,
8) $C_3$-$C_7$ cycloalkyl,
9) $C_3$-$C_7$ cycloalkenyl,
10) haloalkyl,
11) $OR^8$,
12) $NR^9R^{10}$,
13) $SR^8$,
14) $COR^8$,
15) $C(O)OR^8$,
16) $S(O)_mR^8$,
17) $CONR^9R^{10}$,
18) $S(O)_2NR^9R^{10}$,
19) aryl,
20) heteroaryl,
21) heterocyclyl, or
22) heterobicyclyl, wherein the alkyl, alkenyl, alkynyl, cycloalkyl, and cycloalkenyl is optionally substituted with one or more $R^7$ substituents;

$R^{12}$ is
1) haloalkyl,
2) $C_1$-$C_6$ alkyl,
3) $C_2$-$C_6$ alkenyl,
4) $C_2$-$C_4$ alkynyl,
5) $C_3$-$C_7$ cycloalkyl,
6) $C_3$-$C_7$ cycloalkenyl,
7) aryl,
8) heteroaryl,
9) heterocyclyl, or
10) heterobicyclyl, wherein the alkyl, alkenyl, alkynyl, cycloalkyl, cycloalkenyl is optionally substituted with one or more $R^7$ substituents; and wherein the aryl, heteroaryl, heterocyclyl, and heterobicyclyl is optionally substituted with one or more $R^{11}$ substituents;

$R^{13}$ and $R^{14}$ are each independently
1) H, or
2) $C_1$-$C_6$ alkyl; or
$R^{13}$ and $R^{14}$ are combined to form a ring system;
or a prodrug, or a pharmaceutically acceptable salt, or labeled with a detectable label or an affinity tag thereof.

In another aspect of the present invention, there is provided an intermediate compound represented by Formula 1-v:

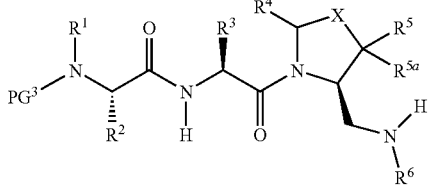

1-v wherein $PG^3$, $R^1$, $R^2$, $R^3$, $R^4$, $R^5$, $R^{5a}$, X, and $R^6$ are as defined herein.

In another aspect of the present invention, there is provided an intermediate compound represented by Formula 5-i:

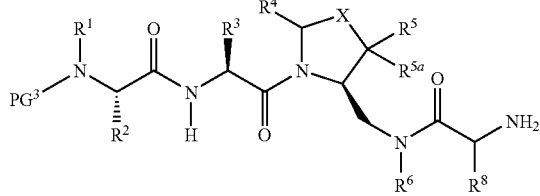

5-I wherein $PG^3$, $R^1$, $R^2$, $R^3$, $R^4$, $R^5$, $R^{5a}$, X, and $R^6$ are as defined herein.

In another aspect of the present invention, there is provided an intermediate compound represented by Formula 6-iv:

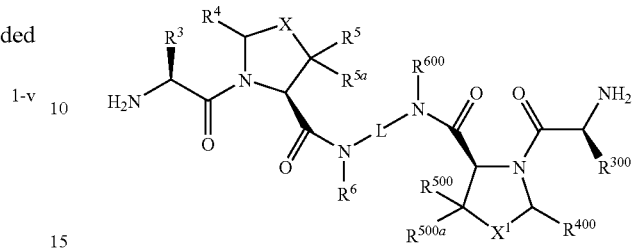

6-iv wherein $R^3$, $R^{300}$, $R^4$, $R^{400}$, $R^5$, $R^{5a}$, $R^{500}$, $R^{500a}$, X, $X^1$ and L are as defined herein.

In another aspect of the present invention, there is provided a process for producing compounds represented by Formula 2-i, described, the process comprising:
a) mixing two intermediates represented by Formula 1-v:

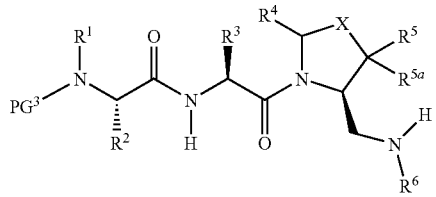

1-v and LG-C(O)-L-C(O)-LG in a solvent with a base; and
b) deprotecting $PG^3$ to provide a compound of Formula 2-i:

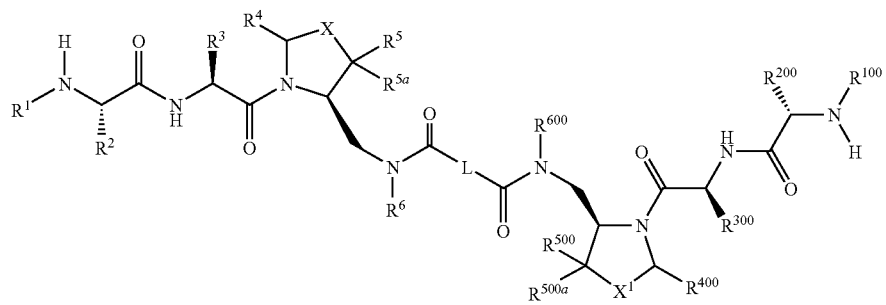

I-ii 2-i wherein $PG^3$, $R^1$, $R^{100}$, $R^2$, $R^{200}$, $R^3$, $R^{300}$, $R^4$, $R^{400}$, $R^5$, $R^{5a}$, $R^{500}$, $R^{500a}$, X, $X^1$ and L are as defined herein.

In another aspect of the present invention, there is provided a process for producing compounds represented by Formula 3-i, described, the process comprising:
a) mixing two intermediates represented by Formula 1-v:

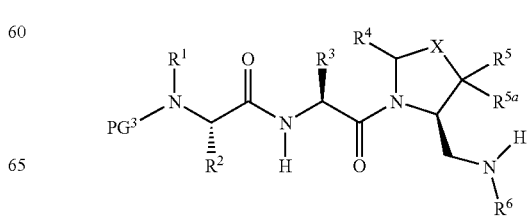

1-v and LG-S(O)$_2$-L-S(O)$_2$-LG in a solvent with a base; and
b) deprotecting PG$^3$ to provide a compound of Formula 3-i:

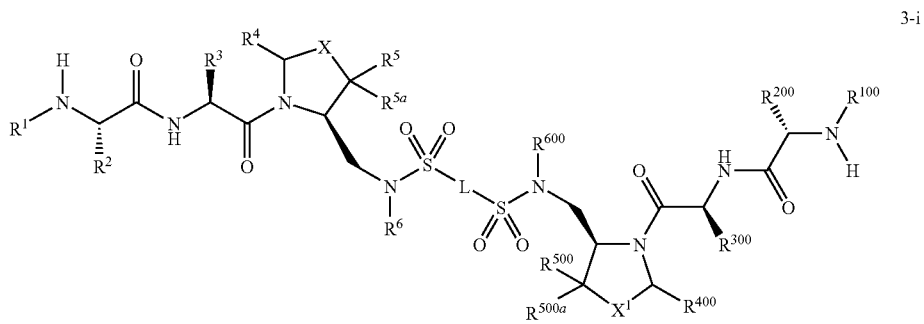

3-i wherein PG$^3$, R$^1$, R$^{100}$, R$^2$, R$^{200}$, R$^3$, R$^{300}$, R$^4$, R$^{400}$, R$^5$, R$^{5a}$, R$^{500}$, R$^{500a}$, X, X and L are as defined herein.

In another aspect of the present invention, there is provided a process for producing compounds represented by Formula 4-i, described, the process comprising:
a) mixing two intermediates represented by Formula 1-v:

1-v

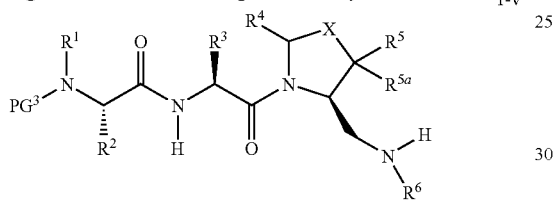

and LG-L-LG in a solvent with a base; and
b) deprotecting PG$^3$ to provide a compound of Formula 4-i:

4-i

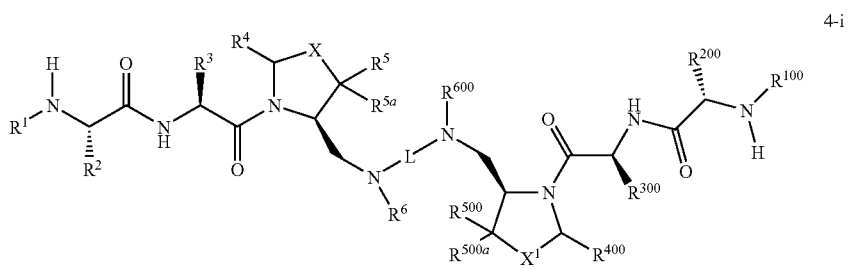

wherein PG$^3$, R$^1$, R$^{100}$, R$^2$, R$^{200}$, R$^3$, R$^{300}$, R$^4$, R$^{400}$, R$^5$, R$^{5a}$, R$^{500}$, R$^{500a}$, X, X and L are as defined herein.

In another aspect of the present invention, there is provided a process for producing compounds represented by Formula 5-ii, described, the process comprising:
a) mixing two intermediates represented by Formula 5-i:

5-i

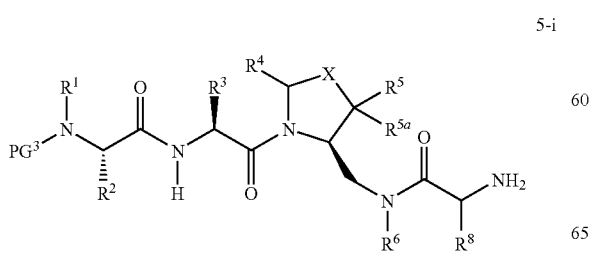

and LG-L-LG in a solvent with a base; and
b) deprotecting $PG^3$ to provide a compound of Formula 5-ii:

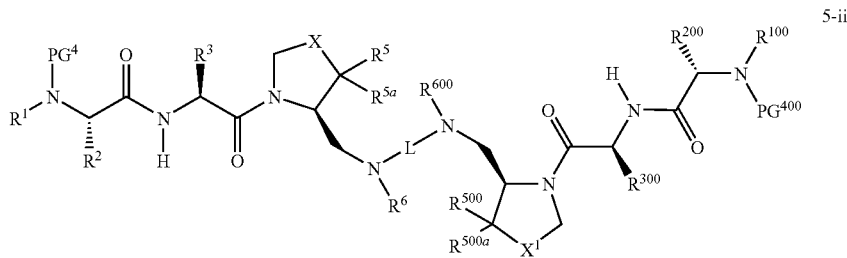

5-ii wherein $PG^3$, $R^1$, $R^{100}$, $R^2$, $R^{200}$, $R^3$, $R^{300}$, $R^4$, $R^{400}$, $R^5$, $R^{5a}$, $R^{500}$, $R^{500a}$, $R^6$, $R^{600}$, $R^8$, $R^{800}$, X, $X^1$ and L are as defined herein.

In another aspect of the present invention, there is provided a process for producing compounds represented by Formula 6-v, described, the process comprising:
a) mixing two intermediates represented by Formula 6-iv:

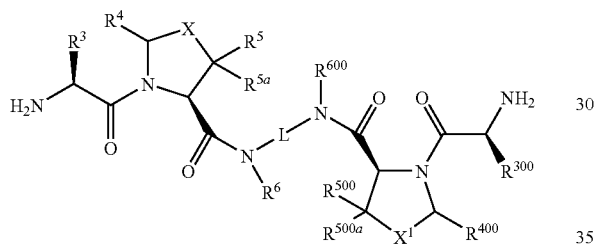

6-iv and

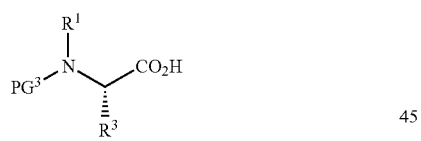

in a solvent with a coupling agent; and
b) deprotecting $PG^3$ to provide a compound of Formula 6-v:

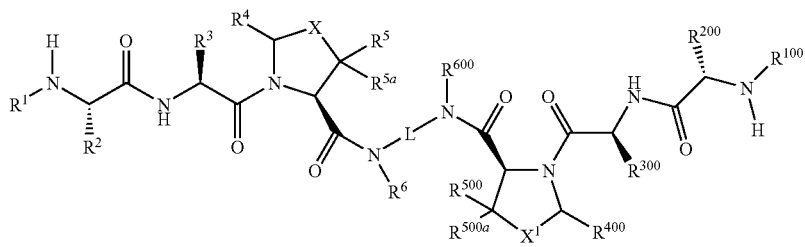

6-v wherein $PG^3$, $R^1$, $R^{100}$, $R^2$, $R^{200}$, $R^3$, $R^{300}$, $R^4$, $R^{400}$, $R^5$, $R^{5a}$, $R^{500}$, $R^{500a}$, $R^6$, $R^{600}$, $R^8$, $R^{800}$, X, $X^1$ and L are as defined herein.

In another aspect of the present invention, there is provided an intermediate compound represented by Formula I-ia:

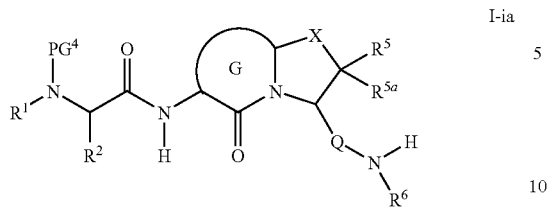
I-ia wherein $PG^4$, $R^1$, $R^2$, $R^3$, $R^4$, $R^5$, $R^{5a}$, X, Q, and $R^6$ are as defined herein.

In another aspect of the present invention, there is provided an intermediate compound represented by Formula I-iia:

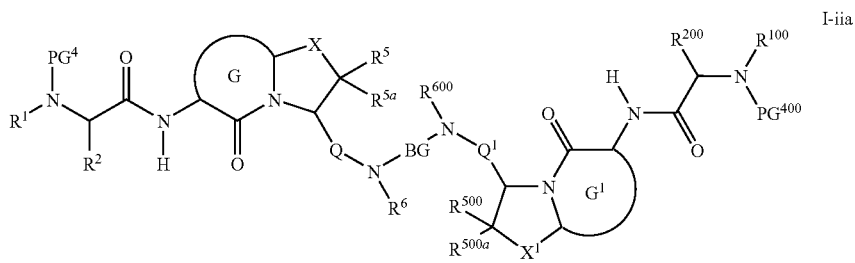
I-iia wherein $PG^4$, $PG^{400}$, $R^1$, $R^{100}$, $R^2$, $R^{200}$, $R^3$, $R^{300}$, $R^4$, $R^{400}$, $R^5$, $R^{5a}$, $R^{500}$, $R^{500a}$, A, $A^1$, Q, $Q^1$, X, $X^1$ and BG are as defined herein.

In another aspect of the present invention, there is provided a process for producing compounds represented by Formula I, described hereinabove, the process comprising:
a) bridging two intermediates represented by Formula 1-ia:

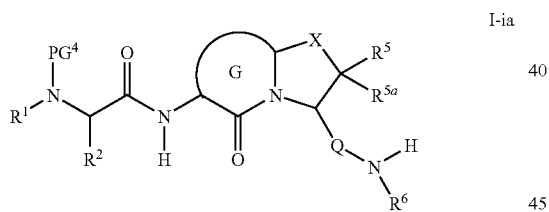
I-ia wherein $PG^4$, $R^1$, $R^2$, $R^3$, $R^4$, $R^5$, $R^{5a}$, X, Q, and $R^6$ are as defined herein, in a solvent to provide an intermediate represented by I-iia

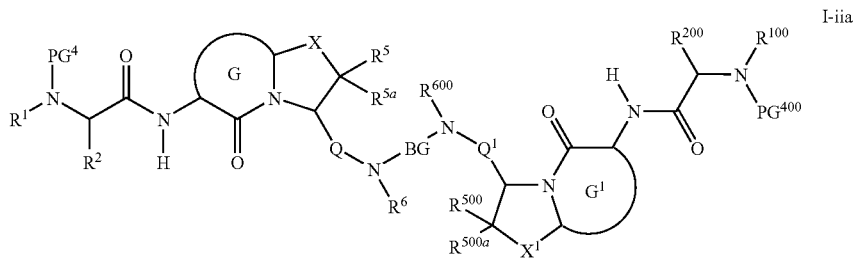
I-iia wherein $PG^4$, $PG^{400}$, $R^1$, $R^{100}$, $R^2$, $R^{200}$, $R^3$, $R^{300}$, $R^4$, $R^{400}$, $R^5$, $R^{5a}$, $R^{500}$, $R^{500a}$, A, $A^1$, Q, $Q^1$, X, $X^1$ and BG are as defined herein, and
b) removing the protecting groups $PG^4$ and $PG^{400}$ so as to form compounds of Formula 1.

In another aspect of the present invention, there is provided an intermediate compound represented by Formula I-ib:

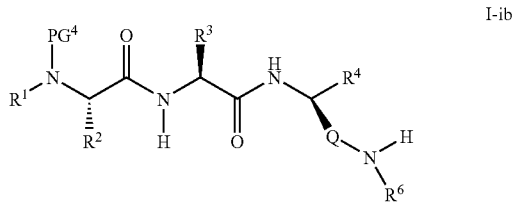

I-ib wherein $PG^4$, $R^1$, $R^2$, $R^3$, $R^4$, $R^5$, $R^{5a}$, X, Q, and $R^6$ are as defined herein.

In another aspect of the present invention, there is provided an intermediate compound represented by Formula I-iib:

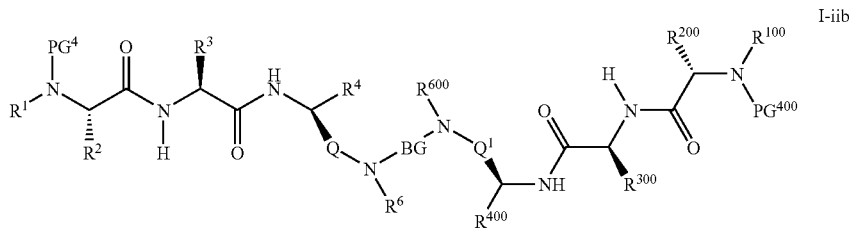

I-iib wherein PG, $PG^4$, $R^1$, $R^{100}$, $R^2$, $R^{200}$, $R^3$, $R^{300}$, $R^4$, $R^{400}$, $R^5$, $R^{5a}$, $R^{500}$, $R^{500a}$, A, $A^1$, Q, $Q^1$, X, $X^1$ and BG are as defined herein.

In another aspect of the present invention, there is provided a process for producing compounds represented by Formula I, described hereinabove, the process comprising:
a) bridging two intermediates represented by Formula 1-ib:

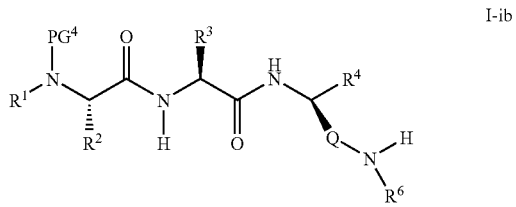

I-ib wherein $PG^4$, $R^1$, $R^2$, $R^3$, $R^4$, $R^5$, $R^{5a}$, X, Q, and $R^6$ are as defined herein, in a solvent to provide an intermediate represented by I-iib

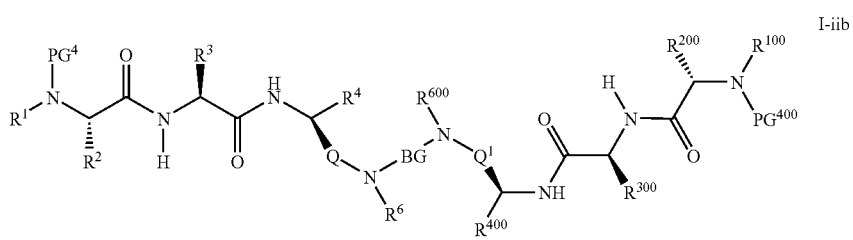

I-iib wherein $PG^4$, $PG^{400}$, $R^1$, $R^{100}$, $R^2$, $R^{200}$, $R^3$, $R^{300}$, $R^4$, $R^{400}$, $R^5$, $R^{5a}$, $R^{500}$, $R^{500a}$, A, $A^1$, Q, $Q^1$, X, $X^1$ and BG are as defined herein.
; and
b) removing the protecting groups $PG^4$ and $PG^{400}$ so as to form compounds of Formula 1.

In another aspect of the present invention, there is provided a method for the preparation of a pharmaceutically acceptable salt of compound of Formula I, by the treatment of a compound of Formula I with 1 to 2 equiv of a pharmaceutically acceptable acid, as defined herein.

In another aspect of the present invention, there is provided a pharmaceutical composition comprising a compound, as described above, mixed with a pharmaceutically acceptable carrier, diluent or excipient.

In another aspect of the present invention, there is provided a pharmaceutical composition adapted for administration as an agent for treating a proliferative disorder in a subject, comprising a therapeutically effective amount of a compound, as described above.

In another aspect of the present invention, there is provided a pharmaceutical composition comprising a compound of Formula I in combination with one or more death receptor agonists, for example, an agonist of TRAIL receptor.

In another aspect of the present invention, there is provided a pharmaceutical composition comprising a compound of Formula I in combination with any therapeutic agent that increases the response of one or more death receptor agonists, for example cytotoxic cytokines such as interferons.

In another aspect of the present invention, there is provided a method of preparing a pharmaceutical composition, the method comprising: mixing a compound, as described above, with a pharmaceutically acceptable carrier, diluent or excipient.

In another aspect of the present invention, there is provided a method of treating a disease state characterized by insufficient apoptosis, the method comprising: administering to a subject in need thereof, a therapeutically effective amount of a pharmaceutical composition, as described above, so as to treat the disease state.

In another aspect of the present invention, there is provided a method of modulating IAP function, the method comprising: contacting a cell with a compound of the present invention so as to prevent binding of a BIR binding protein to an IAP BIR domain thereby modulating the IAP function.

In another aspect of the present invention, there is provided a method of treating a proliferative disease, the method comprising: administering to a subject in need thereof, a therapeutically effective amount of the pharmaceutical composition, as described above, so as to treat the proliferative disease.

In another aspect of the present invention, there is provided a method of treating cancer, the method comprising: administering to a subject in need thereof, a therapeutically effective amount of the pharmaceutical composition, as described above, so as to treat the cancer.

In another aspect of the present invention, there is provided a method of treating cancer, the method comprising: administering to the subject in need thereof, a therapeutically effective amount of a pharmaceutical composition, as described above, in combination or sequentially with an agent selected from:
a) an estrogen receptor modulator,
b) an androgen receptor modulator,
c) retinoid receptor modulator,
d) a cytotoxic agent,
e) an antiproliferative agent,
f) a prenyl-protein transferase inhibitor,
g) an HMG-CoA reductase inhibitor,
h) an HIV protease inhibitor,
i) a reverse transcriptase inhibitor,
k) an angiogenesis inhibitor,
l) a PPAR-$\gamma$ agonist,
m) a PPAR-$\delta$. agonist,
n) an inhibitor of inherent multidrug resistance,
o) an anti-emetic agent,
p) an agent useful in the treatment of anemia,
q) agents useful in the treatment of neutropenia,
r) an immunologic-enhancing drug.
s) a proteasome inhibitor;
t) an HDAC inhibitor;
u) an inhibitor of the chemotrypsin-like activity in the proteasome; or
v) E3 ligase inhibitors;
w) a modulator of the immune system such as, but not limited to, interferon-alpha, Bacillus Calmette-Guerin (BCG), and ionizing radition (UVB) that can induce the release of cytokines, such as the interleukins, TNF, or induce release of death receptor ligands such as TRAIL;
x) a modulator of death receptors TRAIL and TRAIL agonists such as the humanized antibodies HGS-ETR1 and HGS-ETR2;
or in combination or sequentially with radiation therapy, so as to treat the cancer.

In another aspect of the present invention, there is provided a method for the treatment or prevention of a proliferative disorder in a subject, the method comprising: administering to the subject a therapeutically effective amount of the composition, described above.

In another aspect of the present invention, the method further comprises administering to the subject a therapeutically effective amount of a chemotherapeutic agent prior to, simultaneously with or after administration of the composition.

In yet another aspect, the method further comprises administering to the subject a therapeutically effective amount of a death receptor agonist prior to, simultaneously with or after administration of the composition. The death receptor agonist is TRAIL or the death receptor agonist is a TRAIL antibody.

The death receptor agonist is typically administered in an amount that produces a synergistic effect.

In yet another aspect, there is provided use of the compound as described above for the manufacture of a medicament for treating or preventing a disease state characterized by insufficient apoptosis.

In yet another aspect, there is provided use of the compound as described above for the manufacture of a medicament for treating or preventing a proliferative disorder.

In yet another aspect, there is provided use of the compound as described above in combination with an agent for the manufacture of a medicament for treating or preventing a proliferative disorder, wherein the agent is selected from:
a) an estrogen receptor modulator,
b) an androgen receptor modulator,
c) retinoid receptor modulator,
d) a cytotoxic agent,
e) an antiproliferative agent,
f) a prenyl-protein transferase inhibitor,
g) an HMG-CoA reductase inhibitor,
h) an HIV protease inhibitor,
i) a reverse transcriptase inhibitor,
k) an angiogenesis inhibitor,
l) a PPAR-$\gamma$ agonist,
m) a PPAR-$\delta$. agonist,
n) an inhibitor of inherent multidrug resistance,
o) an anti-emetic agent,
p) an agent useful in the treatment of anemia,
q) agents useful in the treatment of neutropenia,
r) an immunologic-enhancing drug.
s) a proteasome inhibitor;
t) an HDAC inhibitor;
u) an inhibitor of the chemotrypsin-like activity in the proteasome; or
v) E3 ligase inhibitors;
w) a modulator of the immune system such as, but not limited to, interferon-alpha, Bacillus Calmette-Guerin (BCG), and ionizing radition (UVB) that can induce the release of cytokines, such as the interleukins, TNF, or induce release of death receptor ligands such as TRAIL;
x) a modulator of death receptors TRAIL and TRAIL agonists such as the humanized antibodies HGS-ETR1 and HGS-ETR2;
or in combination or sequentially with radiation therapy.

In yet another aspect, there is provided use of the compound as described above in combination with a death receptor agonist for the manufacture of a medicament the treatment or prevention of a proliferative disorder in a subject.

In yet another aspect, there is provided a pharmaceutical composition comprising the compound as described above, mixed with a pharmaceutically acceptable carrier, diluent or excipient, for treating or preventing a disease state characterized by insufficient apoptosis.

In yet another aspect, there is provided a pharmaceutical composition comprising the compound as described above in combination with any compound that increases the circulating level of one or more death receptor agonists for preventing or treating a proliferative disorder.

In yet another aspect, there is provided a method of preparing a pharmaceutical composition, the method comprising: mixing the compound as described above, with a pharmaceutically acceptable carrier, diluent or excipient.

In another aspect of the present invention, there is provided a probe, the probe being a compound of Formula I above, the compound being labeled with a detectable label or an affinity tag.

In another aspect of the present invention, there is provided a method of identifying compounds that bind to an IAP BIR domain, the assay comprising:
a) contacting an IAP BIR domain with a probe to form a probe:BIR domain complex, the probe being displaceable by a test compound;
b) measuring a signal from the probe so as to establish a reference level;
c) incubating the probe:BIR domain complex with the test compound;
d) measuring the signal from the probe;
e) comparing the signal from step d) with the reference level, a modulation of the signal being an indication that the test compound binds to the BIR domain,
wherein the probe is a compound of Formula I labeled with a detectable label or an affinity label.

In another aspect of the present invention, there is provided a method of detecting loss of function or suppression of IAPs in vivo, the method comprising: a) administering to a subject, a therapeutically effective amount of a pharmaceutical composition, as defined above; b) isolating a tissue sample from the subject; and c) detecting a loss of function or suppression of IAPs from the sample.

DETAILED DESCRIPTION OF THE INVENTION

In many cancers and other diseases, up-regulation of IAPs in cells, induced by genetic defects or in response to chemotherapeutic agents, has been correlated with an increased resistance to apoptosis. Interestingly, our results show that cancer cells whose IAP levels are decreased are more sensitive to chemotherapeutic agents or TRAIL-induced apoptosis. We describe in this invention, compounds that can directly bind to various IAPs, antagonize their functions and furthermore, cause a down-regulation of certain IAP proteins in cells, thereby sensitizing them to apoptosis. Such molecules, by inducing long duration IAP loss from cells involved in the pathogenesis or progress of disease, will be useful as therapeutic agents, either alone or in a synergistic combination with other inducers of apoptosis. This combination of effects is anticipated to provide clinical advantages of the compounds of the present invention in terms of overcoming resistance to therapy. Also advantageous would be the use of the disclosed compounds in combination therapy with other agents.

In one aspect of the present invention, the compounds of the present invention may also be represented by the following Formula II in which M1 and M2 represent independent BIR binding domains.

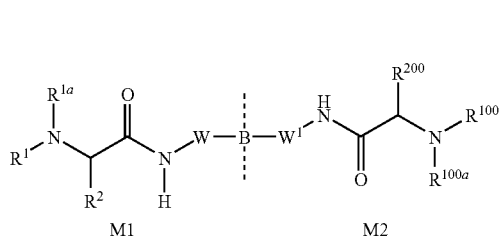

In one subset of Formula II, M1 is the same as M2 and the dotted line denotes a line of symmetry. In another subset, M1 is different from M2.

In one subset, compounds of Formula II are asymmetrical about the dotted line. In another subset the substituents on M1 and M2 are the same. In another subset, the substituents on M1 and M2 are different.

One skilled in the art will recognize that when M1 and M2 are the same, the $R^1$, $R^{1a}$, $R^2$, $R^3$, $R^4$, $R^5$, $R^{5a}$, $R^6$, $R^7$, $R^8$, $R^9$, $R^{10}$, $R^{11}$, $R^{12}$, $R^{13}$, $R^{14}$, n, m, $Y^1$, Q, and X substituents in M1 have the same meaning as the $R^{100}$, $R^{100a}$, $R^{200}$, $R^{300}$, $R^{400}$, $R^{500}$, $R^{600}$, $R^{700}$, $R^{800}$, $R^{900}$, $R^{1000}$, $R^{1100}$, $R^{1300}$, $R^{1400}$, n, m, $Y^{100}$, $Q^1$, and $X^1$ substituents respectively in M2. When M1 and M2 are different, at least one of the aforesaid substituents is different in either of M1 or M2.

Alternatively the substituents in M1 can be defined as $R^1$, $R^{1a}$, $R^2$, $R^3$, $R^4$, $R^5$, $R^{5a}$, $R^6$, $R^7$, $R^8$, $R^9$, $R^{10}$, $R^{11}$, $R^{12}$, $R^{13}$, $R^{14}$, n, m, $Y^1$, Q, and X, and those in M2 can be defined as $R^{100}$, $R^{100a}$, $R^{200}$, $R^{300}$, $R^{400}$, $R^{500}$, $R^{600}$, $R^{700}$, $R^{800}$, $R^{900}$, $R^{1000}$, $R^{1100}$, $R^{1300}$, $R^{1400}$, n, m, $Y^{100}$, $Q^1$, and $X^1$ respectively. In the case where M1 and M2 are the same, the $R^1$, $R^{1a}$, $R^2$, $R^3$, $R^4$, $R^5$, $R^{5a}$, $R^6$, $R^7$, $R^8$, $R^9$, $R^{10}$, $R^{11}$, $R^{12}$, $R^{13}$, $R^{14}$, n, m, $Y^1$, Q, and X substituents in M1 have the same meanings as $R^{100}$, $R^{100a}$, $R^{200}$, $R^{300}$, $R^{400}$, $R^{500}$, $R^{600}$, $R^{700}$, $R^{800}$, $R^{900}$, $R^{1000}$, $R^{1100}$, $R^{1300}$, $R^{1400}$, n, m, $Y^{100}$, $Q^1$, and $X^1$ respectively in M2. In the case where M1 and M2 are different, at least one of the aforesaid substituents is different.

The compounds of the present invention are useful as BIR domain binding compounds in mammalian IAPs and are represented by Formula I.

W and $W^1$:

In one subset of compounds of Formula 1, W is

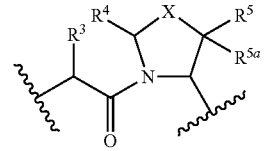

and $W^1$ is

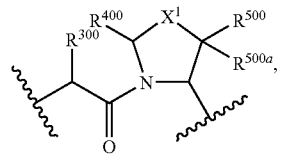

wherein $R^{300}$, $R^{400}$, $R^{500}$, $R^{500a}$, $X^1$ are as defined as $R^3$, $R^4$, $R^5$, $R^{5a}$, and X respectively.

In an alternative subset of compounds of Formula 1, W is

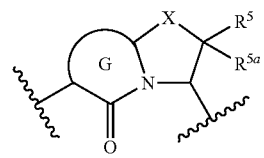

and $W^1$ is

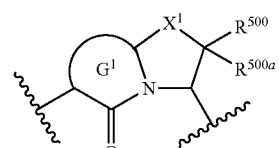

wherein $R^{500}$, $R^{500a}$, $X^1$, $G^1$ are as defined as $R^5$, $R^a$, X and G respectively.

In an alternative subset of compounds of Formula 1, W is and $W^1$ is wherein $R^{500}$, $R^{500a}$, $G^1$ are as defined as $R^5$, $R^{5a}$, and G respectively.

In another alternative subset of compounds of Formula I, W is and $W^1$ is wherein $R^3$, $R^4$ are defined as $R^{300}$, $R^{400}$ respectively.

Any and each individual definition of W and $W^1$ as set out herein may be combined with any and each individual definition of $R^1$, $R^{1a}$, $R^2$, $R^{100}$, $R^{100a}$, $R^2$, $R^{200}$, B.

B:

In one example of the compounds of Formula I, B is wherein A, $A^1$, Q, $Q^1$ and BG are as defined herein.

Any and each individual definition of B as set out herein may be combined with any and each individual definition of $R^1$, $R^{1a}$, $R^2$, $R^{100}$, $R^{100a}$, $R^2$, $R^{200}$, W and $W^1$ as set out herein.

Q and $Q^1$:

In one subset of compounds of Formula I, Q and $Q^1$ are both —$CH_2$—.

In an alternative subset of compounds of Formula I, Q and $Q^1$ are both —C(O)—.

Any and each individual definition of Q and $Q^1$ as set out herein may be combined with any and each individual definition of $R^1$, $R^{1a}$, $R^2$, $R^{100}$, $R^{100a}$, $R^{200}$, W and $W^1$ as set out herein.

A and $A^1$:

In one subset of compounds of Formula I, A and $A^1$ are independently selected from
1) $NR^6$ or
2) $NR^{600}$;

wherein $R^6$ and $R^{600}$ are as defined herein.

Any and each individual definition of A and $A^1$ as set out herein may be combined with any and each individual definition of $R^1$, $R^{1a}$, $R^2$, $R^{100}$, $R^{100a}$, $R^{200}$, W and $W^1$ as set out herein.

BG:

In one subset of compounds of Formula I, BG is —$Y^1$-L-$Y^{100}$—.

In an alternative subset of compounds of Formula I, BG is -L-.

In another alternative subset, BG is —$Y^1$-$L^1$-Z-$L^{100}$-$Y^{100}$—, wherein $L^1$ and $L^{100}$ are equal or $L^1$ and $L^{100}$ are different.

Any and each individual definition of BG as set out herein may be combined with any and each individual definition of $R^1$, $R^{1a}$, $R^2$, $R^{100}$, $R^{100a}$, $R^{200}$, W and $W^1$ as set out herein.

Core:

Therefore, in one subset, the compounds of the present invention comprise compounds of Formula 1A.

wherein $R^1$, $R^{1a}$, $R^2$, $R^2$, $R^3$, $R^4$, $R^5$, $R^{5a}$, X, $X^1$, A, $A^1$, BG, $R^{100}$, $R^{100a}$, $R^{200}$, $R^{300}$, $R^{400}$, $R^{500}$, and $R^{500a}$ are as defined herein.

In one subset, the compounds of the present invention comprise compounds of Formula 1A1:

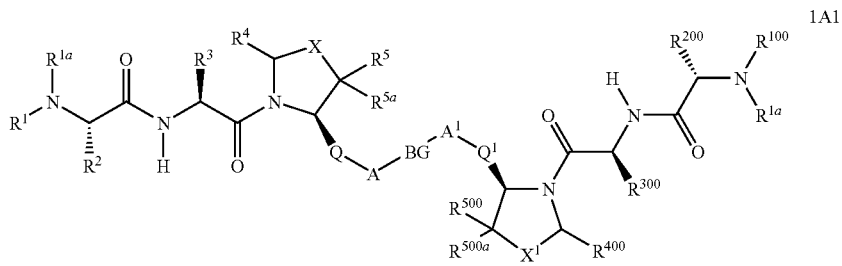

1A1 wherein $R^1$, $R^{1a}$, $R^2$, $R^2$, $R^3$, $R^4$, $R^5$, $R^{5a}$, Q, $Q^1$, A, $A^1$, BG, X, $X^1$, $R^{100}$, $R^{100a}$, $R^{200}$, $R^{300}$, $R^{400}$, $R^{500}$, and $R^{500a}$ are as defined herein.

In another subset, the compounds of the present invention comprise compounds of Formula 1A2:

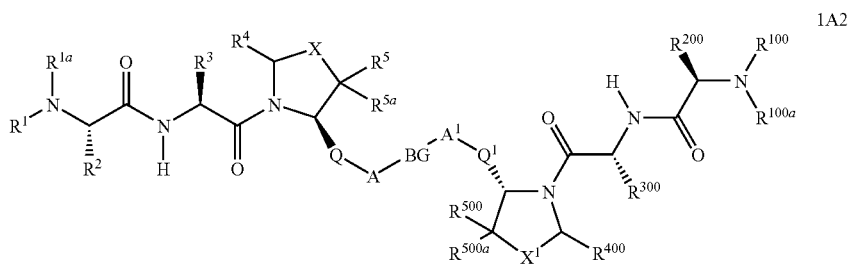

1A2 wherein $R^1$, $R^{1a}$, $R^2$, $R^2$, $R^3$, $R^4$, $R^5$, $R^{5a}$, Q, $Q^1$, A, $A^1$, BG, X, $X^1$, $R^{100}$, $R^{100a}$, $R^{200}$, $R^{300}$, $R^{400}$, $R^{500}$, and $R^{500a}$ are as defined herein.

In another subset, the compounds of the present invention comprise compounds of Formula 1A3:

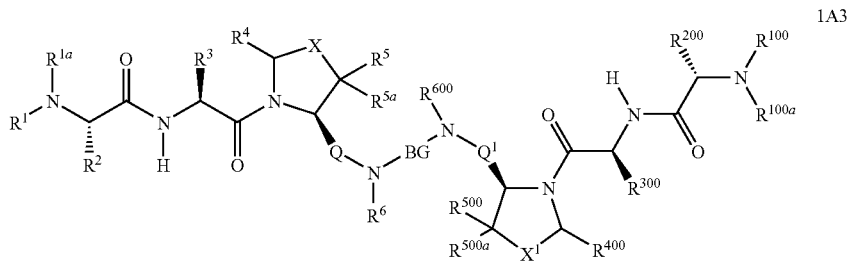

1A3 wherein $R^1$, $R^{1a}$, $R^2$, $R^2$, $R^3$, $R^4$, $R^5$, $R^{5a}$, Q, $Q^1$, BG, X, $X^1$, $R^{100}$, $R^{100a}$, $R^{200}$, $R^{300}$, $R^{400}$, $R^{500}$, $R^{500a}$, $R^6$ and $R^{600}$ are as defined herein.

In another subset, the compounds of the present invention comprise compounds of Formula 1A4:

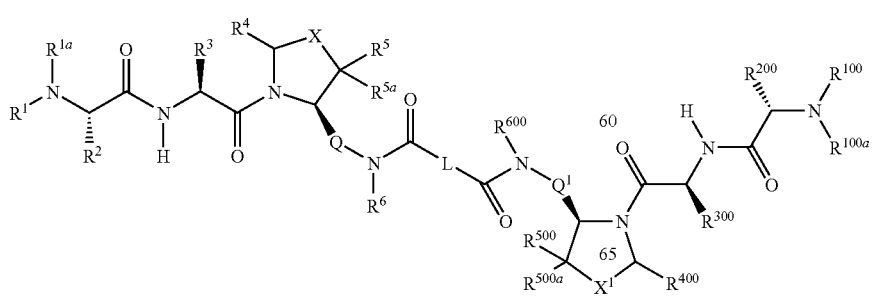

1A4 wherein $R^1$, $R^{1a}$, $R^2$, $R^2$, $R^2$, $R^4$, $R^5$, $R^{5a}$, Q, $Q^1$, L, X, $X^1$, $R^{100}$, $R^{100a}$, $R^{200}$, $R^{300}$, $R^{400}$, $R^{500}$, $R^{500a}$, $R^6$ and $R^{600}$ are as defined herein.

In another subset, the compounds of the present invention comprise compounds of Formula 1A5:

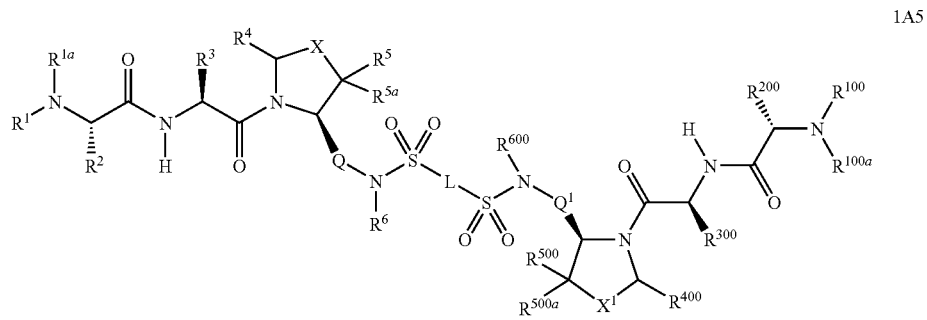

1A5 wherein $R^1$, $R^{1a}$, $R^2$, $R^2$, $R^3$, $R^4$, $R^5$, $R^{5a}$, Q, $Q^1$, L, X, $X^1$, $R^{100}$, $R^{100a}$, $R^{200}$, $R^{300}$, $R^{400}$, $R^{500}$, $R^{500a}$, $R^6$ and $R^{600}$ are as defined herein.

In another subset, the compounds of the present invention comprise compounds of Formula 1A6:

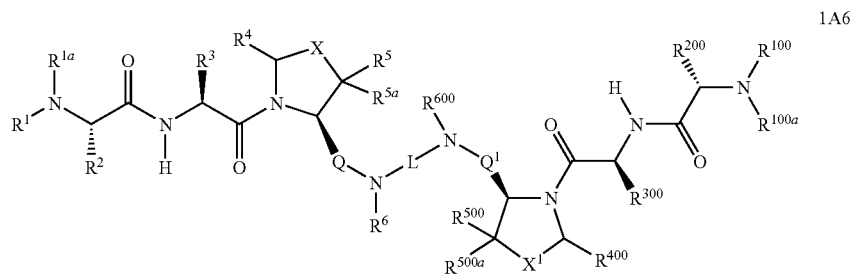

1A6 wherein $R^1$, $R^{1a}$, $R^2$, $R^2$, $R^3$, $R^4$, $R^5$, $R^{5a}$, Q, $Q^1$, X, $X^1$, L, $R^{100}$, $R^{100a}$, $R^{200}$, $R^{300}$, $R^{400}$, $R^{500}$, $R^{500a}$, $R^6$ and $R^{600}$ are as defined herein.

In an alternative subset, the compounds of the present invention comprise compounds of Formula 1B:

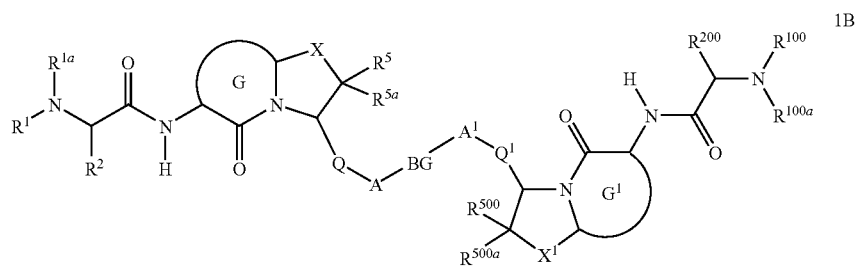

1B wherein $R^1$, $R^{1a}$, $R^2$, $R^{200}$, $R^5$, $R^{5a}$, G, $G^1$, Q, $Q^1$, X, $X^1$, A, $A^1$, $R^{100}$, $R^{100a}$, $R^{200}$, $R^{500}$ and $R^{500a}$ are as defined herein.

In another subset, the compounds of the present invention comprise compounds of the Formula 1B1:

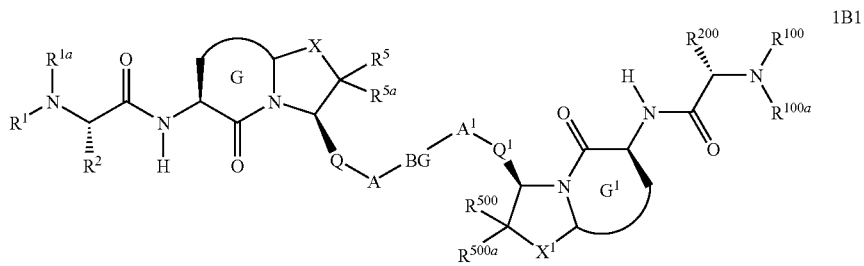

wherein $R^1$, $R^{1a}$, $R^2$, $R^{200}$, $R^5$, $R^{5a}$, G, $G^1$, Q, $Q^1$, BG, X, $X^1$, A, $A^1$, $R^{100}$, $R^{100a}$, $R^{200}$, $R^{500}$ and $R^{500a}$ are as defined herein.

In another subset, the compounds of the present invention comprise compounds of the Formula 1B2:

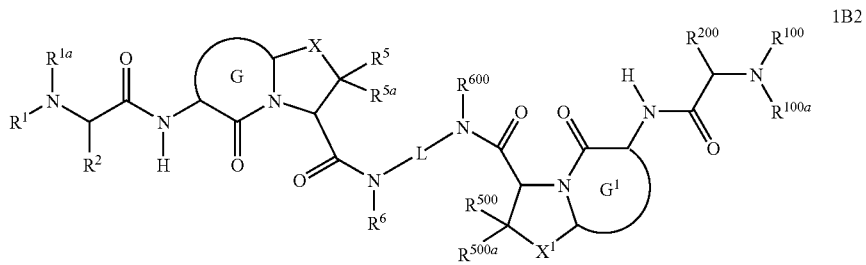

wherein $R^1$, $R^{1a}$, $R^2$, $R^{200}$, $R^5$, $R^{5a}$, G, $G^1$, L, Q, $Q^1$, X, $X^1$, A, $A^1$, $R^{100}$, $R^{100a}$, $R^{200}$, $R^{500}$ and $R^{500a}$ are as defined herein.

In another alternative subset, the compounds of the present invention comprise compounds of the Formula 1C:

wherein $R^1$, $R^{1a}$, $R^2$, $R^2$, $R^5$, $R^{5a}$, BG, G, $G^1$, Q, $Q^1$, A, $A^1$, $R^{100}$, $R^{100a}$, $R^{200}$, $R^{500}$, $R^{500a}$, $R^6$ and $R^{600}$ are as defined herein.

$Y^1$ and $Y^{100}$:

In one subset, $Y^1$ and $Y^{100}$ are both —C(O)—.
In another subset, $Y^1$ and $Y^{100}$ are both —S(O)$_2$—.
In another subset, $Y^1$ and $Y^{100}$ are both —C(O)N($R^8$)—, wherein $R^8$ is as defined herein

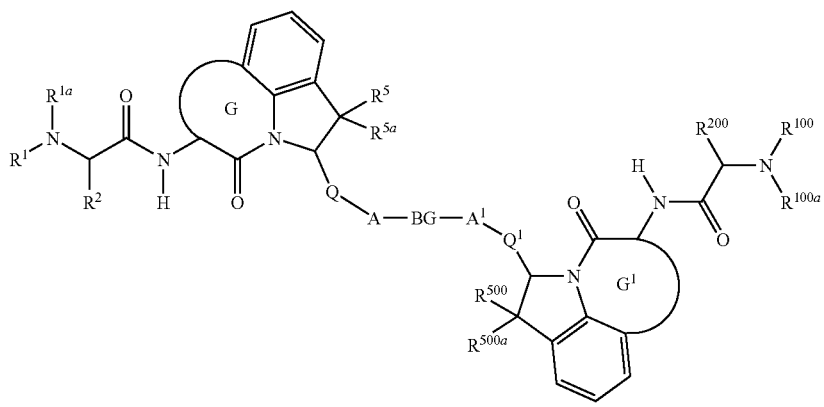

wherein $R^1$, $R^{1a}$, $R^2$, $R^{200}$, $R^5$, $R^{5a}$, G, $G^1$, BG, Q, $Q^1$, X, $X^1$, A, $A^1$, $R^{100}$, $R^{100a}$, $R^{200}$, $R^{500}$ and $R^{500a}$ are as defined herein.

In another alternative subset, the compounds of the present invention comprise compounds of the Formula 1D:

Any and each individual definition of $Y^1$ and $Y^{100}$ as set out herein may be combined with any and each individual definition of Z, $R^1$, $R^{1a}$, $R^2$, $R^3$, $R^4$, $R^5$, $R^{5a}$, $R^6$, $R^7$, $R^8$, $R^9$, $R^{10}$, $R^{11}$, $R^{12}$, $R^{13}$, $R^{14}$, n, m, Q, X $R^{100}$, $R^{100a}$, $R^{200}$, $R^{300}$, $R^{400}$,

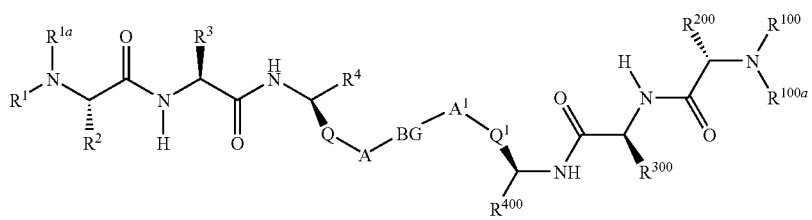

$R^{500}, R^{600}, R^{700}, R^{800}, R^{900}, R^{1000}, R^{1100}, R^{1300}, R^{1400}$, n, m, $Y^{100}, Q^1$, and $X^1$ as set out herein.

$L, L^1$ and $L^{100}$:

In one subset, $L, L^1$ and $L^{100}$ are selected from:
1) —$C_1$-$C_{12}$ alkyl-,
2) —$C_3$-$C_7$ cycloalkyl-,
3) -aryl-,
4) -biphenyl-,
5) -heteroaryl-,
6) -heterocycyl-,
7) —$C_1$-$C_6$ alkyl-($C_3$-$C_7$ cycloalkyl)-$C_1$-$C_6$ alkyl,
8) —$C_1$-$C_6$ alkyl-aryl-$C_1$-$C_6$ alkyl,
9) —$C_1$-$C_6$ alkyl-biphenyl-$C_1$-$C_6$ alkyl,
10) —$C_1$-$C_6$ alkyl-heteroaryl-$C_1$-$C_6$ alkyl,
11) —$C_1$-$C_6$ alkyl heterocycyl-$C_1$-$C_6$ alkyl, or
12) —$C_1$-$C_6$ alkyl-O—$C_1$-$C_6$ alkyl.

wherein the alkyl, and the cycloalkyl are optionally substituted with one or more $R^7$ substituents; and the aryl, the heteroaryl, the biphenyl and the heterocyclyl are optionally substituted with one or more $R^{11}$ substituents.

In another subset, $L, L^1$, and $L^{100}$ are —$N(R^8)C(O)N(R^8)$—, wherein $R^8$ is as defined herein.

In another subset, $L, L^1$ and $L^{100}$ are —$C_1$-$C_6$ alkyl-Z—$C_1$-$C_6$ alkyl-;
wherein the alkyl is optionally substituted with one or more $R^7$ substituents, and Z is as defined herein.

Any and each individual definition of $L, L^1, L^{100}$ as set out herein may be combined with any and each individual definition of $Z, R^1, R^{1a}, R^2, R^3, R^4, R^5, R^{5a}, R^6, R^7, R^8, R^9, R^{10}, R^{11}, R^{12}, R^{13}, R^{14}$, n, m, Y, Q, X $R^{100}, R^{100a}, R^{200}, R^{300}, R^{400}, R^{500}, R^{600}, R^{700}, R^{800}, R^{900}, R^{1000}, R^{1100}, R^{1300}, R^{1400}$, n, m, $Y^{100}, Q^1$, and $X^1$ as set out herein.

Z:

In one subset, Z is selected from:
1) —$N(R^8)CON(R^8)$—,
2) —$N(R^8)C(O)$-aryl-$C(O)N(R^8)$—,
3) —$N(R^8)C(O)$-heteroaryl-$C(O)N(R^8)$—,
4) —$C(O)$—,
5) —$N(R^8)$—$C_1$-$C_{12}$-alkyl-$N(R^8)$—,
6) —$N(R^8)$—$C(O)C(O)$—$N(R^8)$—,
7) —$N(R^8)$—$C(O)$—$C_1$-$C_{12}$-alkyl-$C(O)$—$N(R^8)$—,
8) —$N(R^8)$—$C(O)$-aryl-$C(O)$—$N(R^8)$—,
9) —$N(R^8)$—$C(O)$-aryl-O-aryl-$C(O)$—$N(R^8)$—,
10) —$N(R^8)$—$C(O)$-heteroaryl-$C(O)$—$N(R^8)$—,
11) —$N(R^8)$—$C(O)$-biphenyl-$C(O)$—$N(R^8)$—,
12) —$N(R^8)$—$S(O)_2$—$C_1$-$C_{12}$-alkyl-$S(O)_2$—$N(R^8)$—
13) —$N(R^8)$—$S(O)_2$-aryl-$S(O)_2$—$N(R^8)$—,
14) —$N(R^8)$—$S(O)_2$-heteroaryl-$S(O)_2$—$N(R^8)$—, or
25) —$N(R^8)$—$S(O)_2$-biphenyl-$S(O)_2$—$N(R^8)$—, wherein the alkyl and the cycloalkyl are optionally substituted with one or more $R^7$ substituents, and the aryl, the heteroaryl and the heterocyclyl are optionally substituted with one or more $R^{11}$ substituents; and wherein $R^8$ is as defined herein.

Any and each individual definition of Z as set out herein may be combined with any and each individual definition of $L, L^1, L^{100}, R^1, R^{1a}, R^2, R^3, R^4, R^5, R^{5a}, R^6, R^7, R^8, R^9, R^{10}, R^{11}, R^{12}, R^{13}, R^{14}$, n, m, Y, Q, X, $R^{100}, R^{100a}, R^{200}, R^{300}, R^{400}, R^{500}, R^{600}, R^{700}, R^{800}, R^{900}, R^{1000}, R^{1100}, R^{1300}, R^{1400}$ n, m, $Y^{100}, Q^1$, and $X^1$ as set out herein.

$R^1, R^{1a}, R^{100}$ and $R^{100}$:

In one subset of compounds of Formula I, $R^1, R^{1a}, R^{100}$ and $R^{100}$ are independently selected from H or $CH_3$.

Any and each individual definition of $R^1, R^{1a}, R^{100}, R^{100a}$ as set out herein may be combined with any and each individual definition of $L, L^1, L^{100}, R^2, R^3, R^4, R^5, R^{5a}, R^6, R^7, R^8, R^9, R^{10}, R^{11}, R^{12}, R^{13}, R^{14}$, n, m, Y, Q, X, $R^{200}, R^{300}, R^{400}$, $R^{500}, R^{600}, R^{700}, R^{800}, R^{900}, R^{1000}, R^{1100}, R^{1300}, R^{1400}$, n, m, $Y^{100}, Q^1$, and $X^1$ as set out herein.

$R^2$ and $R^{200}$:

In one subset of compounds of Formula I, both $R^2$ and $R^{200}$ display (S)-stereochemistry Any and each individual definition of $R^2$ and $R^{200}$ as set out herein may be combined with any and each individual definition of $L, L^1, L^{100}, R^1, R^{1a}, R^3, R^4, R^5, R^{5a}, R^6, R^7, R^8, R^9, R^{10}, R^{11}, R^{12}, R^{13}, R^{14}$, n, m, Y, Q, X, $R^{100}, R^{100a}, R^{300}, R^{400}$, $R^{500}, R^{600}, R^{700}, R^{800}, R^{900}, R^{1000}, R^{1100}, R^{1300}, R^{1400}$, n, m, $Y^{100}, Q^1$, and $X^1$ as set out herein.

$R^3$ and $R^{300}$:

In one subset of compounds of Formula I, $R^3$ and $R^{300}$ are independently selected from
1) H, or
2) $C_1$-$C_6$ alkyl optionally substituted with an $R^7$ substituent;

and wherein $R^7$ is as described herein.

Typical examples of $R^3$ and $R^{300}$ include H, (S)-methyl, (S)-ethyl, (S)-tert-butyl, (S)-cyclohexylmethyl, (S)-2-phenylethyl and benzyl (S)-butylcarbamate.

Any and each individual definition of $R^3$ and $R^{300}$ as set out herein may be combined with any and each individual definition of $L, L^1, L^{100}, R^1, R^{1a}, R^2, R^4, R^5, R^{5a}, R^6, R^7, R^8, R^9, R^{10}, R^{11}, R^{12}, R^{13}, R^{14}$, n, m, Y, Q, X, $R^{100}, R^{100a}, R^{200}, R^{400}$, $R^{500}, R^{600}, R^{700}, R^{800}, R^{900}, R^{1000}, R^{1100}, R^{1300}, R^{1400}$, n, m, $Y^{100}, Q^1$, and $X^1$ as set out herein.

$R^6$ and $R^{600}$:

In one subset of compounds of Formula I, $R^6$ and $R^{600}$ are each independently
1) H,
2) ←$C_1$-$C_6$ alkyl,
3) ←aryl, or

4)

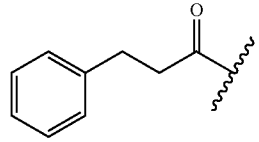

wherein the alkyl is optionally substituted with one or more $R^7$ substituents; and wherein the aryl is optionally substituted with one or more $R^{11}$ substituents.

Typical examples of $R^6$ and $R^{600}$ include H, —$CH(CH_3)_2$, —$CH_2CH_2C(CH_3)_3$,

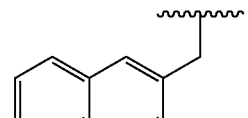 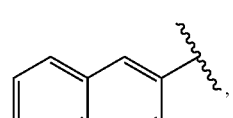

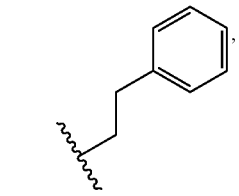 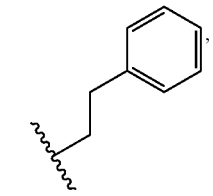

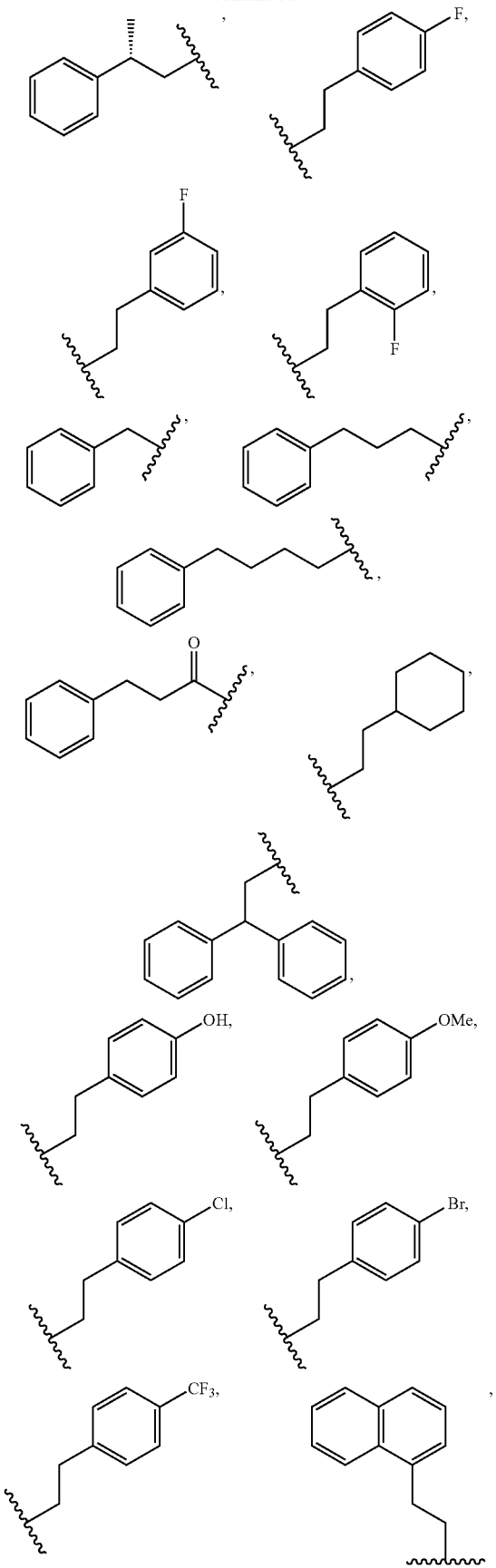

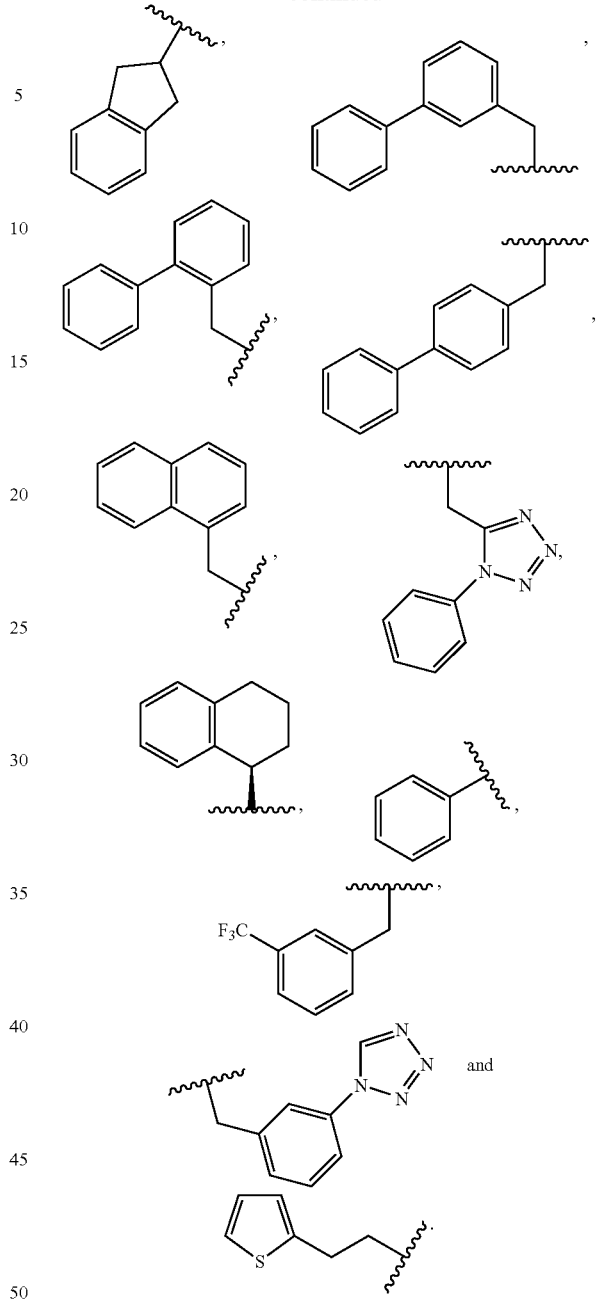

Any and each individual definition of $R^6$ and $R^{600}$ as set out herein may be combined with any and each individual definition of L, $L^1$, $L^{100}$, $R^1$, $R^{1a}$, $R^2$, $R^3$, $R^4$, $R^5$, $R^{5a}$, $R^7$, $R^8$, $R^9$, $R^{10}$, $R^{11}$, $R^{12}$, $R^{13}$, $R^{14}$, n, m, Y, Q, X, $R^{100}$, $R^{100a}$, $R^{200}$, $R^{300}$, $R^{400}$, $R^{500}$, $R^{700}$, $R^{800}$, $R^{900}$, $R^{1000}$, $R^{1100}$, $R^{1300}$, $R^{1400}$, n, m, $Y^{100}$, $Q^1$, and $X^1$ as set out herein.

$R^7$:

In one subset of compounds of Formula I, $R^7$ is
1) $C_3$-$C_7$ cycloalkyl,
2) aryl,
3) heteroaryl, or
4) NHC(O)OCH$_2$phenyl, wherein the aryl and the heteroaryl are optionally substituted with one or more $R^{11}$ substituents; and wherein $R^9$ and $R^{10}$ are as defined herein.

Any and each individual definition of $R^7$ as set out herein may be combined with any and each individual definition of L, $L^1$, $L^{100}$, $R^1$, $R^{1a}$, $R^2$, $R^3$, $R^4$, $R^5$, $R^{5a}$, $R^6$, $R^8$, $R^9$, $R^{10}$, $R^{11}$, $R^{12}$, $R^{13}$, $R^{14}$, n, m, Y, Q, X, $R^{100}$, $R^{100a}$, $R^{200}$, $R^{300}$, $R^{400}$, $R^{500}$, $R^{600}$, $R^{700}$, $R^{800}$, $R^{900}$, $R^{1000}$, $R^{1100}$, $R^{1300}$, $R^{1400}$, n, m, $Y^{100}$, $Q^1$, and $X^1$ as set out herein.

$R^8$:

In one subset, $R^8$ is selected from
1) H,
2) haloalkyl,
3) $C_1$-$C_6$ alkyl,
4) $C_3$-$C_7$ cycloalkyl,
5) aryl,
6) heteroaryl,
7) heterocyclyl, or
8) heterobicyclyl, wherein the alkyl, cycloalkyl, are optionally substituted with one or more $R^7$ substituents; and wherein the aryl, heteroaryl, heterocyclyl, and heterobicyclyl is optionally substituted with one or more $R^{11}$ substituents.

Any and each individual definition of $R^8$ as set out herein may be combined with any and each individual definition of L, $L^1$, $L^{100}$, $R^1$, $R^{1a}$, $R^2$, $R^3$, $R^4$, $R^5$, $R^{5a}$, $R^6$, $R^7$, $R^9$, $R^{10}$, $R^{11}$, $R^{12}$, $R^{13}$, $R^{14}$, n, m, Y, Q, X, $R^{100}$, $R^{100a}$, $R^{200}$, $R^{300}$, $R^{400}$, $R^{500}$, $R^{600}$, $R^{700}$, $R^{800}$, $R^{900}$, $R^{1000}$, $R^{1100}$, $R^{1300}$, $R^{1400}$, n, m, $Y^{100}$, $Q^1$, and $X^1$ as set out herein.

$R^{11}$:

In one subset of compounds of Formula I, $R^{11}$ is
1) halogen,
2) $CF_3$,
3) OH,
4) OMe,
5) aryl, or
6) heteroaryl.

Examples of $R^{11}$ include F, Cl, Br, OH, OMe, $CF_3$, phenyl and tetrazole.

Any and each individual definition of $R^{11}$ as set out herein may be combined with any and each individual definition of L, $L^1$, $L^{100}$, $R^1$, $R^{1a}$, $R^2$, $R^3$, $R^4$, $R^5$, $R^{5a}$, $R^6$, $R^7$, $R^8$, $R^9$, $R^{10}$, $R^{12}$, $R^{13}$, $R^{14}$, n, m, Y, Q, X, $R^{100}$, $R^{100a}$, $R^{200}$, $R^{300}$, $R^{400}$, $R^{500}$, $R^{600}$, $R^{700}$, $R^{800}$, $R^{900}$, $R^{1000}$, $R^{1100}$, $R^{1300}$, $R^{1400}$, n, m, $Y^{100}$, $Q^1$, and $X^1$ as set out herein.

According to other examples of the present invention, W and $W^1$ may each be defined as:

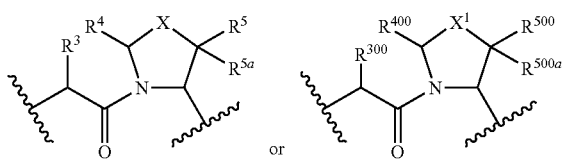

wherein $R^3$, $R^{300}$, $R^4$ and $R^{400}$ are as defined hereinabove.

One subset of compounds of the present invention includes compounds in which W and $W^1$ are defined as:

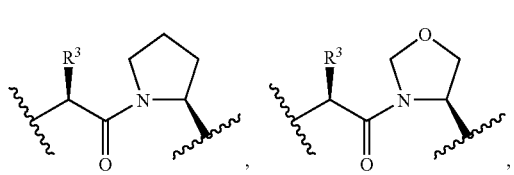

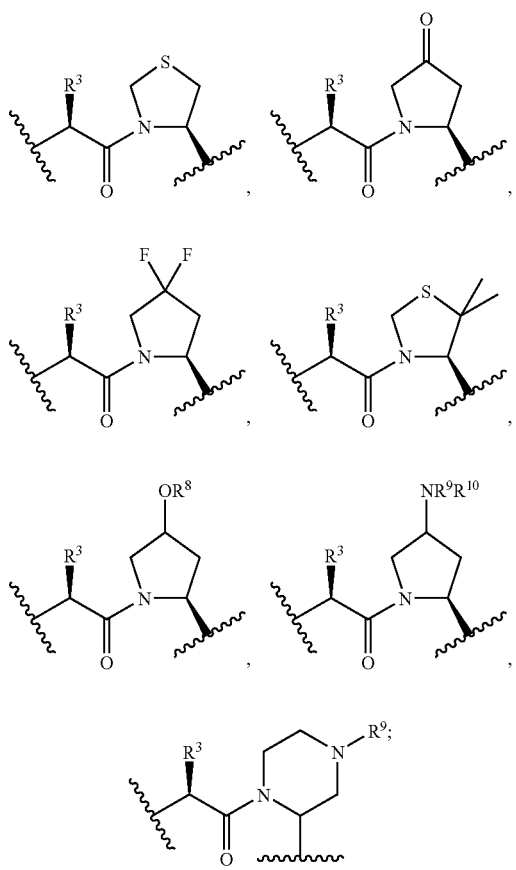

In one example of the present invention, W and W' may each be defined as:

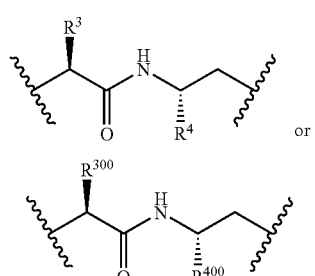

wherein $R^3$, $R^{300}$, $R^4$ and $R^{400}$ are as defined hereinabove.

More specifically, one subset of compounds of the present invention includes compounds in which W and W' are defined as:

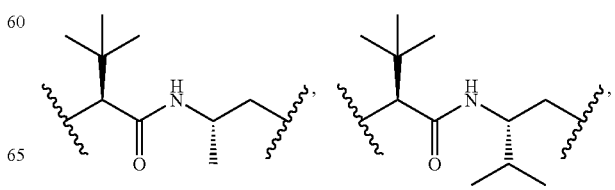

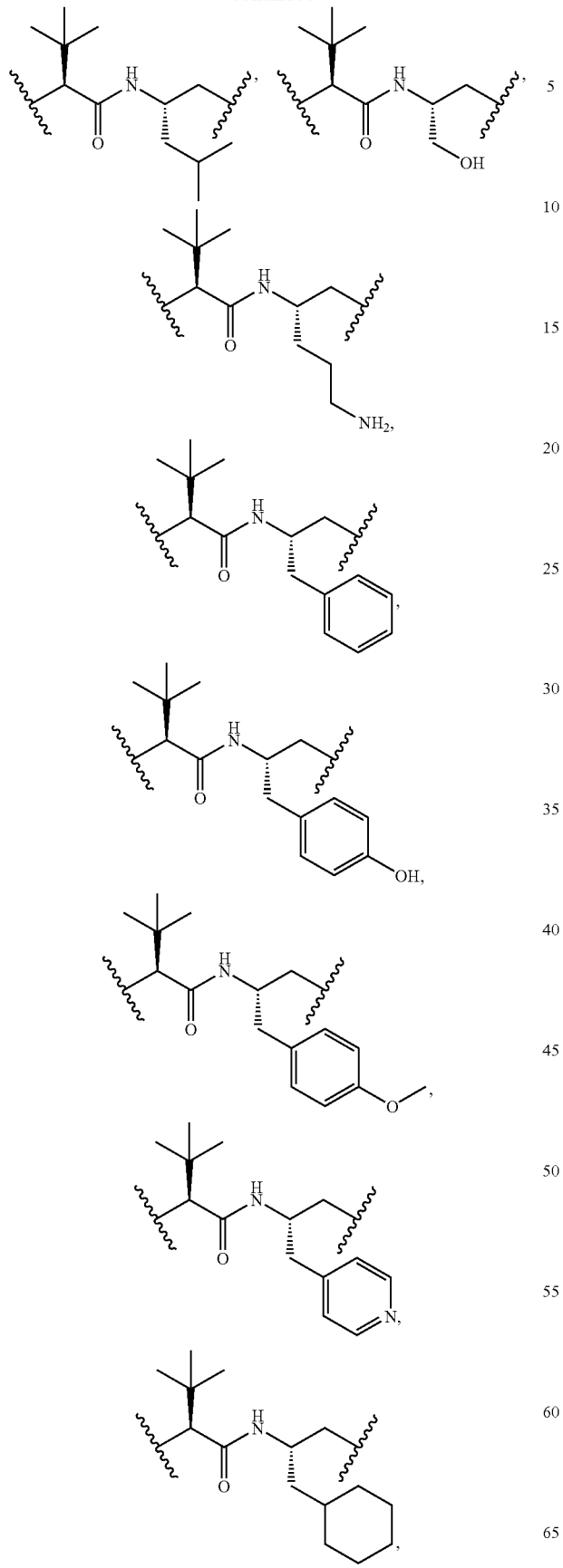
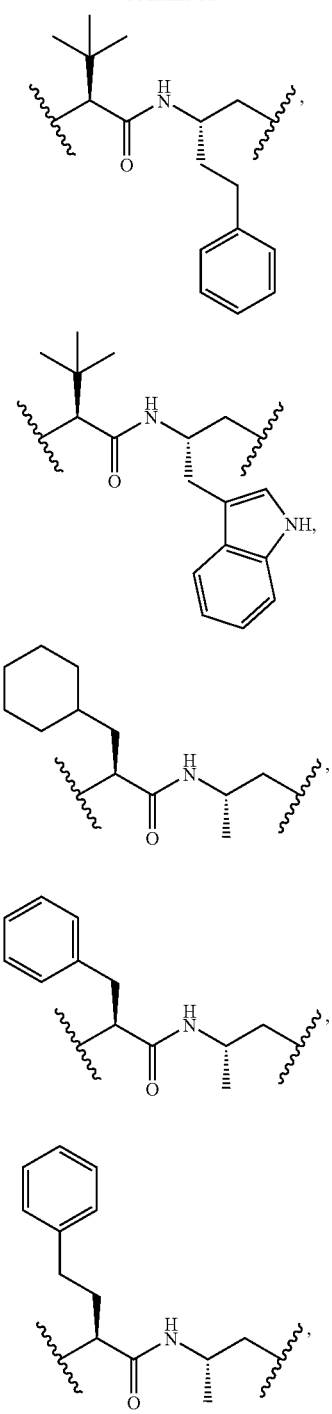
In another aspect of the present invention W and $W^1$ may each be defined as as a β-turn mimetic such as:
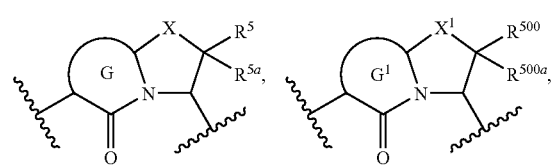

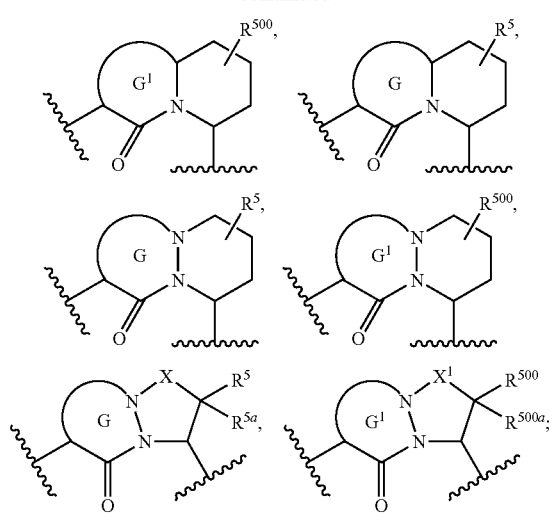

wherein G, G¹, X, X¹, $R^5$, $R^{5a}$, $R^{500}$ and $R^{500a}$ are as defined hereinabove.

More specifically, examples of β-turn mimetics may thus be characterized by the following bicyclic and tricyclic ring systems:

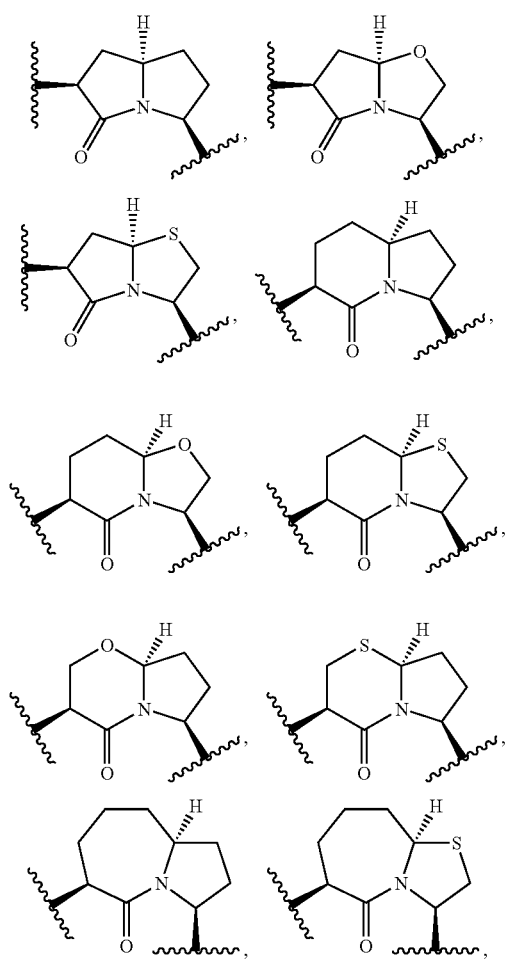

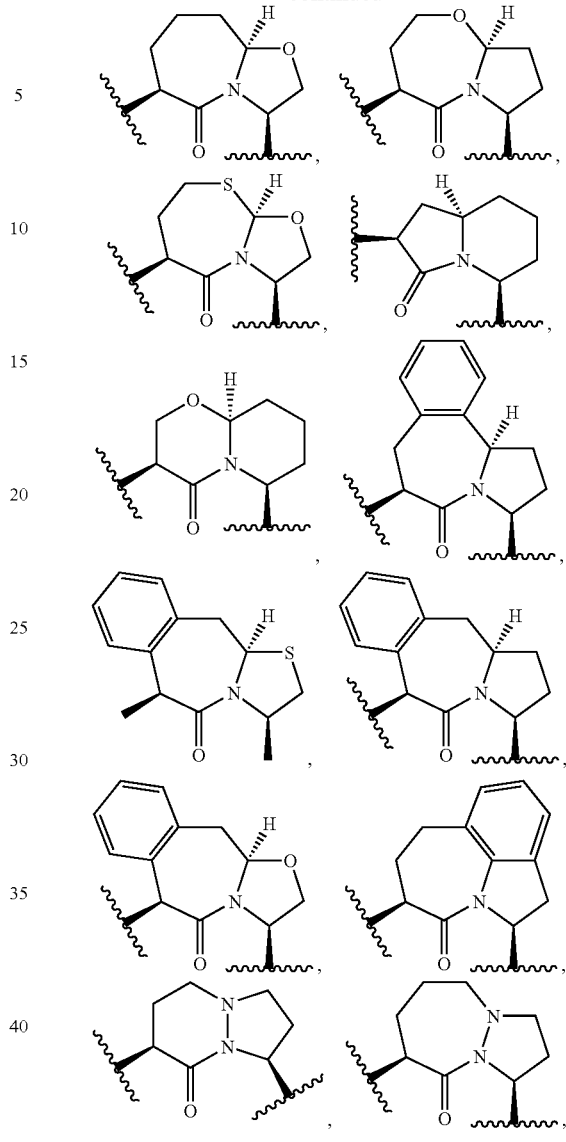

The synthesis of bicyclic and tricyclic ring systems which are capable of acting as β-turn mimetics has been reviewed and synthetic methods for their preparation may be found in the following review article: Cluzeau, J.; Lubell, W. D. Biopolymers-Peptide Synthesis, 2005, 80, 98 and references therein, incorporated in its entirety.

If any variable, such as $R^3$, $R^4$ and the like, occurs more than one time in any constituent structure, the definition of the variable at each occurrence is independent at every other occurrence. If a substituent is itself substituted with one or more substituents, it is to be understood that that the one or more substituents may be attached to the same carbon atom or different carbon atoms. Combinations of substituents and variables defined herein are allowed only if they produce chemically stable compounds.

One skilled in the art will understand that substitution patterns and substituents on compounds of the present invention may be selected to provide compounds that are chemically stable and can be readily synthesized using the chemistry set forth in the examples and chemistry techniques well known in the art using readily available starting materials.

It is to be understood that many substituents or groups described herein have functional group equivalents, which means that the group or substituent may be replaced by another group or substituent that has similar electronic, hybridization or bonding properties.

DEFINITIONS

Unless otherwise specified, the following definitions apply:

The singular forms "a", "an" and "the" include corresponding plural references unless the context clearly dictates otherwise.

As used herein, the term "comprising" is intended to mean that the list of elements following the word "comprising" are required or mandatory but that other elements are optional and may or may not be present.

As used herein, the term "consisting of" is intended to mean including and limited to whatever follows the phrase "consisting of". Thus the phrase "consisting of" indicates that the listed elements are required or mandatory and that no other elements may be present.

As used herein, the term "alkyl" is intended to include both branched and straight chain saturated aliphatic hydrocarbon groups having the specified number of carbon atoms, for example, $C_1$-$C_6$ as in $C_1$-$C_6$-alkyl is defined as including groups having 1, 2, 3, 4, 5 or 6 carbons in a linear or branched arrangement, and $C_1$-$C_4$ as in $C_1$-$C_4$ alkyl is defined as including groups having 1, 2, 3, or 4 carbons in a linear or branched arrangement, and $C_1$-$C_3$ as in $C_1$-$C_3$ alkyl is defined as including groups having 1, 2 or 3 carbons in a linear or branched arrangement, and $C_1$-$C_{12}$ as in $C_1$-$C_{12}$ alkyl is defined as including groups having 1, 2, 3, 4, 5, 6, 7, 8, 9, 10, 11 and 12 carbons in a linear or branched arrangement. Examples of alkyl as defined above include, but are not limited to, methyl, ethyl, n-propyl, i-propyl, n-butyl, t-butyl, i-butyl, pentyl and hexyl.

As used herein, the term, "alkenyl" is intended to mean unsaturated straight or branched chain hydrocarbon groups having the specified number of carbon atoms therein, and in which at least two of the carbon atoms are bonded to each other by a double bond, and having either E or Z regeochemistry and combinations thereof. For example, $C_2$-$C_6$ as in $C_2$-$C_6$ alkenyl is defined as including groups having 2, 3, 4, 5, or 6 carbons in a linear or branched arrangement, at least two of the carbon atoms being bonded together by a double bond. Examples of $C_2$-$C_6$ alkenyl include ethenyl (vinyl), 1-propenyl, 2-propenyl, 1-butenyl and the like.

As used herein, the term "alkynyl" is intended to mean unsaturated, straight chain hydrocarbon groups having the specified number of carbon atoms therein and in which at least two carbon atoms are bonded together by a triple bond. For example $C_2$-$C_4$ as in $C_2$-$C_4$ alkynyl is defined as including groups having 2, 3, or 4 carbon atoms in a chain, at least two of the carbon atoms being bonded together by a triple bond.

As used herein, the term "cycloalkyl" is intended to mean a monocyclic saturated aliphatic hydrocarbon group having the specified number of carbon atoms therein, for example, $C_3$-$C_7$ as in $C_3$-$C_7$ cycloalkyl is defined as including groups having 3, 4, 5, 6 or 7 carbons in a monocyclic arrangement. Examples of $C_3$-$C_7$ cycloalkyl as defined above include, but are not limited to, cyclopropyl, cyclobutyl, cyclopentyl, cyclohexyl and cycloheptyl.

As used herein, the term "cycloalkenyl" is intended to mean a monocyclic saturated aliphatic hydrocarbon group having the specified number of carbon atoms therein, for example, $C_3$-$C_7$ as in $C_3$-$C_7$ cycloalkenyl is defined as including groups having 3, 4, 5, 6 or 7 carbons in a monocyclic arrangement. Examples of $C_3$-$C_7$ cycloalkenyl as defined above include, but are not limited to, cyclopentenyl, and cyclohexenyl.

As used herein, the term "halo" or "halogen" is intended to mean fluorine, chlorine, bromine and iodine.

As used herein, the term "haloalkyl" is intended to mean an alkyl as defined above, in which each hydrogen atom may be successively replaced by a halogen atom. Examples of haloalkyls include, but are not limited to, $CH_2F$, $CHF_2$ and $CF_3$.

As used herein, the term "aryl", either alone or in combination with another radical, means a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, 1-naphthyl, 2-naphthyl and tetrahydronaphthyl. The fused aryls may be connected to another group either at a suitable position on the cycloalkyl ring or the aromatic ring. For example:

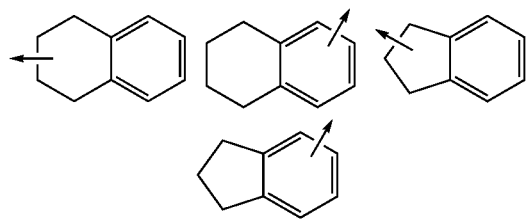

Arrowed lines drawn from the ring system indicate that the bond may be attached to any of the suitable ring atoms.

As used herein, the term "heteroaryl" is intended to mean a monocyclic or bicyclic ring system of up to ten atoms, wherein at least one ring is aromatic, and contains from 1 to 4 hetero atoms selected from the group consisting of O, N, and S. The heteroaryl substituent may be attached either via a ring carbon atom or one of the heteroatoms. Examples of heteroaryl groups include, but are not limited to thienyl, benzimidazolyl, benzo[b]thienyl, furyl, benzofuranyl, pyranyl, isobenzofuranyl, chromenyl, xanthenyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, napthyridinyl, quinoxalinyl, quinazolinyl, cinnolinyl, pteridinyl, isothiazolyl, isochromanyl, chromanyl, isoxazolyl, furazanyl, indolinyl, isoindolinyl, thiazolo[4,5-b]-pyridine, and fluoroscein derivatives such as:

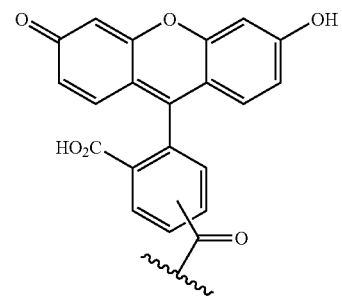

or

-continued

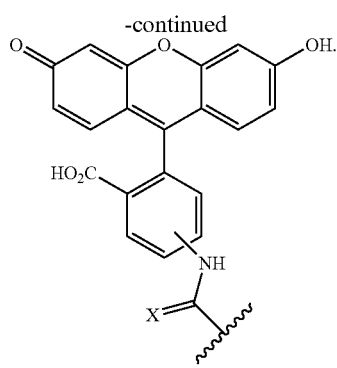

As used herein, the term "heterocycle", "heterocyclic" or "heterocyclyl" is intended to mean a 5, 6, or 7 membered non-aromatic ring system containing from 1 to 4 heteroatoms selected from the group consisting of O, N and S. Examples of heterocycles include, but are not limited to pyrrolidinyl, tetrahydrofuranyl, piperidyl, pyrrolinyl, piperazinyl, imidazolidinyl, morpholinyl, imidazolinyl, pyrazolidinyl, pyrazolinyl, and biotinyl derivatives. As used herein, the term "heterobicycle" either alone or in combination with another radical, is intended to mean a heterocycle as defined above fused to another cycle, be it a heterocycle, an aryl or any other cycle defined herein. Examples of such heterobicycles include, but are not limited to, coumarin, benzo[d][1,3]dioxole, 2,3-dihydrobenzo[b][1,4]dioxine and 3,4-dihydro-2H-benzo[b][1,4]dioepine.

As used herein, the term "detectable label" is intended to mean a group that may be linked to a compound of the present invention to produce a probe or to an IAP BIR domain, such that when the probe is associated with the BIR domain, the label allows either direct or indirect recognition of the probe so that it may be detected, measured and quantified. As used herein, the term "affinity tag" is intended to mean a ligand or group, which is linked to either a compound of the present invention or to an IAP BIR domain to allow another compound to be extracted from a solution to which the ligand or group is attached.

As used herein, the term "probe" is intended to mean a compound of Formula I which is labeled with either a detectable label or an affinity tag, and which is capable of binding, either covalently or non-covalently, to an IAP BIR domain. When, for example, the probe is non-covalently bound, it may be displaced by a test compound. When, for example, the probe is bound covalently, it may be used to form cross-linked adducts, which may be quantified and inhibited by a test compound.

As used herein, the term "optionally substituted with one or more substituents" or its equivalent term "optionally substituted with at least one substituent" is intended to mean that the subsequently described event of circumstances may or may not occur, and that the description includes instances where the event or circumstance occurs and instances in which it does not. The definition is intended to mean from zero to five substituents.

If the substituents themselves are incompatible with the synthetic methods of the present invention, the substituent may be protected with a suitable protecting group (PG) that is stable to the reaction conditions used in these methods. The protecting group may be removed at a suitable point in the reaction sequence of the method to provide a desired intermediate or target compound. Suitable protecting groups and the methods for protecting and de-protecting different substituents using such suitable protecting groups are well known to those skilled in the art; examples of which may be found in T. Greene and P. Wuts, Protecting Groups in Chemical Synthesis (3$^{rd}$ ed.), John Wiley & Sons, NY (1999), which is incorporated herein by reference in its entirety. Examples of protecting groups used throughout include, but are not limited to Alloc, Fmoc, Bn, Boc, CBz and COCF$_3$. In some instances, a substituent may be specifically selected to be reactive under the reaction conditions used in the methods of this invention. Under these circumstances, the reaction conditions convert the selected substituent into another substituent that is either useful in an intermediate compound in the methods of this invention or is a desired substituent in a target compound.

Abbreviations for α-amino acids used throughout are as follows:

| Amino acid | Abbreviation |
| --- | --- |
| α-Amino butyric acid | Abu |
| Alanine | Ala |
| Arginine | Arg |
| Aspartic acid | Asp |
| Asparagine | Asn |
| Cysteine | Cys |
| Glutamic acid | Glu |
| Glutamine | Gln |
| Glycine | Gly |
| Isoleucine | Ile |
| Histidine | His |
| Leucine | Leu |
| Lysine | Lys |
| Methionine | Met |
| Phenylalanine | Phe |
| Proline | Pro |
| Serine | Ser |
| Threonine | Thr |
| Tryptophan | Trp |
| Tyrosine | Tyr |
| Valine | Val |

As used herein, the term "residue" when referring to α-amino acids is intended to mean a radical derived from the corresponding α-amino acid by eliminating the hydroxyl of the carboxy group and one hydrogen of the α-amino group. For example, the terms Gln, Ala, Gly, Ile, Arg, Asp, Phe, Ser, Leu, Cys, Asn, and Tyr represent the residues of L-glutamine, L-alanine, glycine, L-isoleucine, L-arginine, L-aspartic acid, L-phenylalanine, L-serine, L-leucine, L-cysteine, L-asparagine, and L-tyrosine, respectively.

As used herein, the term "subject" is intended to mean humans and non-human mammals such as primates, cats, dogs, swine, cattle, sheep, goats, horses, rabbits, rats, mice and the like.

As used herein, the term "prodrug" is intended to mean a compound that may be converted under physiological conditions or by solvolysis to a biologically active compound of the present invention. Thus, the term "prodrug" refers to a precursor of a compound of the invention that is pharmaceutically acceptable. A prodrug may be inactive or display limited activity when administered to a subject in need thereof, but is converted in vivo to an active compound of the present invention. Typically, prodrugs are transformed in vivo to yield the compound of the invention, for example, by hydrolysis in blood or other organs by enzymatic processing. The prodrug compound often offers advantages of solubility, tissue compatibility or delayed release in the subject (see, Bundgard, H., Design of Prodrugs (1985), pp. 7-9, 21-24 (Elsevier, Amsterdam). The definition of prodrug includes any covalently bonded carriers which release the active compound of the invention in vivo when such prodrug is administered to a subject. Prodrugs of a compound of the present invention may be prepared by modifying functional groups present in the compound of the invention in such a way that the modifications are cleaved, either in routine manipulation or in vivo, to a parent compound of the invention.

As used herein, the term "pharmaceutically acceptable carrier, diluent or excipient" is intended to mean, without limitation, any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, emulsifier, or encapsulating agent, such as a liposome, cyclodextrins, encapsulating polymeric delivery systems or polyethylene glycol matrix, which is acceptable for use in the subject, preferably humans.

As used herein, the term "pharmaceutically acceptable salt" is intended to mean both acid and base addition salts.

As used herein, the term "pharmaceutically acceptable acid addition salt" is intended to mean those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

As used herein, the term "pharmaceutically acceptable base addition salt" is intended to mean those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like.

As used herein, the term "BIR domain binding" is intended to mean the action of a compound of the present invention upon an IAP BIR domain, which blocks or diminishes the binding of IAPs to BIR binding proteins or is involved in displacing BIR binding proteins from an IAP. Examples of BIR binding proteins include, but are not limited to, caspases and mitochondrially derived BIR binding proteins such as Smac, Omi/WTR2A and the like.

As used herein, the term "insufficient apoptosis" is intended to mean a state wherein a disease is caused or continues because cells deleterious to the subject have not apoptosed. This includes, but is not limited to, cancer cells that survive in a subject without treatment, cancer cells that survive in a subject during or following anti-cancer treatment, or immune cells whose action is deleterious to the subject, and includes, neutrophils, monocytes and auto-reactive T-cells.

As used herein, the term "therapeutically effective amount" is intended to mean an amount of a compound of Formula I which, when administered to a subject is sufficient to effect treatment for a disease-state associated with insufficient apoptosis. The amount of the compound of Formula I will vary depending on the compound, the condition and its severity, and the age of the subject to be treated, but can be determined routinely by one of ordinary skill in the art having regard to his own knowledge and to this disclosure.

As used herein, the term "treating" or "treatment" is intended to mean treatment of a disease-state associated with insufficient apoptosis, as disclosed herein, in a subject, and includes: (i) preventing a disease or condition associated with insufficient apoptosis from occurring in a subject, in particular, when such mammal is predisposed to the disease or condition but has not yet been diagnosed as having it; (ii) inhibiting a disease or condition associated with insufficient apoptosis, i.e., arresting its development; or (iii) relieving a disease or condition associated with insufficient apoptosis, i.e., causing regression of the condition.

As used herein, the term "treating cancer" is intended to mean the administration of a pharmaceutical composition of the present invention to a subject, preferably a human, which is afflicted with cancer to cause an alleviation of the cancer by killing, inhibiting the growth, or inhibiting the metastasis of the cancer cells.

As used herein, the term "preventing disease" is intended to mean, in the case of cancer, the post-surgical, post-chemotherapy or post-radiotherapy administration of a pharmaceutical composition of the present invention to a subject, preferably a human, which was afflicted with cancer to prevent the regrowth of the cancer by killing, inhibiting the growth, or inhibiting the metastasis of any remaining cancer cells. Also included in this definition is the prevention of prosurvival conditions that lead to diseases such as asthma, MS and the like.

As used herein, the term "apoptosis" or "programmed cell death" is intended to mean the regulated process of cell death wherein a dying cell displays a set of well-characterized biochemical hallmarks that include cell membrane blebbing, cell soma shrinkage, chromatin condensation, and DNA laddering, as well as any caspase-mediated cell death.

As used herein, the term "BIR domain" or "BIR" are used interchangeably throughout and are intended to mean a domain which is characterized by a number of invariant amino acid residue including conserved cysteines and one conserved hisitidine residue within the sequence Cys-(Xaa1)$_2$Cys-(Xaa1)$_{16}$His-(Xaa1)$_{6-8}$Cys. Typically, the amino acid sequence of the consensus sequence is: Xaa1-Xaa1-Arg-Leu-Xaa1-Thr-Phe-Xaa1-Xaa1-Trp-Pro-Xaa2-Xaa1-Xaa1-Xaa2-Xaa2-Xaa1-Xaa1-Xaa1-Xaa1-Leu-Ala-Xaa1-Ala-Gly-Phe-Tyr-Tyr-Xaa1-Gly-Xaa1-Xaa1-Asp-Xaa1-Val-Xaa1-Cys-Phe-Xaa1-Cys-Xaa1-Xaa1-Xaa1-Xaa1-Xaa1-Xaa1-Trp-Xaa1-Xaa1-Xaa1-Asp-Xaa1-Xaa1-Xaa1-Xaa1-Xaa1-His-Xaa-1-Xaa1-Xaa1-Xaa1-Pro-Xaa1-Cys-Xaa1-Phe-Val, wherein Xaa1 is any amino acid and Xaa2 is any amino acid or is absent. Preferably the sequence is substantially identical to one of the BIR domain sequences provided for XIAP, HIAP1, or HIAP2 herein.

The BIR domain residues are listed below (see Genome Biology (2001) 1-10):

|        | XIAP    | HIAP-1    | HIAP-2    |
|--------|---------|-----------|-----------|
| BIR1   | 21-93   | 41-113    | 24-96     |
| BIR2   | 159-230 | 179-250   | 164-235   |
| BIR3   | 258-330 | 264-336   | 250-322   |
| Seq. # | P98170  | XP-006266 | XP-006267 |

As used herein, the term "ring zinc finger" or "RZF" is intended to mean a domain having the amino acid sequence of the consensus sequence: Glu-Xaa1-Xaa1-Xaa1-Xaa1-Xaa1-Xaa-1-Xaa2-Xaa1-Xaa1-Xaa1-Cys-Lys-Xaa3-Cys-Met-Xaa1-Xaa1-Xaa1-Xaa1-Xaa1-Xaa3-X-aa1-Phe-Xaa1-Pro-Cys-Gly-His-Xaa1-Xaa1-Xaa1-Cys-Xaa1-Xaa1-Cys-Ala-Xaa1-Xaa-1-Xaa1-Xaa1-Xaa1-Cys-Pro-Xaa1-Cys, wherein Xaa1 is any amino acid, Xaa2 is Glu or Asp, and Xaa3 is Val or Ile.

As used herein, the term "IAP" is intended to mean a polypeptide or protein, or fragment thereof, encoded by an IAP gene. Examples of IAPs include, but are not limited to human or mouse NAIP (Birc 1), HIAP-1 (cIAP2, Birc 3), HIAP-2 (cIAP1, Birc 2), XIAP (Birc 4), survivin (Birc 5), livin (ML-IAP, Birc 7), ILP-2 (Birc 8) and Apollon/BRUCE (Birc 6) (see for example U.S. Pat. Nos. 6,107,041; 6,133,437; 6,156,535; 6,541,457; 6,656,704; 6,689,562; Deveraux and Reed, Genes Dev. 13, 239-252, 1999; Kasof and Gomes, J. Biol. Chem., 276, 3238-3246, 2001; Vucic et al., Curr. Biol. 10, 1359-1366, 2000; Ashab et al. FEBS Lett., 495, 56-60, 2001, the contents of which are hereby incorporated by reference).

As used herein, the term "IAP gene" is intended to mean a gene encoding a polypeptide having at least one BIR domain and which is capable of modulating (inhibiting or enhancing) apoptosis in a cell or tissue. The IAP gene is a gene having about 50% or greater nucleotide sequence identity to at least one of human or mouse NAIP (Birc 1), HIAP-1 (cIAP2, Birc 3), HIAP-2 (cIAP1, Birc 2), XIAP (Birc 4), survivin (Birc 5), livin (ML-IAP, Birc 7), ILP-2 (Birc 8) and Apollon/BRUCE (Birc 6). The region of sequence over which identity is measured is a region encoding at least one BIR domain and a ring zinc finger domain. Mammalian IAP genes include nucleotide sequences isolated from any mammalian source.

As used herein, the term "$IC_{50}$" is intended to mean an amount, concentration or dosage of a particular compound of the present invention that achieves a 50% inhibition of a maximal response, such as displacement of maximal fluorescent probe binding in an assay that measures such response.

As used herein, the term "$EC_{50}$" is intended to mean an amount, concentration or dosage of a particular compound of the present invention that achieves a 50% inhibition of cell survival.

As used herein, the term "modulate" or "modulating" is intended to mean the treatment, prevention, suppression, enhancement or induction of a function or condition using the compounds of the present invention. For example, the compounds of the present invention can modulate IAP function in a subject, thereby enhancing apoptosis by significantly reducing, or essentially eliminating the interaction of activated apoptotic proteins, such as caspase-3, 7 and 9, with the BIR domains of mammalian IAPs or by inducing the loss of XIAP protein in a cell.

As used herein, the term "enhancing apoptosis" is intended to mean increasing the number of cells that apoptose in a given cell population either in vitro or in vivo. Examples of cell populations include, but are not limited to, ovarian cancer cells, colon cancer cells, breast cancer cells, lung cancer cells, pancreatic cancer cells, or T cells and the like. It will be appreciated that the degree of apoptosis enhancement provided by an apoptosis-enhancing compound of the present invention in a given assay will vary, but that one skilled in the art can determine the statistically significant change in the level of apoptosis that identifies a compound that enhances apoptosis otherwise limited by an IAP. Preferably "enhancing apoptosis" means that the increase in the number of cells undergoing apoptosis is at least 25%, more preferably the increase is 50%, and most preferably the increase is at least one-fold. Preferably the sample monitored is a sample of cells that normally undergo insufficient apoptosis (i.e., cancer cells). Methods for detecting the changes in the level of apoptosis (i.e., enhancement or reduction) are described in the Examples and include methods that quantify the fragmentation of DNA, methods that quantify the translocation phosphatoylserine from the cytoplasmic to the extracellular side of the membrane, determination of activation of the caspases and methods quantify the release of cytochrome C and the apoptosis inhibitory factor into the cytoplasm by mitochondria.

As used herein, the term "proliferative disease" or "proliferative disorder" is intended to mean a disease that is caused by or results in inappropriately high levels of cell division, inappropriately low levels of apoptosis, or both. For example, cancers such as lymphoma, leukemia, melanoma, ovarian cancer, breast cancer, pancreatic cancer, and lung cancer, and autoimmune disorders are all examples of proliferative diseases.

The compounds of the present invention, or their pharmaceutically acceptable salts may contain one or more asymmetric centers, chiral axes and chiral planes and may thus give rise to enantiomers, diastereomers, and other stereoisomeric forms and may be defined in terms of absolute stereochemistry, such as (R)- or (S)- or, as (D)- or (L)- for amino acids. The present invention is intended to include all such possible isomers, as well as, their racemic and optically pure forms. Optically active (+) and (−), (R)- and (S)-, or (D)- and (L)-isomers may be prepared using chiral synthons or chiral reagents, or resolved using conventional techniques, such as reverse phase HPLC. The racemic mixtures may be prepared and thereafter separated into individual optical isomers or these optical isomers may be prepared by chiral synthesis. The enantiomers may be resolved by methods known to those skilled in the art, for example by formation of diastereoisomeric salts which may then be separated by crystallization, gas-liquid or liquid chromatography, selective reaction of one enantiomer with an enantiomer specific reagent. It will also be appreciated by those skilled in the art that where the desired enantiomer is converted into another chemical entity by a separation technique, an additional step is then required to form the desired enantiomeric form. Alternatively specific enantiomers may be synthesized by asymmetric synthesis using optically active reagents, substrates, catalysts, or solvents or by converting one enantiomer to another by asymmetric transformation.

Certain compounds of the present invention may exist in Zwitterionic form and the present invention includes Zwitterionic forms of these compounds and mixtures thereof.

Utilities

The compounds of the present invention are useful as IAP BIR domain binding compounds and as such the compounds, compositions and method of the present invention include application to the cells or subjects afflicted with or having a predisposition towards developing a particular disease state, which is characterized by insufficient apoptosis. Thus, the compounds, compositions and methods of the present invention are used to treat cellular proliferative diseases/disorders, which include, but are not limited to, i) cancer, ii) autoimmune disease, iii) inflammatory disorders, iv) proliferation induced post medical procedures, including, but not limited to, surgery, angioplasty, and the like.

The compounds of the present invention may also be useful as antiulcerous agents. Down-regulation of the TRAIL (TNF-alpha-related apoptosis inducing ligand) system, in the context of H. pylori infection, may limit exaggerated apoptosis of gastric epithelial cells and destruction of tissue and, therefore, may enable *H. pylori* to maintain its niche, thus the compounds of the present invention may be useful in the treatment of bacterial infection and/or recurrent infection that may have develop due to the down-regulation of the TRAIL system. (see Nou et al. J. Infectious Diseases (2005) 571-8).

The compounds of the present invention may also be useful in the treatment of primary varicosis. Data suggest (see Ducass et al. Eur. J. Vasc. Endovac. Surg (2005) 316-323) that primary varicose veins are associated with inhibition of programmed cell death involving the defect in intrinsic apoptotic pathway. Thus the BIR domain binding compounds of the present invention may be useful in the treatment of this pathology.

The compounds of the present invention may also be useful in the treatment of diseases in which there is a defect in the programmed cell-death or the apoptotic machinery (TRAIL, FAS, apoptosome), such as multiple sclerosis, asthma, artherosclerosis, inflammation, autoimmunity and the like.

The treatment involves administration to a subject in need thereof a compound of the present invention or a pharmaceutically acceptable salt thereof, or a pharmaceutical composition comprising a pharmaceutical carrier and a therapeutically effective amount of a compound of the present invention, or a pharmaceutically acceptable salt thereof. In particular, the compounds, compositions and methods of the present invention are useful for the treatment of cancer including solid tumors such as skin, breast, brain, lung, testicular carcinomas, and the like. Cancers that may be treated by the compounds, compositions and methods of the invention include, but are not limited to the following:

| Tissue | Example |
| --- | --- |
| Adrenal gland | neuroblastoma |
| Bone | osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors |
| Cardiac | sarcoma (angiosarcoma, fibrosarcoma, rhabdomyosarcoma, liposarcoma), myxoma, rhabdomyoma, fibroma, lipoma and teratoma |
| Gastrointestinal | esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma) |
| Genitourinary tract | kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma) |
| Gynecological | uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma) |
| Hematologic | blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma] |
| Liver | hepatoma (hepatocellular carcinoma), cholangiocarcinoma, hepatoblastoma, angiosarcoma, hepatocellular adenoma, hemangioma |
| Lung | bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma |
| Nervous system | skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma) |
| Skin | malignant melanoma, basal cell carcinoma, squamous cell carcinoma, Karposi's sarcoma, moles dysplastic nevi, lipoma, angioma, dermatofibroma, keloids |

The compounds of the present invention, or their pharmaceutically acceptable salts or their prodrugs, may be administered in pure form or in an appropriate pharmaceutical composition, and can be carried out via any of the accepted modes of Galenic pharmaceutical practice.

The pharmaceutical compositions of the present invention can be prepared by admixing a compound of the present invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral (subcutaneous injections, intravenous, intramuscular, intrasternal injection or infusion techniques), sublingual, ocular, rectal, vaginal, and intranasal. Pharmaceutical compositions of the present invention are formulated so as to allow the active ingredients contained therein to be bioavailable upon administration of the composition to a subject. Compositions that will be administered to a subject or patient take the form of one or more dosage units, where for example, a tablet may be a single dosage unit, and a container of a compound of the present invention in aerosol form may hold a plurality of dosage units. Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound of the present invention, or a pharmaceutically acceptable salt thereof, for treatment of a disease-state as described above.

A pharmaceutical composition of the present invention may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, for example inhalatory administration.

For oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, e.g., a gelatin capsule, it may contain, in addition to materials of the above type, a liquid carrier such as polyethylene glycol or oil such as soybean or vegetable oil.

The pharmaceutical composition may be in the form of a liquid, e.g., an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the present invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediamine tetraacetic acid; buffers such as acetates, citrates or phosphates and agents for the adjustment of tonicity such as sodium chloride or dextrose. Solubilization agents may include cyclodextrins such as hydroxypropyl-beta-cyclodextrin. The parenteral preparation can be enclosed in ampoules, disposable syringes or multiple dose vials made of glass or plastic. An injectable pharmaceutical composition is preferably sterile.

A liquid pharmaceutical composition of the present invention used for either parenteral or oral administration should contain an amount of a compound of the present invention such that a suitable dosage will be obtained. Typically, this amount is at least 0.01% of a compound of the present invention in the composition. When intended for oral administration, this amount may be varied to be between 0.1 and about 70% of the weight of the composition. For parenteral usage, compositions and preparations according to the present invention are prepared so that a parenteral dosage unit contains between 0.01 to 1% by weight of the compound of the present invention.

The pharmaceutical composition of the present invention may be used for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the compound of the present invention from about 0.1 to about 10% w/v (weight per unit volume).

The pharmaceutical composition of the present invention may be used for rectal administration to treat for example, colon cancer, in the form, e.g., of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition of the present invention may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the present invention in solid or liquid form may include an agent that binds to the compound of the present invention and thereby assists in the delivery of the compound. Suitable agents that may act in this capacity include, but are not limited to, a monoclonal or polyclonal antibody, a protein or a liposome.

The pharmaceutical composition of the present invention may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the present invention may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine preferred aerosols.

The pharmaceutical compositions of the present invention may be prepared by methodology well known in the pharmaceutical art. For example, a pharmaceutical composition intended to be administered by injection can be prepared by admixing a compound of the present invention with sterile, distilled water so as to form a solution. A surfactant may be added to facilitate the formation of a homogeneous solution or suspension. Surfactants are compounds that non-covalently interact with the compound of the present invention so as to facilitate dissolution or homogeneous suspension of the compound in the aqueous delivery system.

The compounds of the present invention, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy. Generally, a therapeutically effective daily dose may be from about 0.1 mg to about 40 mg/kg of body weight per day or twice per day of a compound of the present invention, or a pharmaceutically acceptable salt thereof.

Combination Therapy

The compounds of the present invention, or pharmaceutically acceptable salts thereof, may also be administered simultaneously with, prior to, or after administration of one or more of the therapeutic agents described below. Such combination therapy may include administration of a single pharmaceutical dosage formulation which contains a compound of the present invention and one or more additional agents given below, as well as administration of the compound of the present invention and each of additional agent in its own separate pharmaceutical dosage formulation. For example, a compound of the present invention and another therapeutic agent can be administered to the patient either together in a single oral dosage composition such as a tablet or capsule, or each agent administered in separate oral dosage formulations or via intravenous injection. Where separate dosage formulations are used, the compounds of the present invention and one or more additional agents can be administered at essentially the same time, i.e., concurrently, or at separately staggered times, i.e., sequentially; combination therapy is understood to include all these regimens.

Thus, the present invention also encompasses the use of the compounds of the present invention in combination with radiation therapy or one or more additional agents such as those described in WO 03/099211 (PCT/US03/15861), which is hereby incorporated by reference.

Examples of such additional therapeutic agents include, but are not limited to the following:
a) an estrogen receptor modulator,
b) an androgen receptor modulator,
c) retinoid receptor modulator,
d) a cytotoxic agent,
e) an antiproliferative agent,
f) a prenyl-protein transferase inhibitor,
g) an HMG-CoA reductase inhibitor,
h) an HIV protease inhibitor,
i) a reverse transcriptase inhibitor,
k) an angiogenesis inhibitor,
l) a PPAR-.γ agonist,
m) a PPAR-.δ. agonist,
n) an inhibitor of inherent multidrug resistance,
o) an anti-emetic agent,
p) an agent useful in the treatment of anemia,
q) agents useful in the treatment of neutropenia,
r) an immunologic-enhancing drug.
s) a proteasome inhibitor such as Velcade and MG132 (7-Leu-Leu-aldehyde) (see He at al. in Oncogene (2004) 23, 2554-2558);
t) an HDAC inhibitor, such as sodium butyrate, phenyl butyrate, hydroamic acids, cyclin tetrapeptide and the like (see Rosato et al., Molecular Cancer Therapeutics 2003, 1273-1284);
u) an inhibitor of the chemotrypsin-like activity in the proteasome; and
v) E3 ligase inhibitors.

More specifically, the compounds of the present invention can also be used in combination with one or more chemotherapeutic agents that disrupts or stabilizes microtubules is particularly effective in treating cancer and other neoplasms. Microtubule-disrupting agents (e.g., vinca alkaloids) and microtubule-stabilizing agents (e.g., taxanes) are described in greater detail below.

Vinca Alkaloids and Related Compounds

Vinca alkaloids that can be used in combination with the nucleobase oligomers of the invention to treat cancer and other neoplasms include vincristine, vinblastine, vindesine, vinflunine, vinorelbine, and anhydrovinblastine.

Dolastatins are oligopeptides that primarily interfere with tubulin at the vinca alkaloid binding domain. These compounds can also be used in combination with the compounds of the invention to treat cancer and other neoplasms. Dolastatins include dolastatin-10 (NCS 376128), dolastatin-15, ILX651, TZT-1027, symplostatin 1, symplostatin 3, and LU103793 (cemadotin).

Cryptophycins (e.g., cryptophycin 1 and cryptophycin 52 (LY355703)) bind tubulin within the vinca alkaloid-binding domain and induce G2/M arrest and apoptosis. Any of these compounds can be used in combination with the compounds of the invention to treat cancer and other neoplasms.

Other microtubule disrupting compounds that can be used in conjunction with the compounds of the invention to treat cancer and other neoplasms are described in U.S. Pat. Nos. 6,458,765; 6,433,187; 6,323,315; 6,258,841; 6,143,721; 6,127,377; 6,103,698; 6,023,626; 5,985,837; 5,965,537; 5,955,423; 5,952,298; 5,939,527; 5,886,025; 5,831,002; 5,741,892; 5,665,860; 5,654,399; 5,635,483; 5,599,902; 5,530,097; 5,521,284; 5,504,191; 4,879,278; and 4,816,444, and U.S. patent application Publication Nos. 2003/0153505 A1; 2003/0083263 A1; and 2003/0055002 A1, each of which is hereby incorporated by reference.

Taxanes and Other Microtubule Stabilizing Compounds

Taxanes such as paclitaxel, doxetaxel, RPR 109881A, SB-T-1213, SB-T-1250, SB-T-101187, BMS-275183, BRT 216, DJ-927, MAC-321, IDN5109, and IDN5390 can be used in combination with the compounds of the invention to treat cancer and other neoplasms. Taxane analogs (e.g., BMS-184476, BMS-188797) and functionally related non-taxanes (e.g., epothilones (e.g., epothilone A, epothilone B (EPO906), deoxyepothilone B, and epothilone B lactam (BMS-247550)), eleutherobin, discodermolide, 2-epi-discodermolide, 2-des-methyldiscodermolide, 5-hydroxymethyldiscoder-molide, 19-des-aminocarbonyldiscodermolide, 9(13)-cyclodiscodermolide, and laulimalide) can also be used in the methods and compositions of the invention.

Other microtubule stabilizing compounds that can be used in combination with the compounds of the invention to treat cancer and other neoplasms are described in U.S. Pat. Nos. 6,624,317; 6,610,736; 6,605,599; 6,589,968; 6,583,290; 6,576,658; 6,515,017; 6,531,497; 6,500,858; 6,498,257; 6,495,594; 6,489,314; 6,458,976; 6,441,186; 6,441,025; 6,414,015; 6,387,927; 6,380,395; 6,380,394; 6,362,217; 6,359,140; 6,306,893; 6,302,838; 6,300,355; 6,291,690; 6,291,684; 6,268,381; 6,262,107; 6,262,094; 6,147,234; 6,136,808; 6,127,406; 6,100,411; 6,096,909; 6,025,385; 6,011,056; 5,965,718; 5,955,489; 5,919,815; 5,912,263; 5,840,750; 5,821,263; 5,767,297; 5,728,725; 5,721,268; 5,719,177; 5,714,513; 5,587,489; 5,473,057; 5,407,674; 5,250,722; 5,010,099; and 4,939,168; and U.S. patent application Publication Nos. 2003/0186965 A1; 2003/0176710 A1; 2003/0176473 A1; 2003/0144523 A1; 2003/0134883 A1; 2003/0087888 A1; 2003/0060623 A1; 2003/0045711 A1; 2003/0023082 A1; 2002/0198256 A1; 2002/0193361 A1; 2002/0188014 A1; 2002/0165257 A1; 2002/0156110 A1; 2002/0128471 A1; 2002/0045609 A1; 2002/0022651 A1; 2002/0016356 A1; 2002/0002292 A1, each of which is hereby incorporated by reference.

Other chemotherapeutic agents that may be administered with a compound of the present invention are listed in the following Table:

| | | |
|---|---|---|
| Alkylating agents | cyclophosphamide | mechlorethamine |
| | lomustine | thiotepa |
| | busulfan | streptozocin |
| | procarbazine | chlorambucil |
| | ifosfamide | temozolomide |
| | altretamine | dacarbazine |
| | melphalan | semustine |
| | estramustine phosphate | carmustine |
| | hexamethylmelamine | |
| Platinum agents | cisplatin | tetraplatin |
| | carboplatinum | BBR-3464 (Hoffmann-La Roche) |
| | oxaliplatin | Ormiplatin |
| | ZD-0473 (AnorMED) | SM-11355 (Sumitomo) |
| | spiroplatinum | iproplatin |
| | lobaplatin (Aeterna) | AP-5280 (Access) |
| | carboxyphthalatoplatinum | |
| | satraplatin (Johnson Matthey) | |
| Antimetabolites | azacytidine | 6-mercaptopurine |
| | tomudex | hydroxyurea |
| | gemcitabine | 6-thioguanine |
| | trimetrexate | decitabine (SuperGen) |
| | capecitabine | cytarabin |
| | deoxycoformycin | clofarabine (Bioenvision) |
| | 5-fluorouracil | 2-fluorodeoxy cytidine |
| | fludarabine | |
| | floxuridine | irofulven (MGI Pharma) |
| | pentostatin | methotrexate |
| | 2-chlorodeoxyadenosine | DMDC (Hoffmann-La Roche) |
| | raltitrexed | idatrexate |
| | | ethynylcytidine (Taiho) |
| Topoisomerase inhibitors | amsacrine | TAS-103 (Taiho) |
| | rubitecan (SuperGen) | Topotecan |
| | epirubicin | elsamitrucin (Spectrum) |
| | exatecan mesylate (Daiichi) | dexrazoxanet (TopoTarget) |
| | etoposide | J-107088 (Merck & Go) |
| | quinamed (ChemGenex) | pixantrone (Novuspharma) |
| | teniposide or mitoxantrone | BNP-1350 (BioNumerik) |
| | gimatecan (Sigma-Tau) | rebeccamycin analogue (Exelixis) |
| | irinotecan (CPT-11) | CKD-602 (Chong Kun Dang) |
| | diflomotecan (Beaufour-Ipsen) | BBR-3576 (Novuspharma) |
| | 7-ethyl-10-hydroxy-camptothecin | KW-2170 (Kyowa Hakko) |
| Antitumor antibiotics | dactinomycin (actinomycin D) | bleomycinic acid |
| | amonafide | idarubicin |
| | doxorubicin (adriamycin) | bleomycin A |
| | azonafide | rubidazone |
| | deoxyrubicin | bleomycin B |
| | anthrapyrazole | plicamycinp |
| | valrubicin | mitomycin C |
| | oxantrazole | porfiromycin |
| | daunorubicin (daunomycin) | MEN-10755 (Menarini) |
| | losoxantrone | cyanomorpholinodoxorubicin |
| | epirubicin | GPX-100 (Gem Pharmaceuticals) |
| | bleomycin sulfate (blenoxane) | mitoxantrone (novantrone) |
| | therarubicin | |
| Antimitotic agents | paclitaxel | RPR 109881A (Aventis) |
| | SB 408075 (GlaxoSmithKline) | ZD 6126 (AstraZeneca) |
| | docetaxel | TXD 258 (Aventis) |

-continued

| | | |
|---|---|---|
| | E7010 (Abbott) | PEG-paclitaxel (Enzon) |
| | Colchicines | epothilone B (Novartis) |
| | PG-TXL (Cell Therapeutics) | AZ10992 (Asahi) |
| | vinblastine | T 900607 (Tularik) |
| | IDN 5109 (Bayer) | IDN-5109 (Indena) |
| | Vincristine | T 138067 (Tularik) |
| | A 105972 (Abbott) | AVLB (Prescient NeuroPharma) |
| | Vinorelbine | cryptophycin 52 (Eli Lilly) |
| | A 204197 (Abbott) | azaepothilone B (BMS) |
| | Vindesine | vinflunine (Fabre) |
| | LU 223651 (BASF) | BNP-7787 (BioNumerik) |
| | dolastatin 10 (NCI) | auristatin PE (Teikoku Hormone) |
| | D 24851 (ASTAMedica) | CA-4 prodrug (OXiGENE) |
| | rhizoxin (Fujisawa) | BMS 247550 (BMS) |
| | ER-86526 (Eisai) | dolastatin-10 (NIH) |
| | mivobulin (Warner-Lambert) | BMS 184476(BMS) |
| | combretastatin A4 (BMS) | CA-4 (OXiGENE) |
| | cemadotin (BASF) | BMS 188797 (BMS) |
| | isohomohalichondrin-B (PharmaMar) | taxoprexin (Protarga) |
| Aromatase inhibitors | Aminoglutethimide | anastrazole |
| | Exemestane | YM-511 (Yamanouchi) |
| | Letrozole | formestane |
| | atamestane (BioMedicines) | |
| Thymidylate synthase inhibitors | pemetrexed (Eli Lilly) | ZD-9331 (BTG) |
| | nolatrexed (Eximias) | CoFactor ™ (BioKeys) |
| DNA antagonists | trabectedin (PharmaMar) | albumin + 32P (Isotope Solutions) |
| | mafosfamide (Baxter International) | O6 benzyl guanine (Paligent) |
| | glufosfamide (Baxter International) | thymectacin (NewBiotics) |
| | apaziquone (Spectrum Pharmaceuticals) | edotreotide (Novartis) |
| Farnesyltransferase inhibitors | arglabin (NuOncology Labs) | perillyl alcohol (DOR BioPharma) |
| | tipifarnib (Johnson & Johnson) | BAY-43-9006 (Bayer) |
| | lonafarnib (Schering-Plough) | |
| Pump inhibitors | CBT-1 (CBA Pharma) | tariquidar (Xenova) |
| | zosuquidar trihydrochloride (Eli Lilly) | biricodar dicitrate (Vertex) |
| | | MS-209 (Schering AG) |
| Histone acetyltransferase inhibitors | tacedinaline (Pfizer) | depsipeptide (Fujisawa) |
| | pivaloyloxymethyl butyrate (Titan) | MS-275 (Schering AG) |
| | SAHA (Aton Pharma) | |
| Metalloproteinase inhibitors | Neovastat (Aeterna Laboratories) | marimastat (British Biotech) BMS-275291 (Celltech) |
| | CMT-3 (CollaGenex) | |
| Ribonucleoside reductase inhibitors | gallium maltolate (Titan) | triapine (Vion) |
| | tezacitabine (Aventis) | didox (Molecules for Health) |
| TNF alpha agonists/antagonists | virulizin (Lorus Therapeutics) | CDC-394 (Celgene) |
| | revimid (Celgene) | |
| Endothelin A receptor antagonist | atrasentan (Abbott) | ZD-4054 (AstraZeneca) |
| | YM-598 (Yamanouchi) | |
| Retinoic acid receptor agonists | fenretinide (Johnson & Johnson) | LGD-1550 (Ligand) |
| | alitretinoin (Ligand) | |
| Immuno-modulators | Interferon | norelin (Biostar) |
| | dexosome therapy (Anosys) | IRX-2 (Immuno-Rx) |
| | oncophage (Antigenics) | BLP-25 (Biomira) |
| | pentrix (Australian Cancer Technology) | PEP-005 (Peplin Biotech) |
| | GMK (Progenics) | MGV (Progenics) |
| | ISF-154 (Tragen) | synchrovax vaccines (CTL Immuno) |
| | adenocarcinoma vaccine (Biomira) cancer vaccine (Intercell) | beta.-alethine (Dovetail) |
| | | melanoma vaccine (CTL Immuno) |
| | | CLL therapy (Vasogen) |
| | CTP-37 (A VI BioPharma) | p21 RAS vaccine (GemVax) |
| Hormonal and antihormonal agents | estrogens | bicalutamide |
| | Prednisone | testosterone propionate; |
| | conjugated estrogens | fluoxymesterone |
| | methylprednisolone | flutamide |
| | ethinyl estradiol | methyltestosterone |
| | prednisolone | octreotide |
| | chlortrianisen | diethylstilbestrol |
| | aminoglutethimide | nilutamide |
| | idenestrol | megestrol |
| | leuprolide | mitotane tamoxifen |
| | hydroxyprogesterone caproate | P-04 (Novogen) |
| | goserelin | Toremofine |
| | medroxyprogesterone | 2-methoxyestradiol (EntreMed) |
| | leuporelin | dexamethasone |
| | testosterone | arzoxifene (Eli Lilly) |

| | | |
|---|---|---|
| Photodynamic agents | talaporfin (Light Sciences) Pd-bacteriopheophorbide (Yeda) Theralux (Theratechnologies) lutetium texaphyrin (Pharmacyclics) | motexafin gadolinium (Pharmacyclics) hypericin |
| Tyrosine Kinase Inhibitors | imatinib (Novartis) kahalide F (PharmaMar) leflunomide (Sugen/Pharmacia) CEP-701 (Cephalon) ZD1839 (AstraZeneca) CEP-751 (Cephalon) erlotinib (Oncogene Science) MLN518 (Millenium) canertinib (Pfizer) PKC412 (Novartis) squalamine (Genaera) phenoxodiol ( ) SU5416 (Pharmacia) trastuzumab (Genentech) SU6668 (Pharmacia) | C225 (ImClone) ZD4190 (AstraZeneca) rhu-Mab (Genentech) ZD6474 (AstraZeneca) MDX-H210 (Medarex) vatalanib (Novartis) 2C4 (Genentech) PKI166 (Novartis) MDX-447 (Medarex) GW2016 (GlaxoSmithKline) ABX-EGF (Abgenix) EKB-509 (Wyeth) IMC-1C11 (ImClone) EKB-569 (Wyeth) |

| Miscellaneous agents | |
|---|---|
| SR-27897 (CCK A inhibitor, Sanofi-Synthelabo) BCX-1777 (PNP inhibitor, BioCryst) tocladesine (cyclic AMP agonist, Ribapharm) ranpirnase (ribonuclease stimulant, Alfacell) alvocidib (CDK inhibitor, Aventis) galarubicin (RNA synthesis inhibitor, Dong-A) CV-247 (COX-2 inhibitor, Ivy Medical) tirapazamine (reducing agent, SRI International) P54 (COX-2 inhibitor, Phytopharm) N-acetylcysteine (reducing agent, Zambon) CapCell ™ (CYP450 stimulant, Bavarian Nordic) R-flurbiprofen (NF-kappaB inhibitor, Encore) GCS-100 (gal3 antagonist, GlycoGenesys) 3CPA (NF-kappaB inhibitor, Active Biotech) G17DT immunogen (gastrin inhibitor, Aphton) seocalcitol (vitamin D receptor agonist, Leo) efaproxiral (oxygenator, Allos Therapeutics) 131-I-TM-601 (DNA antagonist, TransMolecular) PI-88 (heparanase inhibitor, Progen) eflornithine (ODC inhibitor, ILEX Oncology) tesmilifene (histamine antagonist, YM BioSciences) minodronic acid (osteoclast inhibitor, Yamanouchi) histamine (histamine H2 receptor agonist, Maxim) indisulam (p53 stimulant, Eisai) tiazofurin (IMPDH inhibitor, Ribapharm) aplidine (PPT inhibitor, PharmaMar) cilengitide (integrin antagonist, Merck KGaA) rituximab (CD20 antibody, Genentech) SR-31747 (IL-1 antagonist, Sanofi-Synthelabo) | gemtuzumab (CD33 antibody, Wyeth Ayerst) CCI-779 (mTOR kinase inhibitor, Wyeth) PG2 (hematopoiesis enhancer, Pharmagenesis) exisulind (PDE V inhibitor, Cell Pathways) Immunol ™ (triclosan oral rinse, Endo) CP-461 (PDE V inhibitor, Cell Pathways) triacetyluridine (uridine prodrug, Wellstat) AG-2037 (GART inhibitor, Pfizer) SN-4071 (sarcoma agent, Signature BioScience) WX-UK1 (plasminogen activator inhibitor, Wilex) TransMID-107 .TM. (immunotoxin, KS Biomedix) PBI-1402 (PMN stimulant, ProMetic LifeSciences) PCK-3145 (apoptosis promotor, Procyon) bortezomib (proteasome inhibitor, Millennium) doranidazole (apoptosis promotor, Pola) SRL-172 (T cell stimulant, SR Pharma) CHS-828 (cytotoxic agent, Leo) TLK-286 (glutathione S transferase inhibitor, Telik) trans-retinoic acid (differentiator, NIH) PT-100 (growth factor agonist, Point Therapeutics) MX6 (apoptosis promotor, MAXIA) midostaurin (PKC inhibitor, Novartis) apomine (apoptosis promotor, ILEX Oncology) bryostatin-1 (PKC stimulant, GPC Biotech) urocidin (apoptosis promotor, Bioniche) CDA-II (apoptosis promotor, Everlife) Ro-31-7453 (apoptosis promotor, La Roche) SDX-101 (apoptosis promotor, Salmedix) brostallicin (apoptosis promotor, Pharmacia) ceflatonin (apoptosis promotor, ChemGenex) |

Additional combinations may also include agents which reduce the toxicity of the aforesaid agents, such as hepatic toxicity, neuronal toxicity, nephprotoxicity and the like.

Moreover, our in vitro results suggest that the compounds of the present invention may well work with TRAIL. In one example, co-administration of one of the compounds of Formula I of the present invention with a death receptor agonist such as TRAIL, such as a small molecule or an antibody that mimics TRAIL may cause an advantageous synergistic effect of 2 to 3 logs in potency. Moreover, the compounds of the present invention may be used in combination with any compounds that cause an increase in circulating levels of TRAIL.

Screening Assays

The compounds of the present invention may also be used in a method to screen for other compounds that bind to an IAP BIR domain. Generally speaking, to use the compounds of the invention in a method of identifying compounds that bind to an IAP BIR domain, the IAP is bound to a support, and a compound of the invention is added to the assay. Alternatively, the compound of the invention may be bound to the support and the IAP is added.

There are a number of ways in which to determine the binding of a compound of the present invention to the BIR domain. In one way, the compound of the invention, for example, may be fluorescently or radioactively labeled and binding determined directly. For example, this may be done by attaching the IAP to a solid support, adding a detectably labeled compound of the invention, washing off excess reagent, and determining whether the amount of the detectable label is that present on the solid support. Numerous blocking and washing steps may be used, which are known to those skilled in the art.

In some cases, only one of the components is labeled. For example, specific residues in the BIR domain may be labeled. Alternatively, more than one component may be labeled with different labels; for example, using $I^{125}$ for the BIR domain, and a fluorescent label for the probe.

The compounds of the invention may also be used as competitors to screen for additional drug candidates or test compounds. As used herein, the terms "drug candidate" or "test compounds" are used interchangeably and describe any molecule, for example, protein, oligopeptide, small organic molecule, polysaccharide, polynucleotide, and the like, to be tested for bioactivity. The compounds may be capable of directly or indirectly altering the IAP biological activity.

Drug candidates can include various chemical classes, although typically they are small organic molecules having a molecular weight of more than 100 and less than about 2,500 Daltons. Candidate agents typically include functional groups necessary for structural interaction with proteins, for example, hydrogen bonding and lipophilic binding, and typically include at least an amine, carbonyl, hydroxyl, ether, or carboxyl group. The drug candidates often include cyclical carbon or heterocyclic structures and/or aromatic or polyaromatic structures substituted with one or more functional groups.

Drug candidates can be obtained from any number of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means.

Competitive screening assays may be done by combining an IAP BIR domain and a probe to form a probe:BIR domain complex in a first sample followed by adding a test compound from a second sample. The binding of the test is determined, and a change, or difference in binding between the two samples indicates the presence of a test compound capable of binding to the BIR domain and potentially modulating the IAP's activity.

In one case, the binding of the test compound is determined through the use of competitive binding assays. In this embodiment, the probe is labeled with an an affinity label such as biotin. Under certain circumstances, there may be competitive binding between the test compound and the probe, with the probe displacing the candidate agent.

In one case, the test compound may be labeled. Either the test compound, or a compound of the present invention, or both, is added first to the IAP BIR domain for a time sufficient to allow binding to form a complex.

Formation of the probe:BIR domain complex typically require incubations of between 4° C. and 40° C. for between 10 minutes to about 1 hour to allow for high-throughput screening. Any excess of reagents are generally removed or washed away. The test compound is then added, and the presence or absence of the labeled component is followed, to indicate binding to the BIR domain.

In one case, the probe is added first, followed by the test compound. Displacement of the probe is an indication the test compound is binding to the BIR domain and thus is capable of binding to, and potentially modulating, the activity of IAP. Either component can be labeled. For example, the presence of probe in the wash solution indicates displacement by the test compound. Alternatively, if the test compound is labeled, the presence of the probe on the support indicates displacement.

In one case, the test compound may be added first, with incubation and washing, followed by the probe. The absence of binding by the probe may indicate the test compound is bound to the BIR domain with a higher affinity. Thus, if the probe is detected on the support, coupled with a lack of test compound binding, may indicate the test compound is capable of binding to the BIR domain.

Modulation is tested by screening for a test compound's ability to modulate the activity of IAP and includes combining a test compound with an IAP BIR domain, as described above, and determining an alteration in the biological activity of the IAP. Therefore in this case, the test compound should both bind to the BIR domain (although this may not be necessary), and alter its biological activity as defined herein.

Positive controls and negative controls may be used in the assays. All control and test samples are performed multiple times to obtain statistically significant results. Following incubation, all samples are washed free of non-specifically bound material and the amount of bound probe determined. For example, where a radiolabel is employed, the samples may be counted in a scintillation counter to determine the amount of bound compound.

Typically, the signals that are detected in the assay may include fluorescence, resonance energy transfer, time resolved fluorescence, radioactivity, fluorescence polarization, plasma resonance, or chemiluminescence and the like, depending on the nature of the label. Detectable labels useful in performing screening assays in this invention include a fluorescent label such as Fluorescein, Oregon green, dansyl, rhodamine, tetramethyl rhodamine, texas red, $Eu^{3+}$; a chemiluminescent label such as luciferase; calorimetric labels; enzymatic markers; or radioisotopes such as tritium, $I^{125}$ and the like.

We herein disclose the use of two fluorescently labeled BIR binding compounds which can act as probes in a fluorescent polarization assay, as described below.

Affinity tags, which may be useful in performing the screening assays of the present invention include be biotin, polyhistidine and the like.

Synthesis and Methodology

General methods for the synthesis of the compounds of the present invention are shown below and are disclosed merely for the purpose of illustration and are not meant to be interpreted as limiting the processes to make the compounds by any other methods. Those skilled in the art will readily appreciate that a number of methods are available for the preparation of the compounds of the present invention.

General Procedures

Schemes 1, 2, 3, 4, 5 and 6 illustrate general synthetic procedures for the preparation of compounds of the instant invention.

Scheme 1 illustrates general procedures for the preparation of intermediates of general formula 1-v. Intermediate 1-ii was prepared by a reductive amination sequence. As such, compound of general formula 1-i was treated with amine $R^6NH_2$, followed by reduction with an appropriate hydride to provide intermediate 1-ii. Protection of 1-ii with protecting group $PG^5$, followed by deprotection of $PG^1$ yields intermediate 1-iii. $PG^2(H)N(R^3)CHCO_2H$ is coupled to 1-iii using amino acid coupling agents, followed by deprotection of $PG^2$ yields intermediate 1-iv. Similarly, $PG^3(R^1)N(R^2)CHCO_2H$ is coupled to 1-iv using amino acid coupling agents, followed by deprotection of $PG^5$ yields intermediate 1-v.

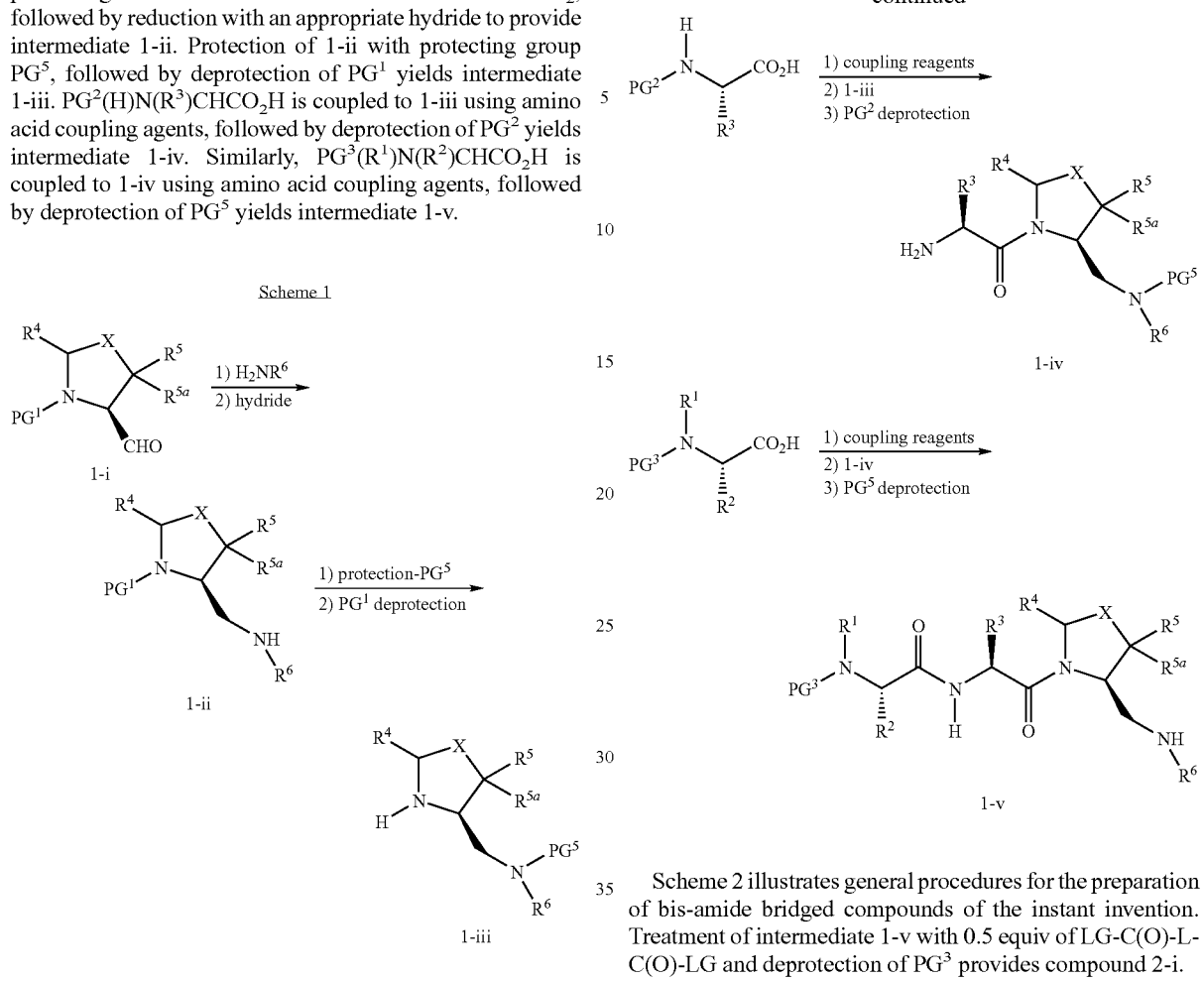

Scheme 2 illustrates general procedures for the preparation of bis-amide bridged compounds of the instant invention. Treatment of intermediate 1-v with 0.5 equiv of LG-C(O)-L-C(O)-LG and deprotection of $PG^3$ provides compound 2-i.

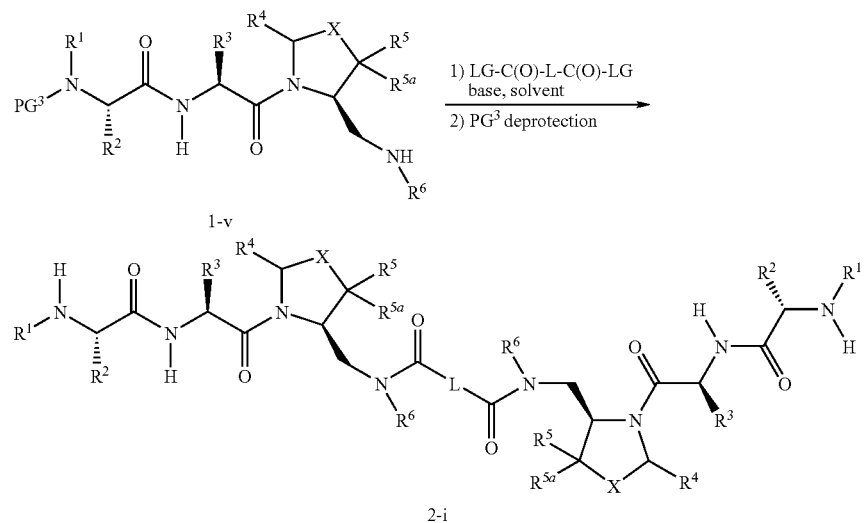

Scheme 3 illustrates general procedures for the preparation of bis-sulfonyl bridged compounds of the instant invention. Treatment of intermediate 1-v with 0.5 equiv of LG-S(O)$_2$-L-S(O)$_2$-LG and deprotection of $PG^3$ provides compound 3-i.

Scheme 3

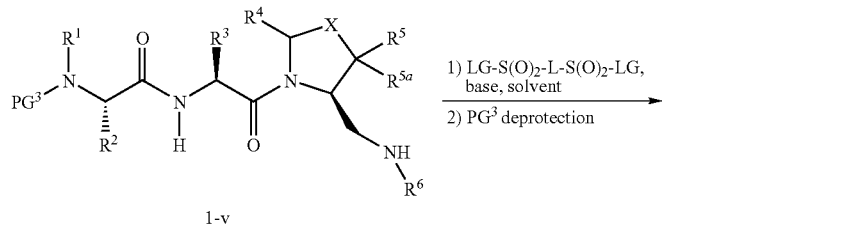

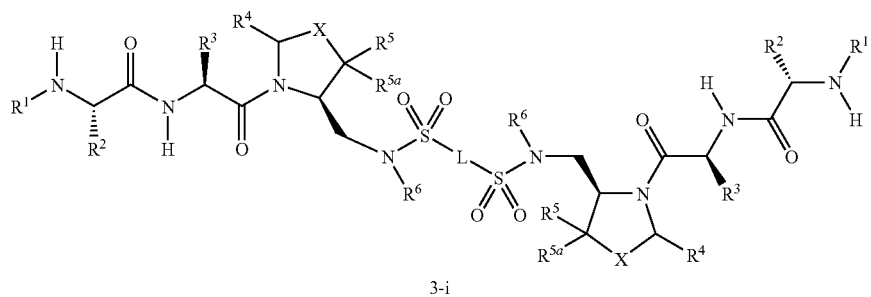

3-i

Scheme 4 illustrates general procedures for the preparation of alkyl bridged compounds of the instant invention. Treatment of intermediate 1-v with 0.5 equiv of LG-L-LG and deprotection of $PG^3$ provides compound 4-i.

Scheme 4

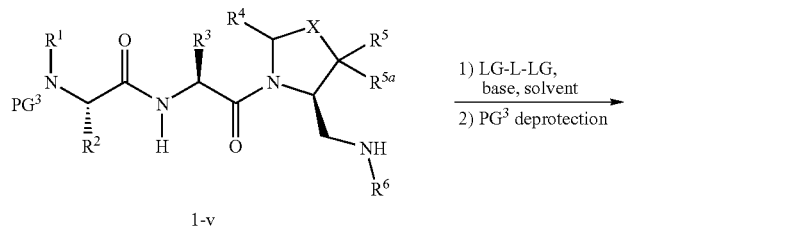

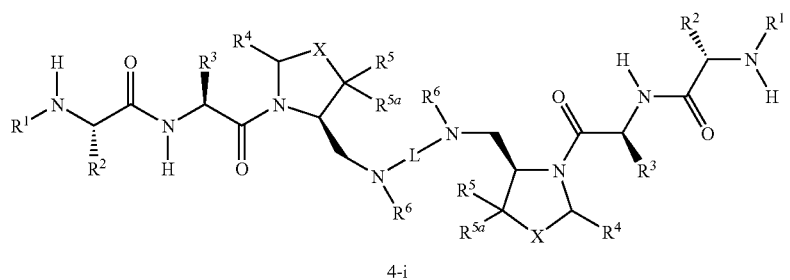

4-i

Scheme 5 illustrates the use of functionalized amino acids as bridging groups. $PG^4(H)N(R^8)CHCO_2H$ is coupled to 1-v using amino acid coupling agents, followed by deprotection of $PG^4$ yields intermediate 4-i. Treatment of 4-i with LG-Z-LG followed by deprotection of $PG^3$ yields compound 5-ii.

Scheme 5

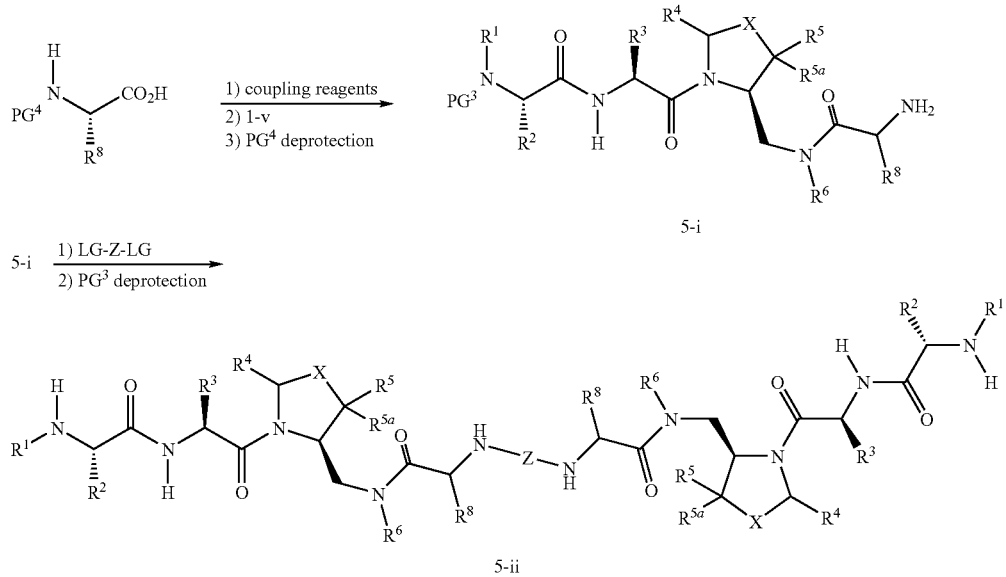

Similar bridging strategies can be used to prepare compounds of formula I from intermediates 1-ia and 1-ib.

Scheme 6 illustrates general procedures for the preparation of bridged compounds of general formula 6-v. Intermediate 6-i was prepared by a reductive amination sequence. A Bis-aldehyde was treated with amine $R^6NH_2$, followed by a reduction with an appropriate hydride to provide intermediate 6-i. A compound of general formula 6-ii is coupled to 6-i using amino acid coupling agents, followed by deprotection of $PG^1$ yields intermediate 6-iii. $PG^2(H)N(R^3)CHCO_2H$ is coupled to 6-iii using amino acid coupling agents, followed by deprotection of $PG^2$ yields intermediate 6-iv. Similarly, $PG^3(R^1)N(R^2)CHCO_2H$ is coupled to 6-iv using amino-acid coupling agents, followed by deprotection of $PG^5$ yields compound 6-v.

Scheme 6

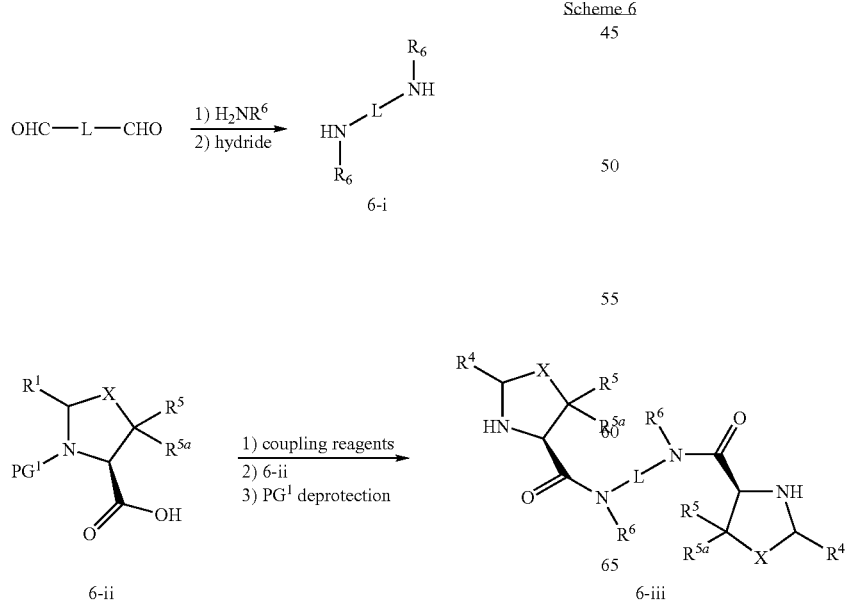

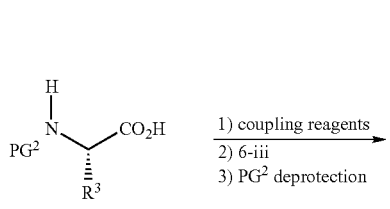
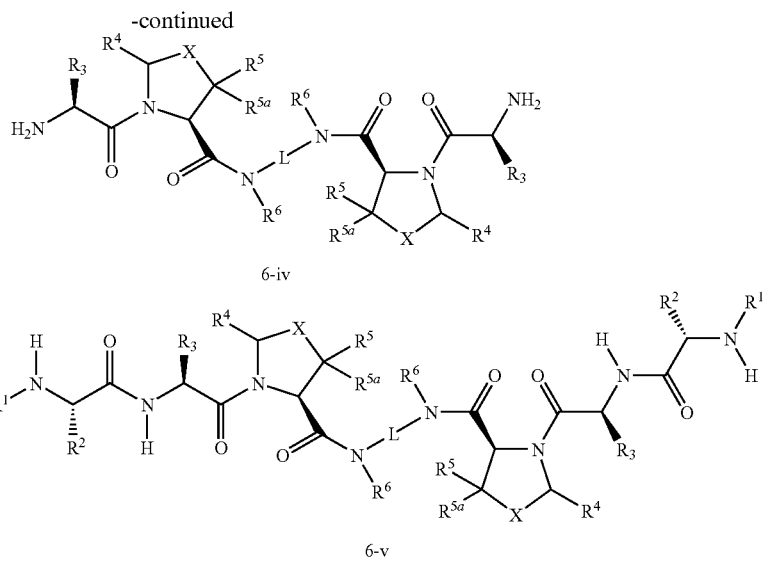

6-iv 6-v

The above schemes are also applicable wherein $R^3$ and $R^4$ are joined to form a heterocyclic ring system, and $R^1$, $R^2$, W, $R^5$, $R^{5a}$, X, L and the like, are as defined herein. LG is a leaving group such as, for example, Cl, Br, I, OTs or OMs.

EXAMPLES

The following abbreviations are used throughout:

| | |
|---|---|
| Boc: | t-butoxycarbonyl; |
| CBz: | benzyloxycarbonyl; |
| DCM: | dichloromethane, $CH_2Cl_2$; |
| DIPEA: | diisopropylethylamine; |
| DMAP: | 4-(dimethylamino)pyridine; |
| DMF: | N,N-dimethylformamide; |
| DTT: | dithiothreitol; |
| EDC: | 3-(dimethylaminopropyl)-3-ethylcarbodiimide hydrochloride; |
| EDTA: | ethylenediaminetetracetic acid; |
| Fmoc: | N-(9-fluorenylmethoxycarbonyl); |
| HBTU: | O-(benzotriazol-1-yl)-N,N,N',N'-tetramethyluronium hexafluorophosphate; |
| HCl: | hydrochloric acid; |
| HOAc: | acetic acid; |
| HOBt: | 1-hydroxybenzotriazole; |
| HPLC: | high performance liquid chromatography; |
| LCMS: | liquid chromatography-mass spectrometer; |
| MeOH: | methanol; |
| $MgSO_4$: | magnesium sulfate; |
| MS: | mass spectrum; |
| Ms: | methanesulfonyl; |
| $NaHCO_3$: | sodium hydrogen carbonate; |
| Pd/C: | palladium on carbon; |
| TEA: | triethylamine; |
| TFA: | trifluoroacetic acid; |
| THF: | tetrahydrofuran; |
| TMEDA: | N,N,N,N-tetramethylethylenediamine; |
| Ts: | para-toluenesulfonyl. |

Synthetic Methods
Preparation of Representative Examples:

The preparation of intermediate 7-7 is illustrated in scheme 7. The conversion of intermediate 7-7 to compounds 1, 13, 20 and 23 is summarized in schemes 8, 9, 10 and 11.

Compound 7-7 was prepared in a manner similar to that described in co-owned U.S. patent application Ser. No. 11/434,166. Reductive amination of Boc-prolinal using phenethylamine and $Na(AcO)_3BH$ provides intermediate 7-1 which was then acylated with benzyl chloroformate, and Boc-deprotected using 4N HCl in 1,4-dioxane to provide intermediate 7-3•HCl. Activation of the carboxyl group of Boc-L-Tle-Gly-OH by treatment with the amide coupling agents HBTU, HOBt, and DIPEA in DMF solvent was followed by the addition of 7-3•HCl to provide intermediate 7-4. Boc deprotection using 4N HCl in 1,4-dioxane provided 7-5•HCl. Activation of the carboxyl group of Boc-NMe-Ala-OH by treatment with the amide coupling agents HBTU, HOBt, and DIPEA in DMF solvent was followed by the addition of 7-5•HCl to provide intermediate 7-6. Cbz deprotection using Pd/C under a hydrogen atmosphere in MeOH provided 7-7.

Scheme 7

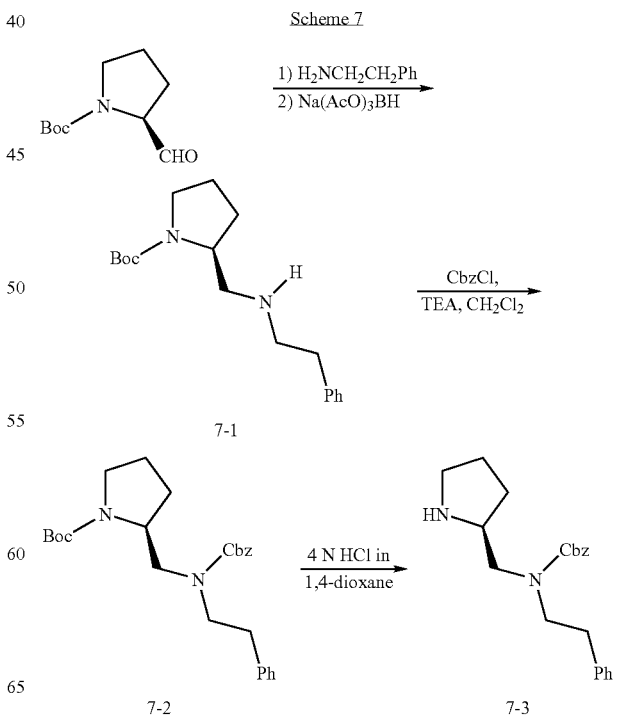

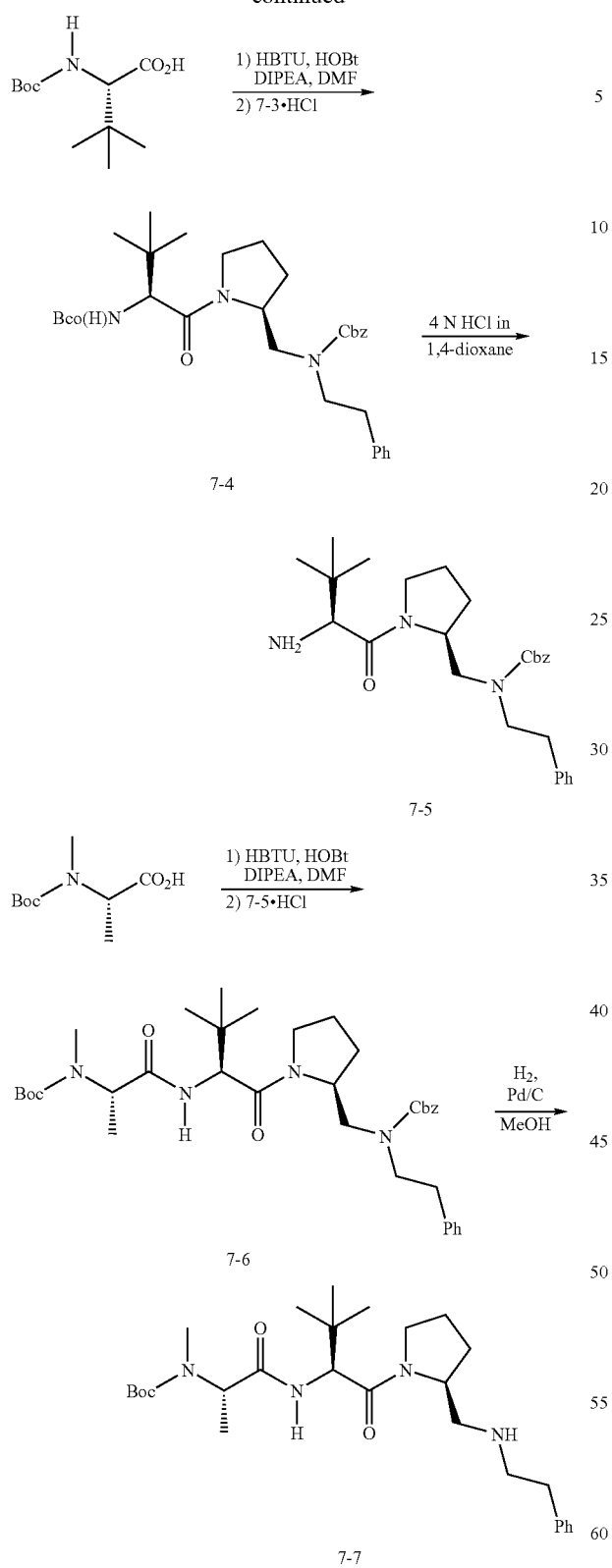

7-4

7-5

7-6

7-7

Scheme 8

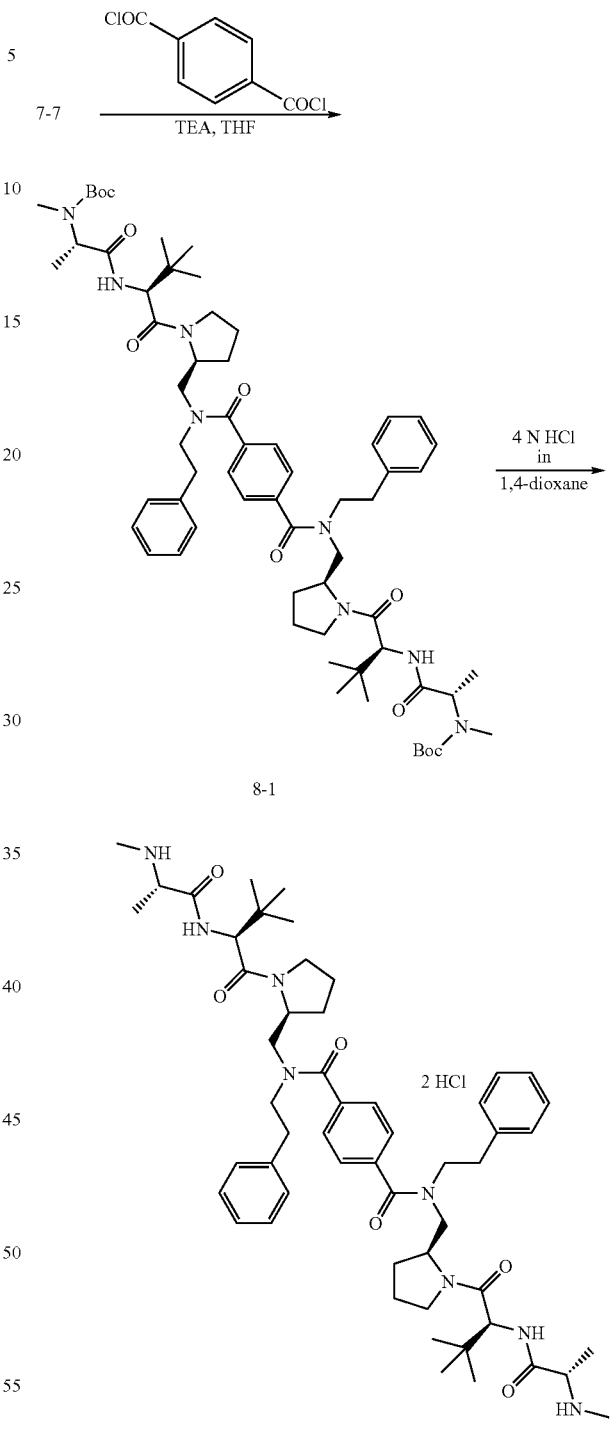

8-1

Compound 1

Treatment of a solution of 7-7 with terephthaloyl chloride and TEA in THF provided intermediate 8-1. Boc-deprotection of intermediate 8-1 using 4N HCl in 1,4-dioxane yields compound 1 as its bis-hydrochloride salt.

Treatment of a solution of 7-7 with 4,4'-biphenyldisulfonyl chloride and TEA in THF provided intermediate 9-1. Boc-deprotection of intermediate 9-1 using 4N HCl in 1,4-dioxane yields compound 13 as its bis-hydrochloride salt.

Scheme 9
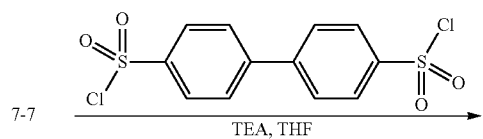
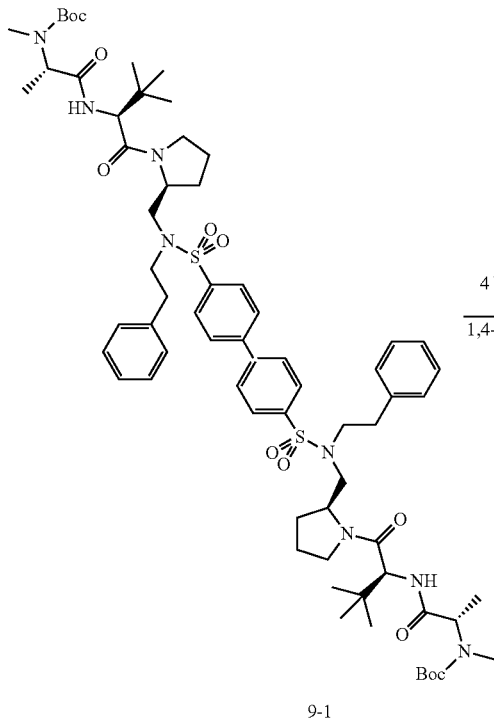
9-1
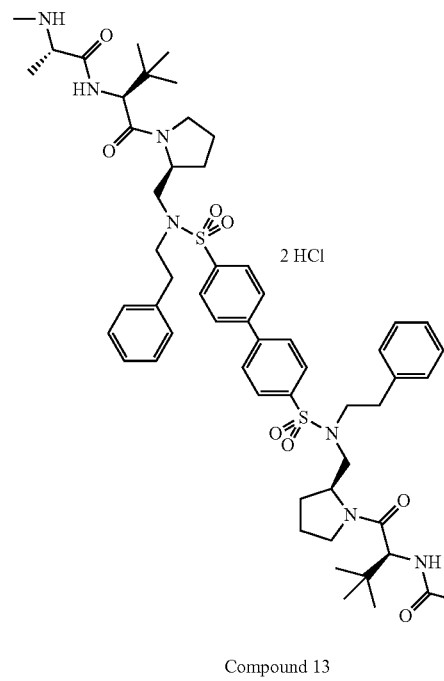
Compound 13
Scheme 10
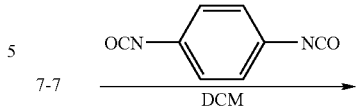
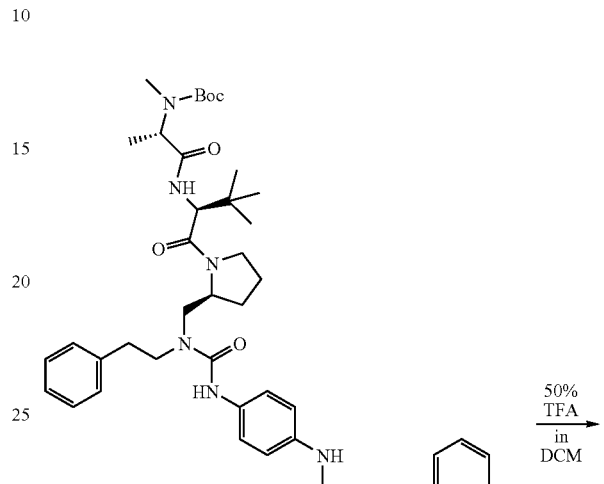
10-1
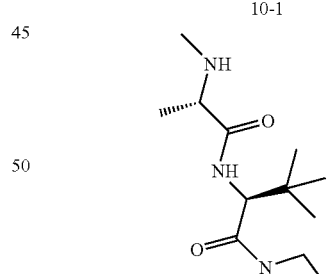
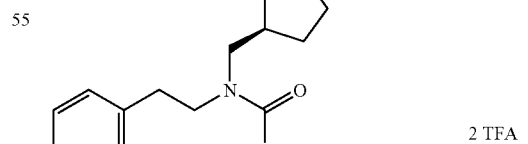
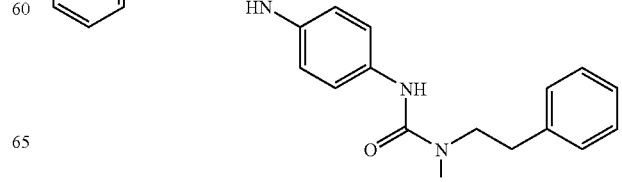
Treatment of a solution of 7-7 with 1,4-phenylenediisocyanate in CH$_2$Cl$_2$ provided intermediate 10-1. Boc-deprotection of intermediate 9-1 using 50% TFA in DCM yields compound 20 as its bis-TFA salt.

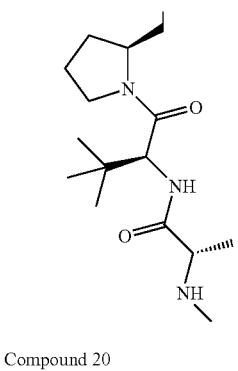

Compound 20

Treatment of a solution of 7-7 with α,α'-dibromo-p-xylene and TEA in DMF provided intermediate 11-1. Boc-deprotection of intermediate 11-1 using 4N HCl in 1,4-dioxane yields compound 23 as its bis-hydrochloride salt.

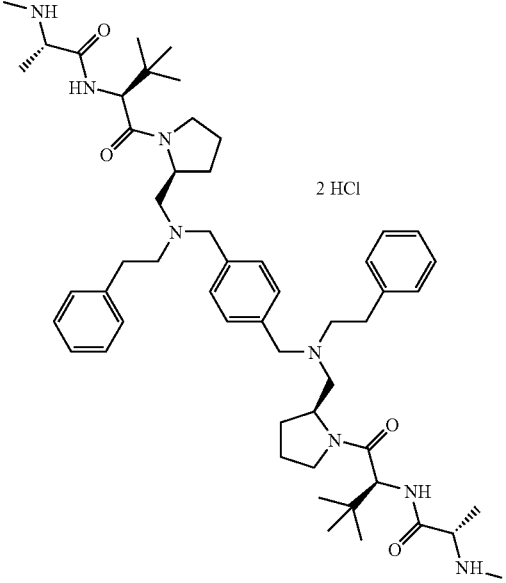

Compound 23

The preparation of intermediate 12-2 is illustrated in scheme 12. The conversion of intermediate 12-2 to compounds 35, 87, and 104 is summarized in schemes 13, 14 and 15.

Activation of the carboxyl group of Cbz-Gly-OH by treatment with the amide coupling agent HBTU and DIPEA in DMF solvent was followed by the addition of 7-7 to provide intermediate 12-1. Cbz deprotection using Pd/C under a hydrogen atmosphere in MeOH provided intermediate 12-2.

Scheme 11

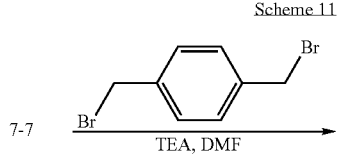

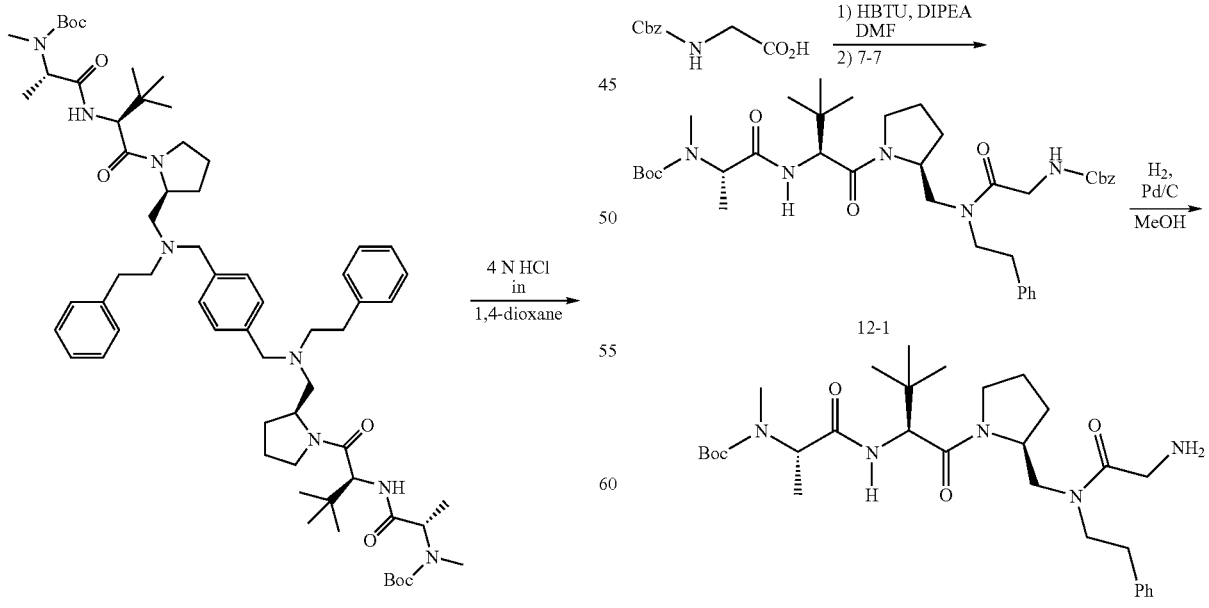

Scheme 12

Treatment of a solution of 12-2 with terephthaloyl chloride and TEA in CH₂Cl₂ provide intermediate 13-1. Boc-deprotection of intermediate 13-1 using 4N HCl in 1,4-dioxane yields compound 91 as its bis-hydrochloride salt.
Scheme 13
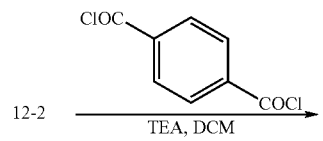
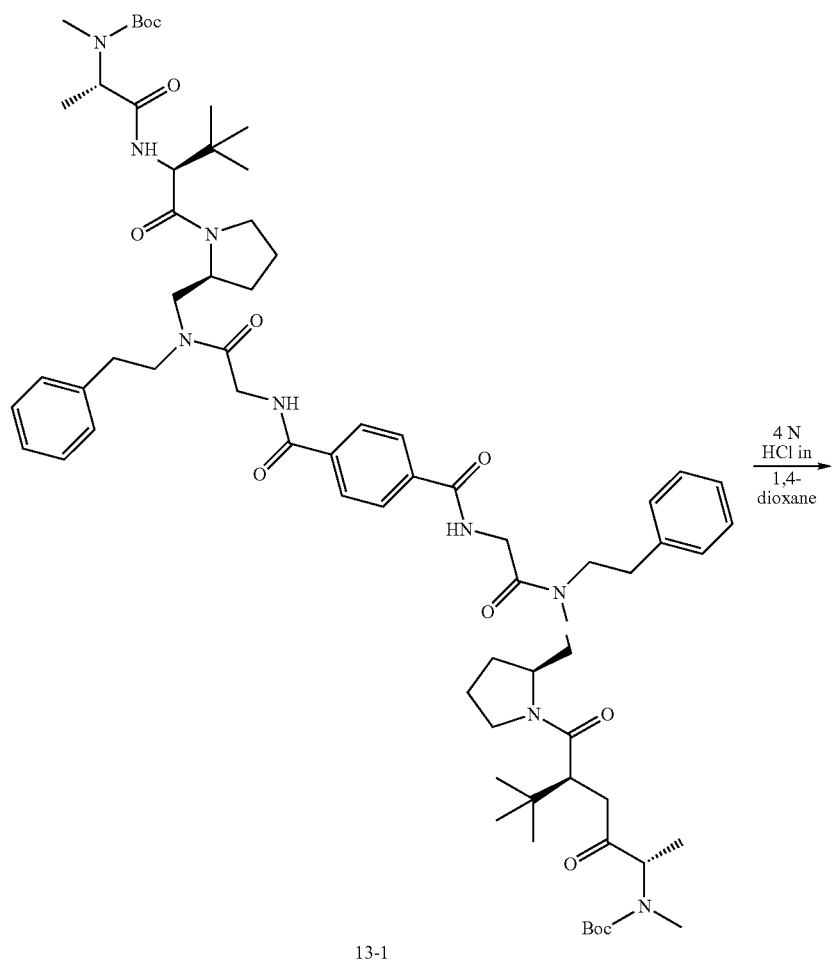
13-1

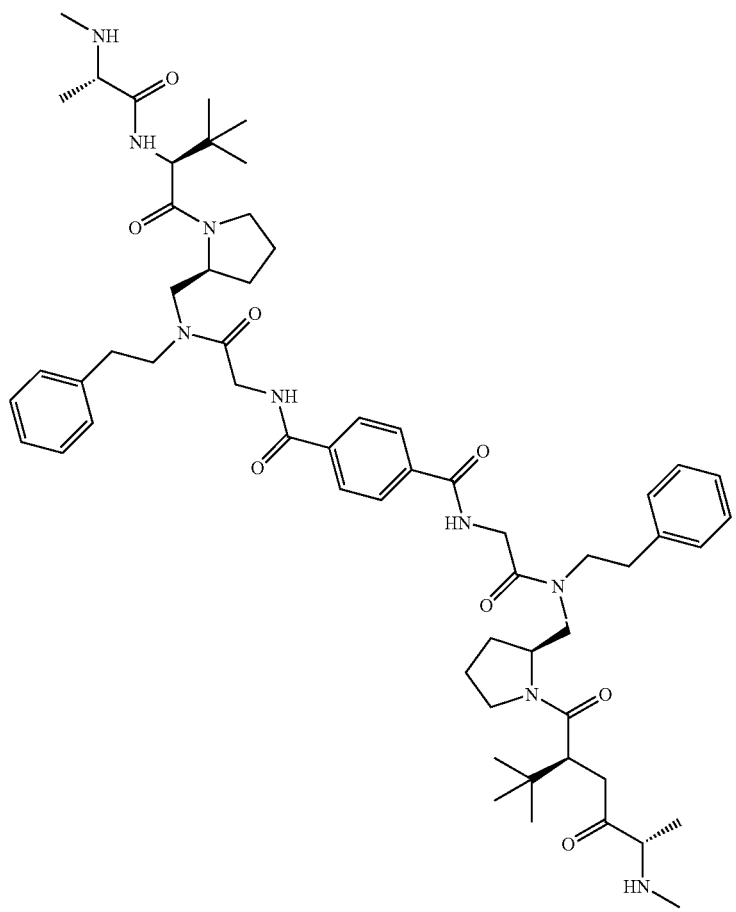
compound 35
Treatment of a solution of 12-2 with 2,6-naphalenedisulfonyl chloride and TEA in CH₂Cl₂ provide intermediate 14-1. Boc-deprotection of intermediate 14-1 using 4N HCl in 1,4-dioxane yields compound 87 as its bis-hydrochloride salt.
Scheme 14
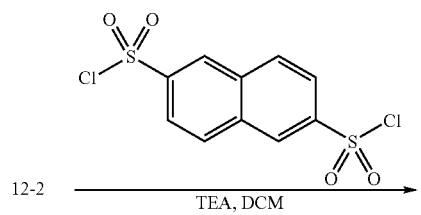

-continued
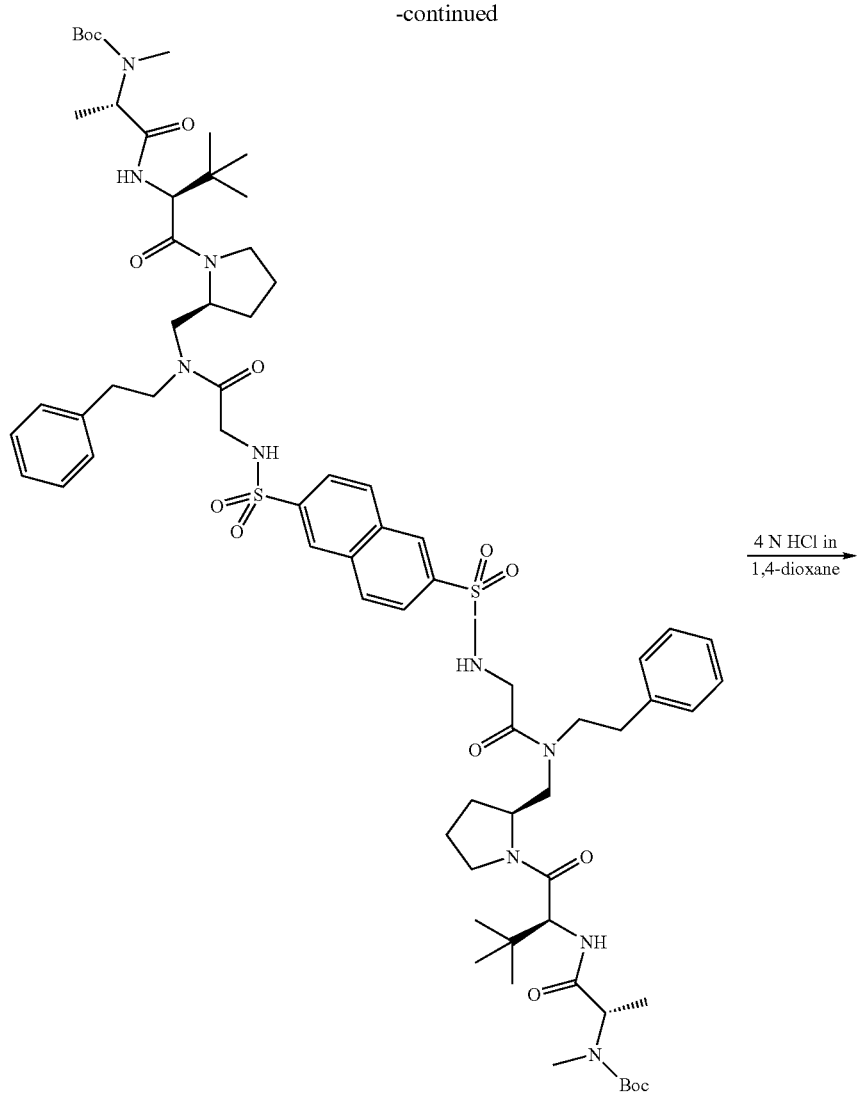
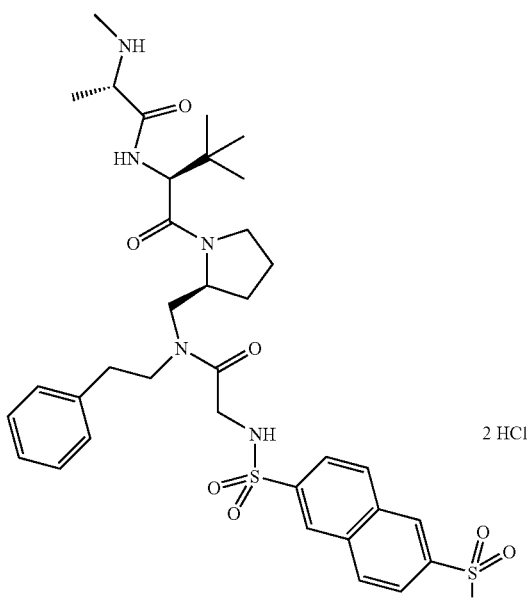
14-1
2 HCl

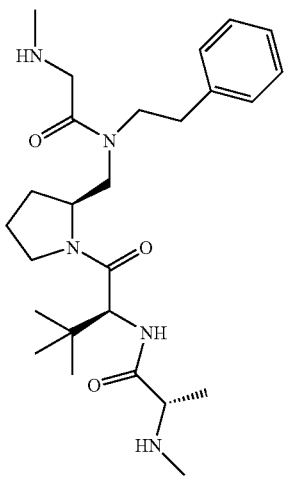
compound 87
Treatment of a solution of 12-2 with 1,4-phenylenediisocyanate in DMF provided intermediate 15-1. Boc-deprotection of intermediate 15-1 using 50% TFA in CH$_2$Cl$_2$ yields compound 104 as its bis-TFA salt.
Scheme 15
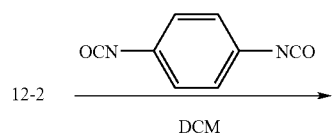
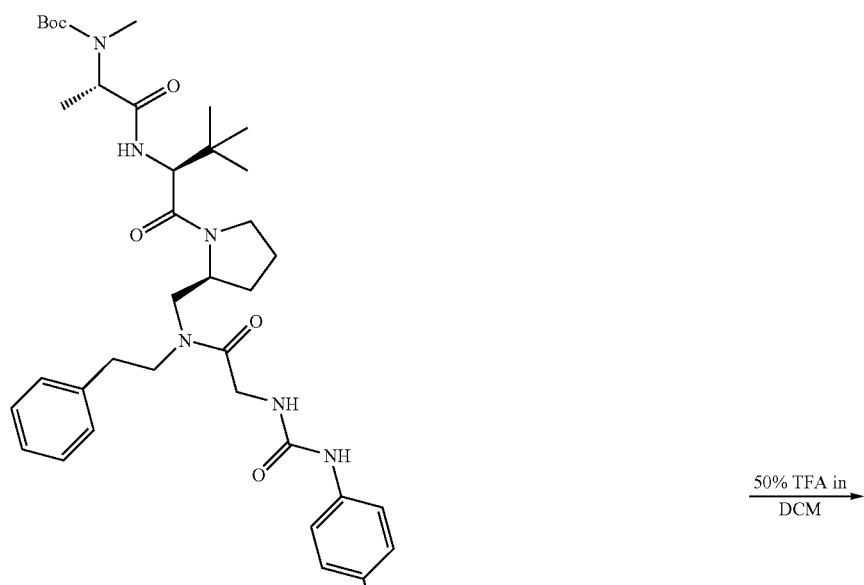

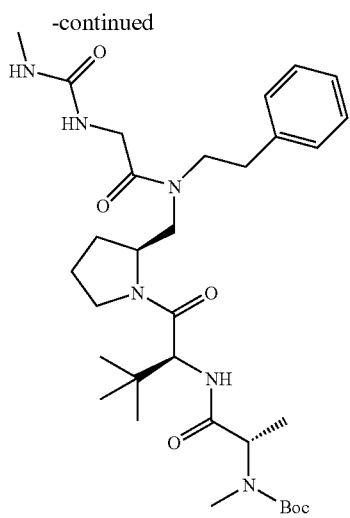
15-1
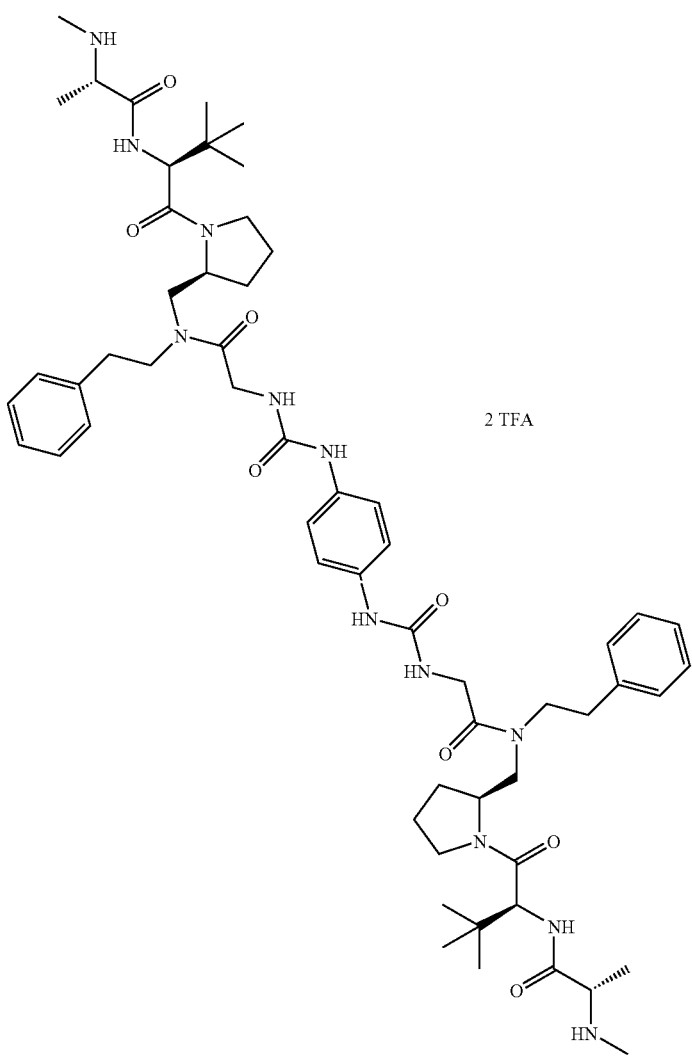
compound 104

The preparation of compound 94 is illustrated in scheme 16. Reductive amination of 4,4'-biphenyldicarboxaldehyde using phenethylamine and Na(AcO)$_3$BH provides intermediate 16-2. Activation of the carboxyl group of proline by treatment with the amide coupling agent HBTU, HOBt, and DIPEA in DMF solvent was followed by the addition of 16-2 to provide intermediate 16-3. Boc deprotection of 16-3 using 4N HCl in 1,4-dioxane provided 16-4•2HCl. Activation of the carboxyl group of Boc-L-Tle-OH by treatment with the amide coupling agents HBTU, HOBt, and DIPEA in DMF solvent was followed by the addition of 16-4•2HCl to provide intermediate 16-5. Boc deprotection using 4N HCl in 1,4-dioxane provided 16-6•2HCl. Activation of the carboxyl group of Boc-N-Me-Ala-OH by treatment with the amide coupling agents EDC, HOBt, and DIPEA in CH$_2$Cl$_2$ solvent was followed by the addition of 16-6•2HCl to provide intermediate 16-7. Boc deprotection using 4N HCl in 1,4-dioxane provided compound 94•2HCl.

Scheme 16

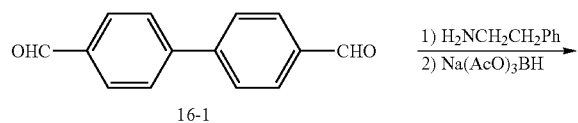

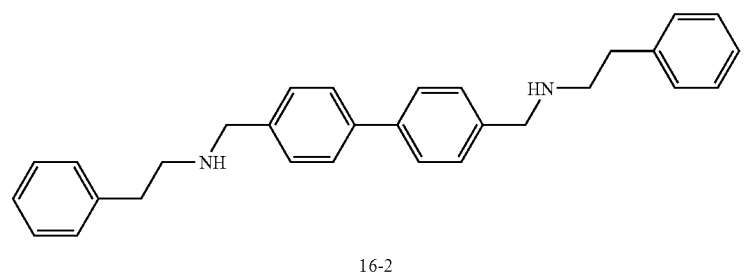

16-2

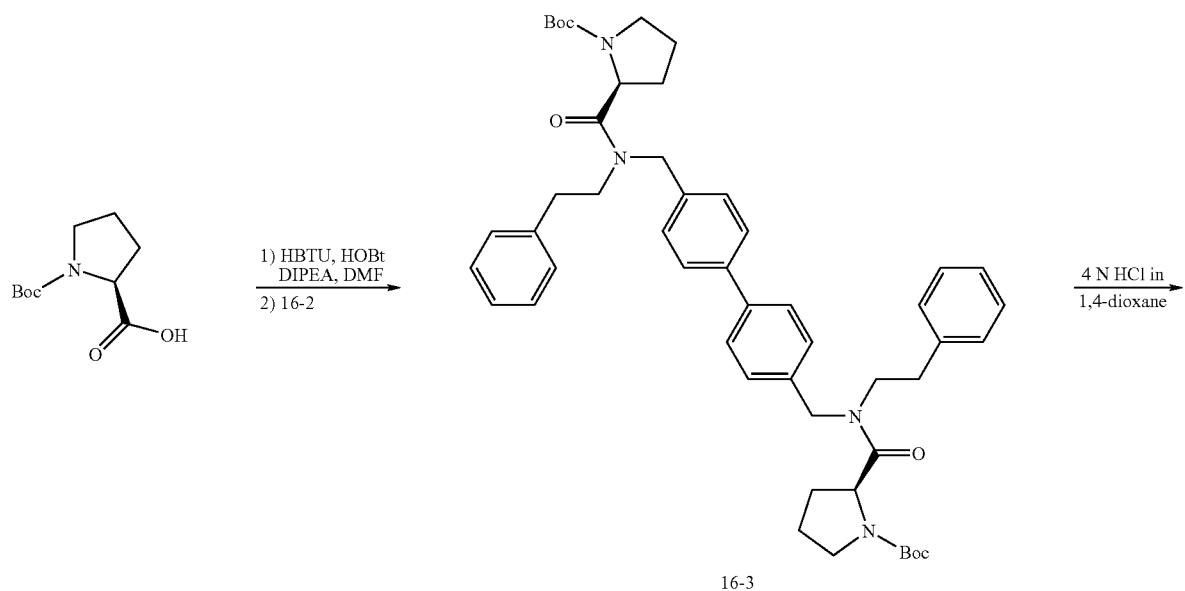

16-3

-continued
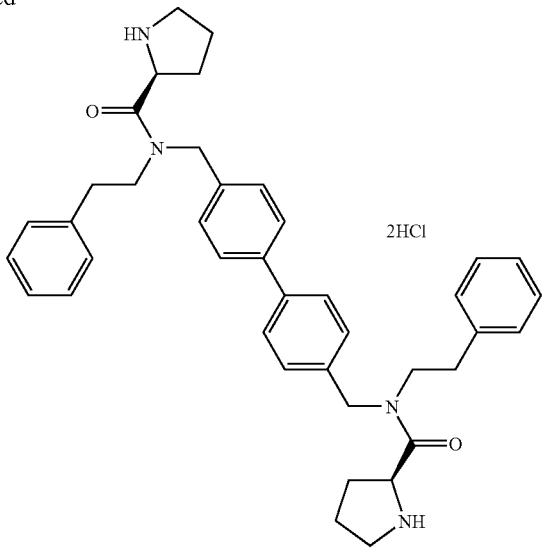
16-4
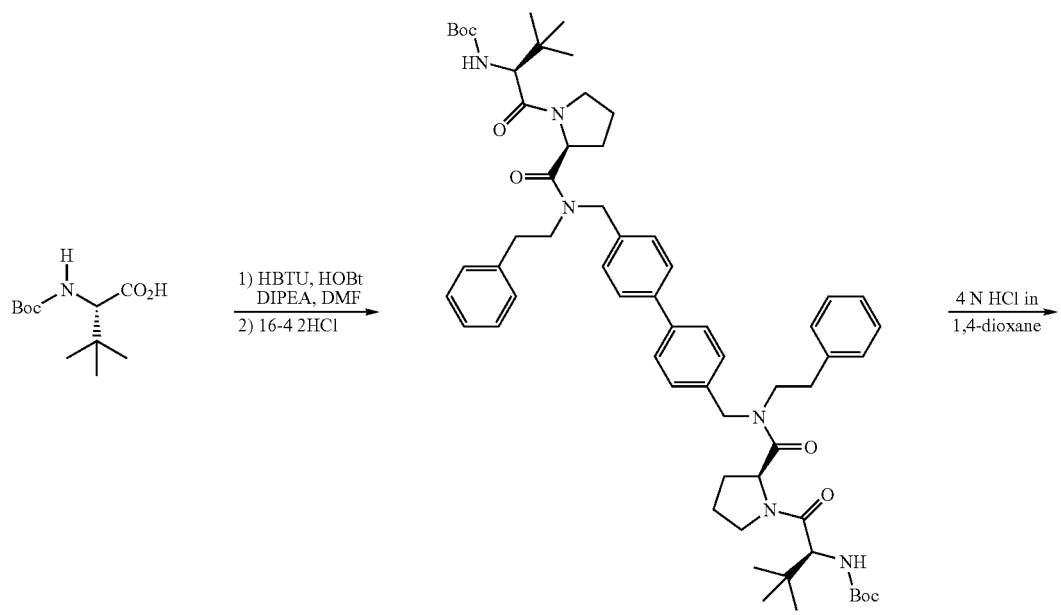
16-5

-continued
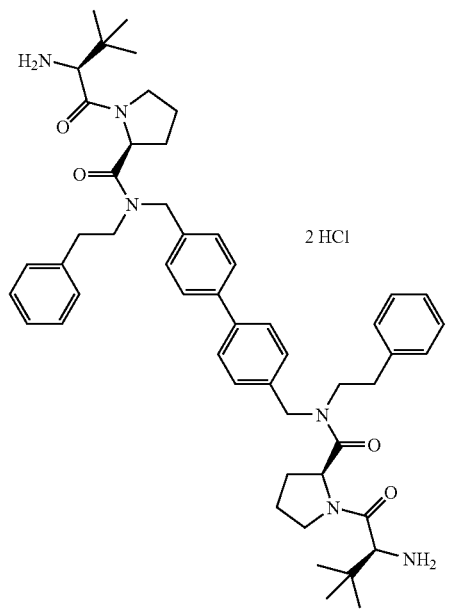
16-6
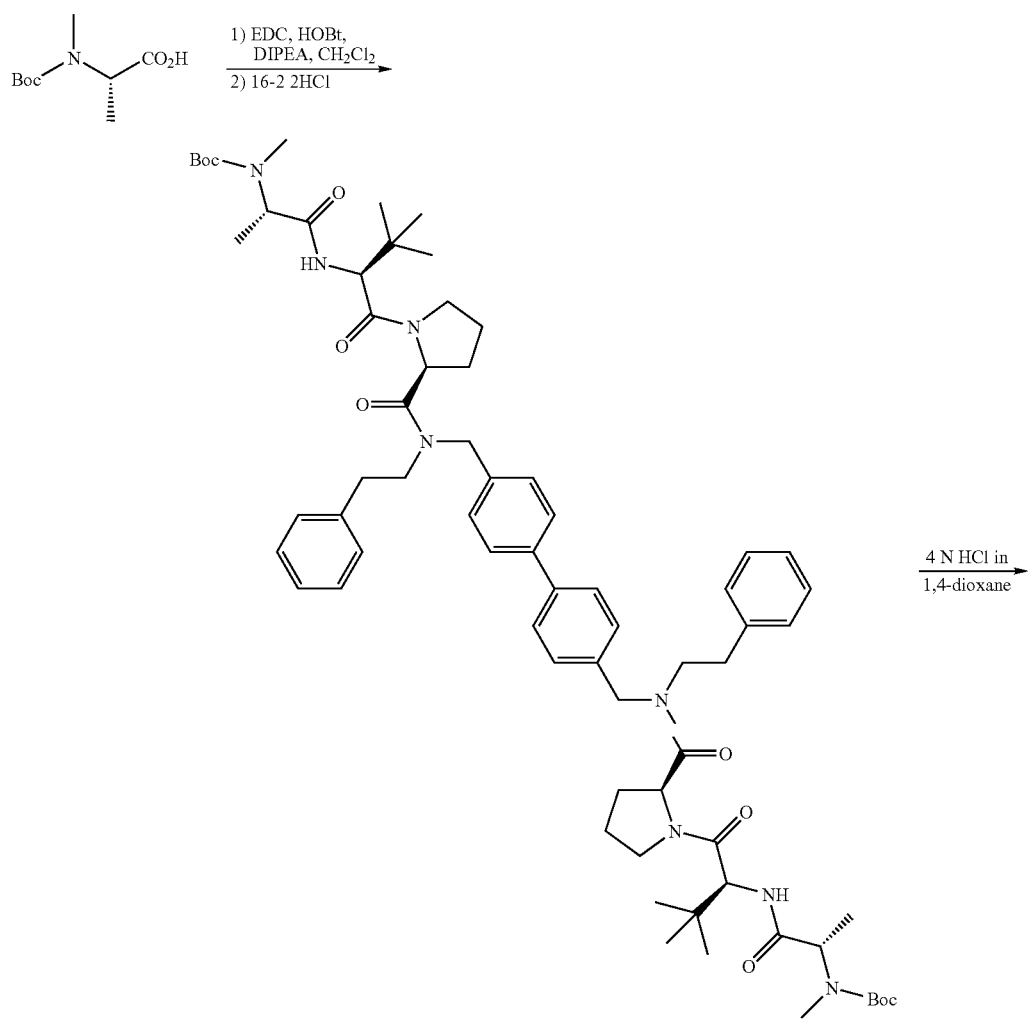
16-7

-continued

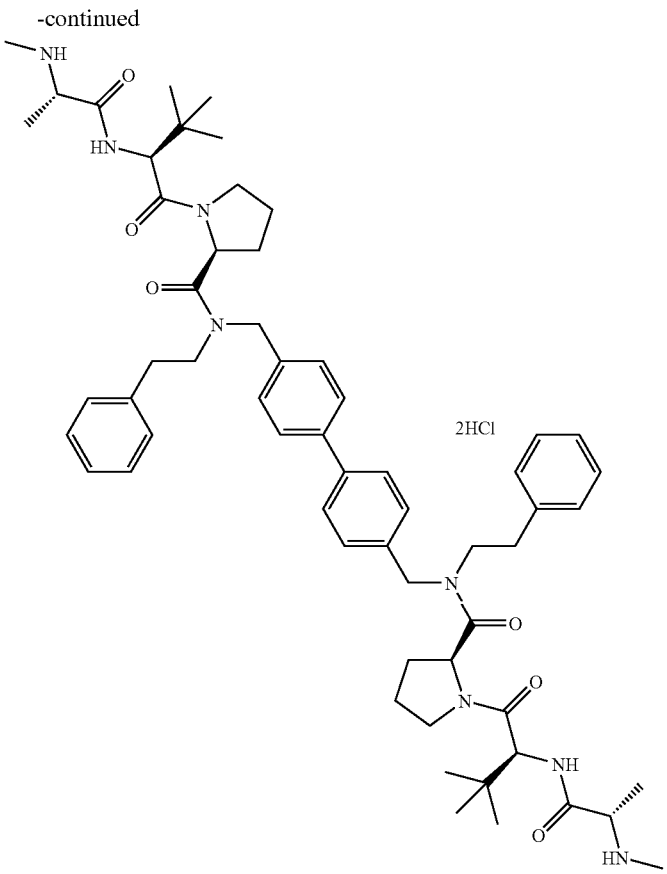

Compound 94

Preparative Methods

Intermediate 7-1

To a solution of N-(tert-butoxycarbonyl)-L-prolinal (10.0 g, 50.2 mmol) in methylene chloride (150 mL) was added phenethylamine (6.52 mL, 50.2 mmol). After stirring for 1 hour at room temperature sodium triacetoxyborohydride (21.0 g, 100.3 mmol) and methanol (50 mL) were added and the reaction mixture was stirred at room temperature overnight. Saturated aqueous NaHCO$_3$ and ethyl acetate were added, the organic layer was separated, washed with brine, dried over anhydrous MgSO$_4$, filtered and concentrated in vacuo. Purification by silica gel chromatography, eluting with a 95:5 to 50:50 hexane/EtOAc, provided intermediate 7-1 as colorless oil. MS (m/z) M+1=305.4

Intermediate 7-2

To a solution of 7-1 (8.10 g, 26.6 mmol) in methylene chloride (80 mL) cooled to 0° C. were sequentially added TEA (7.4 mL, 53.3 mmol), benzyl chloroformate (4.10 mL, 29.3 mmol) and the reaction mixture was stirred for 3 hours at room temperature. Aqueous NaHCO$_3$ and ethyl acetate were added, the organic layer was separated, washed with brine, dried over MgSO$_4$ and concentrated in vacuo. Purification by silica gel chromatography, eluting with a 95:5 to 50:50 hexane/EtOAc gradient, provided intermediate 7-2 as colorless oil.

Intermediate 7-3•HCl

N HCl in 1,4 dioxane (20 mL) was added to intermediate 7-2 (11.5 g, 26.2 mmol) and the solution was stirred for 2 hours at room temperature. Volatiles were removed under reduced pressure and the residue was triturated with diethyl ether to provide intermediate 7-3•HCl as a white solid. MS (m/z) M+1=339.2

Intermediate 7-4

To a solution of Boc-L-Tle-OH (5.70 g, 24.5 mmol) in DMF cooled to 0° C. were sequentially added DIPEA (16.9 mL, 94.3 mmol), HOBt (3.3 g, 24.5 mmol) and HBTU (9.30 g, 24.5 mmol). After stirring for 10 minutes intermediate 7-3•HCl (7.04 g, 18.8 mmol) was added and the reaction mixture was stirred overnight at room temperature. Water and ethyl acetate were added, the organic layer was separated, washed with 10% citric acid, aqueous NaHCO$_3$ and brine, dried over anhydrous MgSO$_4$, filtered and concentrated in vacuo. Purification by silica gel chromatography, eluting with a 95:5 to 50:50 hexane/EtOAc gradient, provided intermediate 7-4 as colorless oil.

Intermediate 7-5•HCl

N HCl in 1,4 dioxane (20 mL) was added to intermediate 7-4 (8.30 g, 15.0 mmol) and the solution was stirred for 2 hours at room temperature. Volatiles were removed under reduced pressure and the residue was triturated with diethyl ether to provide intermediate 7-5•HCl as a white solid. MS (m/z) M+1=452.2.

Intermediate 7-6

To a solution of Boc-N-Me-Ala-OH (4.20 g, 20.7 mmol) in DMF cooled to 0° C. were sequentially added DIPEA (14.3 mL, 79.8 mmol), HOBt (2.8 g, 20.7 mmol) and HBTU (7.90 g, 20.7 mmol). After stirring for 10 minutes intermediate 7-5•HCl (7.76 g, 15.9 mmol) was added and the reaction mixture was stirred overnight at room temperature. Water and ethyl acetate were added, the organic layer was separated, washed with 10% citric acid, aqueous NaHCO$_3$ and brine, dried over anhydrous MgSO$_4$, filtered and concentrated in vacuo. Purification by silica gel chromatography, eluting with a 95:5 to 50:50 hexane/THF gradient, provided intermediate 7-6 as colorless oil.

Intermediate 7-7

To a solution of intermediate 7-6 (3.00 g, 4.7 mmol) in anhydrous MeOH (100 mL) and stirred under N$_2$ was added 10% Pd/C (200 mg). The reaction mixture was purged with H$_2$ and stirred for 1 hour. The reaction was then filtered through celite and the filtrate was concentrated in vacuo. Purification by silica gel chromatography, eluting with a 95:5 to 50:50 hexane/THF gradient, provided intermediate 7-7 as colorless oil. MS (m/z) M+1=503.4

Intermediate 8-1

To a solution of intermediate 7-7 (250 mg, 0.49 mmol) in THF cooled to 0° C. were sequentially added TEA (134 uL, 0.96 mmol) and terephthaloyl chloride (49.7 mg, 0.24 mmol) and the reaction was stirred for 2 hours at room temperature. Water and ethyl acetate were added, the organic layer was separated, washed with 10% citric acid, aqueous NaHCO$_3$ and brine, dried over anhydrous MgSO$_4$, filtered and concentrated in vacuo. Purification by silica gel chromatography, eluting with a 95:5 to 50:50 hexane/THF gradient, provided intermediate 8-1 as a white solid.

Compound 1•2HCl

4N HCl in 1,4-dioxane (3 mL) was added to intermediate 8-1 (120 mg, 0.10 mmol) and the solution was stirred for 2 hours at room temperature. Volatiles were removed under reduced pressure and the residue was triturated with diethyl ether to provide compound 1•2•HCl as a white solid.

Intermediate 9-1

To a solution of intermediate 7-7 (1.22 g, 2.42 mmol) in THF cooled to 0° C. were sequentially added TEA (1.35 mL, 9.70 mmol) and 4,4'-biphenyldisulfonyl chloride (425 mg, 1.21 mmol) and the reaction was stirred for 2 hours at room temperature. Water and ethyl acetate were added, the organic layer was separated, washed with 10% citric acid, aqueous NaHCO$_3$ and brine, dried over anhydrous MgSO$_4$, filtered and concentrated in vacuo. Purification by silica gel chromatography, eluting with a 95:5 to 50:50 hexane/THF gradient, provided intermediate 9-1 as a white solid.

Compound 13•2HCl

4N HCl in 1,4-dioxane (5 mL) was added to intermediate 9-1 (450 mg, 0.35 mmol) and the solution was stirred for 2 hours at room temperature. Volatiles were removed under reduced pressure and the residue was triturated with diethyl ether to provide compound 13•2HCl as a white solid.

Intermediate 10-1

To a solution of intermediate 7-7 (180 mg, 0.36 mmol) in CH$_2$Cl$_2$ was added 1,4-Phenylenediisocyanate (25 mg, 0.16 mmol) and the reaction was stirred overnight at room temperature. Volatiles were removed under reduced pressure and the residue purified by silica gel chromatography, eluting with a 95:5 to 50:50 hexane/THF gradient, to provide intermediate 10-1 as a white solid.

Compound 20•2TFA

Intermediate 10-1 (175 mg, 0.15 mmol) was dissolved in a mixture of CH$_2$Cl$_2$ (3.0 mL) and TFA (3.0 mL). The solution was stirred for 3 hours at room temperature. Volatiles were removed under reduced pressure and the residue was triturated with diethyl ether to provide compound 20•2TFA as a white solid.

Intermediate 11-1

To a solution of intermediate 7-7 (210 mg, 0.42 mmol) in DMF were sequentially added DIPEA (435 μL, 2.50 mmol) and α,α'-dibromo-p-xylene (49 mg, 0.18 mmol) and the reaction was stirred for 2 hours at room temperature. Water and ethyl acetate were added, the organic layer was separated, washed with 10% citric acid, aqueous NaHCO$_3$ and brine, dried over anhydrous MgSO$_4$, filtered and concentrated in vacuo. Purification by silica gel chromatography, eluting with a 95:5 to 30:70 hexane/THF gradient, provided intermediate 11-1 as a white solid.

Compound 23•2HCl

4N HCl in 1,4-dioxane (2 mL) was added to intermediate 11-1 (33 mg, 0.03 mmol) and the solution was stirred for 2 hours at room temperature. Volatiles were removed under reduced pressure and the residue was triturated with diethyl ether to provide compound 23•2HCl as a white solid.

Intermediate 12-1

To a solution of Cbz-Gly-OH (4.16 g, 19.9 mmol) in DMF cooled to 0° C. were sequentially added DIPEA (14.0 mL, 80.4 mmol) and HBTU (7.01 g, 18.5 mmol). After stirring for 5 minutes intermediate 7-7 (8.11 g, 16.1 mmol) was added and the reaction mixture was stirred overnight at room temperature. Water and ethyl acetate were added, the organic layer was separated, washed with 10% citric acid, aqueous NaHCO$_3$ and brine, dried over anhydrous MgSO$_4$, filtered and concentrated in vacuo. Purification by silica gel chromatography, eluting with a 95:5 to 50:50 hexane/THF gradient, provided intermediate 12-1 as a white solid Intermediate 12-2

To a solution of intermediate 12-1 (4.21 g, 6.07 mmol) in anhydrous MeOH (120 mL) and stirred under N$_2$ was added 10% Pd/C (500 mg). The reaction mixture was purged with H$_2$ and stirred for 6 hours. The reaction was then filtered throuht celite and the filtrates were concentrated in vacuo to provide intermediate 12-2 as a white solid. MS (m/z) M+1=560.4

Intermediate 13-1

To a solution of intermediate 12-2 (200 mg, 0.36 mmol) in DCM cooled to 0° C. were sequentially added TEA (100 uL, 0.71 mmol) and terephthaloyl chloride (36 mg, 0.18 mmol) and the reaction was stirred for 6 hours at room temperature. Water and ethyl acetate were added, the organic layer was separated, washed with 10% citric acid, aqueous NaHCO$_3$ and brine, dried over anhydrous MgSO$_4$, filtered and concentrated in vacuo. Purification by silica gel chromatography, eluting with a 95:5 to 50:50 hexane/THF gradient, provided intermediate 13-1 as a white solid.

Compound 35•2HCl

4N HCl in 1,4-dioxane (3.0 mL) was added to intermediate 13-1 (195 mg, 0.18 mmol) and the solution was stirred for 2 hours at room temperature. Volatiles were removed under reduced pressure and the residue was triturated with diethyl ether to provide compound 35•2HCl as a white solid.

Intermediate 14-1

To a solution of intermediate 12-2 (245 mg, 0.44 mmol) in DCM cooled to 0° C. were sequentially added TEA (130 uL, 0.93 mmol), 2,6-naphalenedisulfonyl chloride (66 mg, 0.20 mmol) and the reaction was stirred overnight at room temperature. Water and ethyl acetate were added, the organic layer was separated, washed with 10% citric acid, aqueous NaHCO$_3$ and brine, dried over anhydrous MgSO$_4$, filtered and concentrated in vacuo. Purification by silica gel chromatography, eluting with a 95:5 to 50:50 hexane/THF gradient, provided intermediate 14-1 as a white solid.

Compound 87•2HCl

4N HCl in 1,4-dioxane (5.0 mL) was added to intermediate 14-1 (160 mg, 0.11 mmol) and the solution was stirred for 2 hours at room temperature. Volatiles were removed under Intermediate 15-1

To a solution of intermediate 12-2 (142 mg, 0.25 mmol) in THF was added 1,4-Phenylene diisocyanate (41 mg, 0.25 mmol) and the reaction was stirred at room temperature for 3 hours. Volatiles were removed under reduced pressure and the residue purified by silica gel chromatography, eluting with a 95:5 to 50:50 hexane/THF gradient, to provide intermediate 15-1 as a white solid.

Compound 104•2TFA

Intermediate 15-1 (96 mg, 0.07 mmol) was dissolved in a mixture of CH$_2$Cl$_2$ (1.0 mL) and TFA (1.0 mL). The solution was stirred for 1 hour at room temperature. Volatiles were removed under reduced pressure and the residue was triturated with diethyl ether to provide compound 104•2TFA as a white solid.

Intermediate 16-2

To a solution of 4,4'-biphenyldicarboxaldehyde (1.50 g, 7.13 mmol) in methylene chloride (25 mL) was added phenethylamine (1.72 g, 14.3 mmol). After stirring for 1 hour at room temperature sodium triacetoxyborohydride (4.53 g, 21.4 mmol) and methanol (25 mL) were added and the reaction mixture was stirred at room temperature overnight. Saturated aqueous NaHCO$_3$ and ethyl acetate were added, the organic layer was separated, washed with brine, dried over anhydrous MgSO$_4$, filtered and concentrated in vacuo. Purification by silica gel chromatography, eluting with a 95:5 to 50:50 hexane/EtOAc, provided intermediate 16-2 as a yellow solid.

Intermediate 16-3

To a solution of Boc-Pro-OH (3.64 g, 16.1 mmol) in DMF cooled to 0° C. were sequentially added DIPEA (11.06 mL, 61.8 mmol), HOBt (2.50 g, 18.5 mmol) and HBTU (7.03 g, 18.5 mmol). After stirring for 10 minutes intermediate 16-2 (2.60 g, 6.18 mmol) was added and the reaction mixture was stirred for 3 days at room temperature. Water and ethyl acetate were added, the organic layer was separated, washed with 10% citric acid, aqueous NaHCO$_3$ and brine, dried over anhydrous MgSO$_4$, filtered and concentrated in vacuo. Purification by silica gel chromatography, eluting with a 95:5 to 50:50 hexane/EtOAc gradient, provided intermediate 16-3 as a white solid.

Intermediate 16-4•2HCl

4N HCl in 1,4 dioxane (10 mL) was added to intermediate 16-3 (3.10 g, 3.80 mmol) and the solution was stirred for 2 hours at room temperature. Volatiles were removed under reduced pressure and the residue was triturated with diethyl ether to provide intermediate 16-4•2HCl as a white solid.

Intermediate 16-5

To a solution of Boc-L-Tle-OH (2.18 g, 9.45 mmol) in DMF cooled to 0° C. were sequentially added DIPEA (6.50 mL, 36.3 mmol), HOBt (1.47 g, 10.89 mmol) and HBTU (4.12 g, 10.89 mmol). After stirring for 10 minutes intermediate 16-4 2HCl (2.50 g, 3.63 mmol) was added and the reaction mixture was stirred overnight at room temperature. Water and ethyl acetate were added, the organic layer was separated, washed with 10% citric acid, aqueous NaHCO$_3$ and brine, dried over anhydrous MgSO$_4$, filtered and concentrated in vacuo. Purification by silica gel chromatography, eluting with a 95:5 to 50:50 hexane/EtOAc gradient, provided intermediate 16-5 as a white solid.

Intermediate 16-6•2HCl

4N HCl in 1,4 dioxane (5 mL) was added to intermediate 16-5 (1.60 g, 1.54 mmol) and the solution was stirred for 2 hrs at room temperature. Volatiles were removed under reduced pressure and the residue was triturated with diethyl ether to provide intermediate 16-6•2HCl as a white solid.

Intermediate 16-7

To a solution of Boc-N-Me-Ala-OH (404 mg, 1.99 mmol) in CH$_2$Cl$_2$ cooled to 0° C. were sequentially added DIPEA (1.36 mL, 7.60 mmol), HOBt (308 mg, 2.28 mmol) and EDC (437 mg, 2.28 mmol). After stirring for 10 minutes intermediate 16-6•2HCl (700 mg, 0.76 mmol) was added and the reaction mixture was stirred overnight at room temperature. Water and ethyl acetate were added, the organic layer was separated, washed with 10% citric acid, aqueous NaHCO$_3$ and brine, dried over anhydrous MgSO$_4$, filtered and concentrated in vacuo. Purification by silica gel chromatography, eluting with a 95:5 to 50:50 hexane/THF gradient, provided intermediate 16-7 as a white solid.

Compound 94•2HCl

4N HCl in 1,4-dioxane (3 mL) was added to intermediate 16-7 (243 g, 0.20 mmol) and the solution was stirred for 2 hrs at room temperature. Volatiles were removed under reduced pressure and the residue was triturated with diethyl ether to provide compound 94•2HCl as a white solid.

Compound 94•2HCl

4N HCl in 1,4-dioxane (3 mL) was added to intermediate 16-7 (243 g, 0.20 mmol) and the solution was stirred for 2 hrs at room temperature. Volatiles were removed under reduced pressure and the residue was triturated with diethyl ether to provide compound 94•2HCl as a white solid.

Compound 49

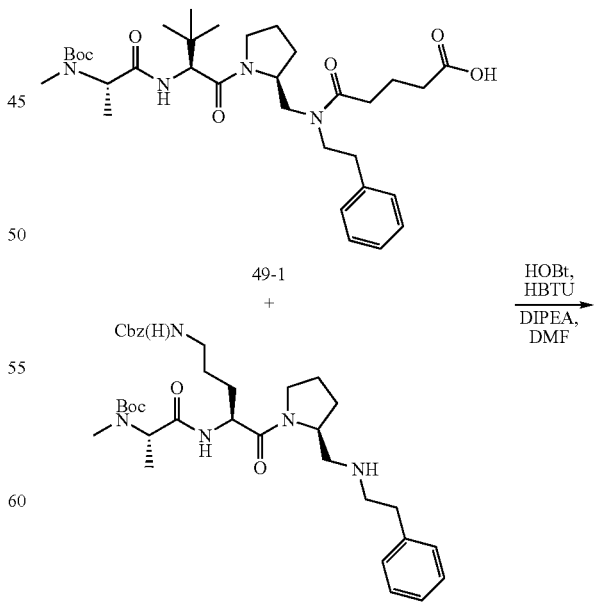

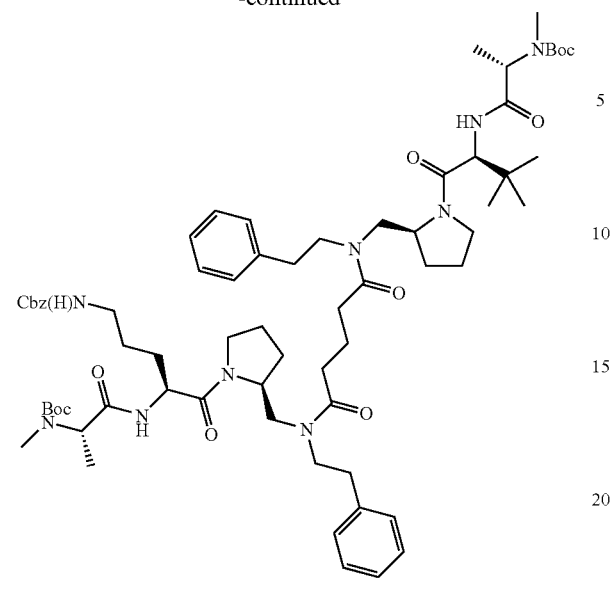

49-3

49-3 →(4 N HCl / 1,4-dioxane)

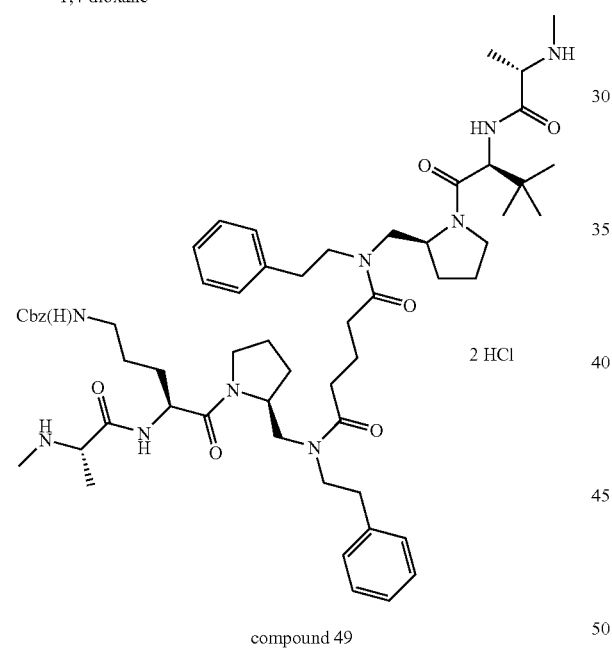

compound 49

2 HCl 49-1 and 49-2 were coupled using HOBt, HBTU and DIPEA in DMF solvent, in a manner similar to that described for the conversion of 75- to 7-6, to provide intermediate 49-3.

Intermediate 9-3 was deprotected using 4N HCl in 1,4-dioxane to provide compound 49·2HCl. MS (m/z) (M+2)/2=519.0.

Compound 106—Probe P2:

49-3 →a)

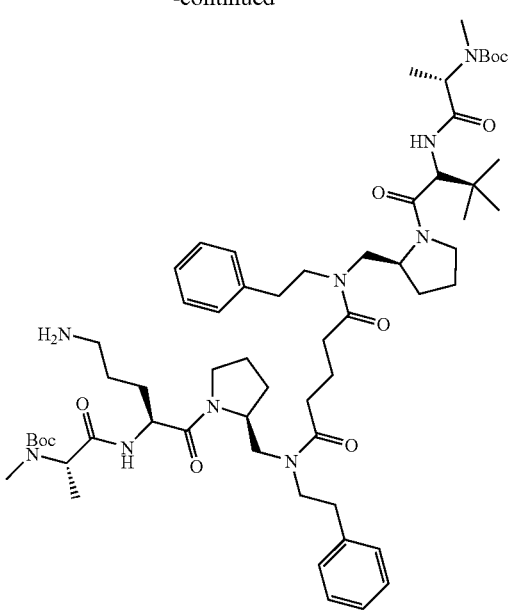

106-1

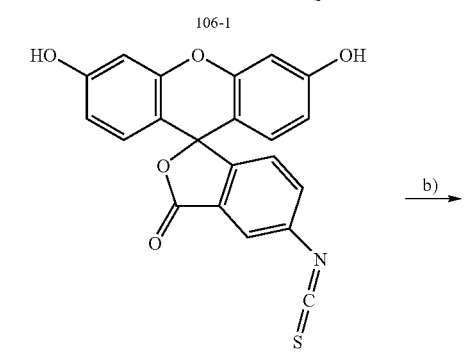

106-1 + → b)

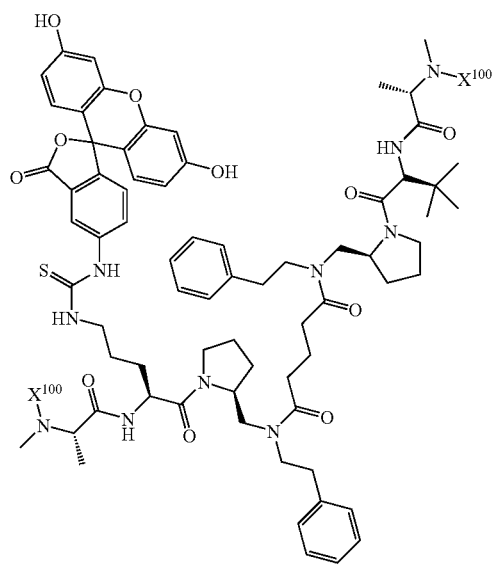

c) ⎡ 106-2; $X^{100}$ = Boc
   ⎣ compound 106·2TFA; $X^{100}$ = H

Step a)

Intermediate 49-3 and 5% Pd/C (10 wt %) were suspended in MeOH and placed under a hydrogen atmosphere (1 atm).

After stirring for 16 hours, the solution was filtered through celite and concentrated under reduced pressure to provide intermediate 106-1.

Step b)

To a solution of 106-1 (100 mg, 0.09 mmol) in anhydrous dichloromethane (5 ml) stirred under $N_2$ was added fluorescein isothiocyanate (35 mg, 0.09 mmol) and triethylamine (20 µl). The reaction mixture was then stirred for 2 hours at room temperature. Ethyl acetate was added and washed twice with 10% citric acid, the organic layer was separated, washed with brine, dried over anhydrous $MgSO_4$, filtered and concentrated in vacuo to provide intermediate 106-2 as a yellow solid. MS (m/z) (M+2)/2=746.6.

Step c)

Dichloromethane (3 ml) and TFA (3 ml) were added to 106-2 (60 mg, 0.04 mmol) and the solution was stirred for 40 min at room temperature. Volatiles were removed under reduced pressure and the residue was triturated with diethyl ether. Purification by reverse phase chromatography eluting with a water/acetonitrile gradient provided the expected compound 106-2TFA as a yellow solid. MS (m/z) M+1=1291.6.

Representative compounds of the present invention were prepared according to the above procedures and are illustrated in Table 1:

TABLE 1

| Cmpd # | Structure | MS |
|---|---|---|
| 1 | 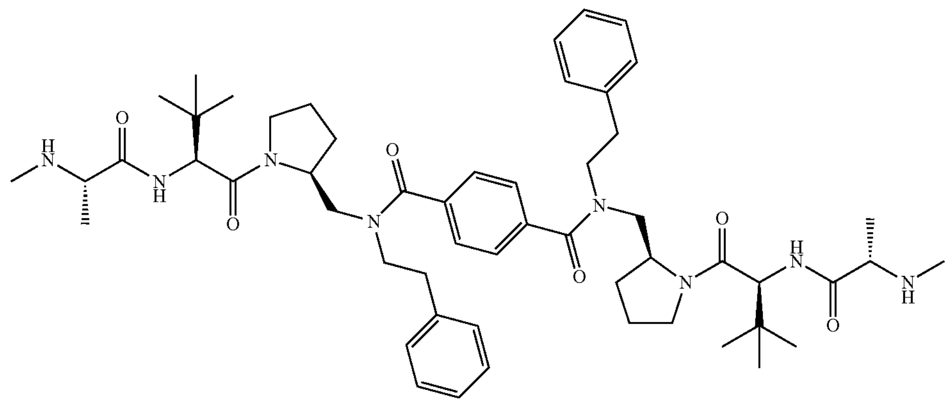 | (M + 2)/2 = 468.4 |
| 2 | 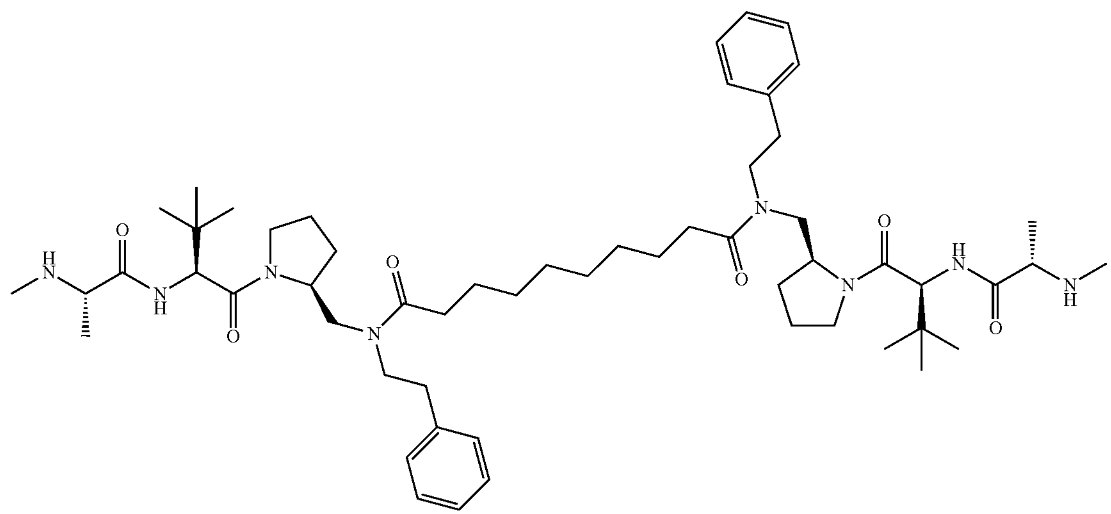 | (M + 2)/2 = 486.4 |

TABLE 1-continued

| Cmpd # | Structure | MS |
|---|---|---|
| 3 | 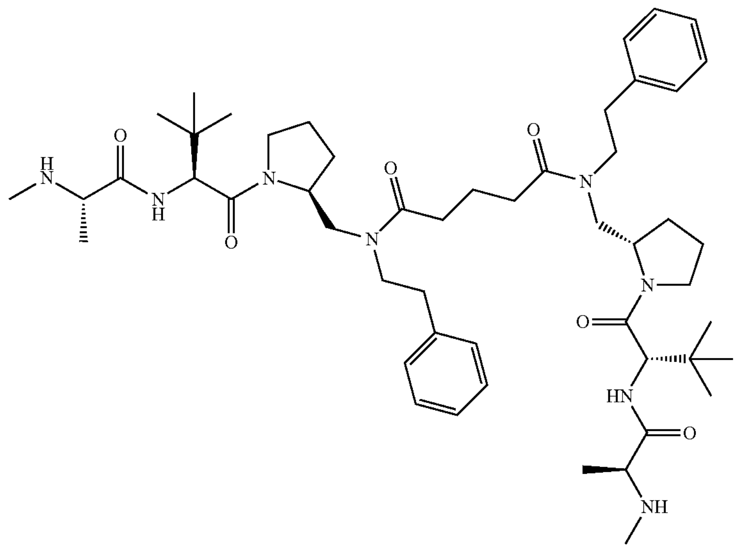 | (M + 2)/2 = 451.4 |
| 4 | 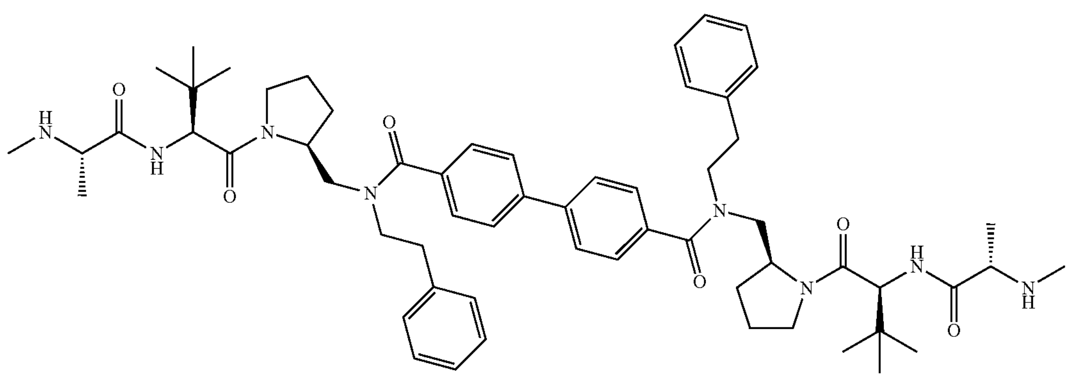 | (M + 2)/2 = 506.4 |

TABLE 1-continued

| Cmpd # | Structure | MS |
|---|---|---|
| 5 | 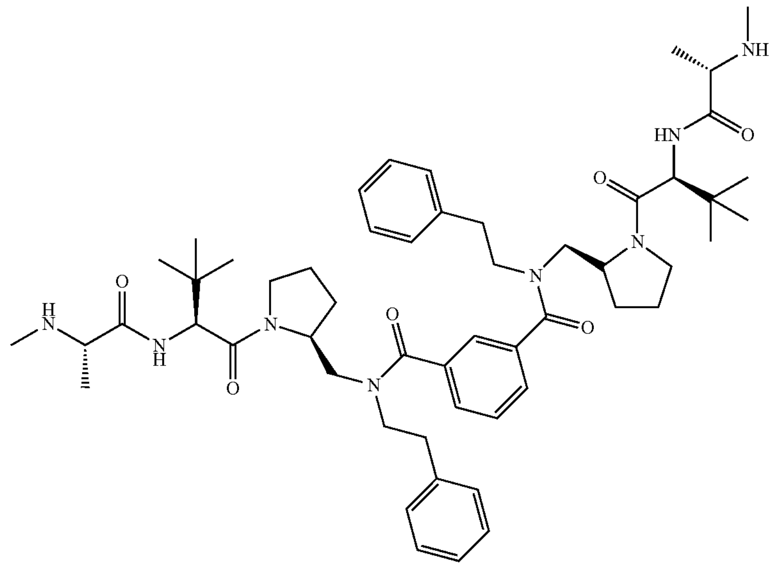 | (M + 2)/2 = 468.4 |
| 6 | 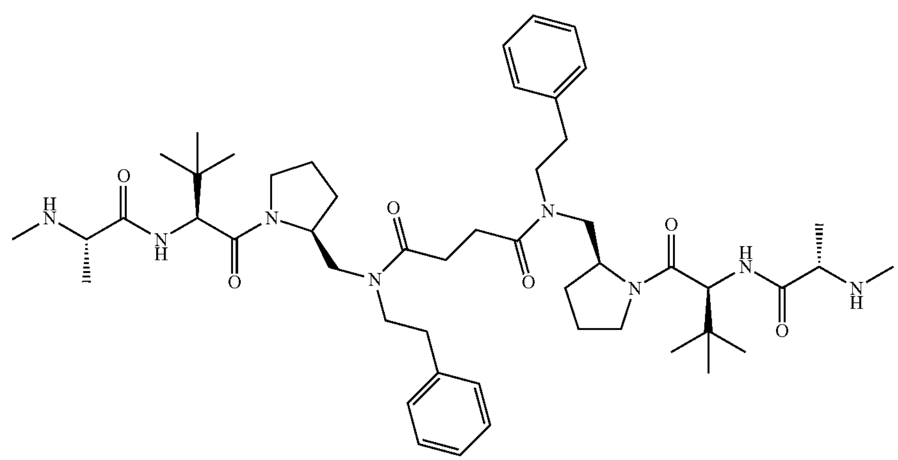 | (M + 2)/2 = 444.4 |

TABLE 1-continued

| Cmpd # | Structure | MS |
|---|---|---|
| 7 | 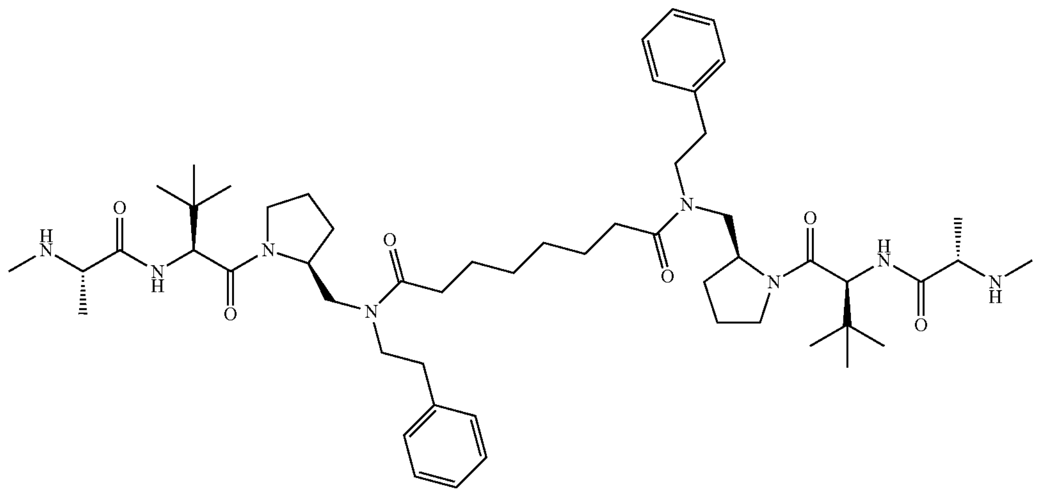 | (M + 2)/2 = 472.4 |
| 8 | 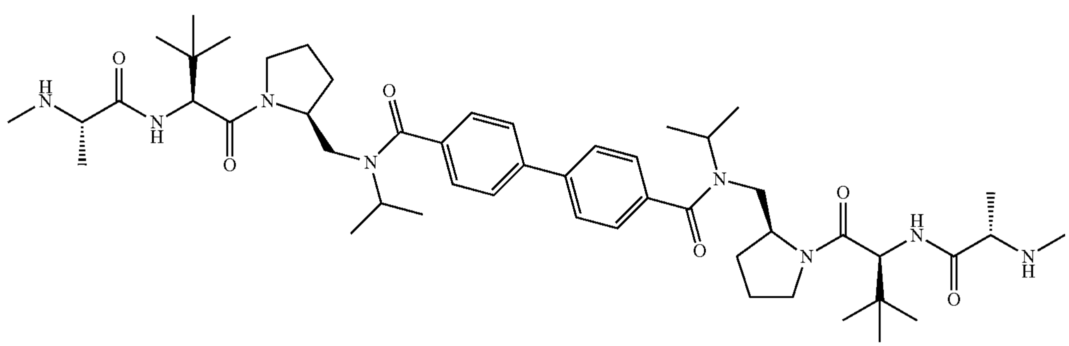 | (M + 2)/2 = 444.4 |

TABLE 1-continued

| Cmpd # | Structure | MS |
|---|---|---|
| 9 | 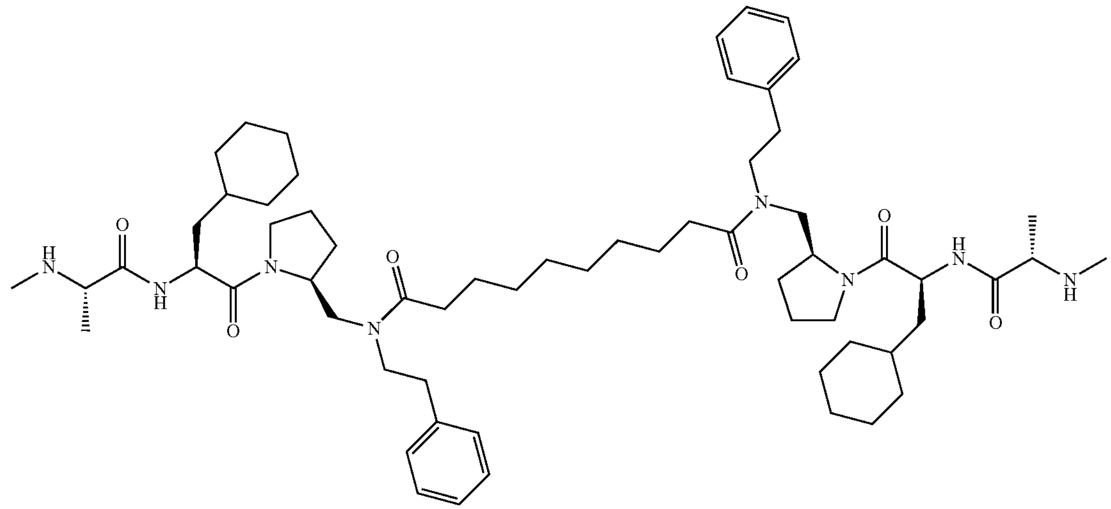 | (M + 2)/2 = 526.4 |
| 10 | 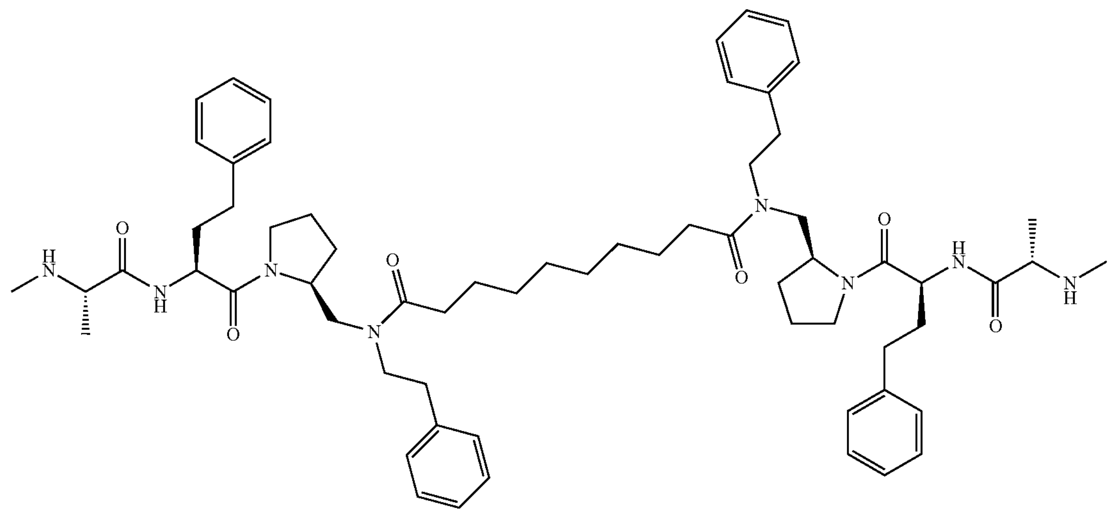 | (M + 2)/2 = 534.4 |

TABLE 1-continued

| Cmpd # | Structure | MS |
|---|---|---|
| 11 | 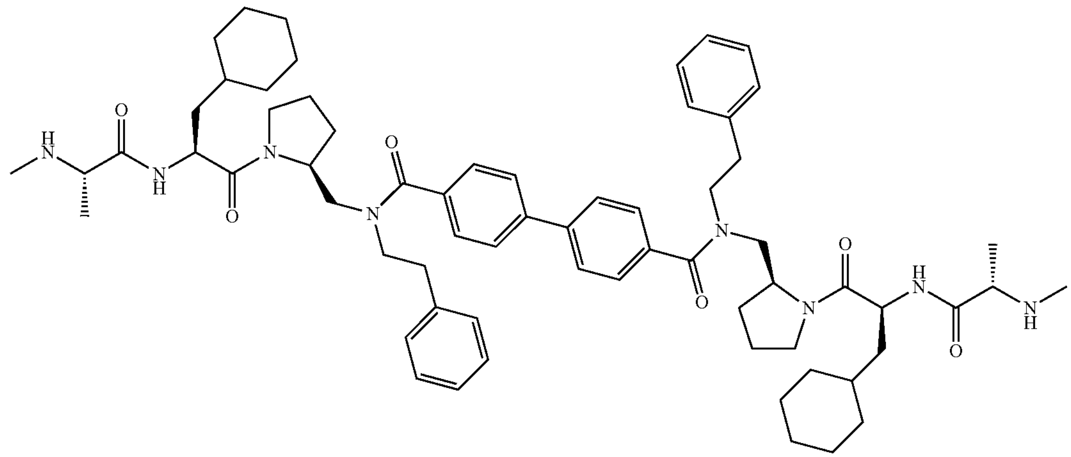 | (M + 2)/2 = 546.4 |
| 12 | 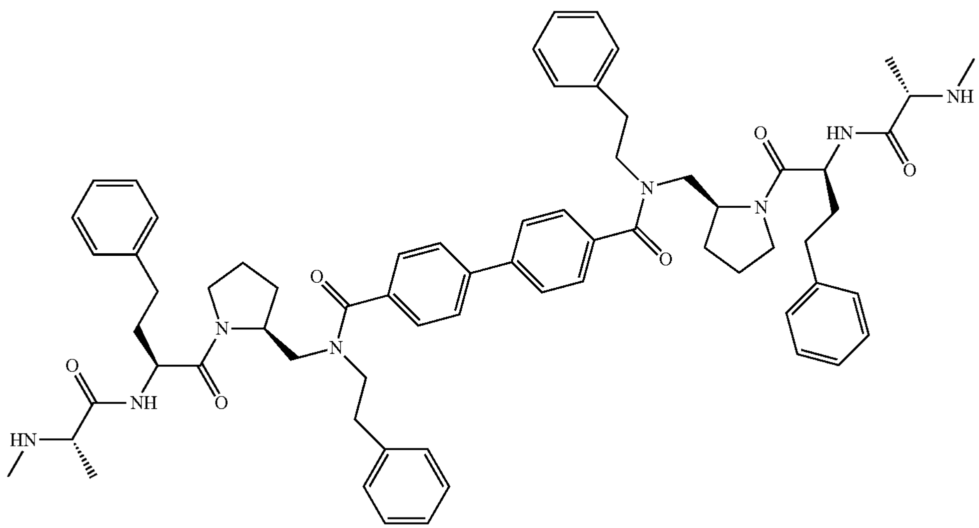 | (M + 2)/2 = 554.4 |

TABLE 1-continued

| Cmpd # | Structure | MS |
|---|---|---|
| 13 | 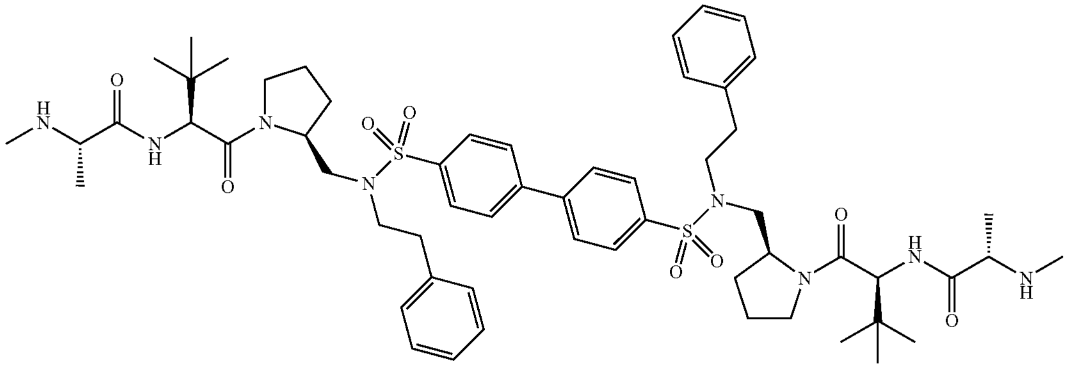 | (M + 2)/2 = 542.4 |
| 14 | 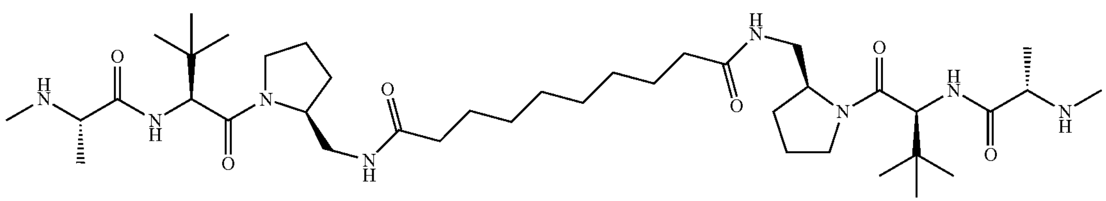 | M + 1 = 763.6<br>(M + 2)/2 = 382.4 |

TABLE 1-continued

| Cmpd # | Structure | MS |
|---|---|---|
| 15 | 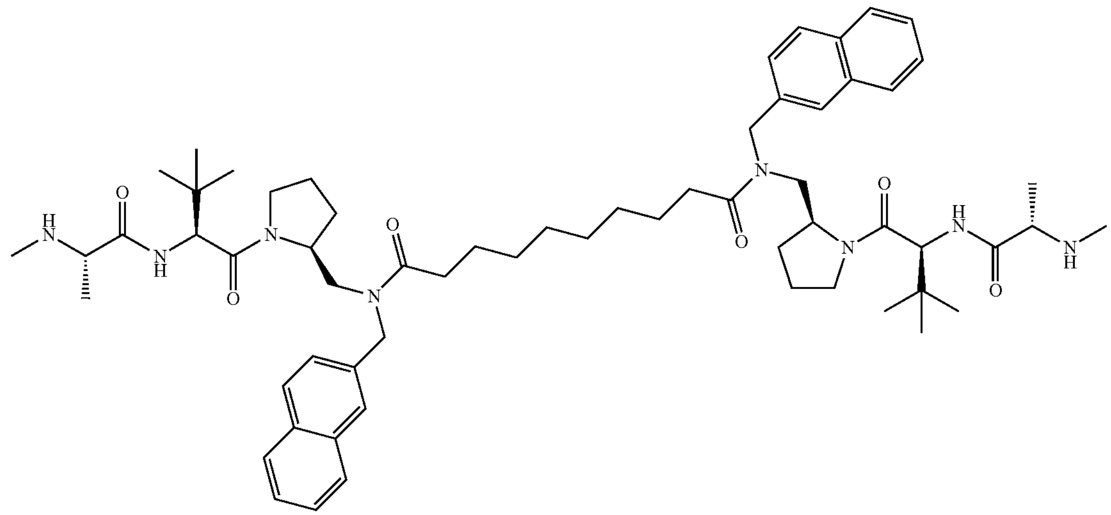 | M + 1 = 1043.8<br>(M + 2)/2 = 522.4 |
| 16 | 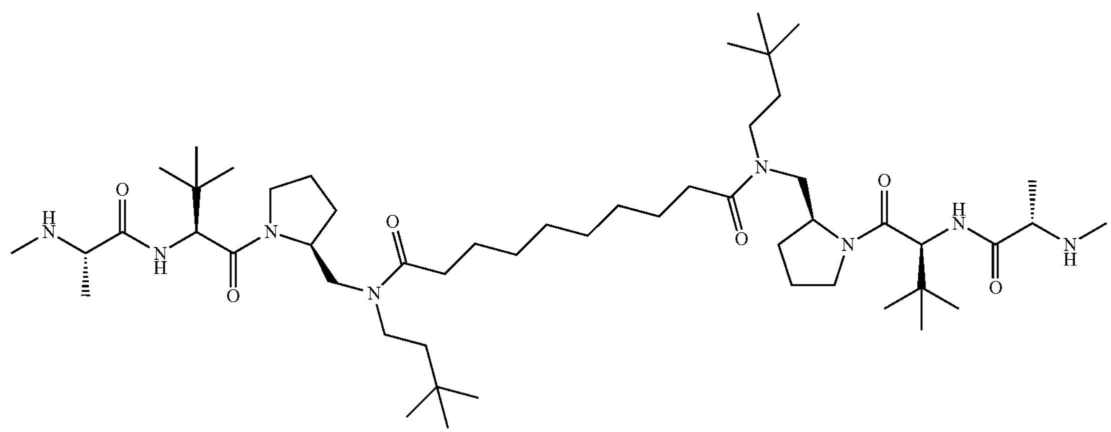 | M + 1 = 931.8<br>(M + 2)/2 = 466.4 |

TABLE 1-continued
| Cmpd # | Structure | MS |
|---|---|---|
| 17 | 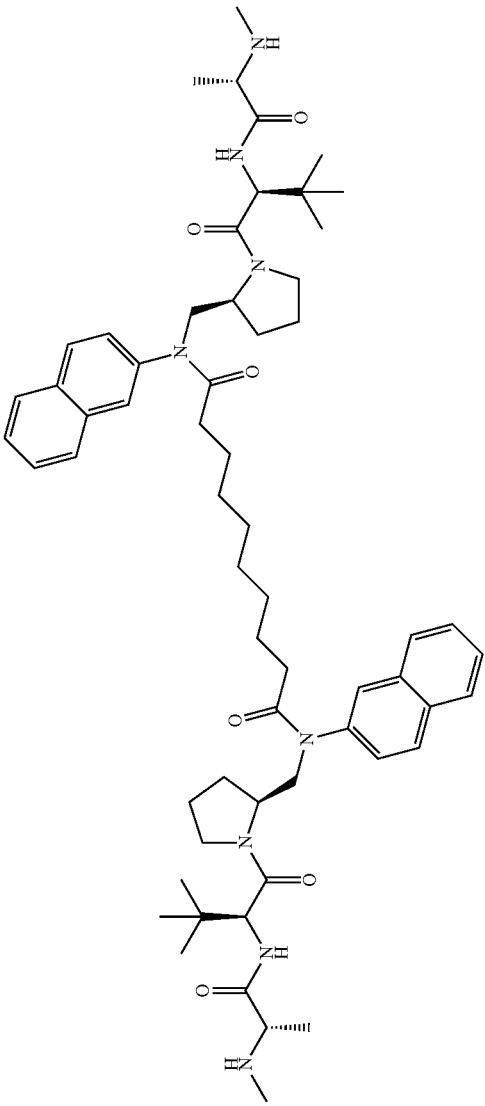 | M + 1 = 1015.6<br>(M + 2)/2 = 508.6 |

TABLE 1-continued
| Cmpd # | Structure | MS |
|---|---|---|
| 18 | 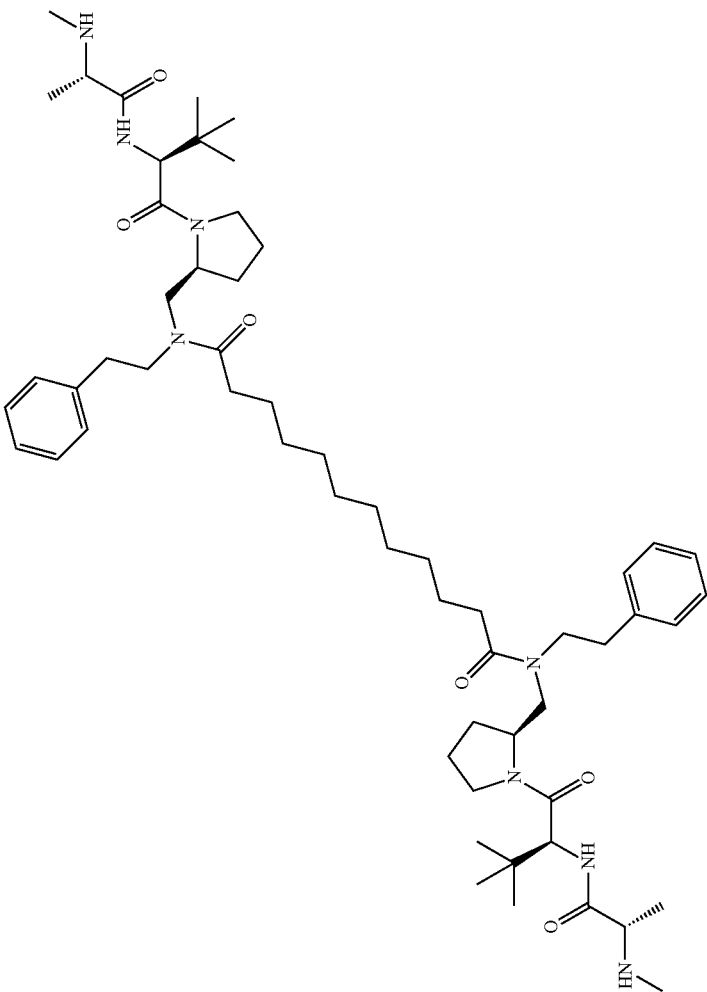 | M + 1 = 999.6<br>(M + 2)/2 = 500.6 |

TABLE 1-continued

| Cmpd # | Structure | MS |
|---|---|---|
| 19 | 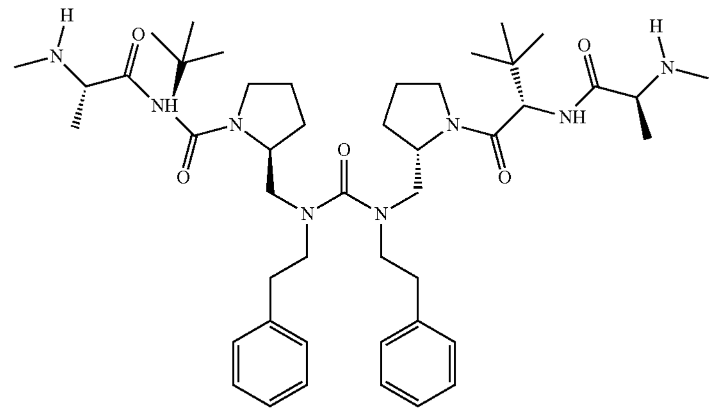 | M + 1 = 831.6 (M + 2)/2 = 416.4 |
| 20 | 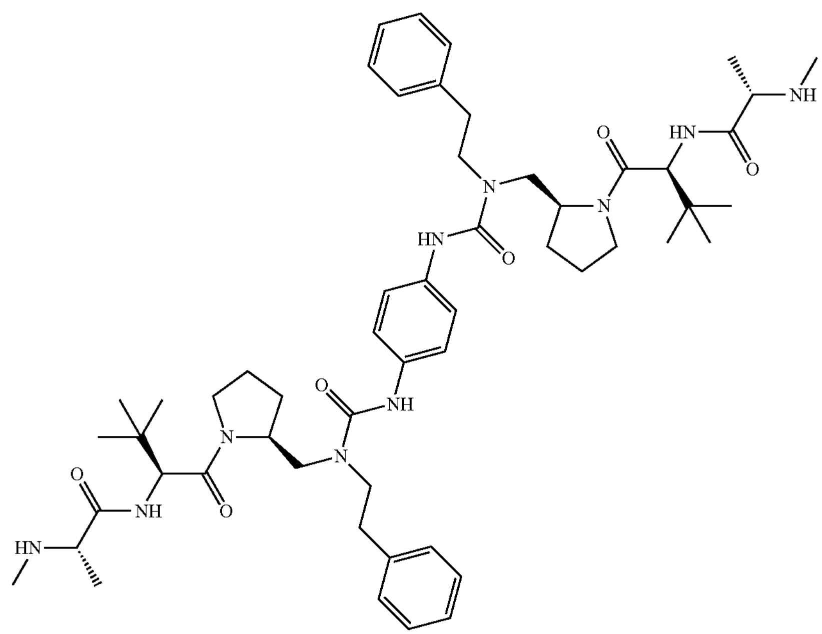 | M + 1 = 965.6 (M + 2)/2 = 483.4 |

TABLE 1-continued

| Cmpd # | Structure | MS |
|---|---|---|
| 21 | (structure image) | M + 1 = 999.8<br>(M + 2)/2 = 500.6 |

TABLE 1-continued
| Cmpd # | Structure | MS |
|---|---|---|
| 22 | 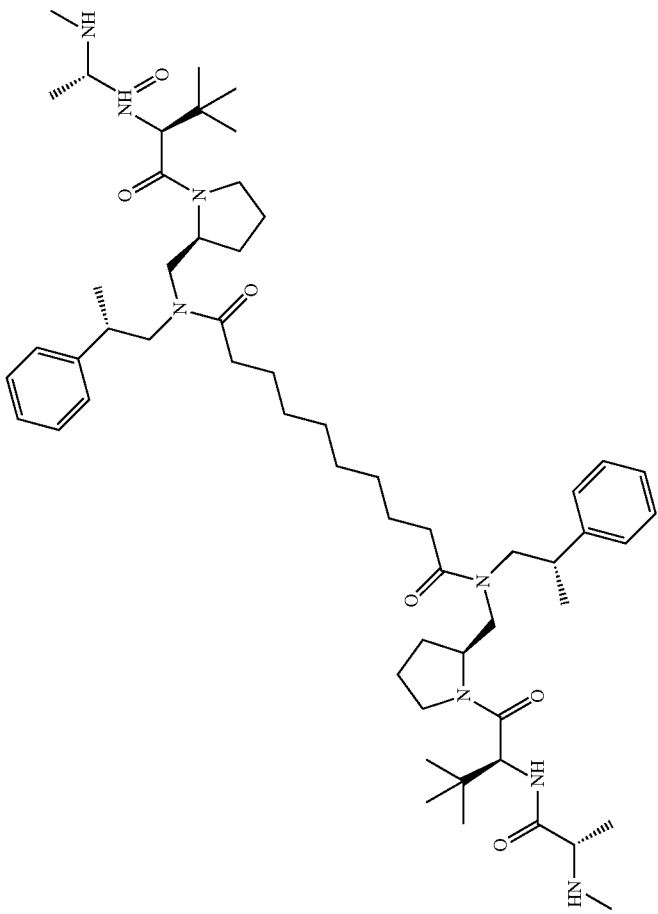 | M + 1 = 999.8<br>(M + 2)/2 = 500.6 |

TABLE 1-continued
| Cmpd # | Structure | MS |
|---|---|---|
| 23 | 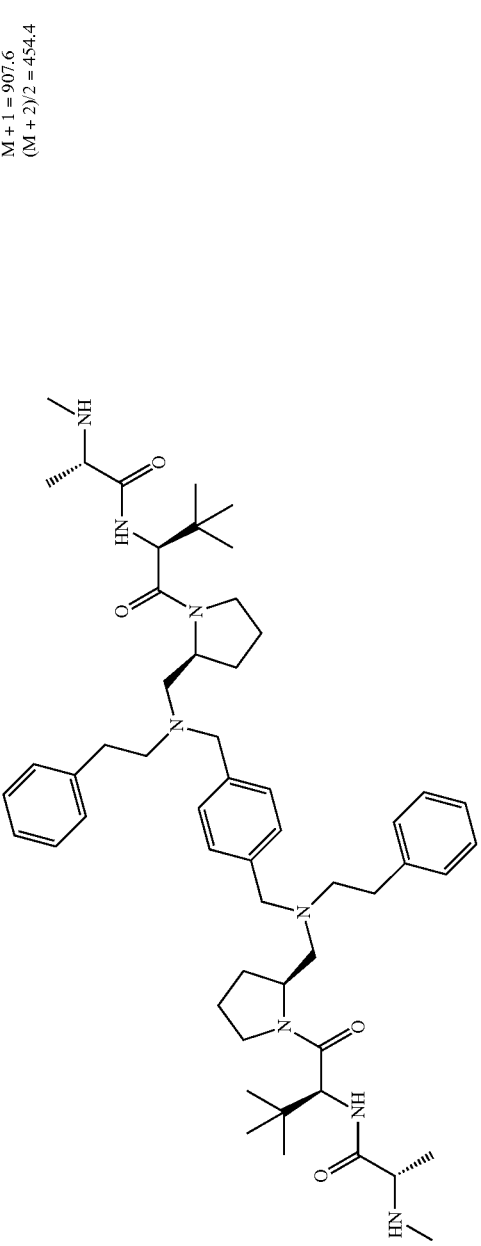 | M + 1 = 907.6<br>(M + 2)/2 = 454.4 |
| 24 | 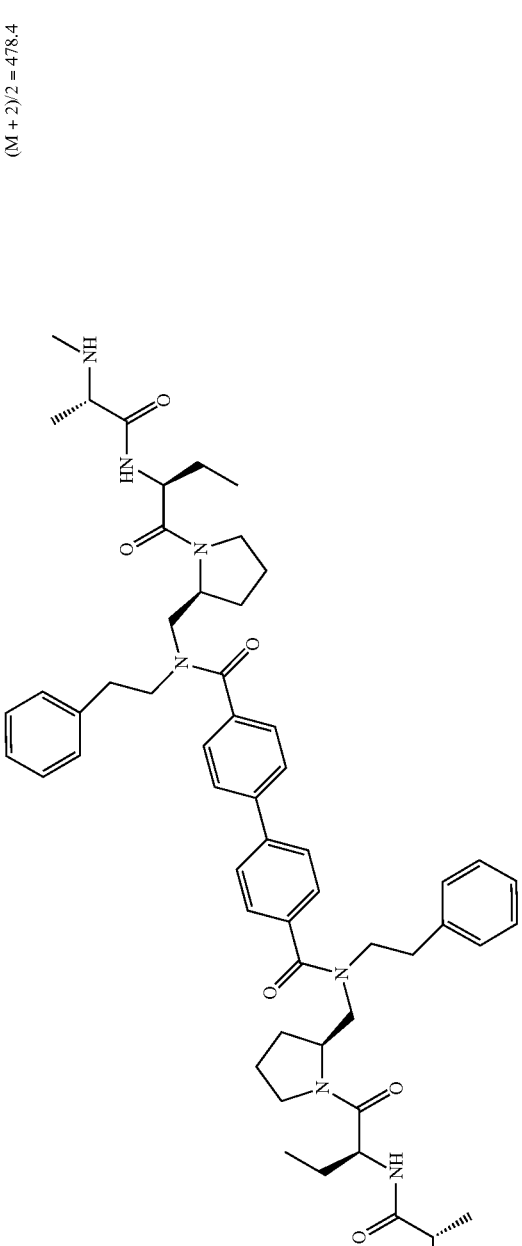 | (M + 2)/2 = 478.4 |

TABLE 1-continued
| Cmpd # | Structure | MS |
|---|---|---|
| 25 | 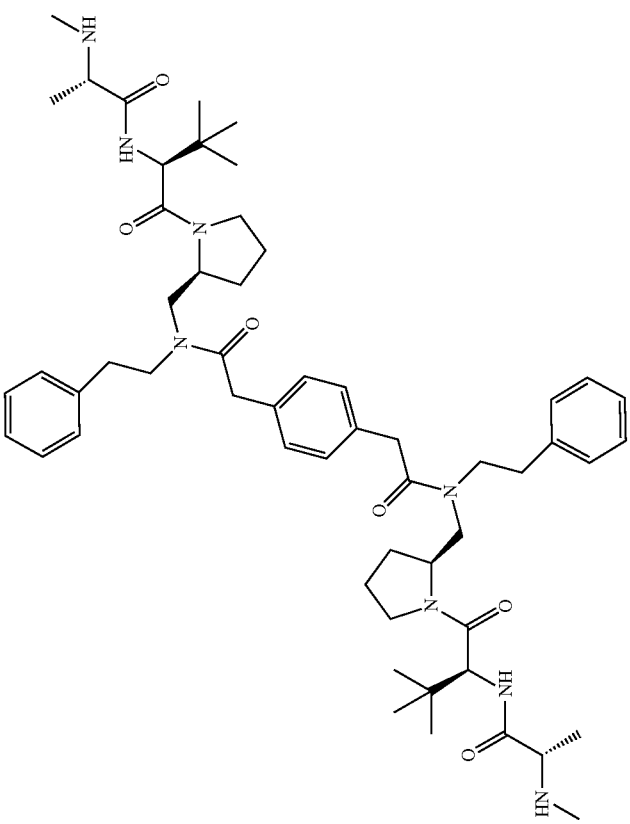 | M + 1 = 963.6<br>(M + 2)/2 = 482.4 |

TABLE 1-continued

| Cmpd # | Structure | MS |
|---|---|---|
| 26 | 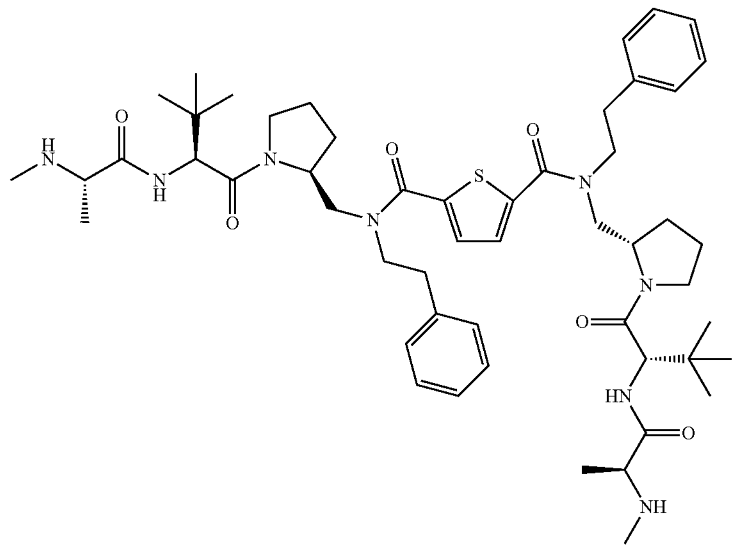 | M + 1 = 941.6<br>(M + 2)/2 = 471.4 |
| 27 | 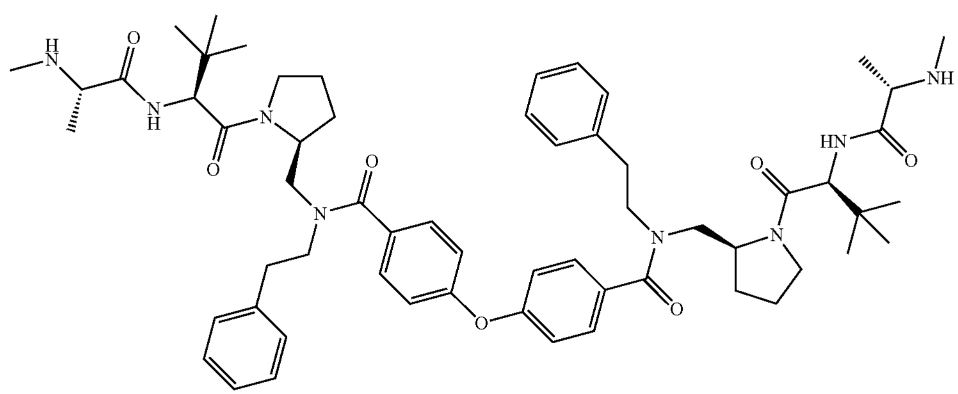 | M + 1 = 1027.6<br>(M + 2)/2 = 514.4 |

TABLE 1-continued
| Cmpd # | Structure | MS |
|---|---|---|
| 28 | 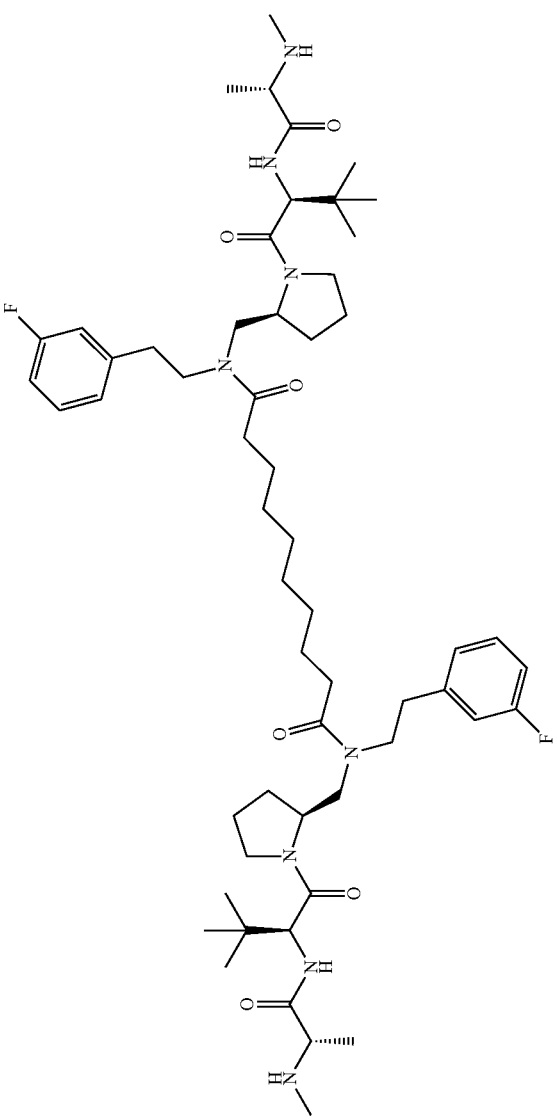 | M + 1 = 1007.6<br>(M + 2)/2 = 504.4 |

TABLE 1-continued
| Cmpd # | Structure | MS |
|---|---|---|
| 29 | 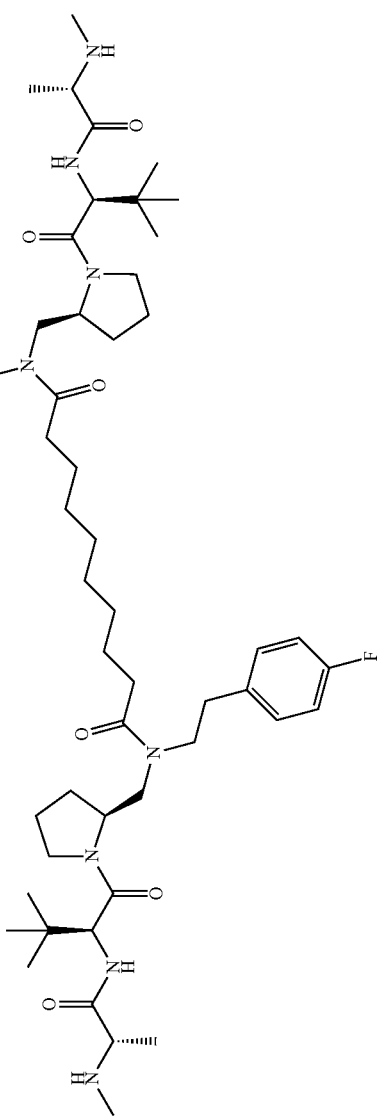 | M + 1 = 1007.6<br>(M + 2)/2 = 504.4 |

TABLE 1-continued

| Cmpd # | Structure | MS |
|---|---|---|
| 30 | 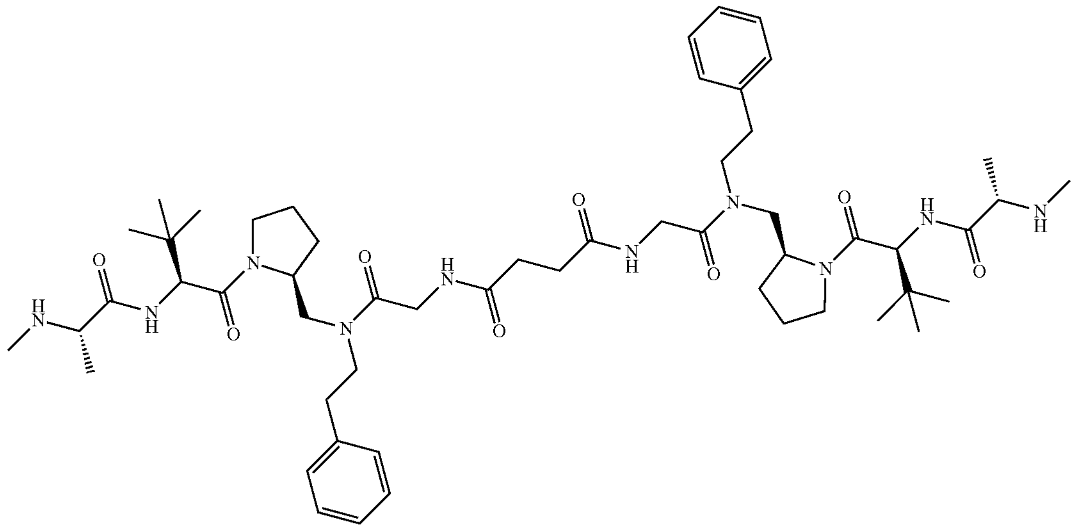 | M + 1 = 1002.6<br>(M + 2)/2 = 501.4 |
| 31 | 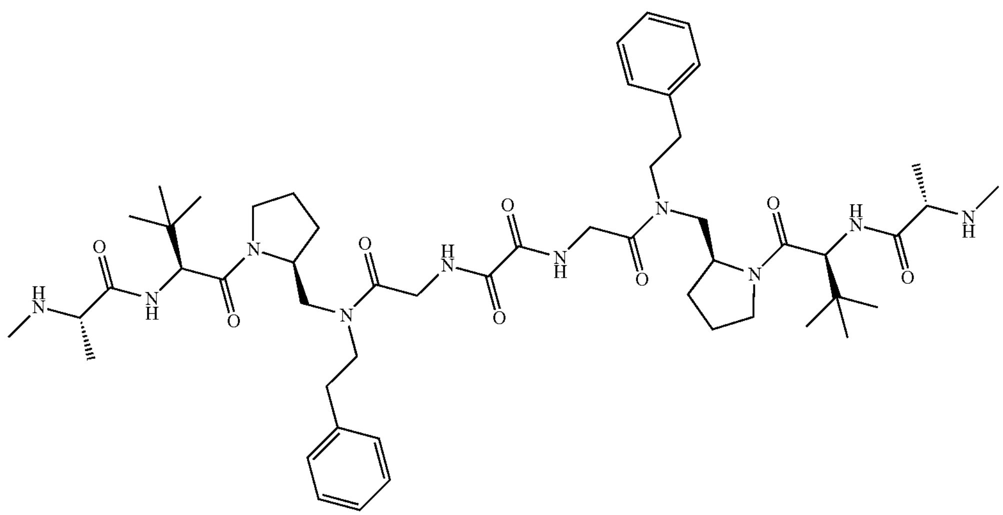 | M + 1 = 973.6<br>(M + 2)/2 = 487.4 |

TABLE 1-continued

| Cmpd # | Structure | MS |
|---|---|---|
| 32 | 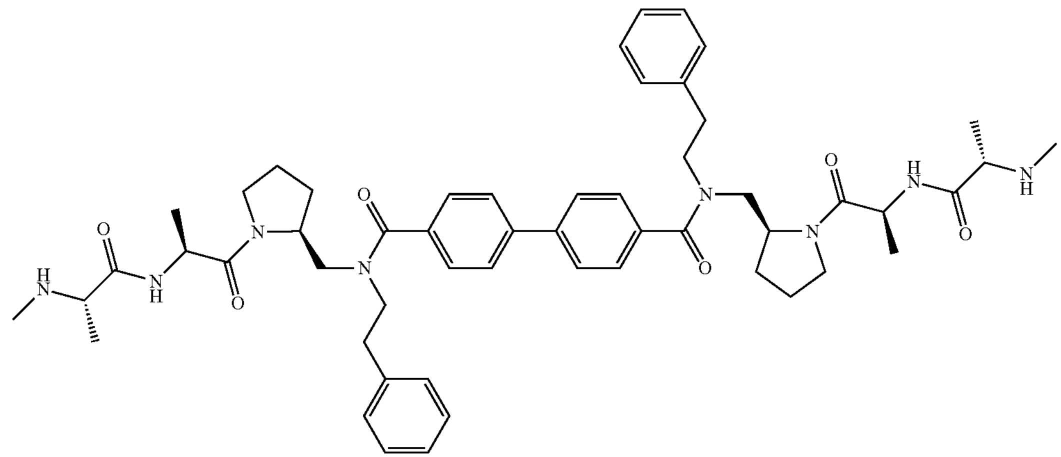 | (M + 2)/2 = 464.4 |
| 33 | 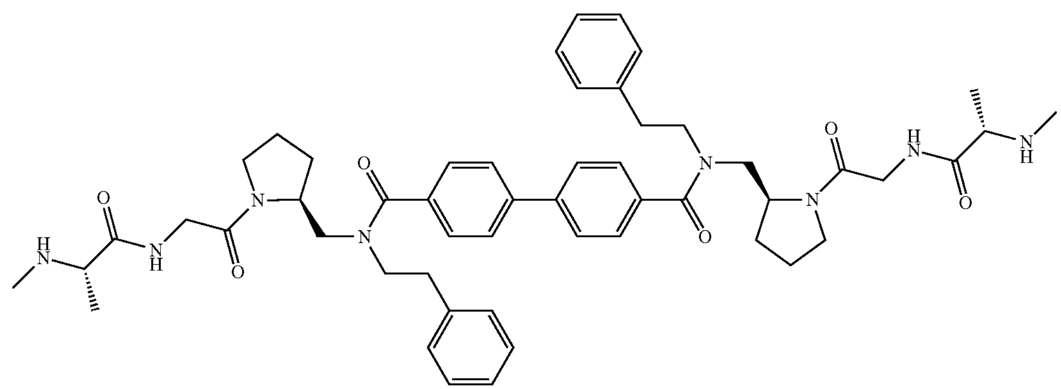 | (M + 2)/2 = 450.4 |

TABLE 1-continued
| Cmpd # | Structure | MS |
|---|---|---|
| 34 | 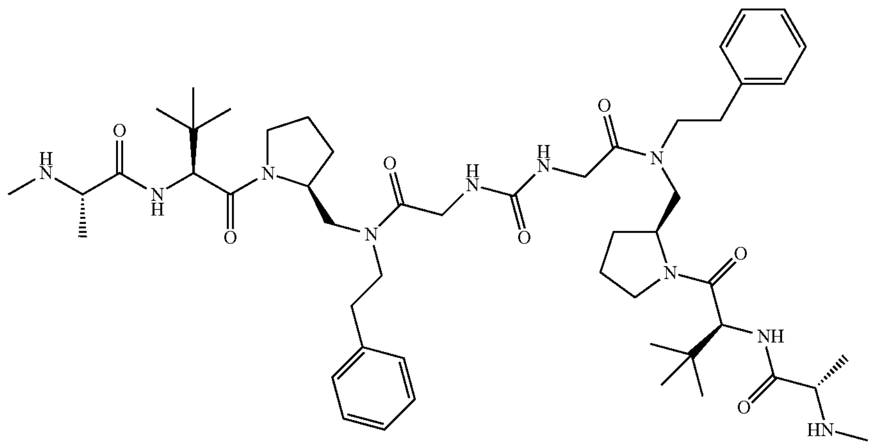 | M + 1 = 945.6<br>(M + 2)/2 = 473.4 |
| 35 | 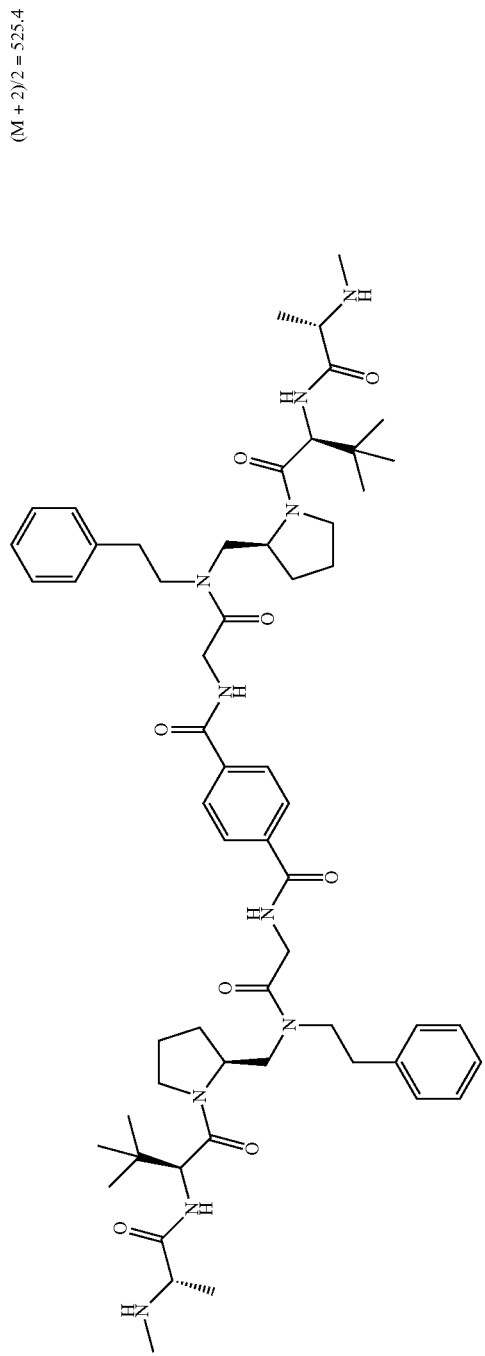 | (M + 2)/2 = 525.4 |

TABLE 1-continued
| Cmpd # | Structure | MS |
|---|---|---|
| 36 | 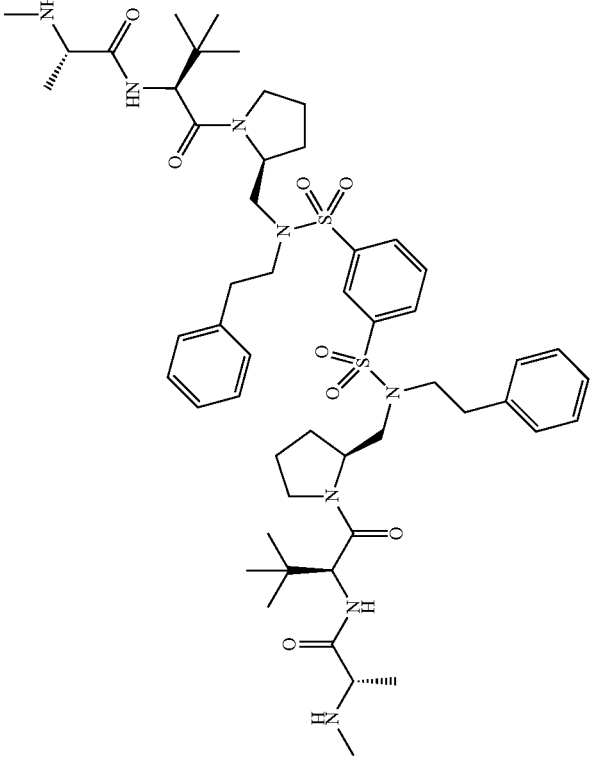 | M + 1 = 1007.4<br>(M + 2)/2 = 504.4 |
| 37 | 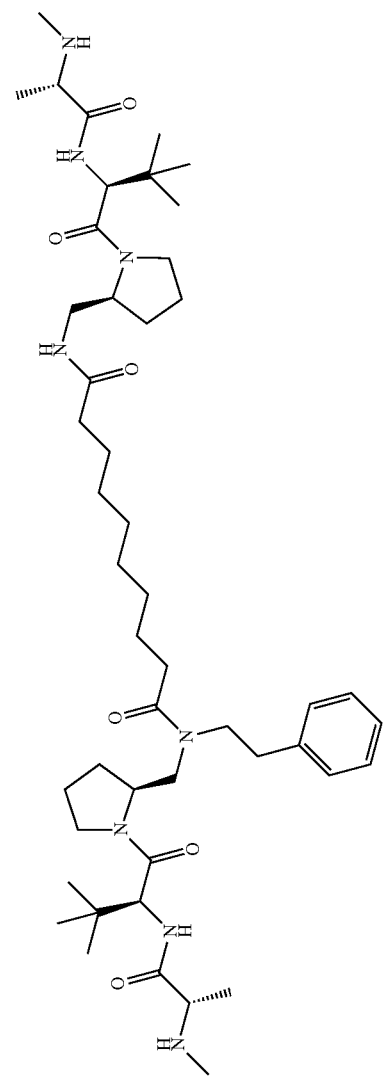 | M + 1 = 867.6<br>(M + 2)/2 = 434.4 |

TABLE 1-continued

| Cmpd # | Structure | MS |
|---|---|---|
| 38 | 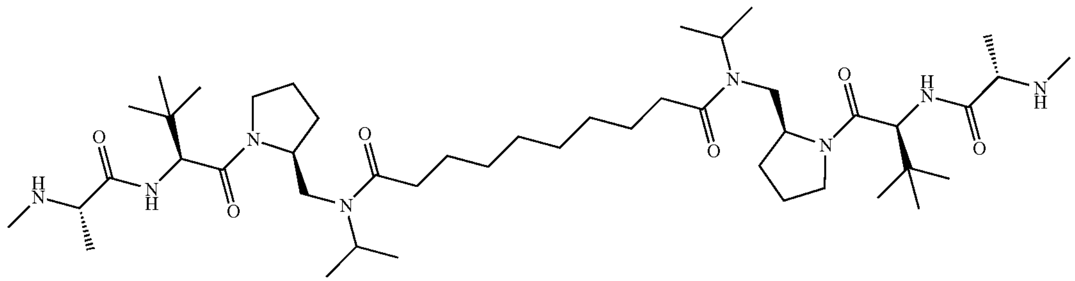 | M + 1 = 847.6<br>(M + 2)/2 = 424.4 |
| 39 | 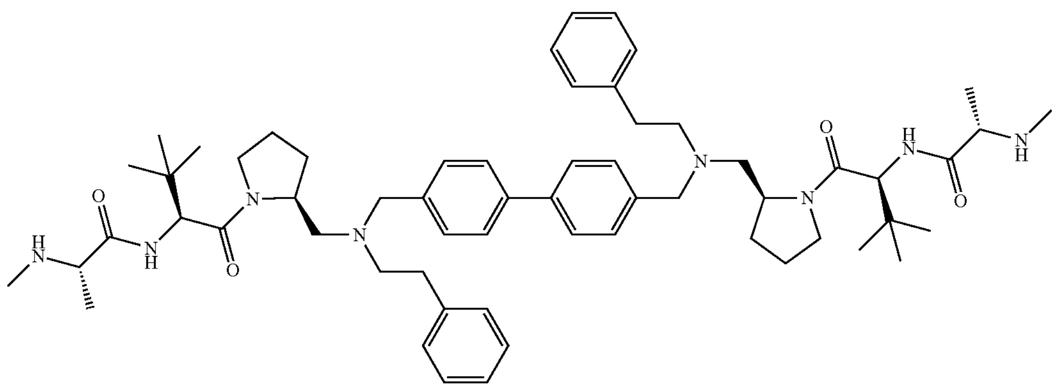 | M + 1 = 983.6<br>(M + 2)/2 = 492.4 |

TABLE 1-continued

| Cmpd # | Structure | MS |
|---|---|---|
| 40 | 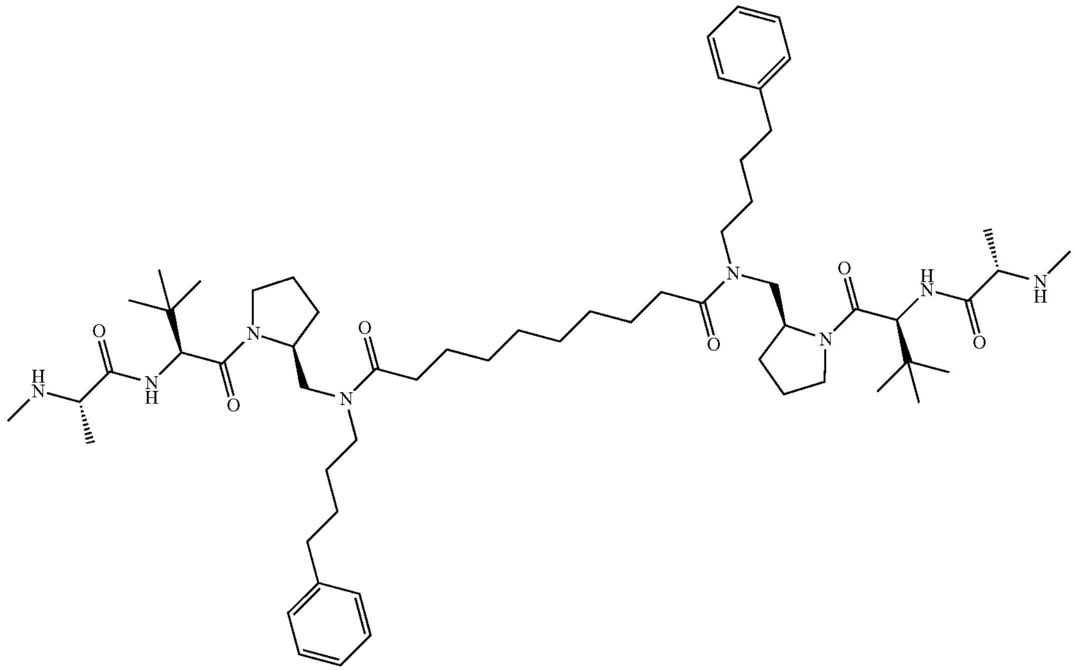 | M + 1 = 1027.8<br>(M + 2)/2 = 514.4 |

TABLE 1-continued
| Cmpd # | Structure | MS |
|---|---|---|
| 41 | 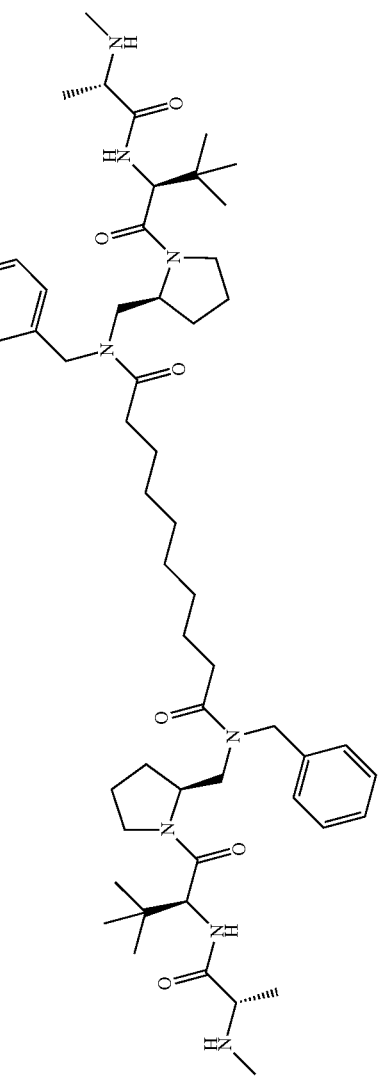 | M + 1 = 943.6<br>(M + 2)/2 = 472.4 |
| 42 | 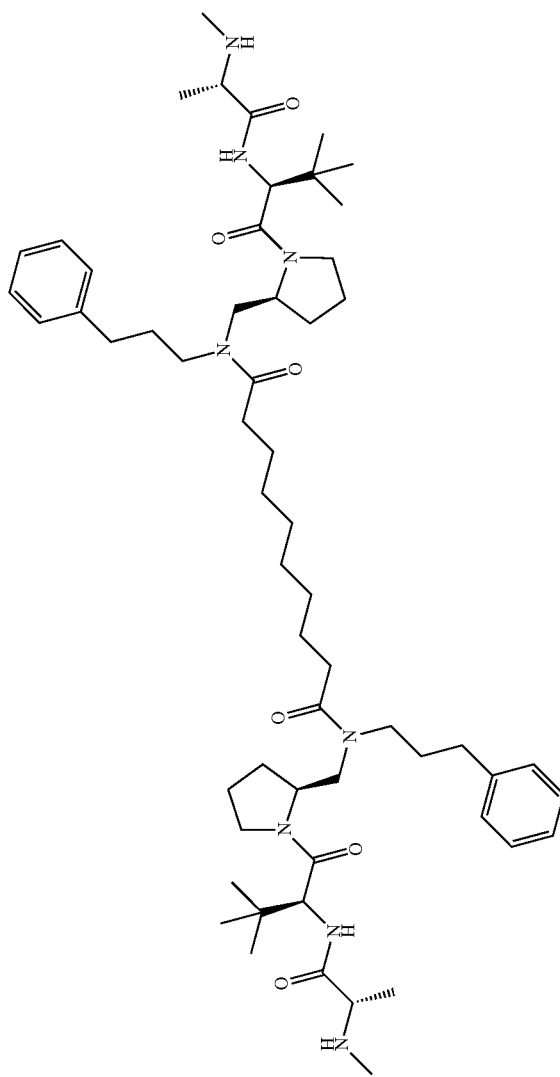 | M + 1 = 999.6<br>(M + 2)/2 = 500.4 |

TABLE 1-continued

| Cmpd # | Structure | MS |
|---|---|---|
| 43 | 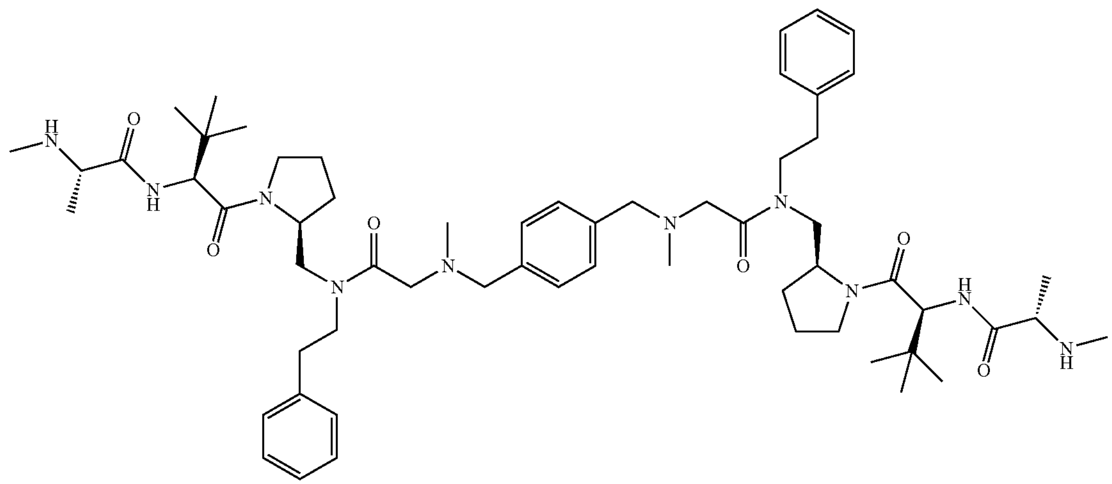 | M + 1 = 1049.6<br>(M + 2)/2 = 525.4 |
| 44 | 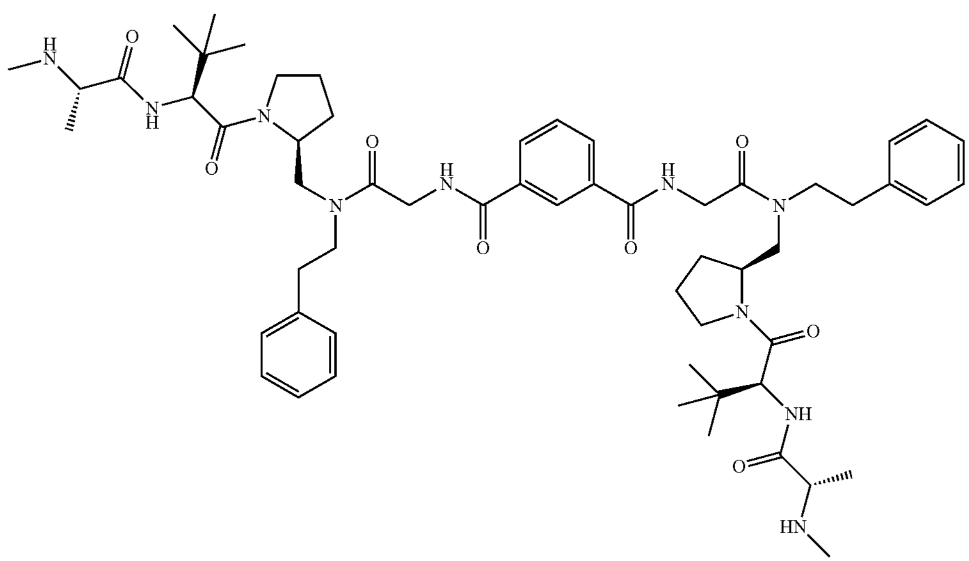 | M + 1 = 1049.4<br>(M + 2)/2 = 525.2 |

TABLE 1-continued

| Cmpd # | Structure | MS |
|---|---|---|
| 45 | 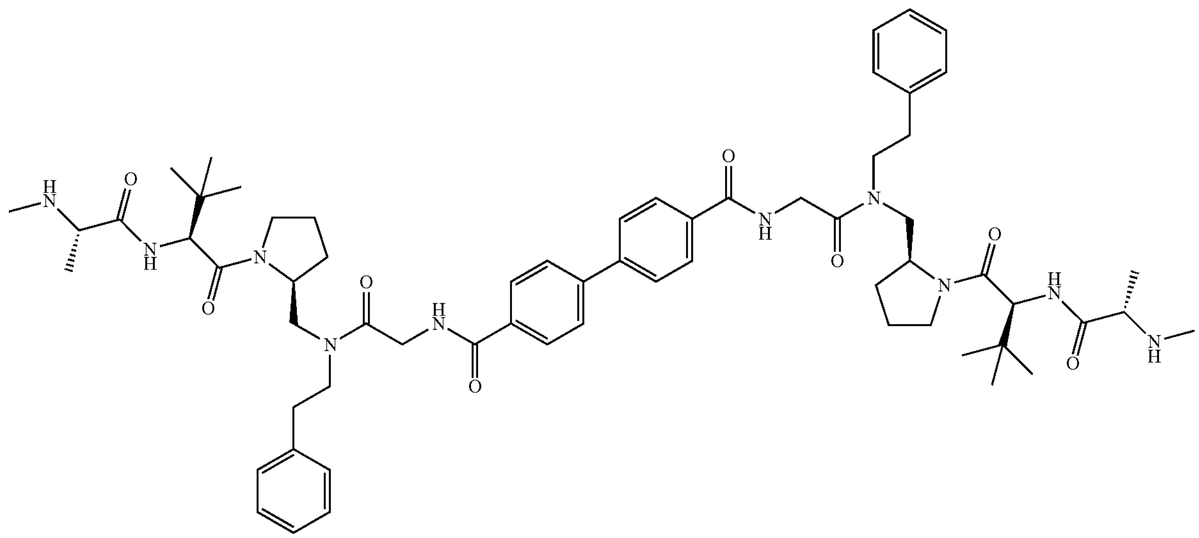 | M + 1 = 1125.4<br>(M + 2)/2 = 563.4 |
| 46 | 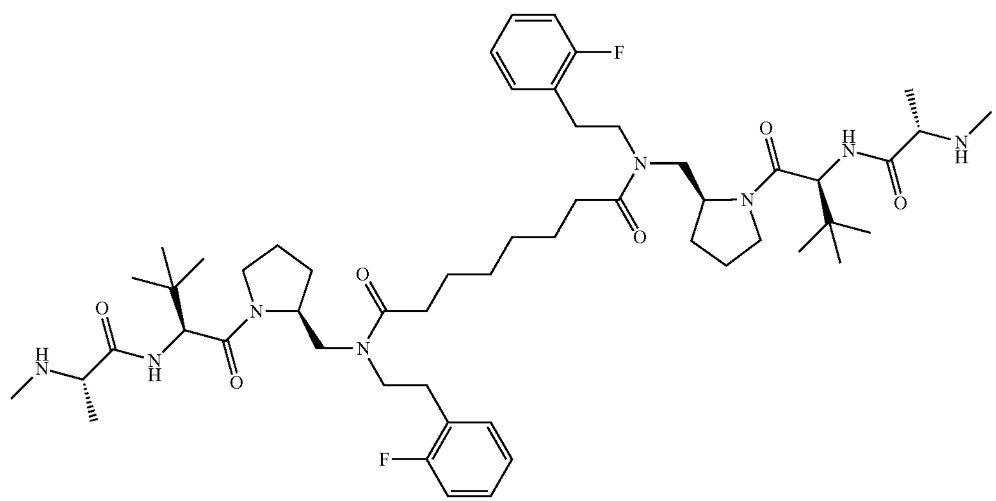 | M + 1 = 1007.6<br>(M + 2)/2 = 504.4 |

TABLE 1-continued

| Cmpd # | Structure | MS |
|---|---|---|
| 47 | 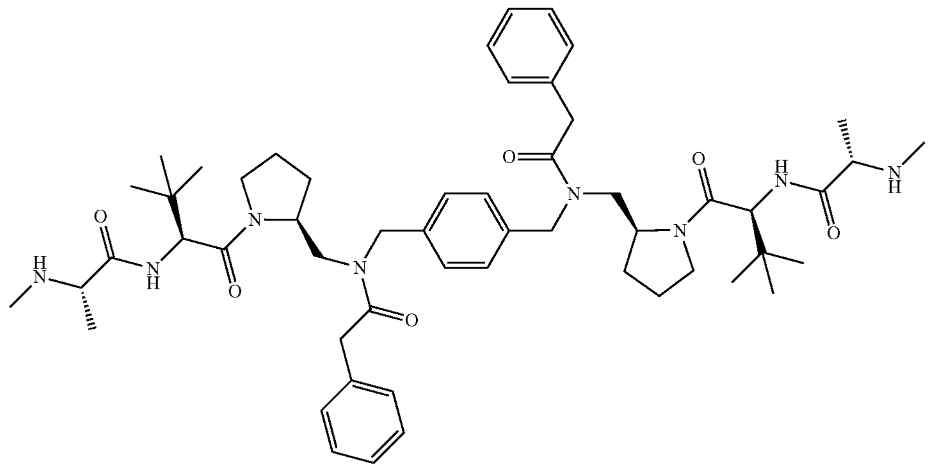 | M + 1 = 935.6<br>(M + 2)/2 = 468.4 |
| 48 | 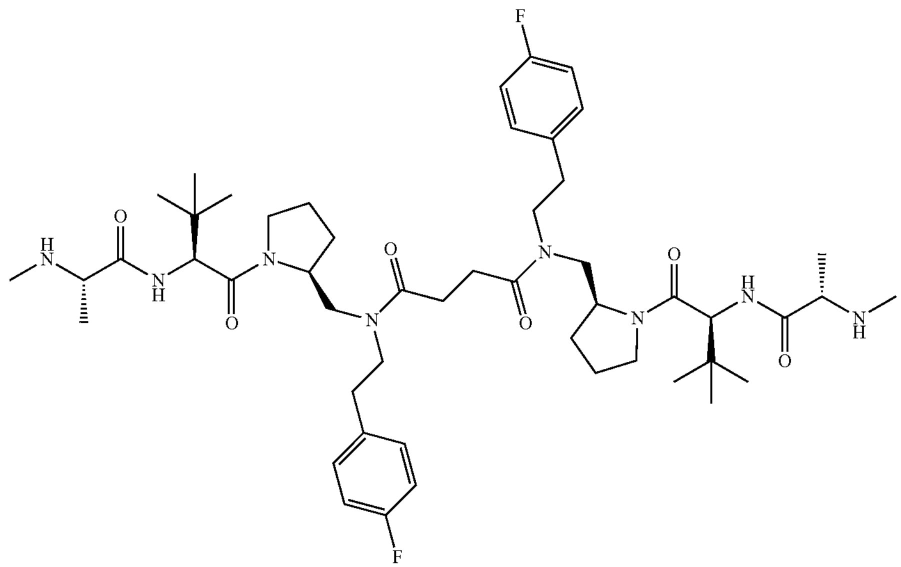 | M + 1 = 923.2<br>(M + 2)/2 = 462.2 |

TABLE 1-continued
| Cmpd # | Structure | MS |
|---|---|---|
| 49 | 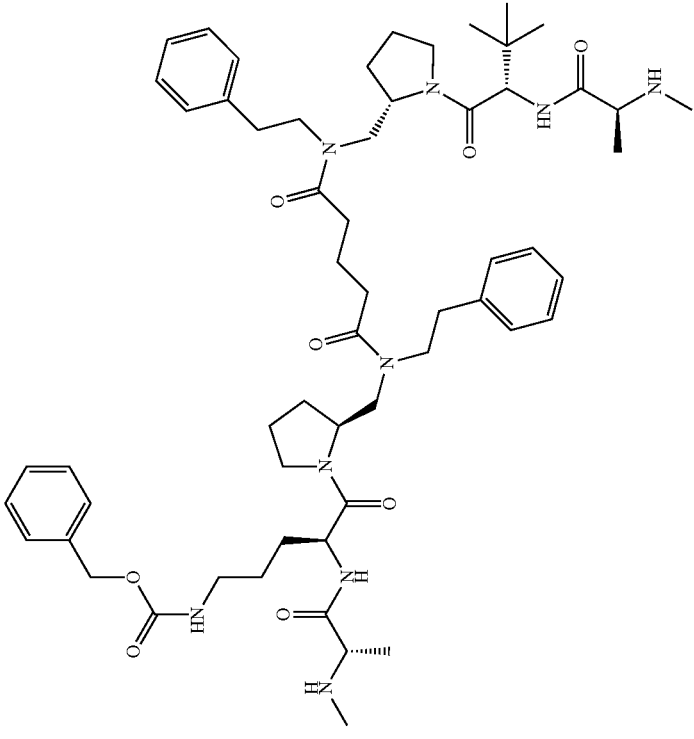 | (M + 2)/2 = 519.0 |

TABLE 1-continued
| Cmpd # | Structure | MS |
|---|---|---|
| 50 | 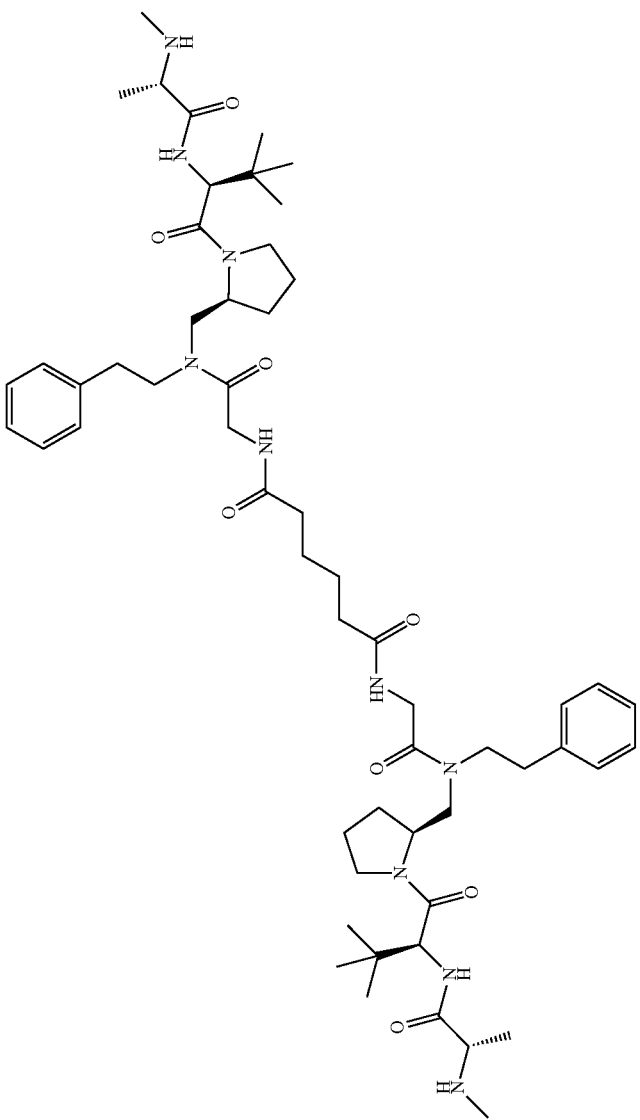 | M + 1 = 1029.6<br>(M + 2)/2 = 515.4 |

TABLE 1-continued

| Cmpd # | Structure | MS |
|---|---|---|
| 51 | 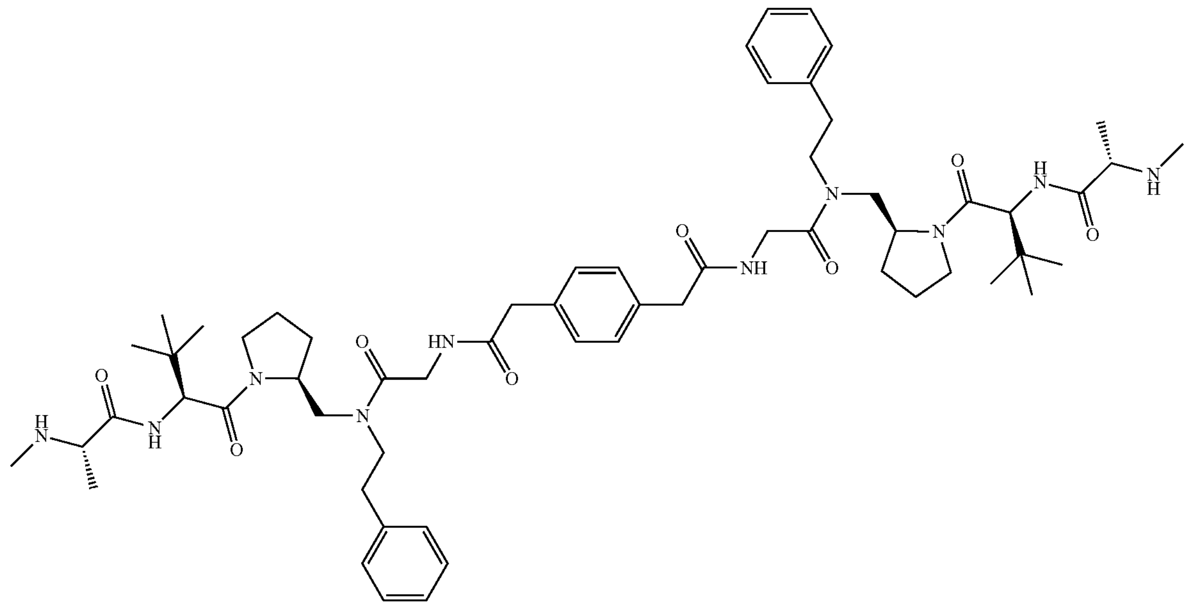 | (M + 2)/2 = 539.4 |

TABLE 1-continued
| Cmpd # | Structure | MS |
|---|---|---|
| 52 | 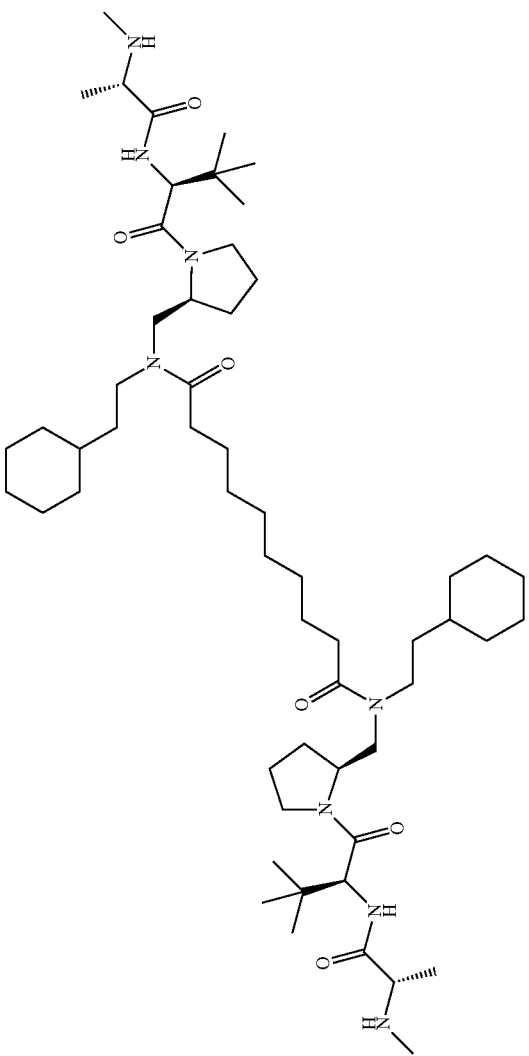 | M + 1 = 983.6<br>(M + 2)/2 = 492.4 |

TABLE 1-continued
| Cmpd # | Structure | MS |
|---|---|---|
| 53 | 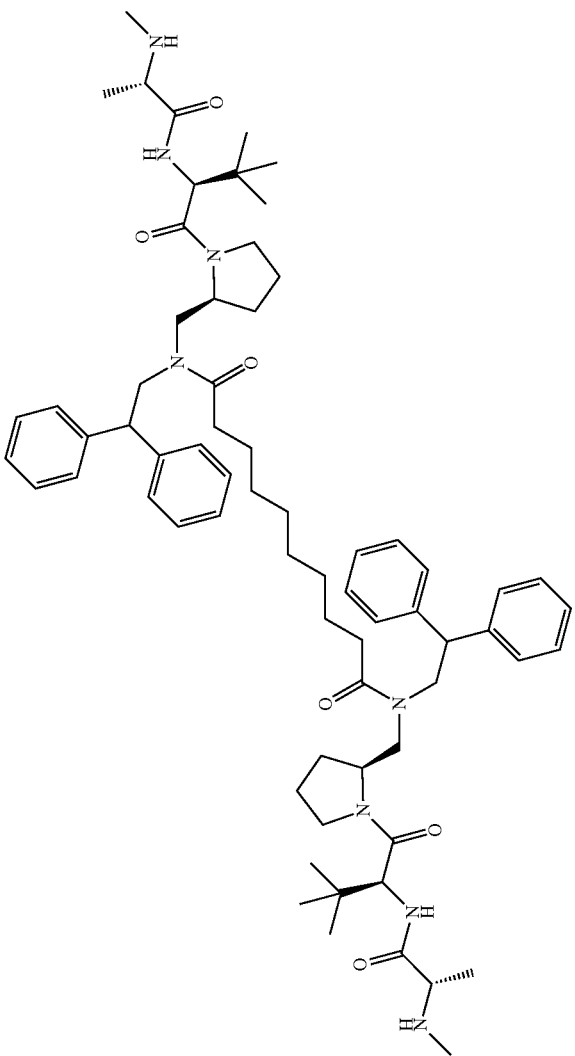 | M + 1 = 1123.6<br>(M + 2)/2 = 562.4 |

TABLE 1-continued
| Cmpd # | Structure | MS |
|---|---|---|
| 54 | 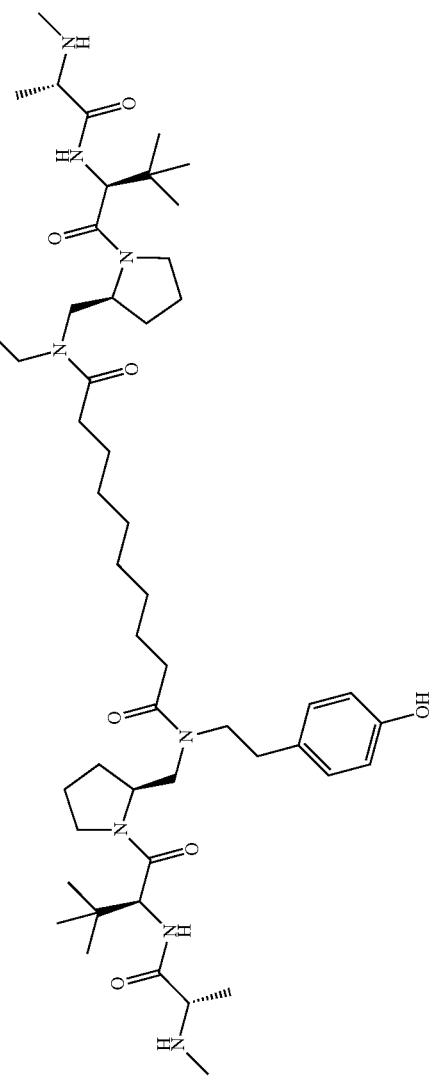 | M + 1 = 1003.6<br>(M + 2)/2 = 502.4 |

TABLE 1-continued
| Cmpd # | Structure | MS |
|---|---|---|
| 55 | 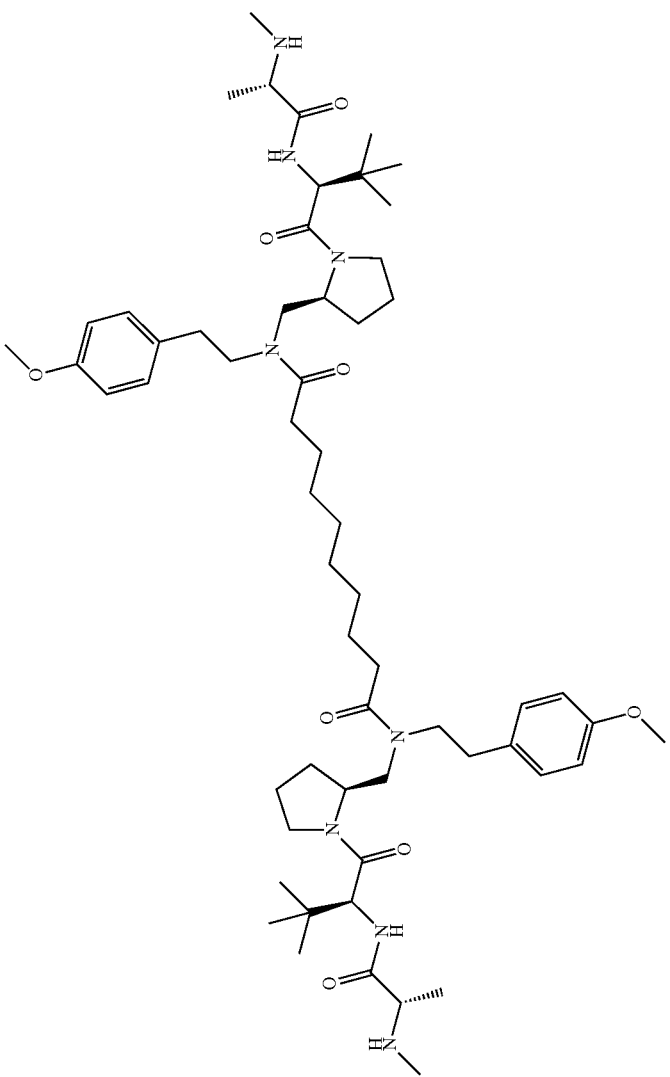 | M + 1 = 1031.6<br>(M + 2)/2 = 516.4 |

TABLE 1-continued
| Cmpd # | Structure | MS |
|---|---|---|
| 56 | 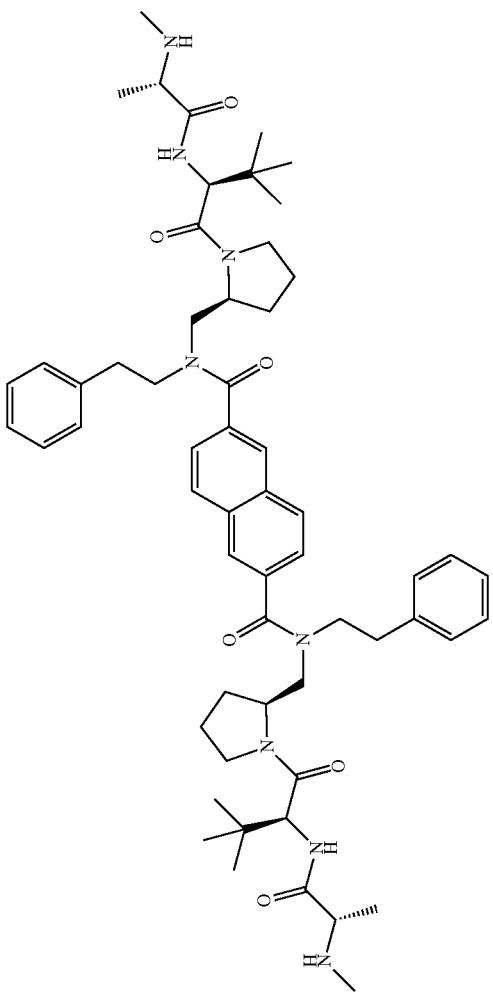 | M + 1 = 985.4<br>(M + 2)/2 = 493.4 |

TABLE 1-continued
| Cmpd # | Structure | MS |
|---|---|---|
| 57 | 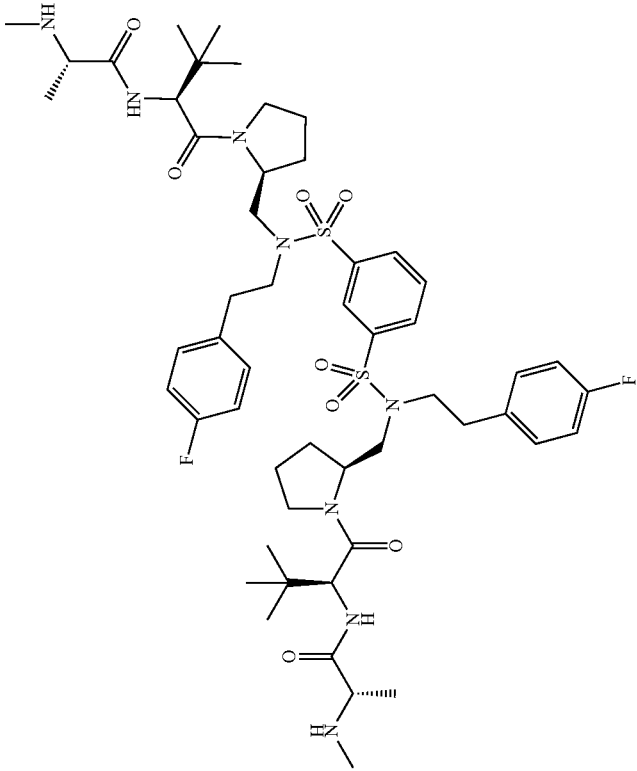 | M + 1 = 1043.4<br>(M + 2)/2 = 522.2 |

TABLE 1-continued
| Cmpd # | Structure | MS |
|---|---|---|
| 58 | 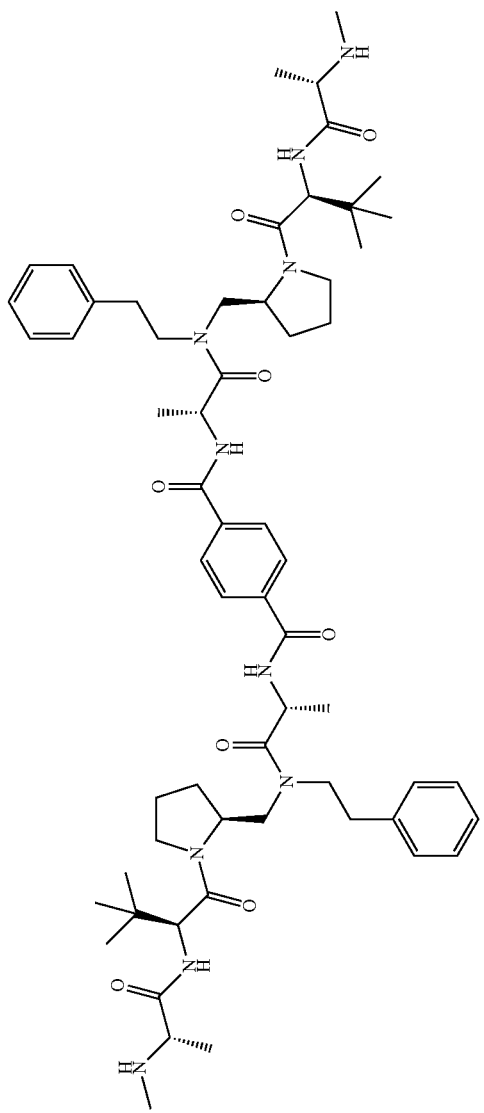 | M + 1 = 1047.6<br>(M + 2)/2 = 524.4 |
| 59 | 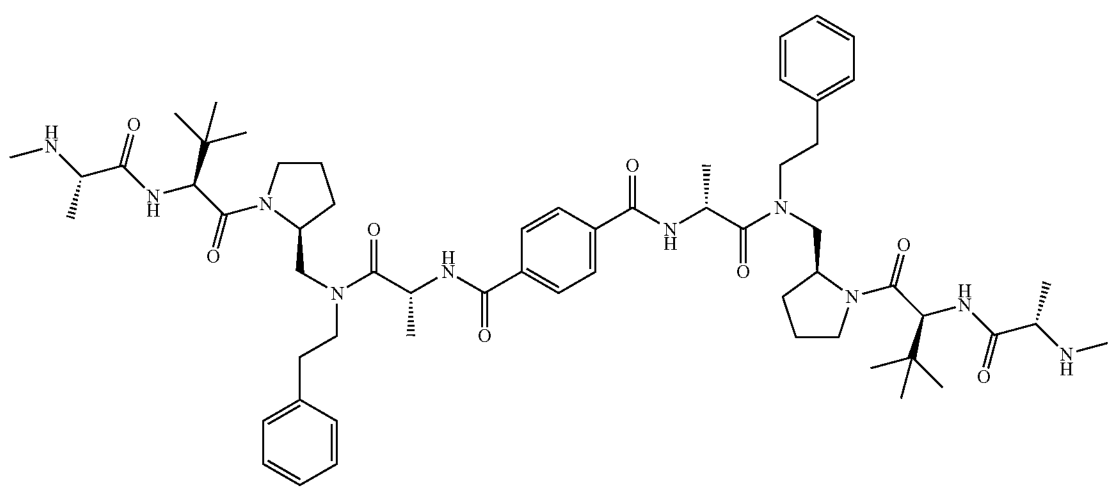 | (M + 2)/2 = 539.4 |

TABLE 1-continued
| Cmpd # | Structure | MS |
|---|---|---|
| 60 | 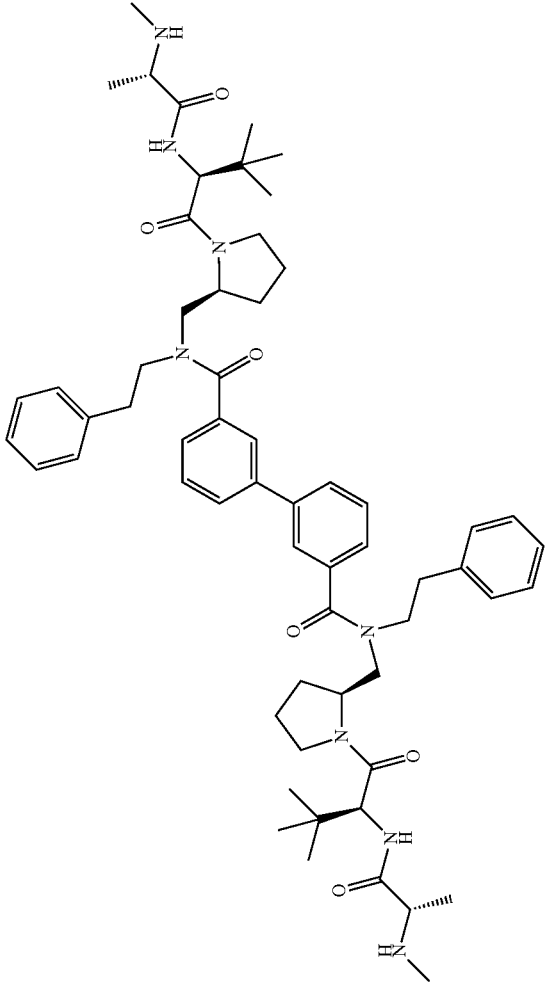 | M + 1 = 1101.4<br>(M + 2)/2 = 506.4 |
| 61 | 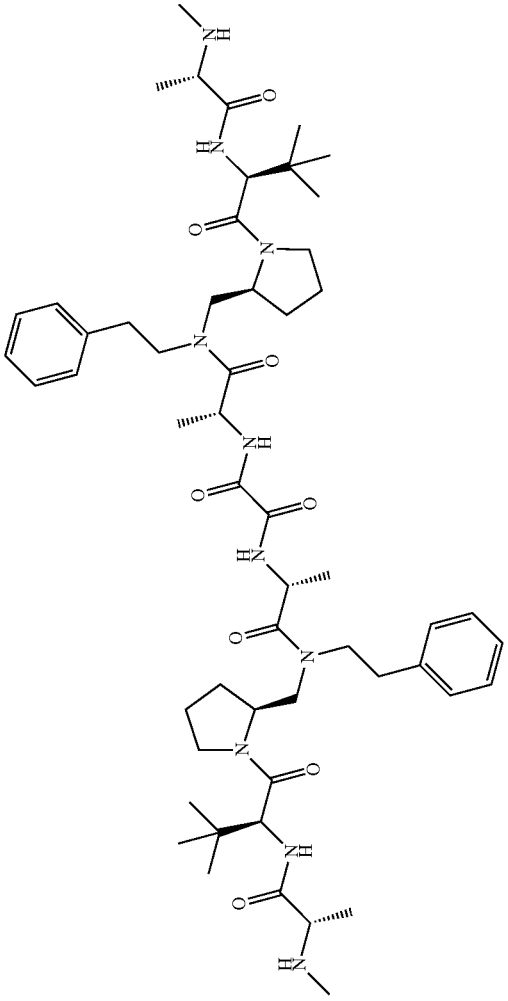 | (M + 2)/2 = 501.4 |

TABLE 1-continued
| Cmpd # | Structure | MS |
|---|---|---|
| 62 | 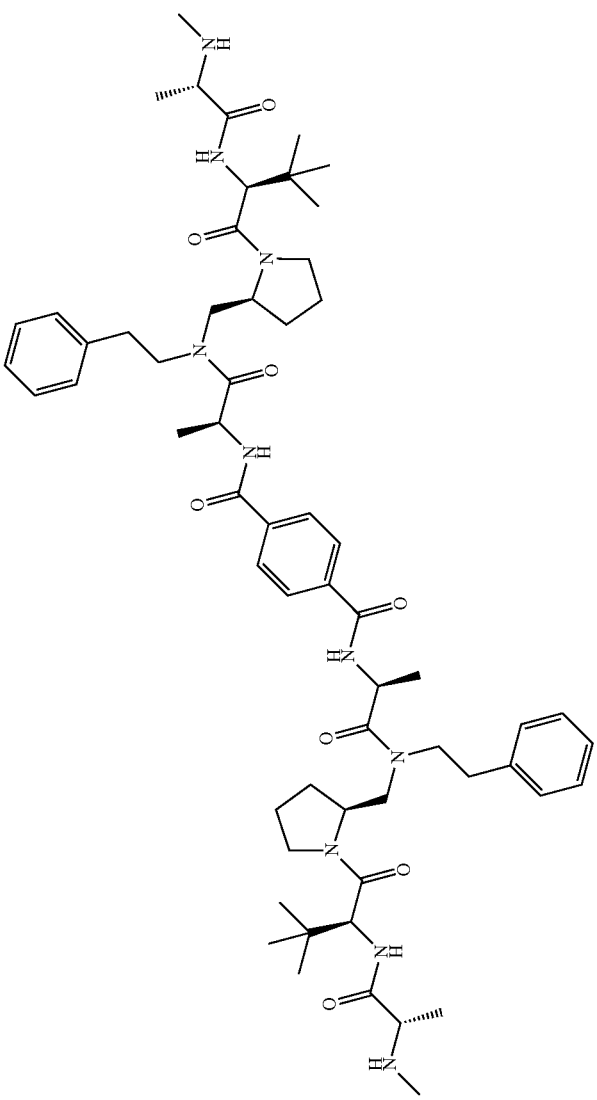 | (M + 2)/2 = 539.4 |

TABLE 1-continued
| Cmpd # | Structure | MS |
|---|---|---|
| 63 | 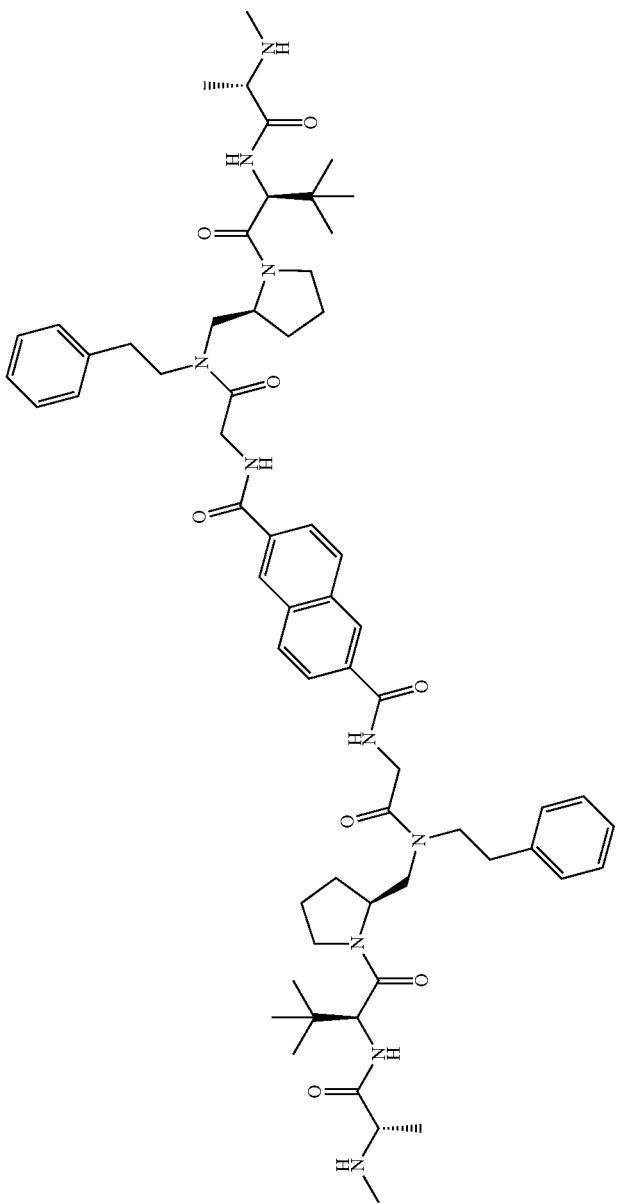 | (M + 2)/2 = 550.4 |
| 64 | 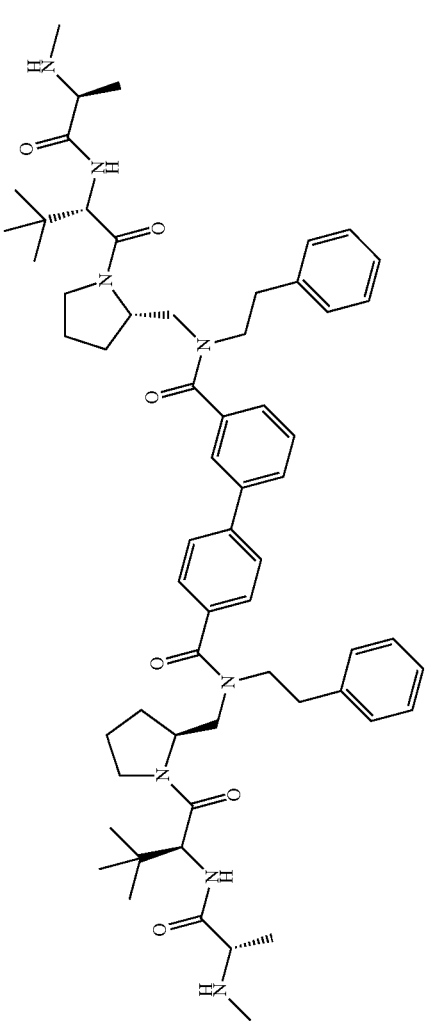 | M + 1 = 1011.4<br>(M + 2)/2 = 506.4 |

TABLE 1-continued
| Cmpd # | Structure | MS |
|---|---|---|
| 65 | 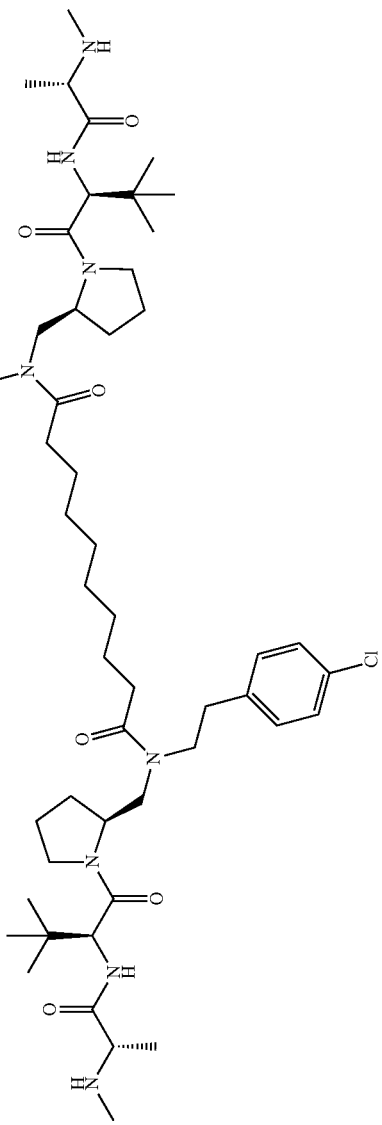 | M + 1 = 1039.4<br>(M + 2)/2 = 520.4 |

TABLE 1-continued
| Cmpd # | Structure | MS |
|---|---|---|
| 66 | 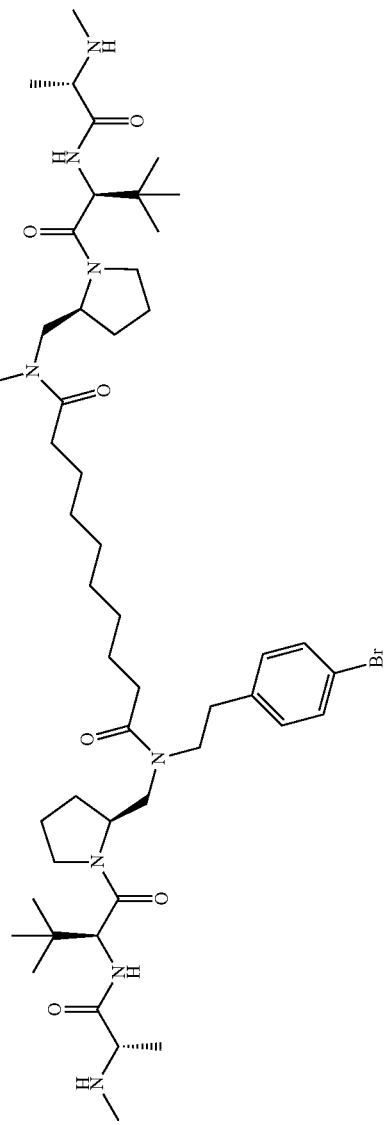 | M + 1 = 1129.4<br>(M + 2)/2 = 565.2 |

TABLE 1-continued
| Cmpd # | Structure | MS |
|---|---|---|
| 67 | 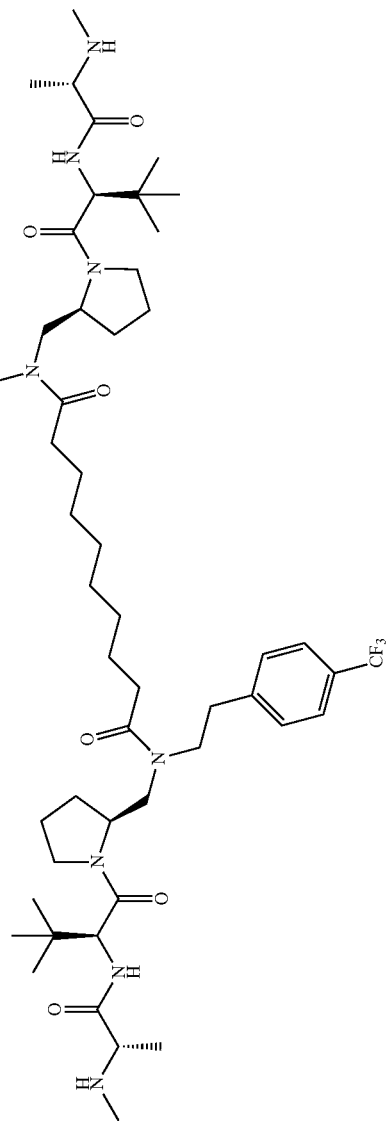 | M + 1 = 1107.6<br>(M + 2)/2 = 554.4 |
| 68 | 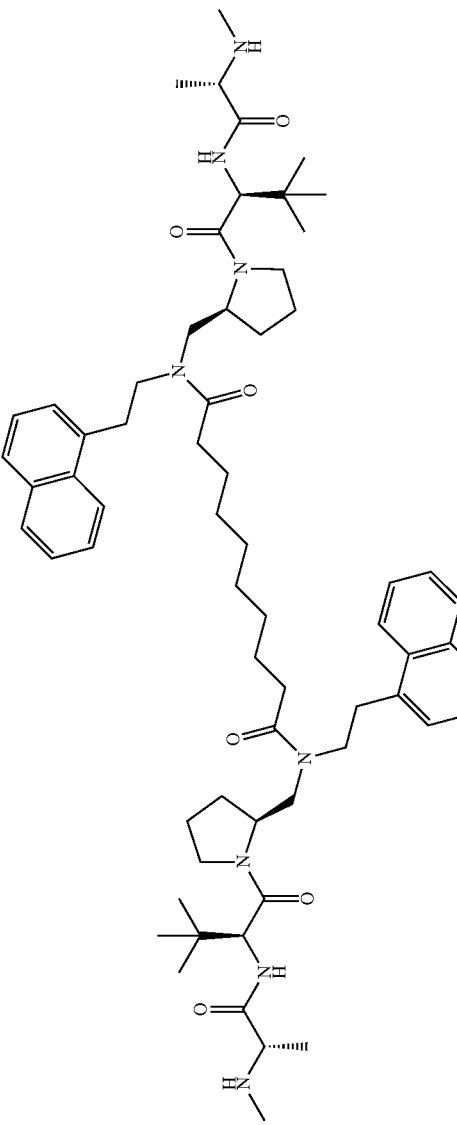 | M + 1 = 1071.6<br>(M + 2)/2 = 536.4 |

TABLE 1-continued

| Cmpd # | Structure | MS |
|---|---|---|
| 69 | 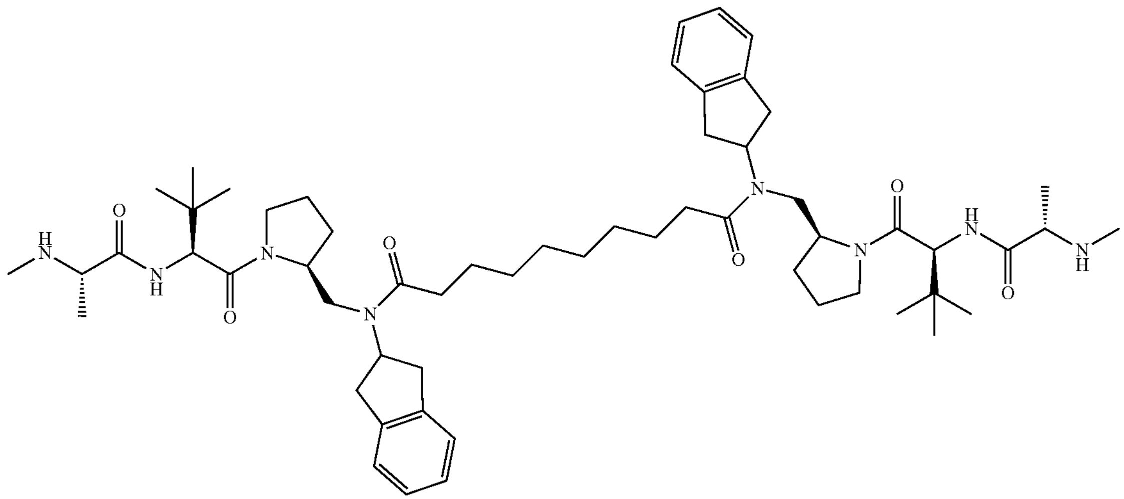 | M + 1 = 995.6<br>(M + 2)/2 = 498.4 |
| 70 | 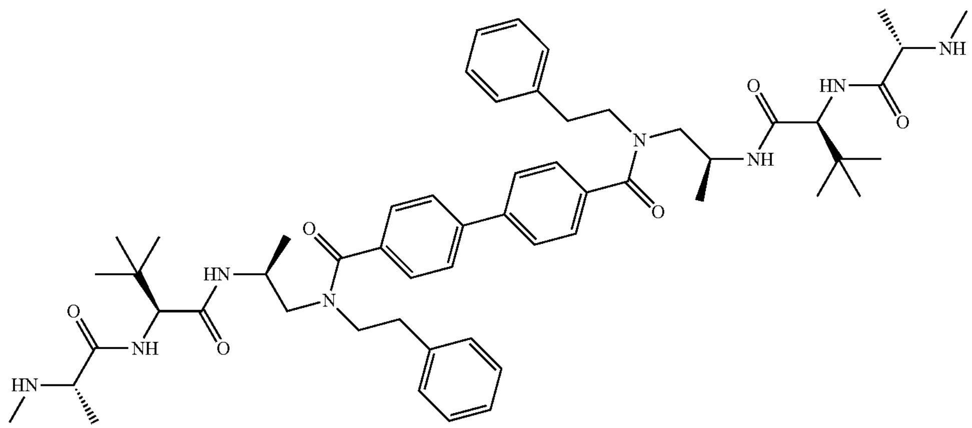 | (M + 2)/2 = 480.4 |

TABLE 1-continued

| Cmpd # | Structure | MS |
|---|---|---|
| 71 | 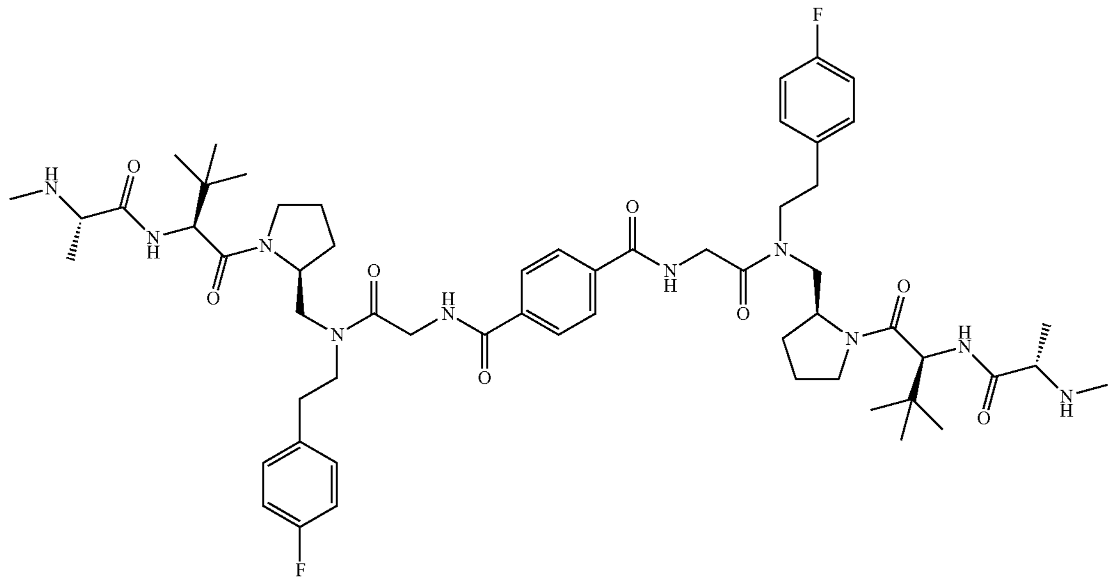 | (M + 2)/2 = 543.4 |
| 72 | 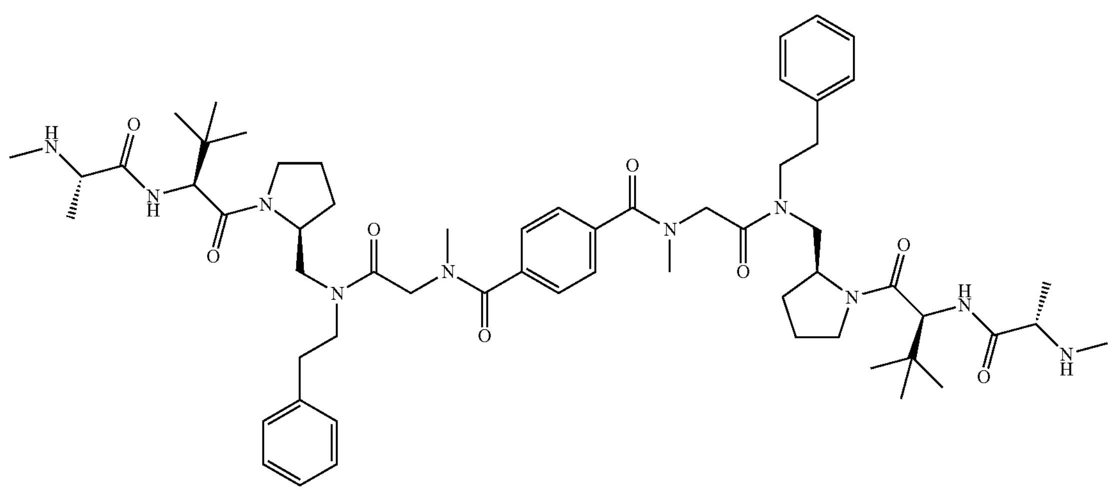 | M + 1 = 1077.6<br>(M + 2)/2 = 539.4 |

TABLE 1-continued
| Cmpd # | Structure | MS |
|---|---|---|
| 73 | 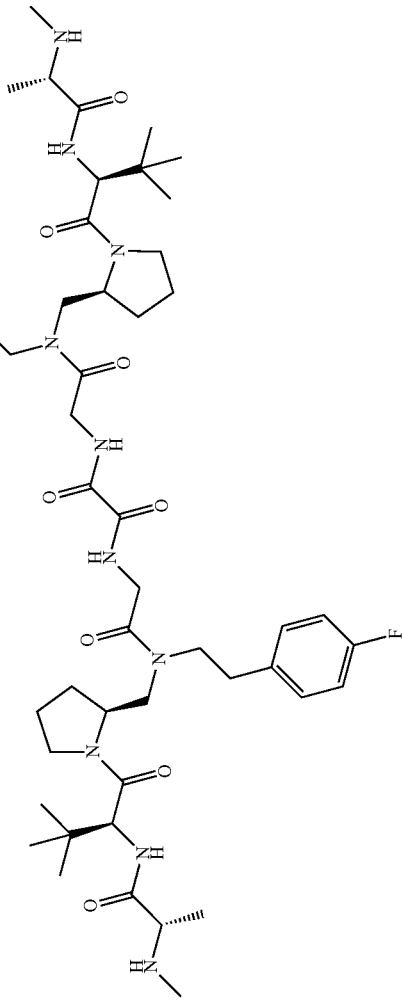 | M + 1 = 1009.6<br>(M + 2)/2 = 505.4 |

TABLE 1-continued
| Cmpd # | Structure | MS |
|---|---|---|
| 74 | 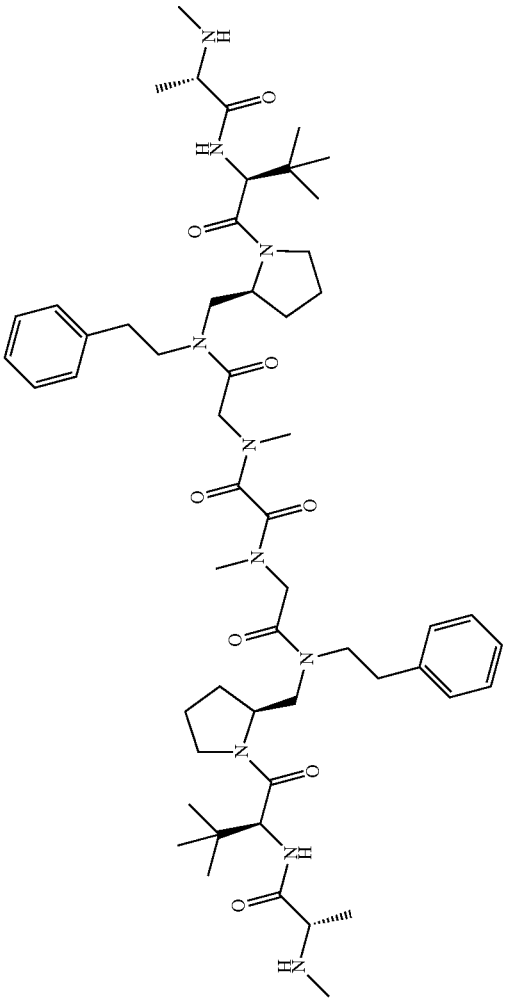 | M + 1 = 1001.6<br>(M + 2)/2 = 501.4 |

TABLE 1-continued
| Cmpd # | Structure | MS |
|---|---|---|
| 75 | 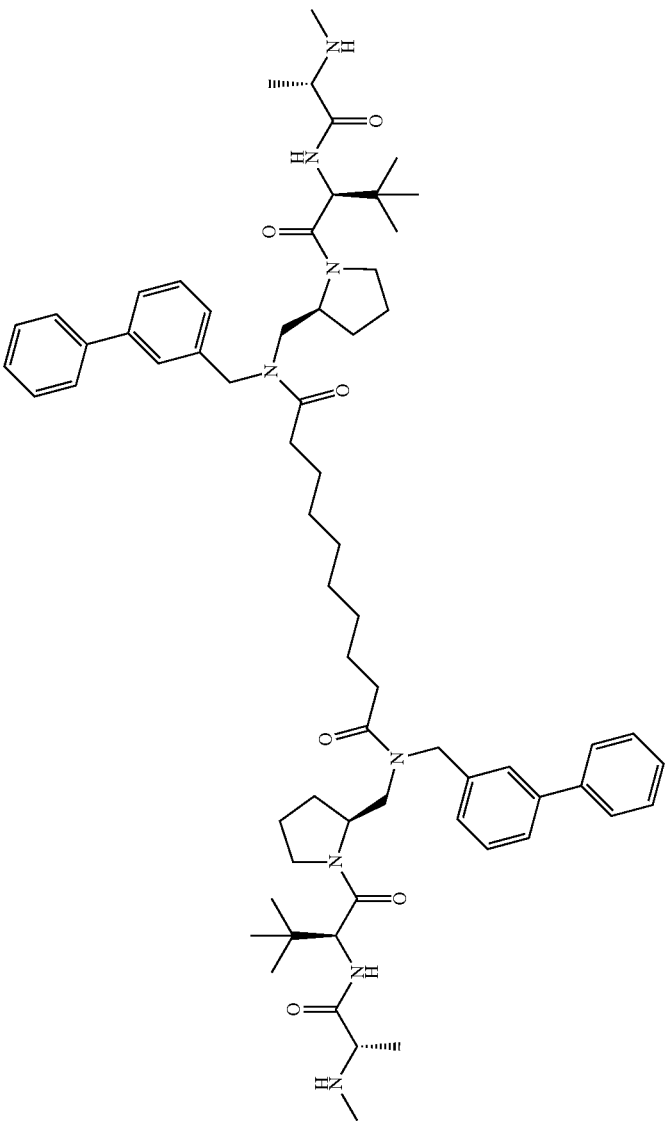 | M + 1 = 1095.6<br>(M + 2)/2 = 548.4 |

TABLE 1-continued
| Cmpd # | Structure | MS |
|---|---|---|
| 76 | 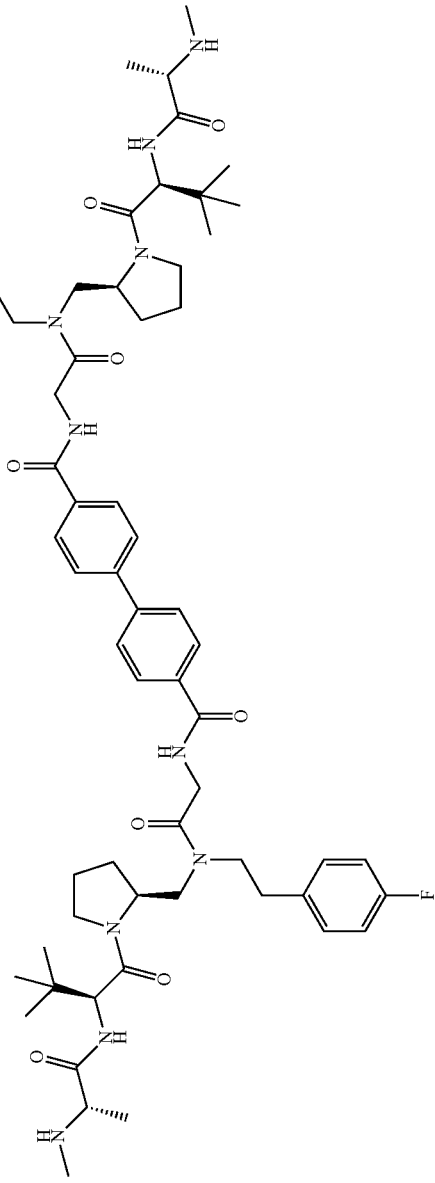 | (M + 2)/2 = 581.4 |

TABLE 1-continued
| Cmpd # | Structure | MS |
|---|---|---|
| 77 | 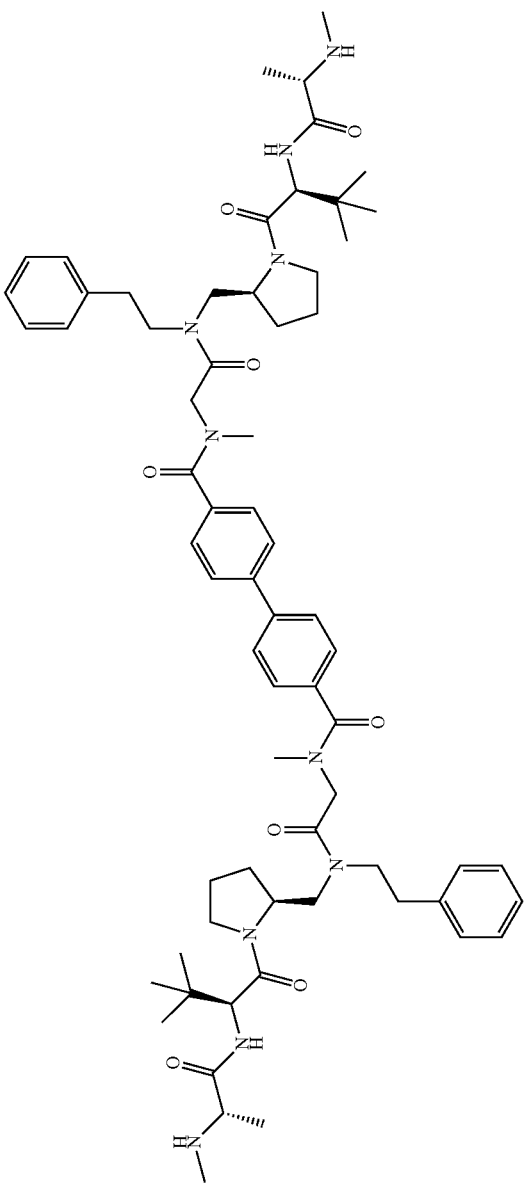 | M + 1 = 1153.6<br>(M + 2)/2 = 577.4 |
| 78 | 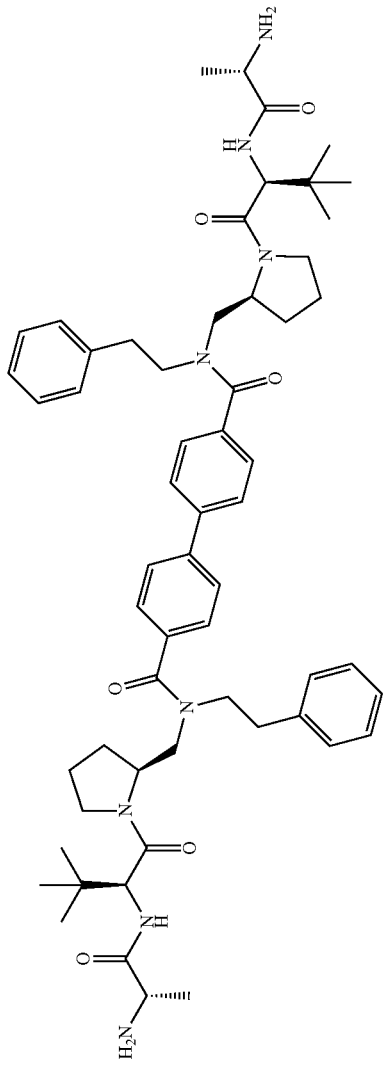 | M + 1 = 983.6<br>(M + 2)/2 = 492.4 |

TABLE 1-continued

| Cmpd # | Structure | MS |
|---|---|---|
| 79 | 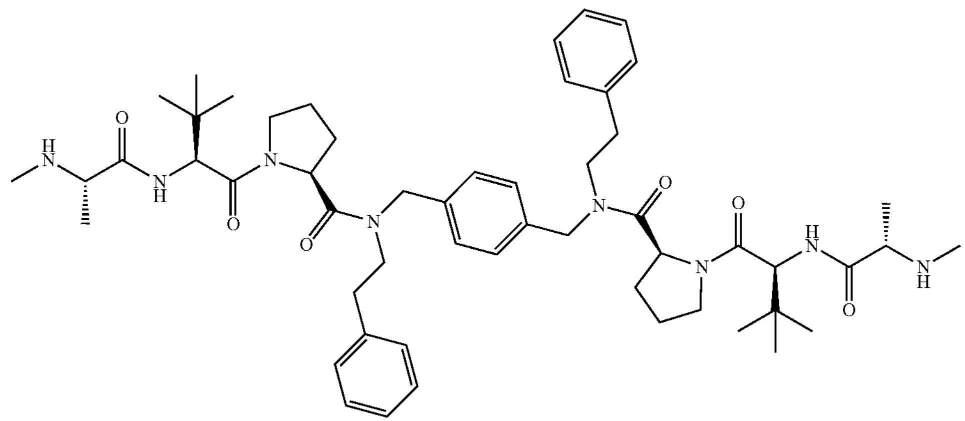 | (M + 2)/2 = 468.4 |
| 80 | 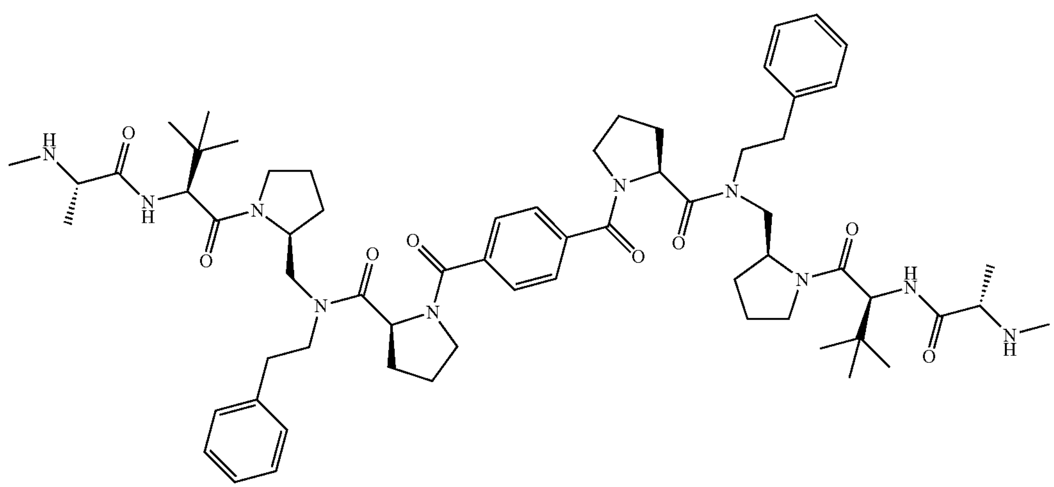 | M + 1 = 1129.6<br>(M + 2)/2 = 565.4 |

TABLE 1-continued

| Cmpd # | Structure | MS |
|---|---|---|
| 81 | 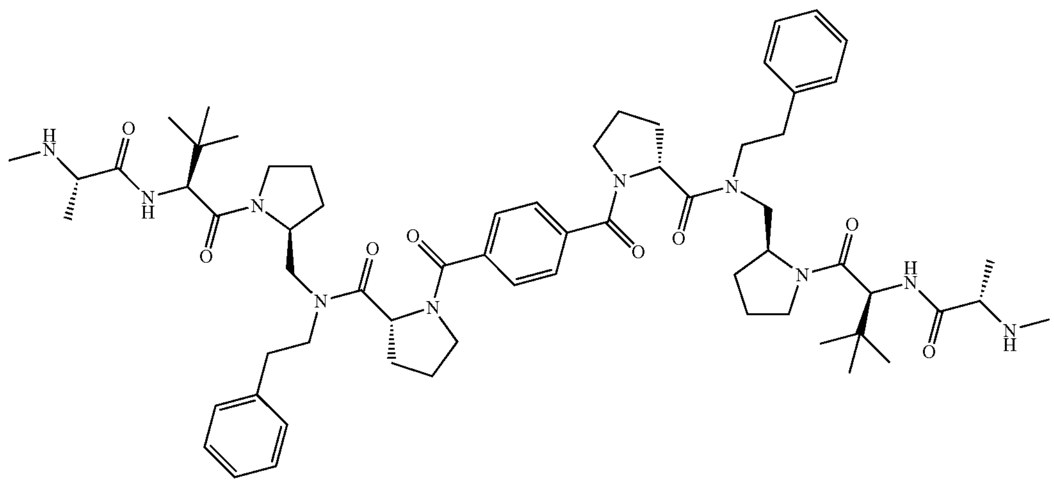 | M + 1 = 1129.6<br>(M + 2)/2 = 565.4 |
| 82 | 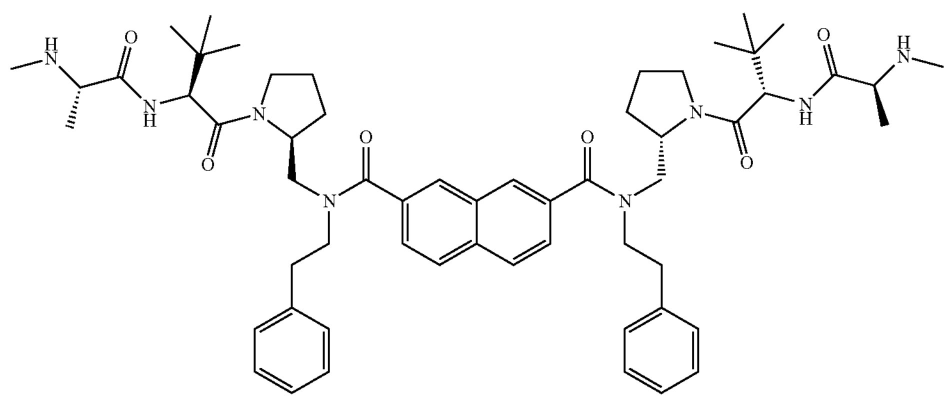 | M + 1 = 985.6<br>(M + 2)/2 = 493.6 |

TABLE 1-continued

| Cmpd # | Structure | MS |
|---|---|---|
| 83 | 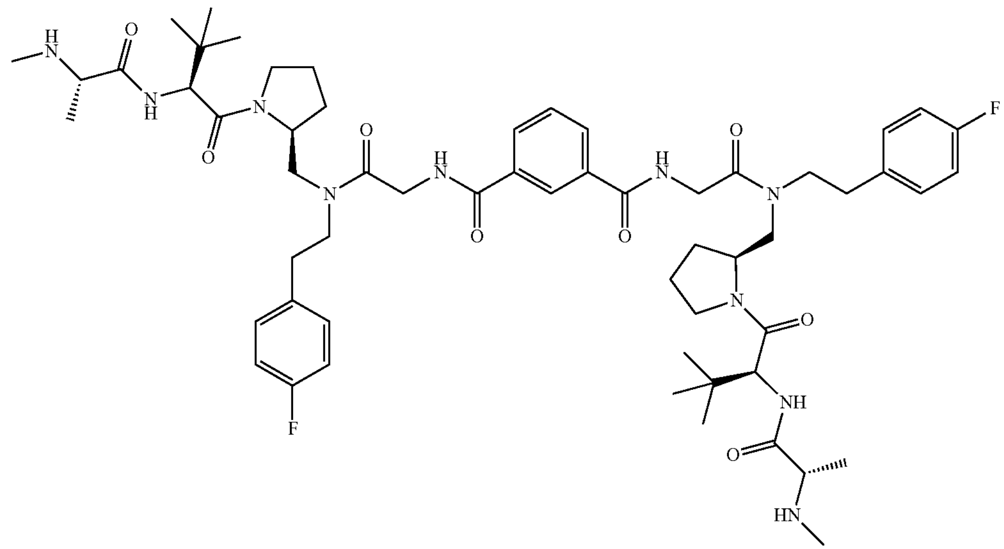 | M + 1 = 1085.8<br>(M + 2)/2 = 543.4 |
| 84 | 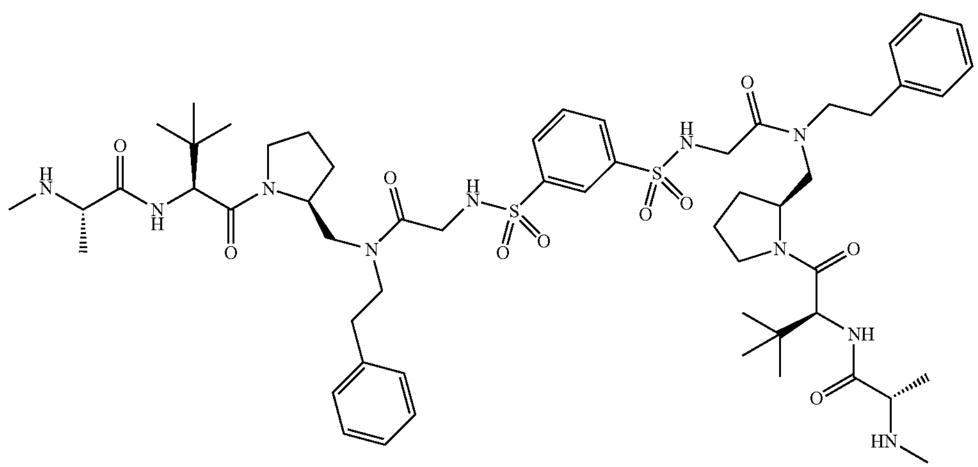 | M + 1 = 1121.6<br>(M + 2)/2 = 561.4 |

| Cmpd # | Structure | MS |
|---|---|---|
| 85 | 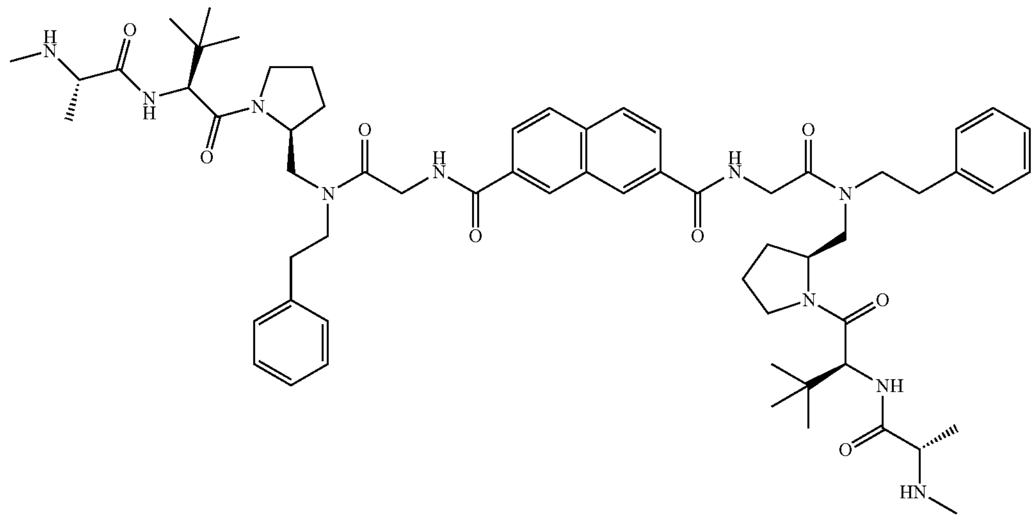 | M + 1 = 1099.6<br>(M + 2)/2 = 550.6 |
| 86 | 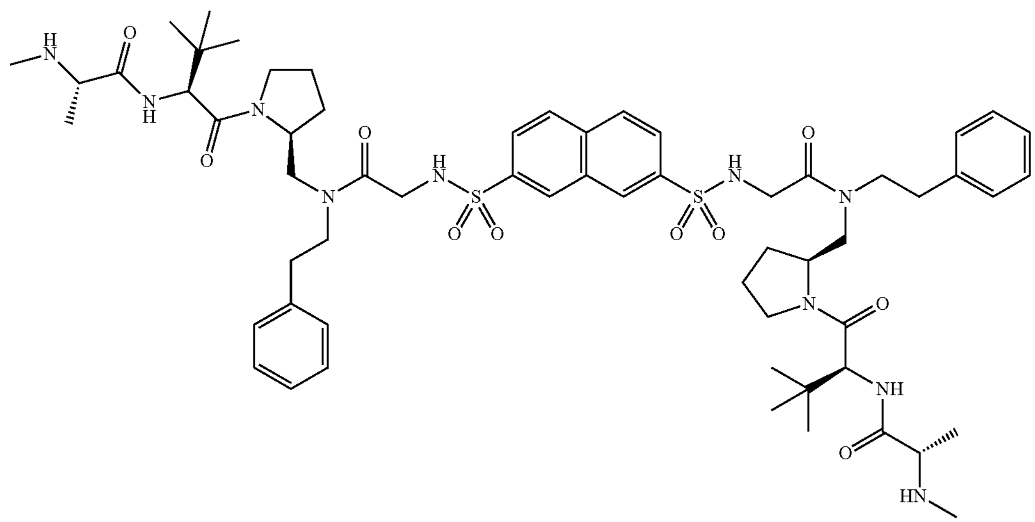 | M + 1 = 1171.8<br>(M + 2)/2 = 586.6 |

TABLE 1-continued

| Cmpd # | Structure | MS |
|---|---|---|
| 87 | 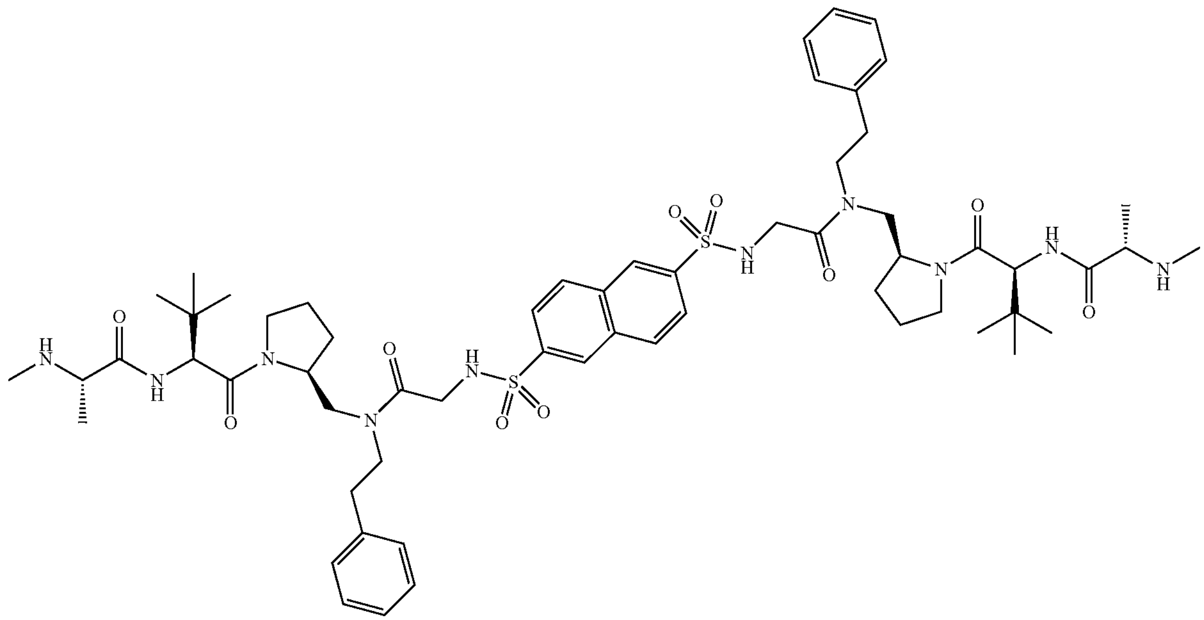 | M + 1 = 1171.8<br>(M + 2)/2 = 586.6 |
| 88 | 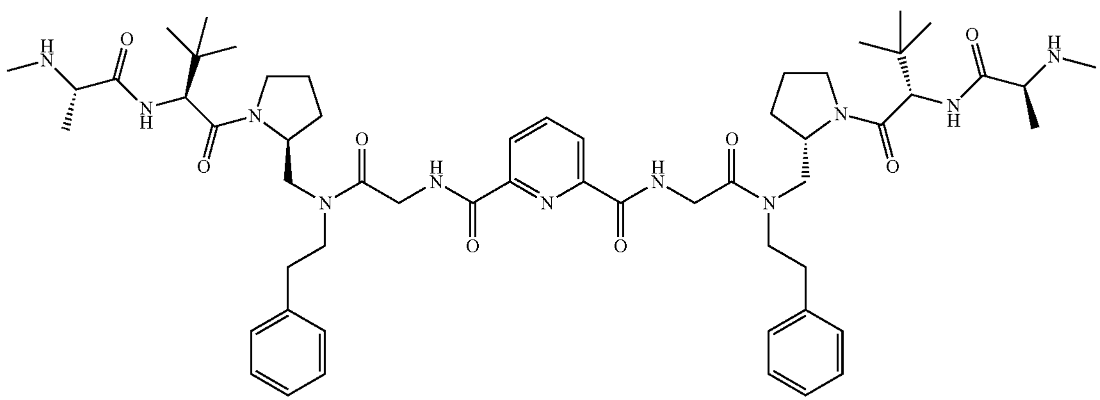 | M + 1 = 1050.8<br>(M + 2)/2 = 526.0 |

TABLE 1-continued
| Cmpd # | Structure | MS |
|---|---|---|
| 89 | 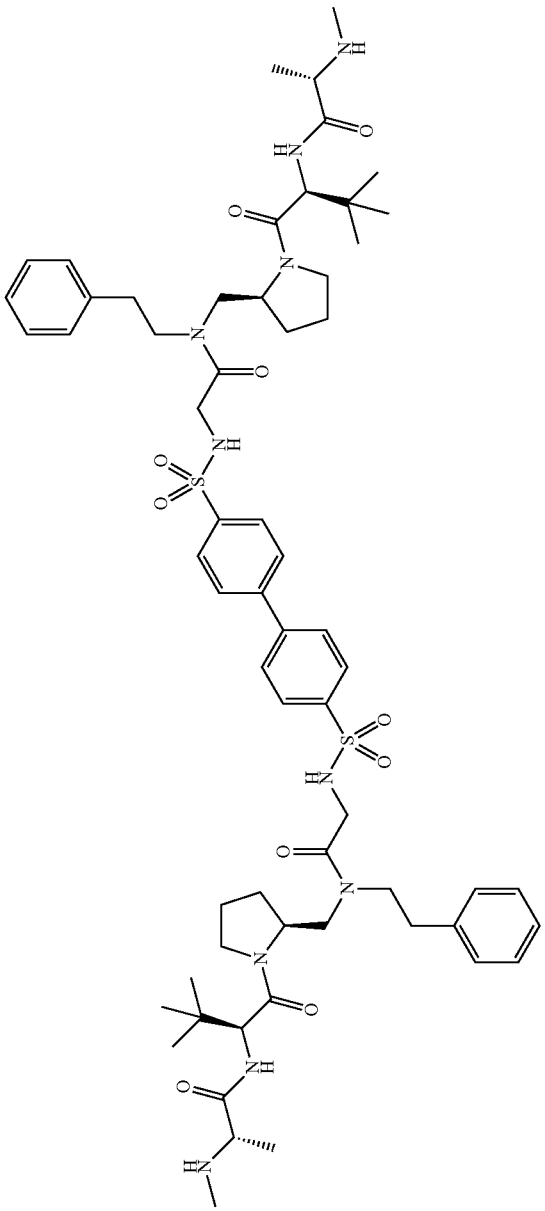 | M + 1 = 1197.8 (M + 2)/2 = 599.6 |
| 90 | 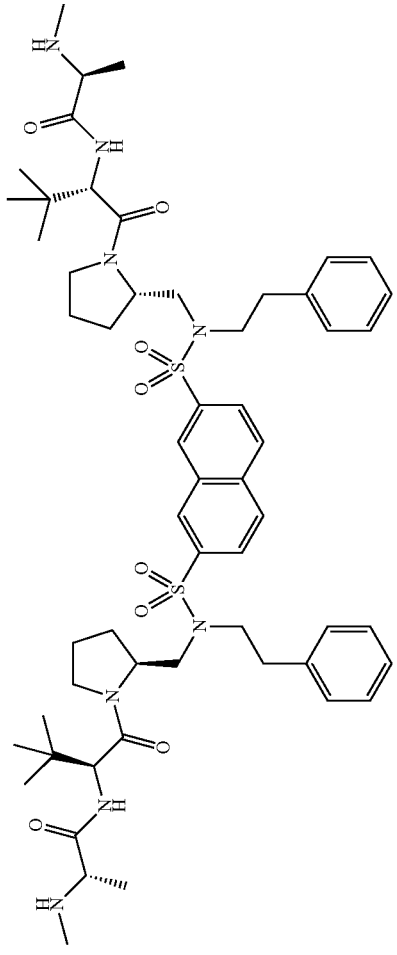 | M + 1 = 1057.6 (M + 2)/2 = 529.4 |

TABLE 1-continued

| Cmpd # | Structure | MS |
|---|---|---|
| 91 | 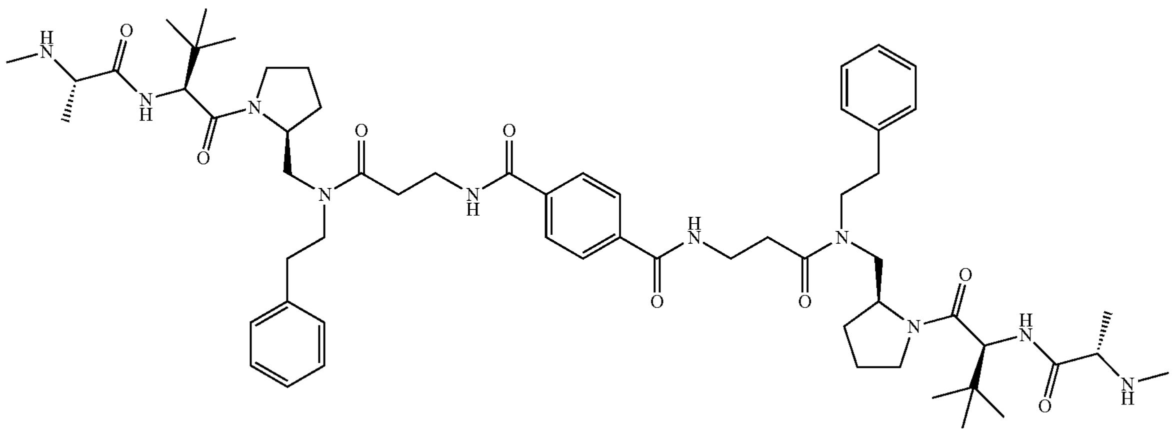 | M + 1 = 1077.8<br>(M + 2)/2 = 539.4 |
| 92 | 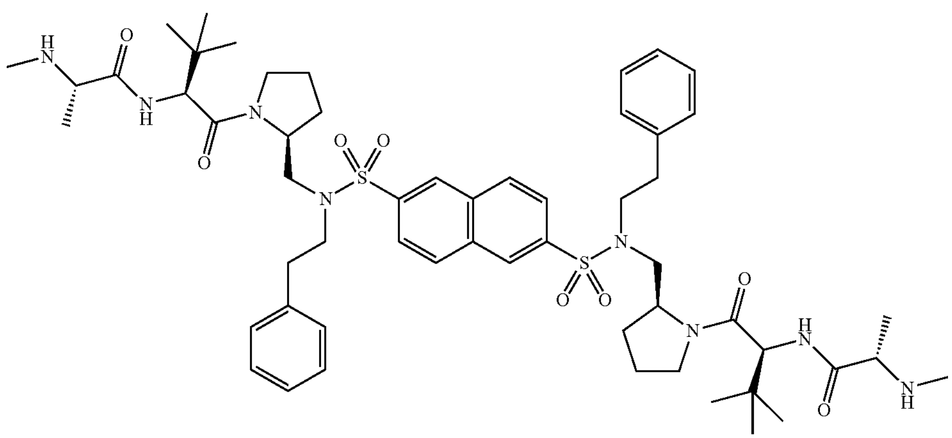 | M + 1 = 1057.4<br>(M + 2)/2 = 529.4 |

TABLE 1-continued

| Cmpd # | Structure | MS |
|---|---|---|
| 93 | 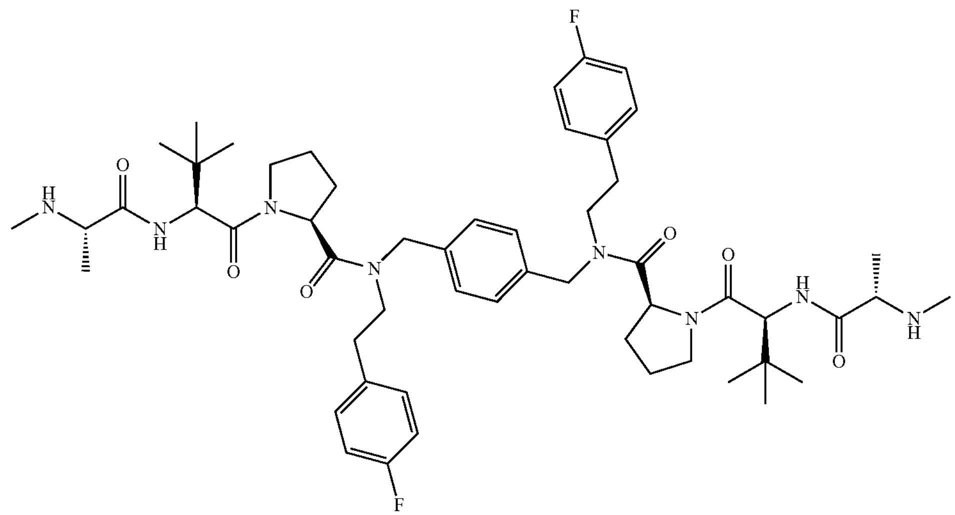 | (M + 2)/2 = 486.4 |
| 94 | 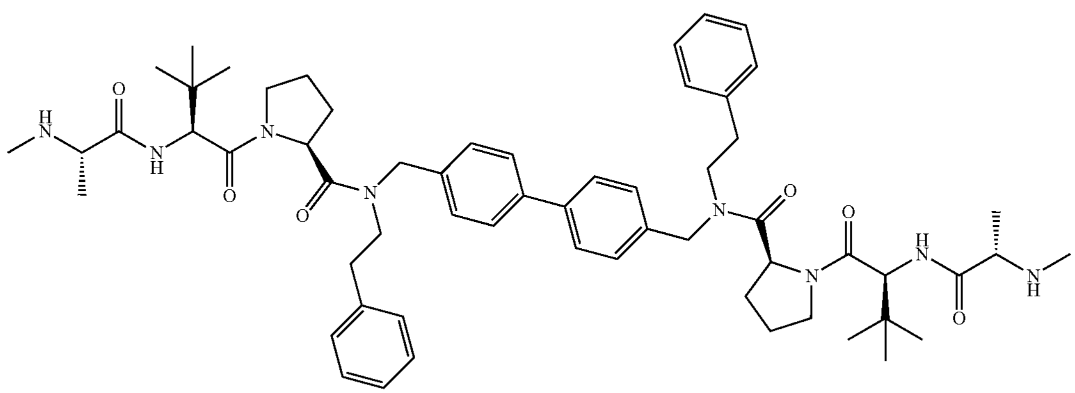 | M + 1 = 1011.8<br>(M + 2)/2 = 506.4 |

TABLE 1-continued
| Cmpd # | Structure | MS |
|---|---|---|
| 95 | 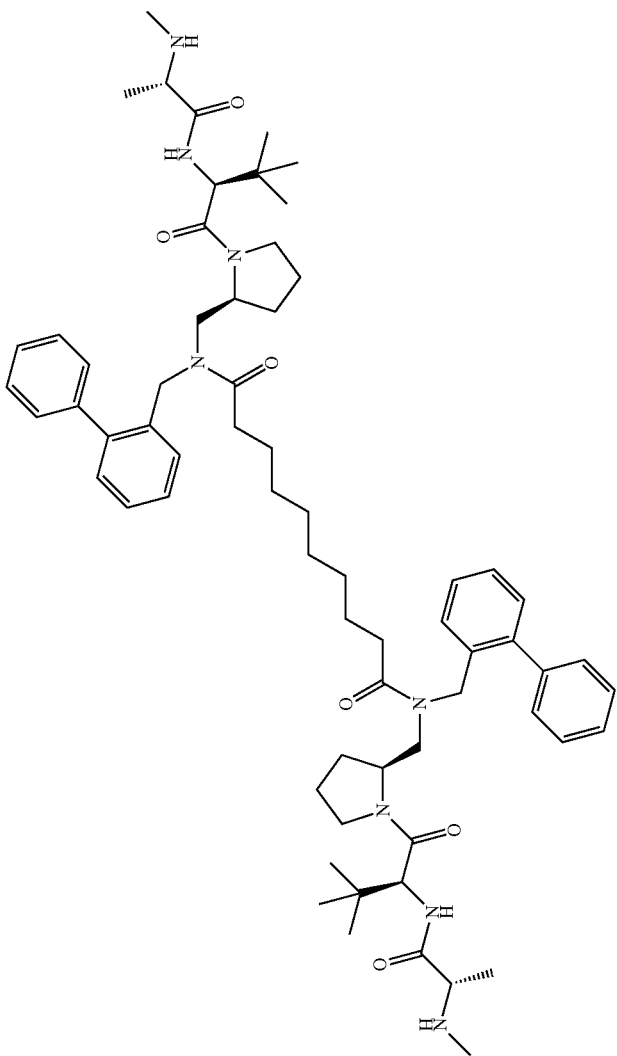 | M + 1 = 1095.8<br>(M + 2)/2 = 548.6 |

TABLE 1-continued

| Cmpd # | Structure | MS |
|---|---|---|
| 96 | 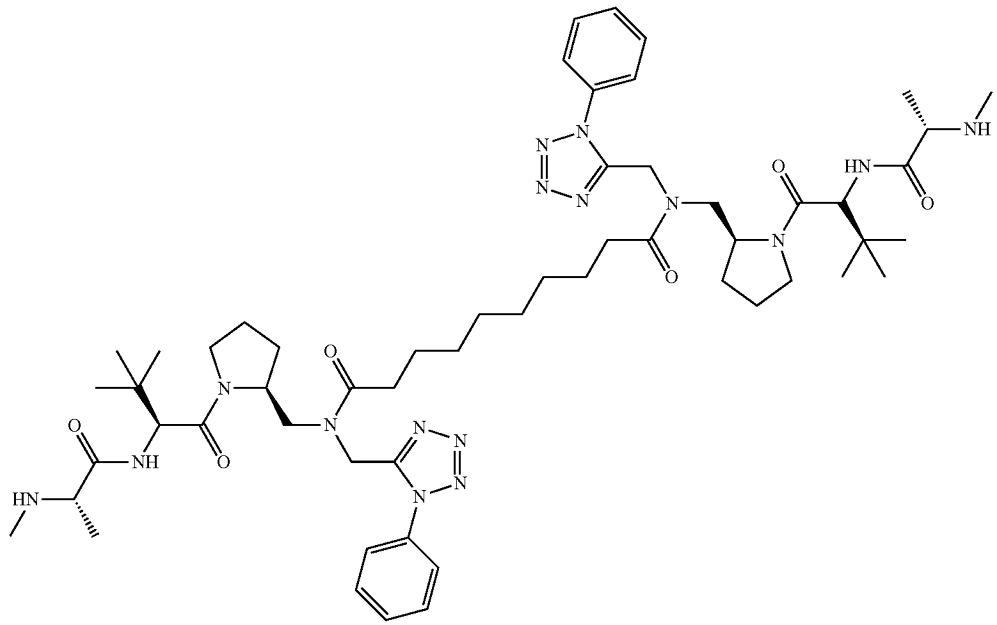 | M + 1 = 1079.8 (M + 2)/2 = 540.6 |
| 97 | 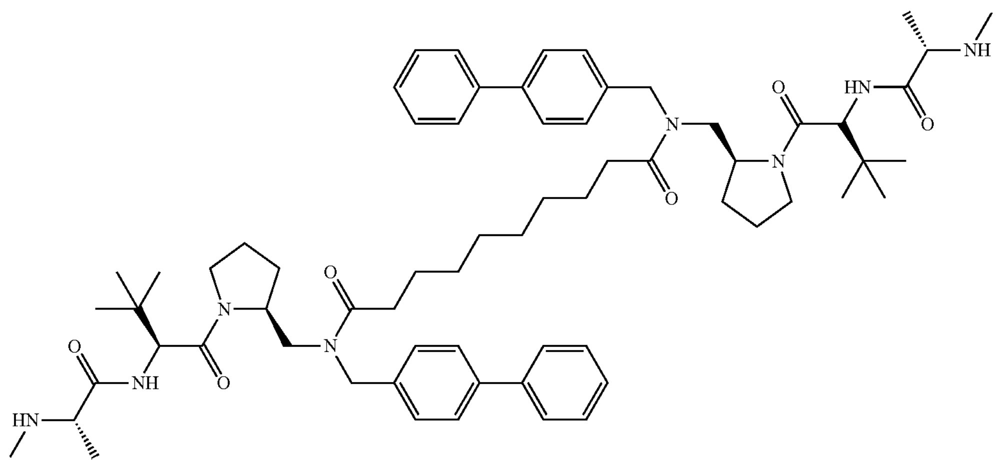 | M + 1 = 1095.8 (M + 2)/2 = 548.6 |

TABLE 1-continued

| Cmpd # | Structure | MS |
|---|---|---|
| 98 | 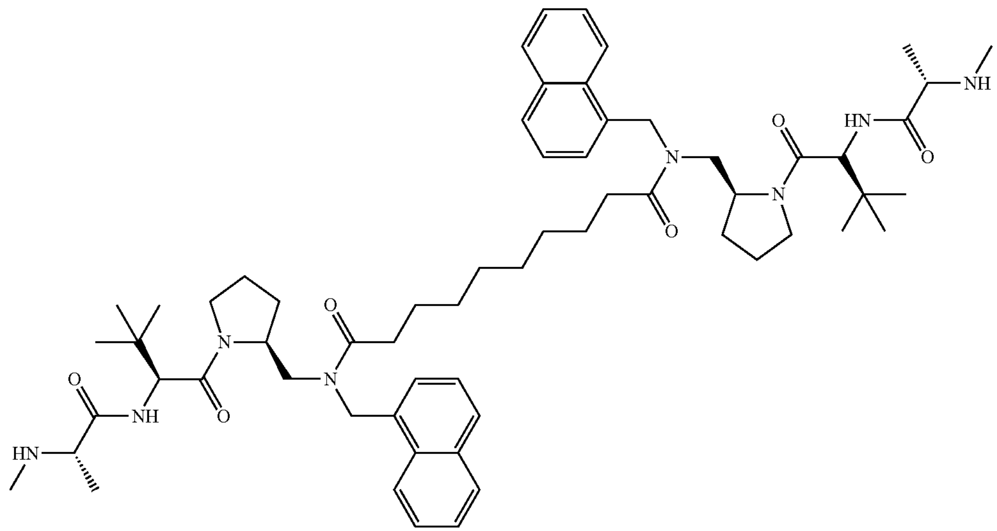 | M + 1 = 1043.8<br>(M + 2)/2 = 522.6 |
| 99 | 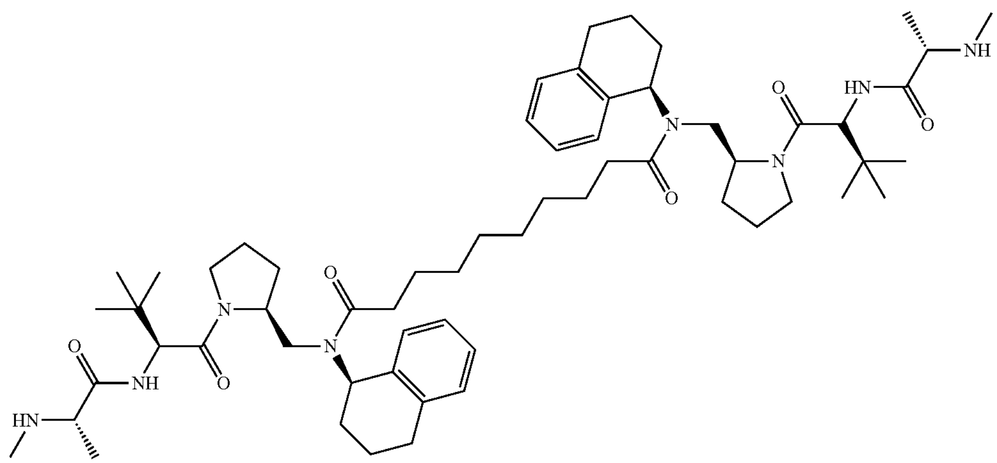 | M + 1 = 1023.8<br>(M + 2)/2 = 512.4 |

TABLE 1-continued
| Cmpd # | Structure | MS |
|---|---|---|
| 100 | 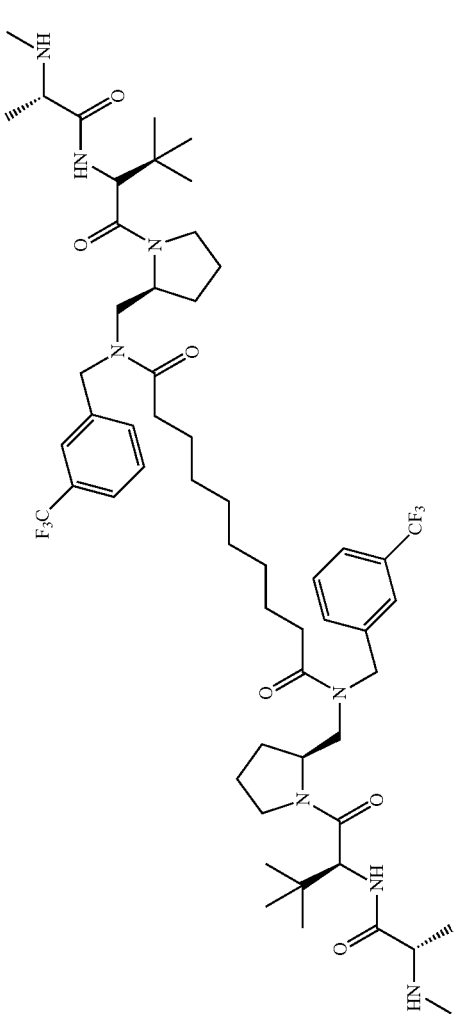 | M + 1 = 1079.6 (M + 2)/2 = 540.4 |
| 101 | 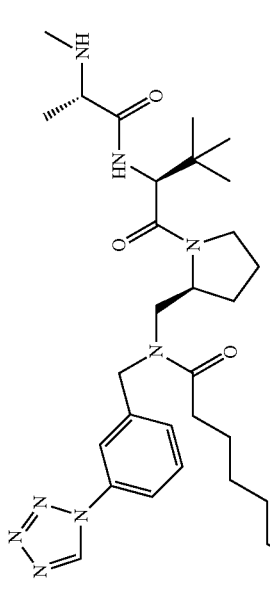 | M + 1 = 1079.8 (M + 2)/2 = 540.4 |

TABLE 1-continued
| Cmpd # | Structure | MS |
|---|---|---|
| 102 | 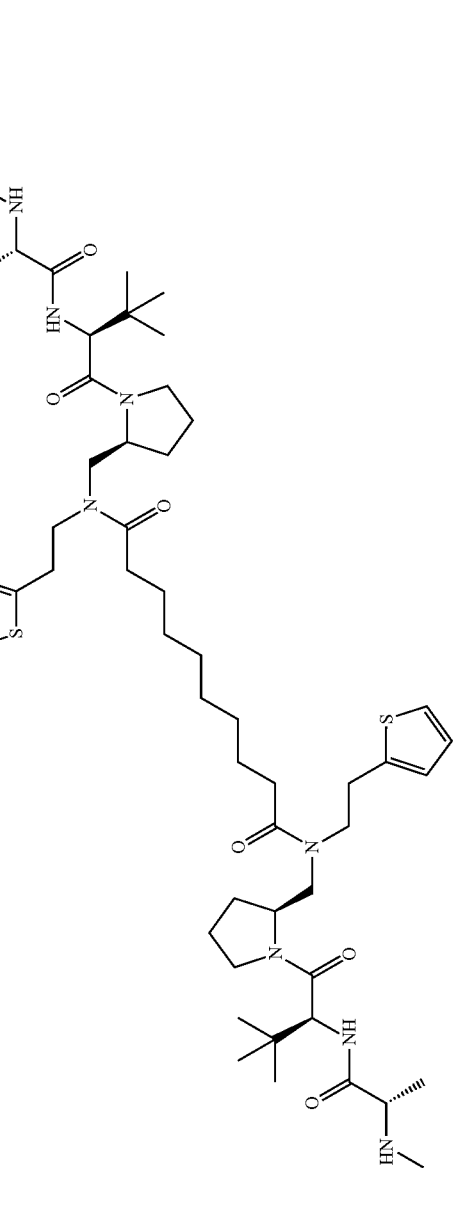 | M + 1 = 983.8 (M + 2)/2 = 492.4 |
| 103 | 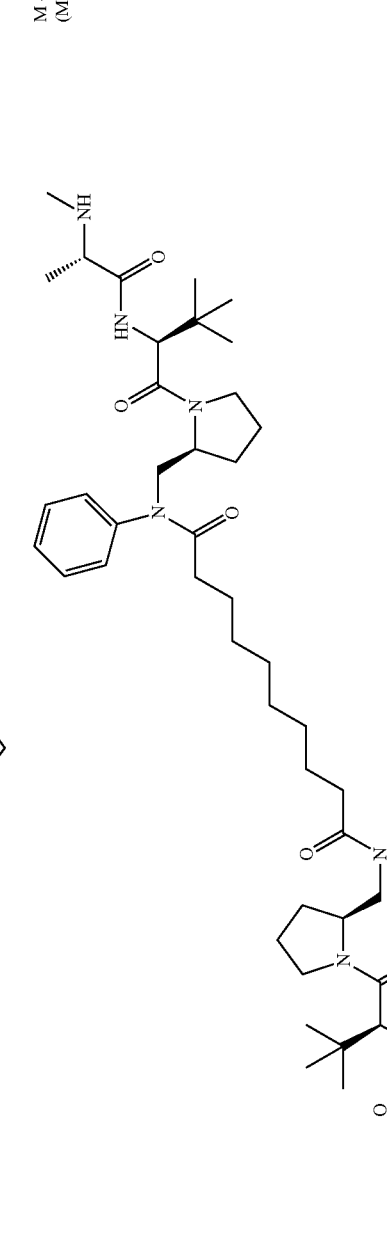 | M + 1 = 915.8 (M + 2)/2 = 458.4 |

TABLE 1-continued
| Cmpd # | Structure | MS |
|---|---|---|
| 104 | 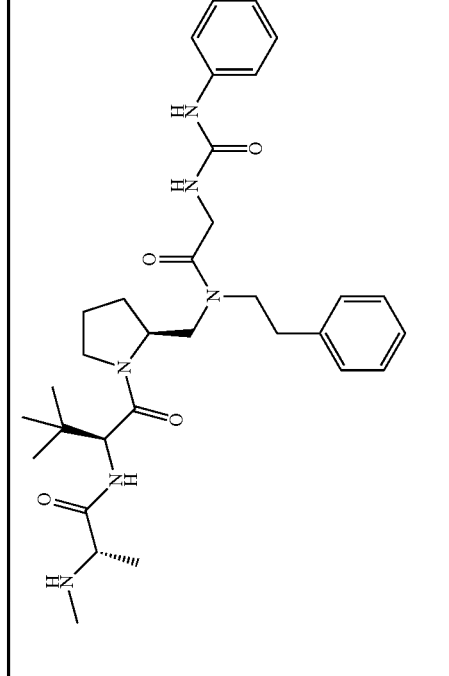 | M + 1 = 1079.8<br>(M + 2)/2 = 540.4 |
| 105 | 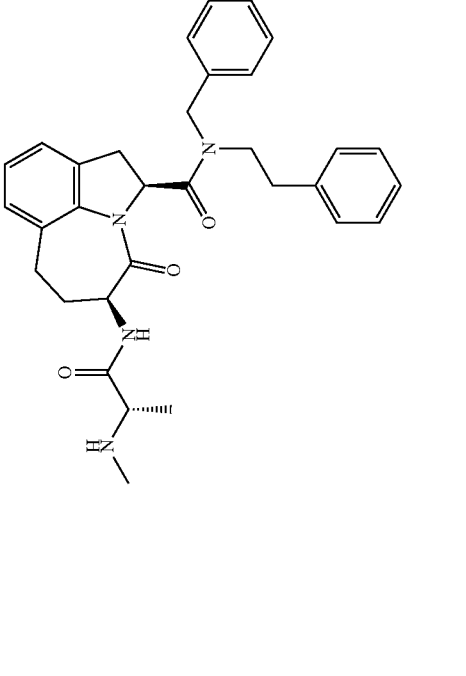 | M + 1 = 971.6<br>(M + 2)/2 = 486.4 |

Representative compounds of the present invention which can be prepared by simple modification of the above procedures are illustrated in Table 2:
TABLE 2
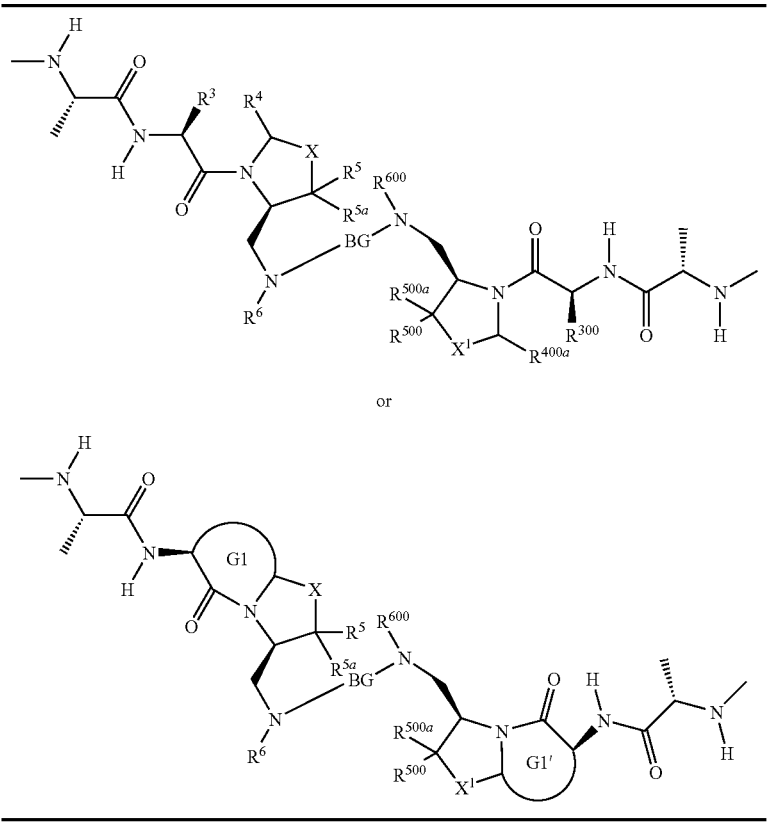
X may be chosen from $CH_2$, $CF_2$, O or S;
and n may be 1, 2, or 3;
and BG may be chosen from the groups consisting of:
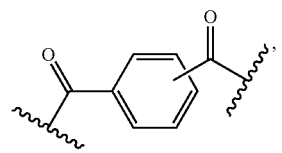
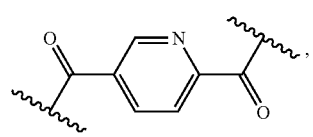
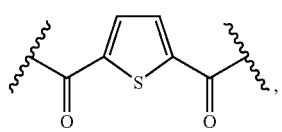
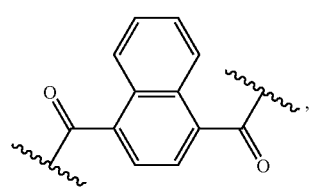
-continued
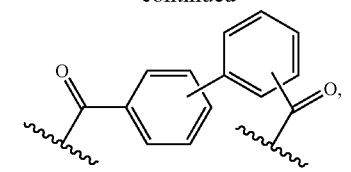
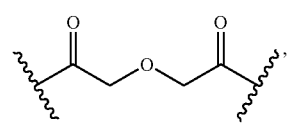
n = 1-11
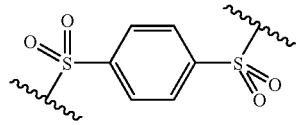

235
-continued
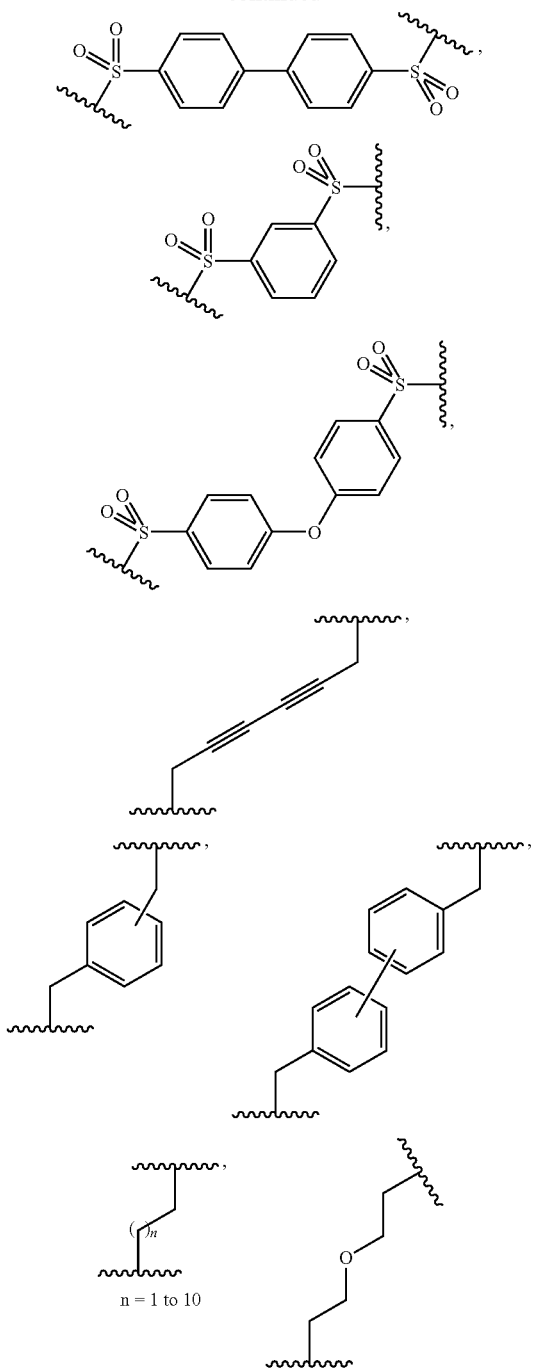
n = 1 to 10
and $R^{3/300}$ are as defined herein
and $R^{6/600}$ are independently chosen from H, alkyl or:
236
-continued
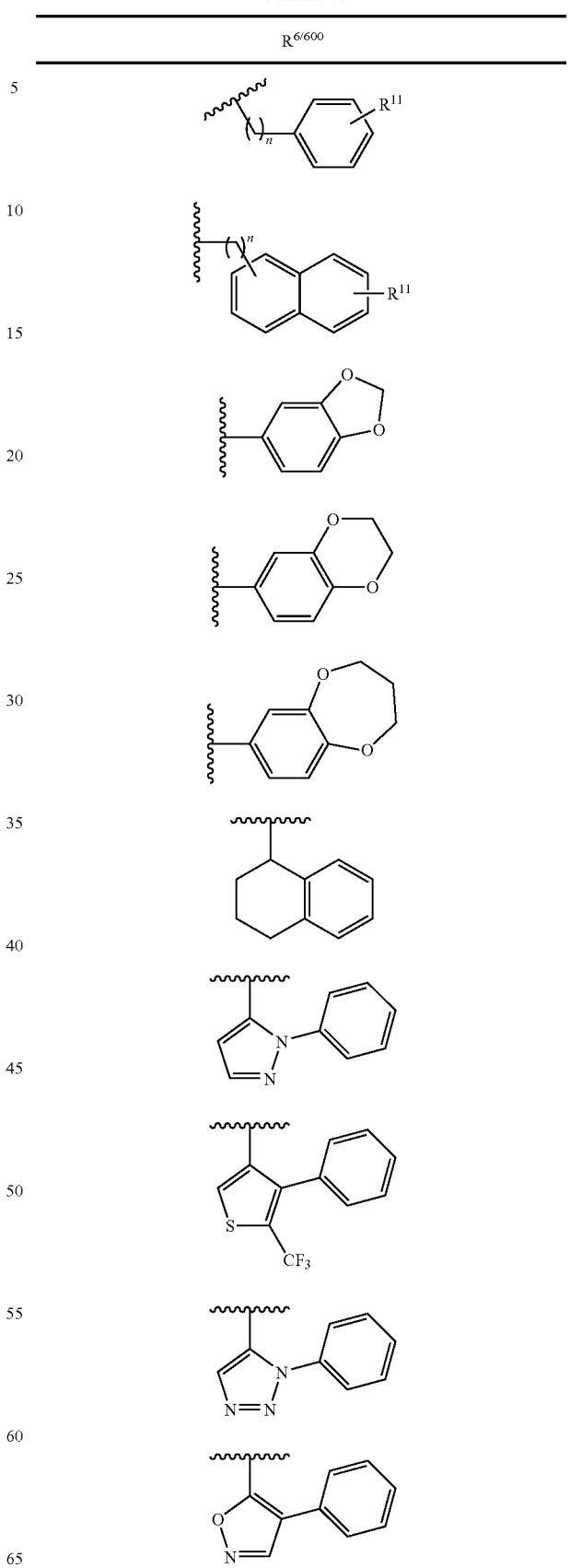

-continued $R^{6/600}$

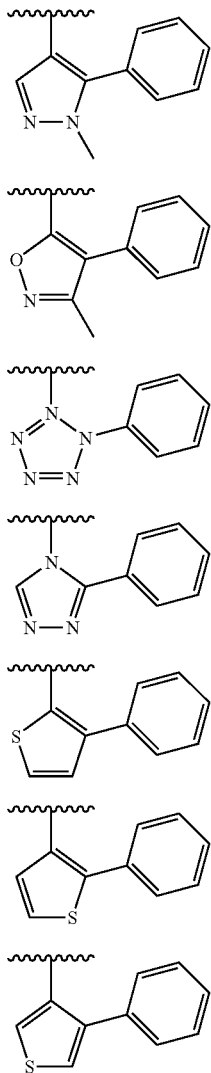

Representative compounds of the present invention which can be prepared by simple modification of the above procedures are illustrated below:

Wherein $R^4$, $R^5$, $R^{5a}$, $R^6$, $R^{400}$, $R^{500}$, $R^{500a}$, $R^{600}$, X, $X^{100}$ and BG are defined herein;

and $R^3$ and $R^{300}$ are independently chosen from the following: —CHOR$^7$, —C(CH$_3$)OR$^7$, or —CH$_2$CH$_2$OR$^7$; wherein $R^7$ is defined as —C(O)R$^8$, and $R^8$ is alkyl, aryl, or heteroaryl, wherein the alkyl may be further substituted by $R^7$, and the aryl and heteroaryl may be further substituted by $R^{11}$.

Assays

Molecular Constructs for Expression

GST-XIAP BIR3RING: XIAP coding sequence amino acids 246-497 cloned into PGEX2T1 via BamH1 and AVA I. The plasmid was transformed into E. coli DH5α for use in protein expression and purification.

GST-HIAP2 (cIAP-1) BIR 3: HIAP2 coding sequence from amino acids 251-363 cloned into PGex4T3 via BamH1 and XhoI. The plasmid was transformed into E. coli DH5a for use in protein expression and purification.

GST-HIAP1 (cIAP-2) BIR 3: HIAP1 coding sequence from amino acids 236-349, cloned into PGex4T3 via BamH1 and XhoI. The plasmid was transformed into E. coli DH5α for use in protein expression and purification.

GST-linker BIR 2 BIR3Ring: XIAP coding sequence from amino acids 93-497 cloned into PGex4T1 via BamH1 and XhoI. Amino acids 93-497 were amplified from full length XIAP in pGex4t3, using the primers: TTAATAGGATCCAT-CAACGGCTTTTATC and GCTGCATGTGTGTCAGAGG, using standard PCR conditions. The PCR fragment was TA cloned into pCR-2.1 (Invitrogen). Linker BIR 2 BIR 3Ring was subcloned into pGex4T1 by BamHI/XhoI digestion. The plasmid was transformed into E. coli DH5α for use in protein expression and purification.

Full-length human XIAP, AEG plasmid number 23. XIAP coding sequence amino acids 1-497 cloned into GST fusion vector, PGEX4T1 via BamH1 and Xho I restriction sites. The plasmid was transformed into E. coli DH5α for use in protein purification.

GST-XIAP linker BIR 2: XIAP linker BIR 2 coding sequence from amino acids 93-497 cloned into pGex4T3 via BamHI and XhoI. The plasmid was transformed into E. coli DH5α for use in protein expression and purification.

Synthesis of Fluorescent Probe for FP Assay

A fluorescent peptide probe, Fmoc-Ala-Val-Pro-Phe-Tyr(t-Bu)-Leu-Pro-Gly(t-Bu)-Gly-OH was prepared using standard Fmoc chemistry on 2-chlorotrityl chloride resin (Int. J. Pept. Prot. Res. 38:555-561, 1991). Cleavage from the resin was performed using 20% acetic acid in dichloromehane (DCM), which left the side chain still blocked. The C-terminal protected carboxylic acid was coupled to 4'-(aminom-

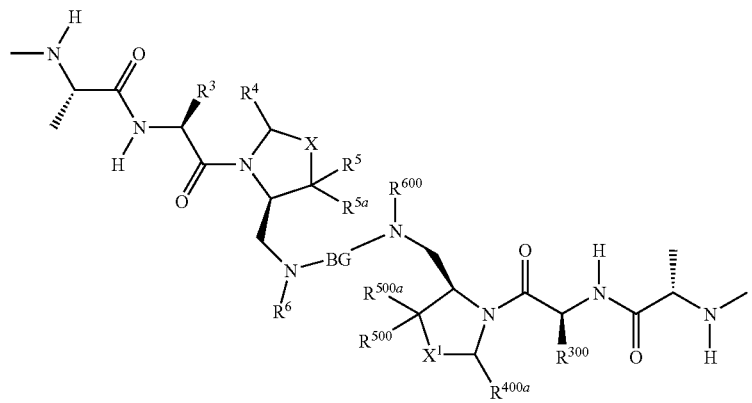

ethy)fluorescein (Molecular Probes, A-1351; Eugene, Oreg.) using excess diisopropylcarbodiimide (DIC) in dimethylformamide (DMF) at room temperature and was purified by silica gel chromatography (10% methanol in DCM). The N-terminal Fmoc protecting group was removed using piperidine (20%) in DMF, and purified by silica gel chromatography (20% methanol in DCM, 0.5% HOAc). Finally, the t-butyl side chain protective groups were removed using 95% trifluoroacetic acid containing 2.5% water and 2.5% triisopropyl silane. The peptide obtained displayed a single peak by HPLC (>95% pure).

Fluorescent probes may be prepared using monomeric BIR binding units or bridged BIR binding compounds of the instant invention by means of the chemistries described herein, to yield probes characterized by compound 106.
Probe P2:

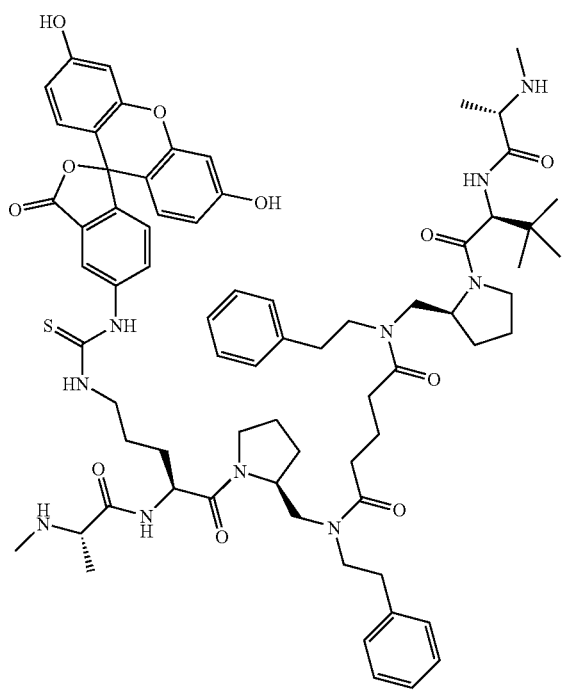

106

Expression and Purification of Recombinant Proteins
A. Recombinant Proteins Expression Glutathione S-transferase (GST) tagged proteins were expressed in *Escherichia coli* strains DH5-alpha. For expression full length XIAP, individual or combinations of XIAP-BIR domains, cIAP-1, cIAP-2 and Livin transformed bacteria were cultured overnight at 37° C. in Luria Broth (LB) medium supplemented with 50 ug/ml of ampicillin. The overnight culture was then diluted 25 fold into fresh LB ampicillin supplemented media and bacteria were grown up to $A_{600}$=0.6 then induced with 1 mM isopropyl-D-1-thiogalactopyranoside for 3 hours. Upon induction, cells were centrifuged at 5000 RPM for 10 minutes and the media was removed. Each pellet obtained from a 1 liter culture received 10 ml of lysis buffer (50 mM Tris-HCl, 200 mM NaCl, 1 mM DTT, 1 mM PMSF, 2 mg/ml of lysozyme, 100 μg/ml)), was incubated at 4° C. with gentle shaking. After 20 minutes of incubation, the cell suspension was placed at −80° C. overnight or until needed.

B. Purification of Recombinant Proteins

For purification of recombinant proteins, the IPTG-induced cell lysate was thawed vortexed and then disrupted by flash freezing in liquid nitrogen two times with vortexing after each thaw. The cells were disrupted further by passing the extract four times through a Bio-Neb Cell disruptor device (Glas-col) set at 100 psi with Nitrogen gas. The extract was clarified by centrifugation at 4 C at 15000 RPM in a SS-34 Beckman rotor for 30 minutes. The resulting supernatant was then mixed with 2 ml of glutathione-Sepharose beads (Pharmacia) per 500 ml cell culture (per 1000 ml culture for full length XIAP) for 1 hour at 4 C. Afterwards, the beads were washed 3 times with 1× Tris-Buffered Saline (TBS) to remove unbound proteins. The retained proteins were eluted with 2 washes of 2 ml of 50 mM TRIS pH 8.0 containing 10 mM reduced glutathione. The eluted proteins were pooled and precipitated with 604 g/liter of ammonium sulfate and the resulting pellet re-suspended into an appropriate buffer. As judged by SDS-PAGE the purified proteins were >90% pure. The protein concentration of purified proteins was determined from the Bradford method.

His-tag proteins were expressed in the *E. Coli* strain in *E. coli* AD494 cells using a pet28ACPP32 construct. The soluble protein fraction was prepared as described above. For protein purification, the supernatant was purified by affinity chromatography using chelating-Sepharose (Pharmacia) charged with $NiSO_4$ according to the manufacturer's instructions. Purity of the eluted protein was >90% pure as determined by SDS-PAGE. The protein concentration of purified proteins was determined from the Bradford assay.
Binding Assay
Fluorescence Polarization-Based Competition Assay For all assays, the fluorescence and fluorescence-polarization was evaluated using a Tecan Polarion instrument with the excitation filter set at 485 nm and the emission filter set at 535 nm. For each assay, the concentration of the target protein was first established by titration of the selected protein in order to produce a linear dose-response signal when incubated alone in the presence of the fluorescent probe. Upon establishing these conditions, the compounds potency ($IC_{50}$) and selectivity, was assessed in the presence of a fix defined-amount of target protein and fluorescent probe and a 10 point serial dilution of the selected compounds. For each $IC_{50}$ curve, the assays were run as followed: 25 uL well of diluted compound in 50 mM MES buffer pH 6.5 were added into a black 96 well plate then 25 uL well of bovine serum albumin (BSA) at 0.5 mg/ml in 50 mM MES pH 6.5. Auto-fluorescence for each compound was first assessed by performing a reading of the compound/BSA solution alone. Then 25 uL of the fluorescein probe diluted into 50 mM MES containing 0.05 mg/ml BSA were added and a reading to detect quenching of fluorescein signal done. Finally 25 uL/well of the target or control protein (GST-BIRS) diluted at the appropriate concentration in 50 mM MES containing 0.05 mg/ml BSA were added and the fluorescence polarization evaluated.
Determination of $IC_{50}$ and Inhibitory Constants For each assay the relative polarization-fluorescence units were plotted against the final concentrations of compound and the $IC_{50}$ calculated using the Grad pad prism software and/or Cambridge soft. The $k_i$ value were derived from the calculated $IC_{50}$ value as described above and according to the equation described in Nikolovska-Coleska, Z. (2004) Anal Biochem 332, 261-273.

Selected compound of the instant invention were shown to bind to the BIR3 domain of c-IAP1, c-IAP2 and XIAP, and to the linker-BIR2-BIR3-RING of XIAP with $k_i$s of <1 uM.

Caspase-3 Full Length XIAP, Linker BIR2 or Linker-BIR2-BIR3-Ring Derepression Assay In order to determine the relative activity of the selected compound against XIAP-Bir2, we setup an in vitro assay where caspase-3 was inhibited by GST fusion proteins of XIAP linker-Bir2, XIAP Linker Bir2-Bir3-RING or full-length XIAP. Caspase 3 (0.125 uL) and 12.25-34.25 nM (final concentration) of GST-XIAP fusion protein (GST-Bir2, GST-Bir2Bir3RING or full-length XIAP) were co-incubated with serial dilutions of compound (200 uM-5 pM). Caspase 3 activity was measured by overlaying 25 uL of a 0.4 mM DEVD-AMC solution. Final reaction volume was 100 ul. All dilutions were performed in caspase buffer (50 mM Hepes pH 7.4, 100 mM NaCl, 10% sucrose, 1 mM EDTA, 10 mM DTT, 0.1% CHAPS (Stennicke, H. R., and Salvesen, G. S. (1997). Biochemical characteristics of caspase-3, -6, -7, and -8. J. Biol. Chem. 272, 25719-25723).

The fluorescent AMC released from the caspase-3 hydrolysis of the substrate was measured in a TECAN spectrophotometer at 360 nm excitation and 444 nm emission, after 15 minutes of incubation at room temperature. $IC_{50}$ values were calculated on a one or two-site competition model using GraphPad v4.0, using the fluorescence values after 15 minutes of incubation plotted against the log 10 concentration of compound.

Cell-Free Assay
Caspase De-Repression Assay Using Cellular Extracts (Apoptosome)

100 ug of 293 cell S100 extract and 0.25 uM to 20 uM of GST-XIAP fusion protein (XIAP-Bir3RING, XIAP-Bir2Bir3RING, or full-length XIAP) were co-incubated with serial dilutions of compound (40 uM-50 pM). Caspases present in the extracts were activated by adding 1 mM dATP, 0.1 mM ALLN, 133 ug Cytochrome C (final concentrations), and incubating at 37° C. for 25 minutes. All reactions and dilutions used S100 buffer (50 mM Pipes pH 7.0, 50 mM KCl, 0.5 mM EGTA pH 8.0, 2 mM $MgCl_2$ supplemented with 1/1000 dilutions of 2 mg/ml Cytochalisin B, 2 mg/ml Chymotstatin, Leupeptin, Pepstatin, Antipain, 0.1M PMSF, 1M DTT). Final reaction volume was 30 ul. Caspase-3 activity was measured by overlaying 30 ul of a 0.4 mM DEVD-AMC solution. Released AMC cleavage was measured in a TECAN spectrophotometer at 360 nm excitation and 444 nm emissions, on a kinetic cycle of 1 hour with readings taken every 5 minutes. Caspase activity was calculated as $V_o$ of AMC fluorescence/sec. Caspase de-repression by our compounds was compared to fully activated extract and activated extract repressed by the presence of XIAP fusion protein.

Cell Culture and Cell Death Assays
A. Cell Culture

MDA-MD-231 (breast), SKOV-3 (ovarian) and H460 (lung) cancer cells were cultured in RPMI1640 media supplemented with 10% FBS and 100 units/mL of Penicillin and Streptomycin.

B. Assays

Survival assays were preformed on the following transformed human cancer cell lines, MDA-MB-231, SKOV-3, H460, PC3, HCT-116, and SW480 cells. Cells were seeded in 96 well plates at a respective density of 5000 and 2000 cells per well and incubated at 37° C. in presence of 5% $CO_2$ for 24 hours. Selected compounds were diluted into the media at various concentration ranging from 0.00001 uM up to 100 uM. Diluted compounds were added to the culture media. For the MDA-MB-231 SKOV3, H460, PC3, HCT-116, and SW480 cells, the compounds were added either alone or in presence of 1-3 ng/ml of TRAIL. After 48-72 hours cellular viability was evaluated by MTS based assays. A solution of [3-(4,5-dimethylthiazol-2-yl)-5-(3-carboxymethoxyphenyl)-2-(4-sulfophenyl)-2H-tetrazolium, inner salt; MTS] was added onto cells for a period of 1 to 4 hours. Upon incubation the amount of converted MTS was evaluated using a Tecan spectrophotometer set at 570 nm.

MDA-MB-231 and SKOV-3 cells were treated with selected compounds of the present invention and found to have $EC_{50}$s below 200 nM.

Survival MTT Assay

One day prior the treatment with compound, 2000 to 4000 cells per well were plated in a tissue culture treated 96 well format dish with 100 uL of media and incubated at 37° C., 5% $CO_2$. On the day of compound treatment, compounds were diluted with cell culture media to a working stock concentration of 2×. 100 ul of diluted compound were then added to each well. The treated plate was incubated for 72 hours at 37° C., 5% $CO_2$. Upon incubation, the cell viability was assessed as follows; 20 uL of MTT reagent (5 mg/mL) were added per well to cell plate. The plate was incubated for 2 hrs at 37° C. in presence of 5% $CO_2$. The supernatant was then removed from the plate and 100 uL of isopropanol was added. The absorbance was measured in a TECAN spectrophotometer at 570 nm. The percentage of viability was expressed in percentage of the signal obtained with non treated cells.

Table 7 summarizes some of the SAR from compounds represented in Table 1 hereinabove. As such, compounds displayed $EC_{50}$ values against MDA-MB-231 and SKOV-3 cells of <1 μM with many compounds displaying $EC_{50}$ of <50 nM.

TABLE 7

| Compound | MDA-MB231 $EC_{50}$ (nM) | SKOV-3 $EC_{50}$ (nM) |
| --- | --- | --- |
| 1 |  | B |
| 2 |  | A |
| 3 |  | B |
| 4 |  | A |
| 6 |  | C |
| 7 |  | B |
| 9 |  | C |
| 13 |  | B |
| 18 |  | B |
| 20 | A | B |
| 21 | A | A |
| 22 |  | C |
| 26 | A | B |
| 27 |  | C |
| 29 | A | B |
| 31 | A | A |
| 35 | A | A |
| 36 |  | A |
| 43 |  | B |
| 44 |  | A |
| 45 |  | A |
| 46 |  | A |
| 48 |  | B |
| 50 |  | B |
| 56 |  | A |
| 57 |  | B |
| 58 |  | B |
| 59 |  | A |
| 62 |  | C |
| 63 |  | A |
| 64 |  | B |
| 71 |  | A |
| 73 |  | A |
| 75 |  | B |
| 76 |  | A |
| 77 |  | B |
| 79 |  | B |
| 81 |  | C |
| 83 |  | A |

TABLE 7-continued

| Compound | MDA-MB231 EC$_{50}$ (nM) | SKOV-3 EC$_{50}$ (nM) |
|---|---|---|
| 85 | | A |
| 88 | | C |
| 90 | | B |
| 91 | | B |
| 92 | | A |

A - EC$_{50}$ < 10 nM
B - EC$_{50}$ 10-25 nM
C - EC$_{50}$ > 25 nM

Further, treatment of cells with 10 nM of compounds 31 and 35 potentiated TRAIL efficacy on HCT116 colorectal and A2780S ovarian cells by approximately 2 logs, respectively.
Apoptosis Assay Measurement of Caspase-3 Activity from Cultured Cells.

One day, prior to the treatment, 10 000 cells per well were plated in a white tissue culture treated 96 well plate with 100 ul of media. On the day of compound treatment, compounds were diluted with cell culture media to a working stock concentration of 2× and 100 uL of diluted compound were added to each well and the plate was incubated for 5 h at 37° C. in presence of 5% CO$_2$. Upon incubation, the plate was washed twice with cold TRIS Buffered Saline (200 uL, TBS) buffer. Cells were lysed with 50 uL of Caspase assay buffer (20 mM), Tris-HCl pH 7.4, 0.1% NP-40, 0.1% Chaps, 1 mM DTT, 0.1 mM EDTA, 0.1 mM PMSF, 2 mg/mL Chymotstatin, Leupeptin, Pepstatin, Antipain) then incubated at 4° C. with shaking for 30 minutes. Caspase assay buffer (45 uL) and Ac-DEVD-AMC (5 uL, 1 mg/mL) were added to each well and the plate was shaken and incubated for 16 hour at 37° C. The amount of release AMC was measured in a TECAN spectrophotometer at with the excitation and emission filter set at 360 nm and 444 nm. The percentage of Caspase-3 activity was expressed in comparison of the signal obtained with the non-treated cells.
Cellular Biochemistry:
A. Detection of XIAP, c-IAP1, c-IAP2, PARP, Caspase-3 and Caspase-9

Detection of cell expressed XIAP and PARP were done by western blotting. Cells were plated at 300 000 cells/well in a 60 mm wells (6 wells plate dish). The next day the cells were treated with selected compound at the indicated concentration. 24 hours later cells the trypsinized cells, pelleted by centrifugation at 1800 rpm at 4° C. The resulting pellet was rinsed twice with cold TBS. The final washed pellet of cells was the lysed with 250 ul Lysis buffer (NP-40, glycerol, 1% of a protease inhibitor cocktail (Sigma)), placed at 4° C. for 25 min with gentle shaking. The cells extract was centrifuged at 4° C. for 10 min at 10 000 rpm. Both the supernatant and the pellet were kept for western blotting analysis as described below. From the supernatant, the protein content was evaluated and about 50 ug of protein was fractionated onto a 10% SDS-PAGE. Pellets were washed with the lysis buffer and re-suspend into 50 ul of Lamelli buffer 1×, boiled and fractionated on SDS-PAGE. Upon electrophoresis each gel was electro-transferred onto a nitrocellulose membrane at 0.6 A for 2 hours. Membrane non-specific sites were blocked for 1 hours with 5% Skim milk in TBST (TBS containing 0.1% (v/v) Tween-20) at RT. For protein immuno-detection, membranes were incubated overnight with primary antibodies raised against various IAPs or caspase-3 or caspase-9 primary antibodies were incubated at 4° C. with shaking at dilutions as follows:

Upon overnight incubation, the membranes received three washes of 15 min in TBST then were incubated for 1 hour at room temperature in the presence of a secondary antibody coupled with HRP-enzyme (Chemicon) and diluted at 1/5 000. Upon incubation each membrane were washed three times with TBST and the immunoreactive bands were detected by addition of a luminescent substrate (ECL kit Amersham) and capture of signal on a X-RAY film for various time of exposure. Active compounds were shown to induce the cleavage of PARP and induce a loss of c-IAP1 and c-IAP2 from cells.

More specifically, c-IAP1 levels were reduced in HCT116 cells following overnight treatment with compounds 45, 100, 31, 59, 44, 40, 67, 91.
Hollow Fiber Model Hollow fiber in vivo model are used to demonstrate in vivo efficacy of selected compounds against selected cell lines as single agent therapy or in combination with selected cytotoxic agents. At day 1, selected cell lines are cultured and the fiber filled at a cell density of about 40,000 cells/fiber. At the day of operation (day 4), three fibers are implanted sub-cutaneous into 28-35 Nu/Nu CD-1 male mice. On day 5, mice start to receive daily injection via sub-cutaneous route of control vehicle or vehicle containing the selected compound at the appropriate concentration and/or injection of cytotoxic agent via intra-peritoneal route. Upon 4 days of consecutive treatments, the animals are sacrificed, each fiber is removed and the metabolic viability of the remaining cells determined by MTT assay. Efficacy of the compound is define as the difference between the vehicle-treated animal and the animal treated with the compound alone or the compound given in combination of the cytotoxic agent Compound 31 and compound 56 caused a 70% decrease in MTT signal in fibers from treated mice as compared to fibers from vehicle treated control mice.
Combination Anti-Cancer Therapy In Vivo with Taxotere Female CD-1 nude mice (approximately 20-25 g) are sub-cutaneously injected with 1×10$^6$H460 cells in the right flank. Animals are balanced into groups based on tumor size and drug therapy began when tumors were ~30-50 mm$^3$. Animals that have no tumor or that were deemed outliers because of excessive tumor size at this time were removed from the study. The remaining animals received Taxotere (or equivalent volume of vehicle) at 30 mg/kg, ip 2 times, one week apart. The compound is given two times per day (at 10 mg/kg, sc, approximately 6 hrs apart), starting at the time of Taxotere, and continuing daily for the duration of the experiment. Tumor size was measured three times per week. Health assessments were performed at the time of the compound's delivery.
SKOV-3 Human Ovarian Cancer Cell Line Xenograpt Study Female CD-1 nude mice (approximately 20-25 g) are sub-cutaneously injected 5×10$^6$ SKOV-3 human ovarian tumor cells in 50% matrigel subcutaneously in the right flank. On day 55, when tumors are approximately 100 mm$^3$, treatment was initiated with compound on a 5 on/2 off treatment schedule for the duration of the experiment. Tumor size was measured with digital calipers and calculated as V=(a×b$^2$)/2, wherein, a is the longest dimension and b is the width.
MDA-MB-231 Human Mammary Cancer Cell Line Xenograph Study Female CD-1 nude mice (approximately 20-25 g) are sub-cutaneously injected 1×10$^6$ MDA-MB-231 human mammary tumor cells in the right flank. On day 71, when tumors were approximately 90 mm$^3$, treatment was initiated with compound 3 on a 5 on/2 off treatment schedule for the duration of the experiment. Tumor size was measured with digital calipers and calculated as V=(a×b$^2$)/2, wherein, a is the longest dimension and b is the width.

245

Pharmacokinetic Studies

Selected compounds are dissolved into aqueous media and given at various doses using different route of administration, including intravenous bolus, intravenous infusion, oral and subcutaneous injection.

Compounds of the instant invention display acceptable pharmacokinetic profiles when administered by various clinically relevant routes.

DISCUSSION

Without wishing to be bound by theory, we believe that the compounds of the present invention bind within the BIR domains of XIAP and prevent the interaction of the activated caspases with XIAP and cause a loss of XIAP protein in cells. Specifically, our data supports the notion that the compounds of the present invention can significantly reduce or essentially eliminate the interaction of XIAP with active caspase-9 and with active caspase-3. Since caspase-7 can also bind to the BIR2 site of XIAP, it is possible that the compounds can also prevent activated caspase-7 from binding to XIAP. Other data show also that the compounds of the present invention induce a loss of cIAP-1 and -2 in cells within 1 to 5 hours of compound addition. Thus a possible mechanism is that in many cancer cells, the compounds of the present invention bind to cIAPs and via ubiquitin mediated degradation induced a loss of there function and facilitate or prime the target cells to apopotosis. In summary, the compounds of the present invention through a direct contact on IAPs, inhibit IAP function in cells, induce or prime cells to apoptosis, and in certain cells, synergize the activity of inducers of apoptosis.

All literature, patents, published patent applications cited herein are hereby incorporated by reference in their entirety.

While specific embodiments have been described, those skilled in the art will recognize many alterations that could be made within the spirit of the invention, which is defined solely according to the following claims:

We claim:
1. A compound of Formula IA:

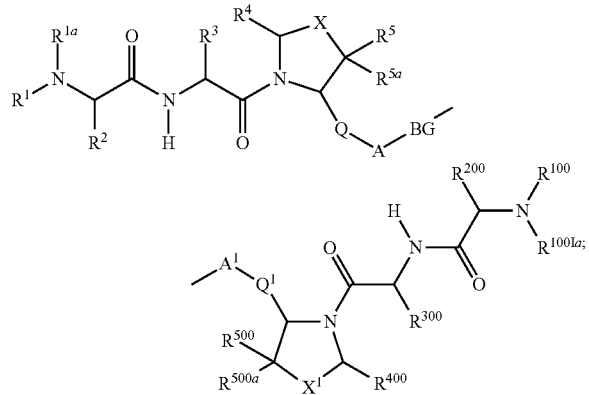

1A including any enantiomer, diastereoisomer or tautomer thereof,
wherein:
n is 0 or 1;
m is 0, 1 or 2;
Y is NH, O or S;
Q and $Q^1$ are, independently:
1) —$CH_2$—,
2) —$CH_2CH_2$—,

246

3) —$CH(C_1-C_6$ alkyl)-,
4) —$CH(C_3-C_7$ cycloalkyl)-,
5) —$C_3-C_7$ cycloalkyl-,
6) —$CH(C_1-C_6$ alkyl-$C_3-C_7$ cycloalkyl)-; or
7) —C(O)—;

A and $A^1$ are, independently:
1) $NR^6$, or
2) $NR^{600}$;

BG is
1) —$Y^1$-L-$Y^{100}$—; or
2) -L-;
or BG is —$Y^1$-$L^1$-Z-$L^{100}$-$Y^{100}$-, wherein $L^1$ and $L^{100}$ are equal or $L^1$ and $L^{100}$ are different;

$Y^1$ and $Y^{100}$ are, independently:
1) —C(O)—,
2) —$S(O)_2$—, or
3) —C(O)N($R^8$)—;

L, $L^1$ and $L^{100}$ are, independently:
1) —$C_1-C_{12}$ alkyl-,
2) —$C_2-C_{12}$ alkenyl-,
3) —$C_2-C_{12}$ alkynyl-,
4) —$C_3-C_7$ cycloalkyl-,
5) —$C_3-C_7$ cycloalkenyl-,
5) -aryl-,
6) -biphenyl-,
7) -heteroaryl-,
8) -heterocycyl-,
9) —$C_1-C_6$ alkyl-($C_2-C_6$ alkenyl)-$C_1-C_6$ alkyl-,
10) —$C_1-C_6$ alkyl-($C_2-C_4$ alkynyl)-$C_1-C_6$ alkyl,
11) —$C_1-C_6$ alkyl-($C_3-C_7$ cycloalkyl)-$C_1-C_6$ alkyl,
12) —$C_1-C_6$ alkyl-aryl-$C_1-C_6$ alkyl,
13) —$C_1-C_6$ alkyl-biphenyl-$C_1-C_6$ alkyl,
14) —$C_1-C_6$ alkyl-heteroaryl-$C_1-C_6$ alkyl,
15) —$C_1-C_6$ alkyl heterocycyl-$C_1-C_6$ alkyl, or
16) —$C_1-C_6$ alkyl-O—$C_1-C_6$ alkyl;
17) —N($R^8$)C(O)N($R^8$)—, or
18) —$C_1-C_6$ alkyl-Z—$C_1-C_6$ alkyl-;

wherein the alkyl, the alkenyl, the alkynyl, the cycloalkyenyl and the cycloalkyl are optionally substituted with one or more $R^7$ substituents; and the aryl, the heteroaryl, the biphenyl and the heterocyclyl are optionally substituted with one or more $R^{11}$ substituents;

Z is selected from:
1) —N($R^8$)CON($R^8$)—,
2) —N($R^8$)C(O)-aryl-C(O)N($R^8$)—,
3) —N($R^8$)C(O)-heteroaryl-C(O)N($R^8$)—,
4) —C(O)—,
5) —$S(O)_2$—,
6) —N($R^8$)C(O)—,
7) —C(O)N($R^8$)—,
8) —OC(O)N($R^8$)—,
9) —$S(O)_2$N($R^8$)—,
10) —N($R^8$)—$C_1-C_{12}$-alkyl-N($R^8$)—,
11) —N($R^8$)—C(O)C(O)—N($R^8$)—,
12) —N($R^8$)—C(O)—$C_1-C_{12}$-alkyl-C(O)—N($R^8$)—,
13) —N($R^8$)—C(O)-aryl-O-aryl-C(O)—N($R^8$)—,
14) —N($R^8$)—C(O)-biphenyl-C(O)—N($R^8$)—,
15) —N($R^8$)—$S(O)_2$—$C_1-C_{12}$-alkyl-$S(O)_2$—N($R^8$)—,
16) —N($R^8$)—$S(O)_2$-aryl-$S(O)_2$—N($R^8$)—,
17) —N($R^8$)—$S(O)_2$-heteroaryl-$S(O)_2$—N($R^8$)—,
18) —N($R^8$)—$S(O)_2$-biphenyl-$S(O)_2$—N($R^8$)—,
19) N($R^8$)-aryl-N($R^8$)—,
20) —N($R^8$)-heteroaryl-N($R^8$)—, or
21) —N($R^8$)-biphenyl-N($R^8$)—;

wherein the alkyl and the cycloalkyl are optionally substituted with one or more $R^7$ substituents, and the aryl, heteroaryl and heterocyclyl are optionally substituted with one or more $R^{11}$ substituents;

$R^1$, $R^{1a}R^{100}$, and $R^{100a}$ are, independently:
  1) H, or
  2) $C_1$-$C_6$ alkyl optionally substituted with one or more $R^7$ substituents;

$R^2$, $R^3$, $R^4$, $R^5$, $R^{5a}$, $R^{200}$, $R^{300}$, $R^{400}$, $R^{500}$ and $R^{500a}$ are each independently H or $C_1$-$C_6$ alkyl optionally substituted with one or more $R^7$ substituents;

$R^6$ and $R^{600}$ are each, independently:
  1) H,
  2) haloalkyl,
  3) $C_1$-$C_6$ alkyl,
  4) $C_2$-$C_6$ alkenyl,
  5) $C_2$-$C_4$ alkynyl,
  6) $C_3$-$C_7$ cycloalkyl,
  7) $C_3$-$C_7$ cycloalkenyl,
  8) aryl,
  9) heteroaryl,
  10) heterocyclyl,
  11) heterobicyclyl,
  12) —C(O)(O)$_n$—$R^{12}$,
  13) —C(=Y)NR$^9$R$^{10}$, or
  14) —S(O)$_2$—$R^{12}$, wherein the alkyl, alkenyl, alkynyl, cycloalkyl, and cycloalkenyl are optionally substituted with one or more $R^7$ substitutents; and wherein the aryl, heteroaryl, heterocyclyl, and heterobicyclyl are optionally substituted with one or more $R^{11}$ substituents;

$R^7$ is
  1) halogen,
  2) NO$_2$,
  3) CN,
  4) haloalkyl,
  5) $C_1$-$C_6$ alkyl,
  6) $C_2$-$C_6$ alkenyl,
  7) $C_2$-$C_4$ alkynyl,
  8) $C_3$-$C_7$ cycloalkyl,
  9) $C_3$-$C_7$ cycloalkenyl,
  10) aryl,
  11) heteroaryl,
  12) heterocyclyl,
  13) heterobicyclyl,
  14) —OR$^8$,
  15) —S(O)$_m$R$^8$,
  16) —NR$^9$R$^{10}$,
  17) —NR$^9$S(O)$_2$R$^{12}$,
  18) —COR$^8$,
  19) —C(O)OR$^8$,
  20) —CONR$^9$R$^{10}$,
  21) —S(O)$_2$NR$^9$R$^{10}$,
  22) —OC(O)R$^8$,
  23) —OC(O)Y—R$^{12}$,
  24) —SC(O)R$^8$, or
  25) —NC(Y)R$^9$R$^{10}$, wherein the aryl, heteroaryl, heterocyclyl, and heterobicyclyl are optionally substituted with one or more $R^{11}$ substituents;

$R^8$ is
  1) H,
  2) haloalkyl,
  3) $C_1$-$C_6$ alkyl,
  4) $C_2$-$C_6$ alkenyl,
  5) $C_2$-$C_4$ alkynyl,
  6) $C_3$-$G_7$ cycloalkyl,
  7) $C_3$-$C_7$ cycloalkenyl,
  8) aryl,
  9) heteroaryl,
  10) heterocyclyl,
  11) heterobicyclyl,
  12) —NC(=Y)R$^9$R$^{10}$, or
  13) $C_1$-$C_6$ alkyl-$C_2$-$C_4$ alkenyl, or
  14) $C_1$-$C_6$ alkyl-$C_2$-$C_4$ alkynyl, wherein the alkyl, alkenyl, alkynyl, cycloalkyl, and cycloalkenyl are optionally substituted with one or more $R^7$ substituents; and wherein the aryl, heteroaryl, heterocyclyl, and heterobicyclyl are optionally substituted with one or more $R^{11}$ substituents;

$R^9$ and $R^{10}$ are each, independently:
  1) H,
  2) haloalkyl,
  3) $C_1$-$C_6$ alkyl,
  4) $C_2$-$C_6$ alkenyl,
  5) $C_2$-$C_4$ alkynyl,
  6) $C_3$-$C_7$ cycloalkyl,
  7) $C_3$-$C_7$ cycloalkenyl,
  8) aryl,
  9) heteroaryl,
  10) heterocyclyl,
  11) heterobicyclyl,
  12) —C(O)R$^{12}$,
  13) —C(O)Y—R$^{12}$, or
  14) —S(O)$_2$—R$^{12}$, wherein the alkyl, alkenyl, alkynyl, cycloalkyl, and cycloalkenyl are optionally substituted with one or more $R^7$ substituents; and wherein the aryl, heteroaryl, heterocyclyl, and heterobicyclyl are optionally substituted with one or more $R^{11}$ substituents;

or $R^9$ and $R^{10}$ together with the nitrogen atom to which they are bonded form a five, six or seven membered heterocyclic ring optionally substituted with one or more $R^7$ substituents;

$R^{11}$ is
  1) halogen,
  2) NO$_2$,
  3) CN,
  4) —B(OR$^{13}$)(OR$^{14}$),
  5) $C_1$-$C_6$ alkyl,
  6) $C_2$-$C_6$ alkenyl,
  7) $C_2$-$C_4$ alkynyl,
  8) $C_3$-$C_7$ cycloalkyl,
  9) $C_3$-$C_7$ cycloalkenyl,
  10) haloalkyl,
  11) —OR$^8$,
  12) —NR$^9$R$^{10}$,
  13) —SR$^8$,
  14) —COR$^8$,
  15) —C(O)OR$^8$,
  16) —S(O)$_m$R$^8$,
  17) —CONR$^9$R$^{10}$,
  18) —S(O)$_2$NR$^9$R$^{10}$,
  19) aryl,
  20) heteroaryl,
  21) heterocyclyl, or
  22) heterobicyclyl, wherein the alkyl, alkenyl, alkynyl, cycloalkyl, and cycloalkenyl are optionally substituted with one or more $R^7$ substituents;

$R^{12}$ is
  1) haloalkyl,
  2) $C_1$-$C_6$ alkyl,
  3) $C_2$-$C_6$ alkenyl,
  4) $C_2$-$C_4$ alkynyl,
  5) $C_3$-$C_7$ cycloalkyl, 6) $C_3$-$C_7$ cycloalkenyl,
7) aryl,
8) heteroaryl,
9) heterocyclyl, or
10) heterobicyclyl, wherein the alkyl, alkenyl, alkynyl, cycloalkyl, and cycloalkenyl are optionally substituted with one or more $R^7$ substituents; and wherein the aryl, heteroaryl, heterocyclyl, and heterobicyclyl are optionally substituted with one or more $R^{11}$ substituents;

$R^{13}$ and $R^{14}$ are each, independently:
1) H, or
2) $C_1$-$C_6$ alkyl;
or $R^{13}$ and $R^{14}$ are combined to form a ring system;
or a pharmaceutically acceptable salt thereof.

2. The compound, according to claim 1, of Formula 1A1:

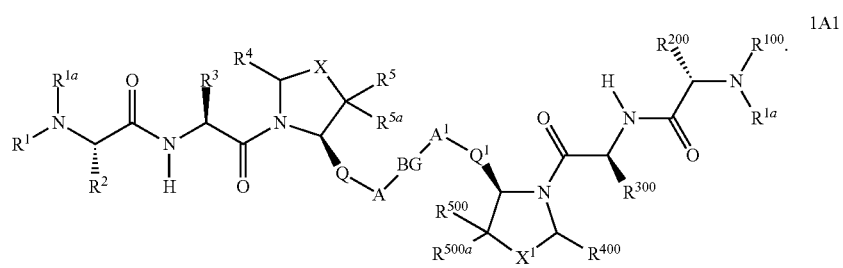

1A1

3. The compound, according to claim 1, of (a) Formula 1A4:

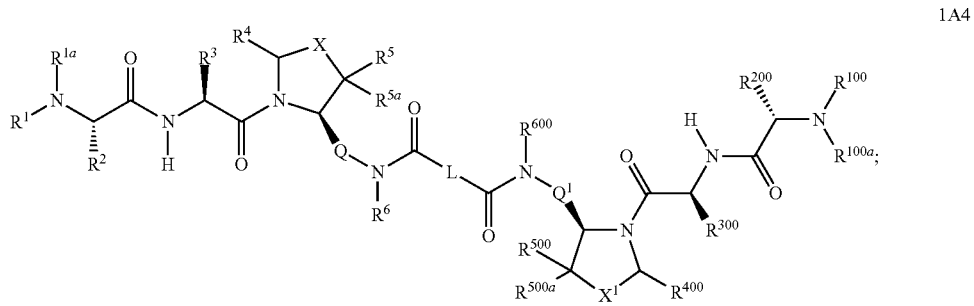

1A4

(b) Formula 1A5:

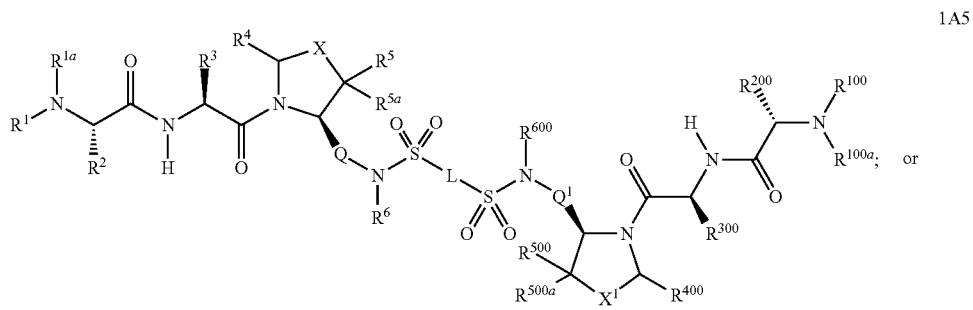

1A5

(c) Formula 1A6:

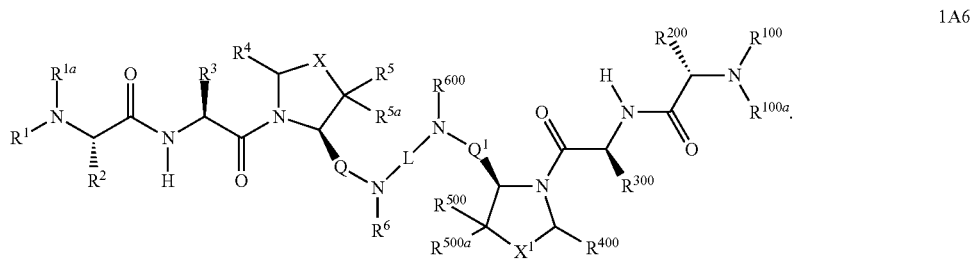

1A6

4. The compound, according to claim 1, in which L, $L^1$ and $L^{100}$ are:
 1) —$C_1$-$C_{12}$ alkyl-,
 2) —$C_3$-$C_7$ cycloalkyl-,
 3) -aryl-,
 4) -biphenyl-,
 5) -heteroaryl-,
 6) -heterocycyl-,
 7) —$C_1$-$C_6$ alkyl-($C_3$-$C_7$ cycloalkyl)-$C_1$-$C_6$ alkyl,
 8) —$C_1$-$C_6$ alkyl-aryl-$C_1$-$C_6$ alkyl,
 9) —$C_1$-$C_6$ alkyl-biphenyl-$C_1$-$C_6$ alkyl,
 10) —$C_1$-$C_6$ alkyl-heteroaryl-$C_1$-$C_6$ alkyl,
 11) —$C_1$-$C_6$ alkyl heterocycyl-$C_1$-$C_6$ alkyl, or
 12) —$C_1$-$C_6$ alkyl-O—$C_1$-$C_6$ alkyl,
wherein the alkyl, and the cycloalkyl are optionally substituted with one or more $R^7$ substituents; and the aryl, the heteroaryl, the biphenyl and the heterocyclyl are optionally substituted with one or more $R^{11}$ substituents.

5. The compound, according to claim 1, in which L, $L^1$, and $L^{100}$ are —$N(R^8)C(O)N(R^8)$—.

6. The compound, according to claim 1, in which L, $L^1$ and $L^{100}$ are —$C_1$-$C_6$ alkyl-Z—$C_1$-$C_6$ alkyl-, wherein the alkyl is optionally substituted with one or more $R^7$ substituents.

7. The compound, according to claim 6, in which Z is:
 1) —$N(R^8)CON(R^8)$—,
 2) —$N(R^8)C(O)$-aryl-$C(O)N(R^8)$—,
 3) —$N(R^8)C(O)$-heteroaryl-$C(O)N(R^8)$—,
 4) —C(O)—,
 5) —$N(R^8)$—$C_1$-$C_{12}$-alkyl-$N(R^8)$—,
 6) —$N(R^8)$—C(O)C(O)—$N(R^8)$—,
 7) —$N(R^8)$—C(O)—$C_1$-$C_{12}$-alkyl-C(O)—$N(R^8)$—,
 8) —$N(R^8)$—C(O)-aryl-O-aryl-C(O)—$N(R^8)$—,
 9) —$N(R^8)$—C(O)-heteroaryl-C(O)—$N(R^8)$—,
 10) —$N(R^8)$—C(O)-biphenyl-C(O)—$N(R^8)$—,
 11) —$N(R^8)$—$S(O)_2$—$C_1$-$C_{12}$-alkyl-$S(O)_2$—$N(R^8)$—,
 12) —$N(R^8)$—$S(O)_2$-aryl-$S(O)_2$—$N(R^8)$—,
 13) —$N(R^8)$—$S(O)_2$-heteroaryl-$S(O)_2$—$N(R^8)$—, or
 14) —$N(R^8)$—$S(O)_2$-biphenyl-$S(O)_2$—$N(R^8)$—,
wherein the alkyl and the cycloalkyl are optionally substituted with one or more $R^7$ substituents, and the aryl, the heteroaryl and the heterocyclyl are optionally substituted with one or more $R^{11}$ substituents.

8. The compound, according to claim 1, in which $R^1$, $R^{1a}$, $R^{100}$ and $R^{100a}$ are independently H or $CH_3$.

9. The compound, according to claim 1, in which $R^3$ and $R^{300}$ are H, (S)-methyl, (S)-ethyl, (S)-tert-butyl, (S)-cyclohexylmethyl, (S)-2-phenylethyl or benzyl(S)-butylcarbamate.

10. The compound, according to claim 1, in which $R^6$ and $R^{600}$ are each independently
 1) H,
 2) $C_1$-$C_6$ alkyl, or
 3) aryl,
wherein the alkyl is optionally substituted with one or more $R^7$ substituents; and wherein the aryl is optionally substituted with one or more $R^{11}$ substituents.

11. The compound, according to claim 10, in which $R^6$ and $R^{600}$ are:

H, —$CH(CH_3)_2$, —$CH_2CH_2C(CH_3)_3$,

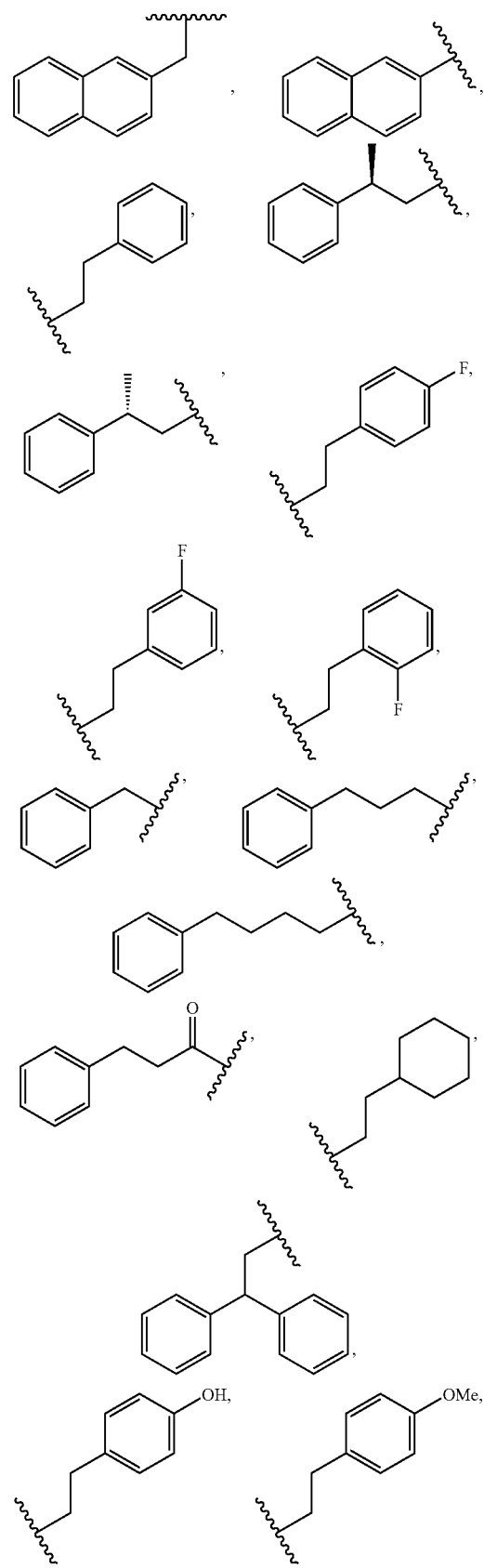

-continued

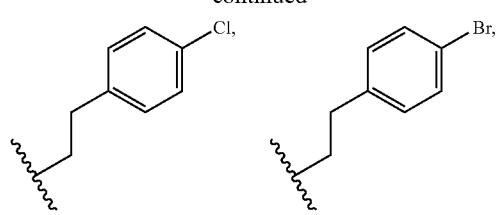

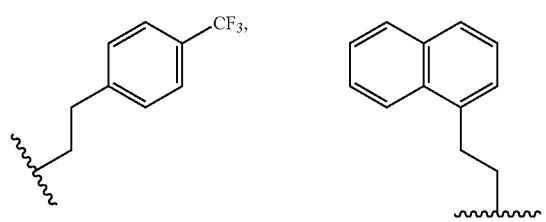

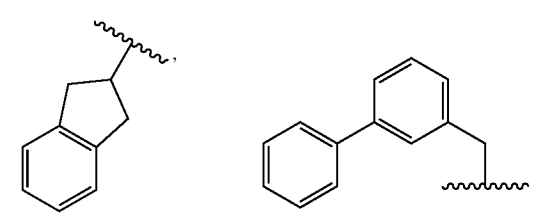

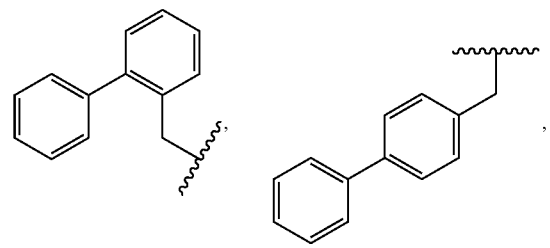

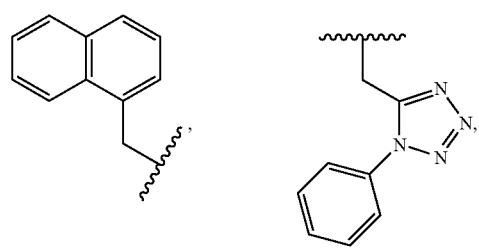

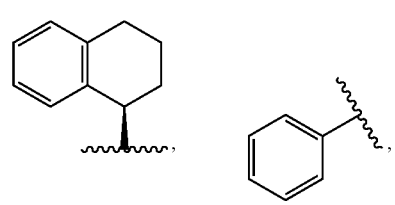

-continued

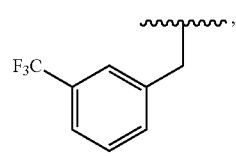

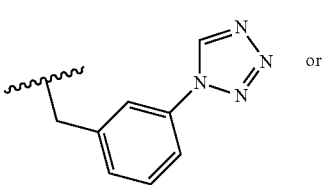 or

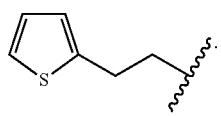

12. The compound, according to claim 1, in which $R^7$ is
1) $C_3$-$C_7$ cycloalkyl,
2) aryl,
3) heteroaryl, or
4) —NHC(O)OCH$_2$-phenyl,
wherein the aryl and the heteroaryl are optionally substituted with one or more $R^{11}$ substituents.

13. The compound, according to claim 1, in which $R^8$ is
1) H,
2) haloalkyl,
3) $C_1$-$C_6$ alkyl,
4) $C_3$-$C_7$ cycloalkyl,
5) aryl,
6) heteroaryl,
7) heterocyclyl, or
8) heterobicyclyl,
wherein the alkyl, cycloalkyl, are optionally substituted with one or more $R^7$ substituents; and
wherein the aryl, heteroaryl, heterocyclyl, and heterobicyclyl are is optionally substituted with one or more $R^{11}$ substituents.

14. The compound, according to claim 1, in which $R^{11}$ is
1) halogen,
2) $CF_3$,
3) OH,
4) OMe,
5) aryl, or
6) heteroaryl.

15. A compound, according to claim 1, wherein the compound is:
| Cmpd # | Structure |
|---|---|
| 5 | 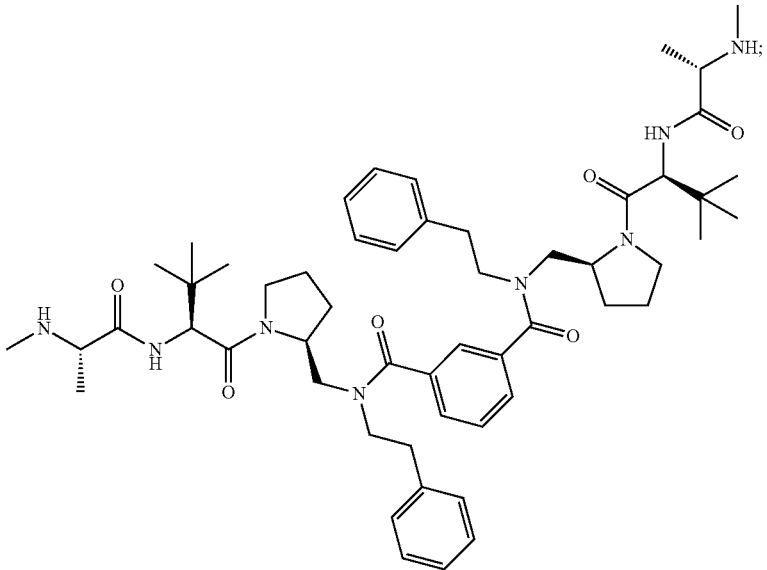 |
| 6 | 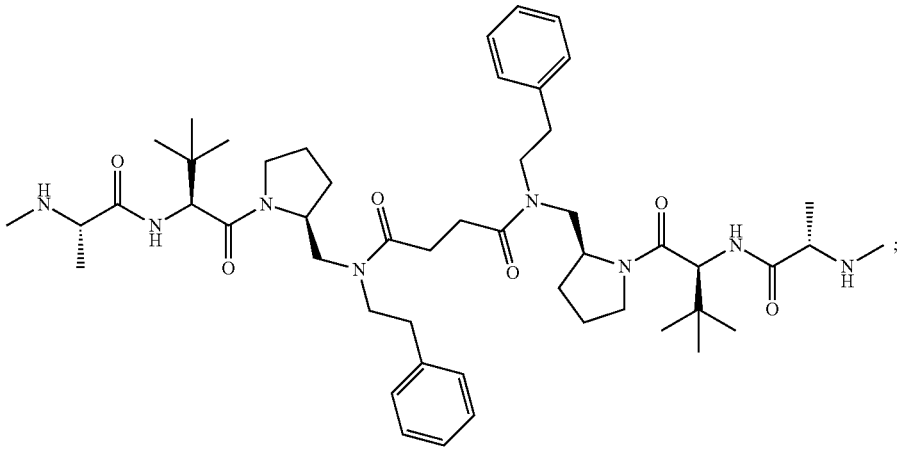 |
| 7 | 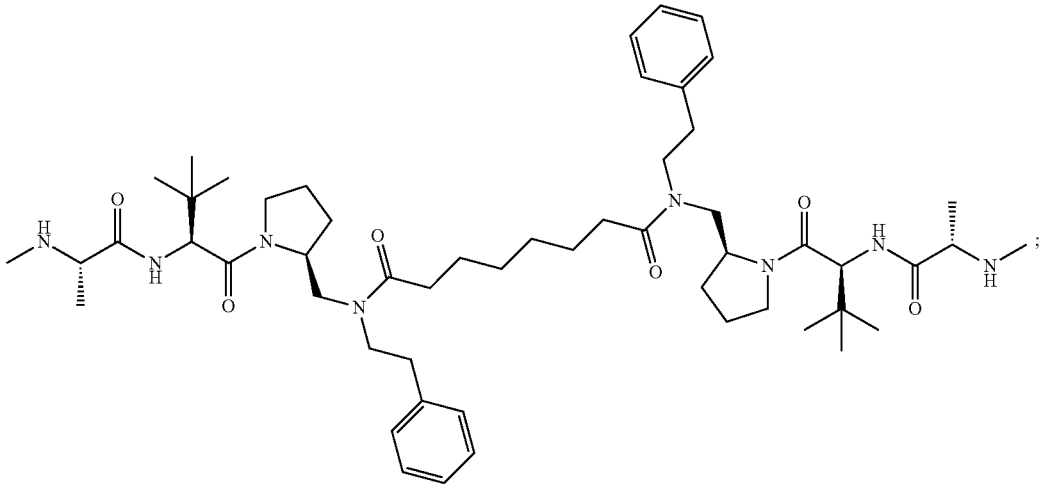 |

| Cmpd # | Structure |
|---|---|
| 8 | 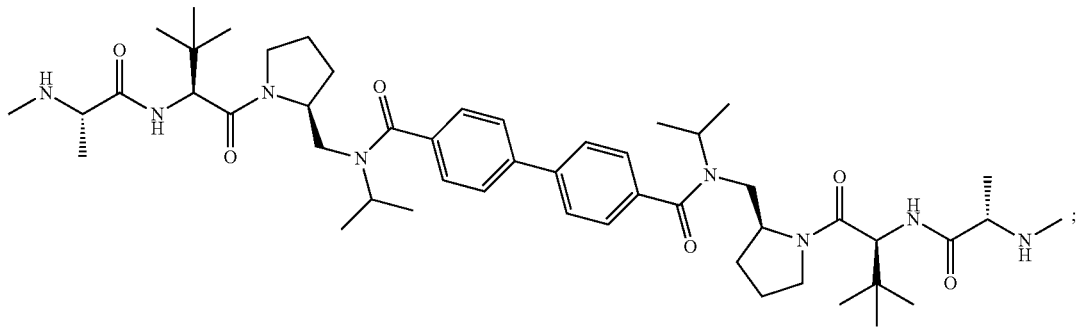 |
| 9 | 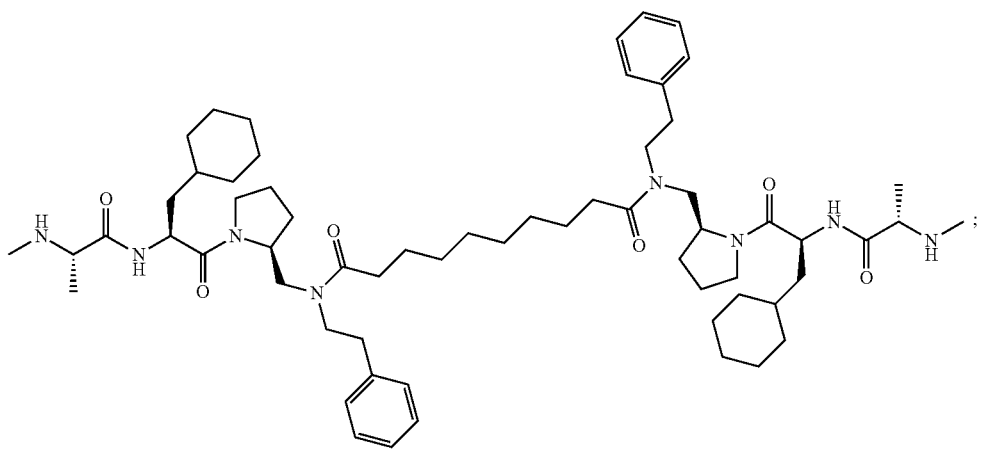 |
| 10 | 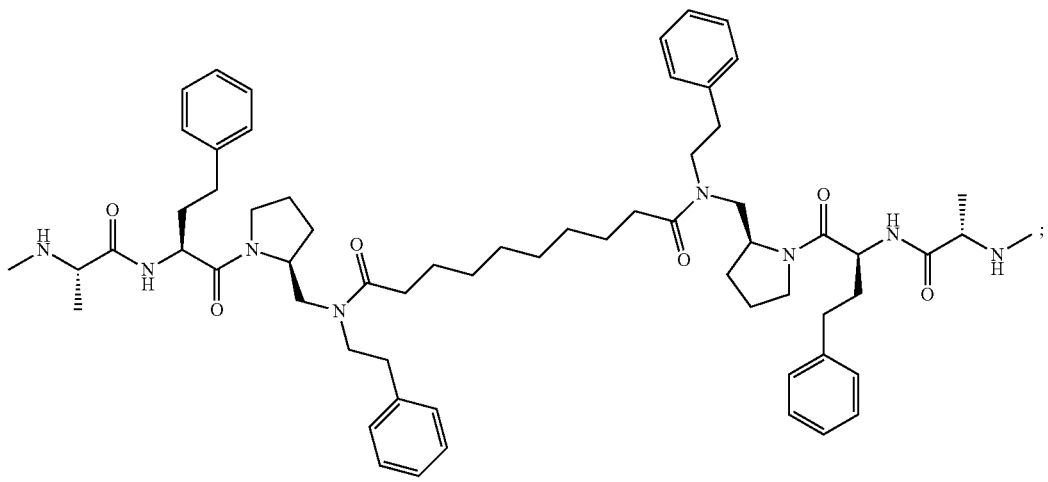 |

| Cmpd # | Structure |
|---|---|
| 11 | 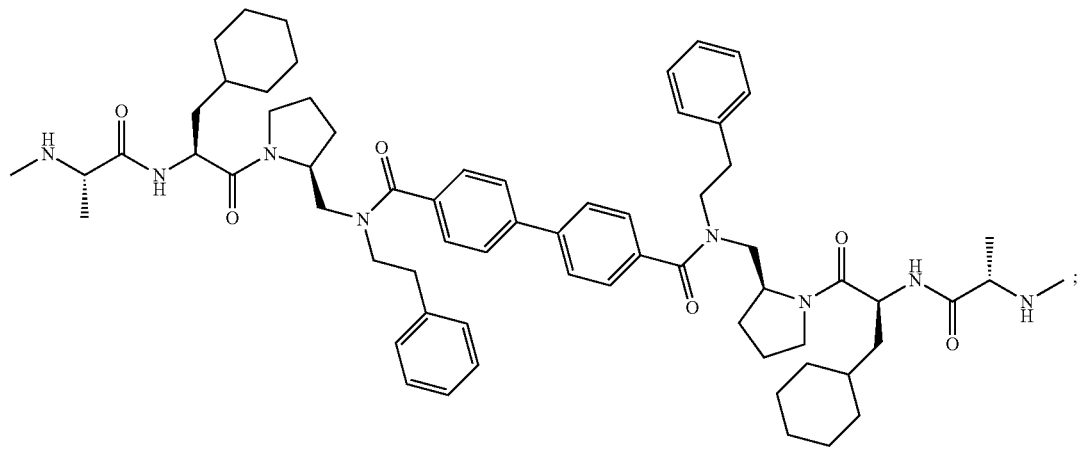 |
| 12 | 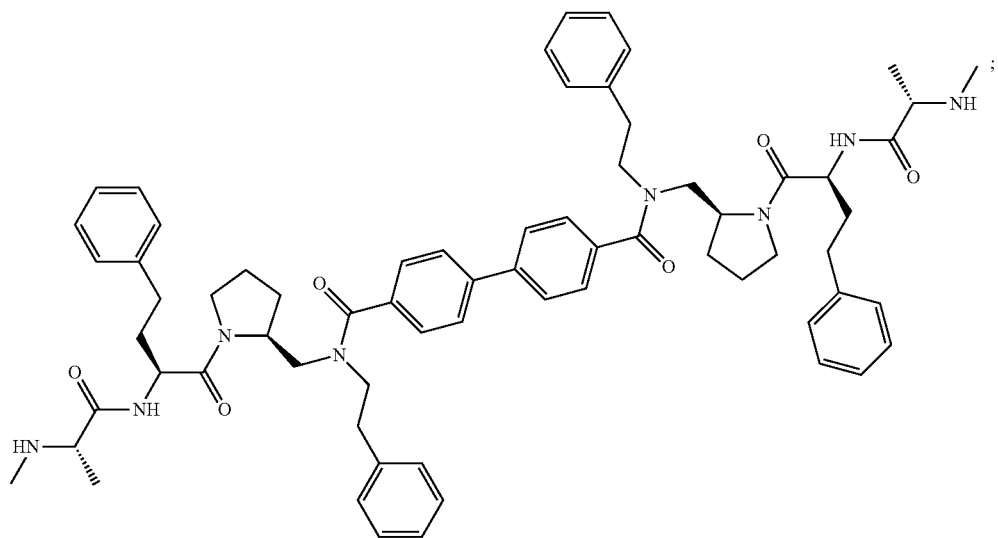 |
| 13 | 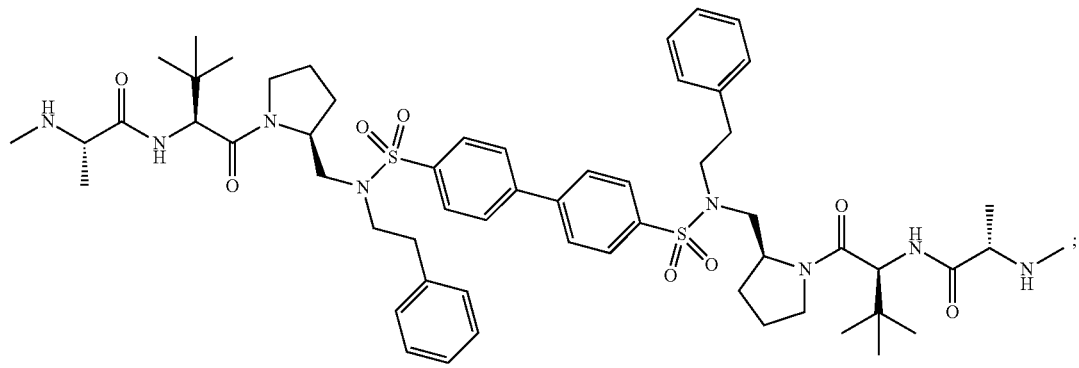 |
| 14 | 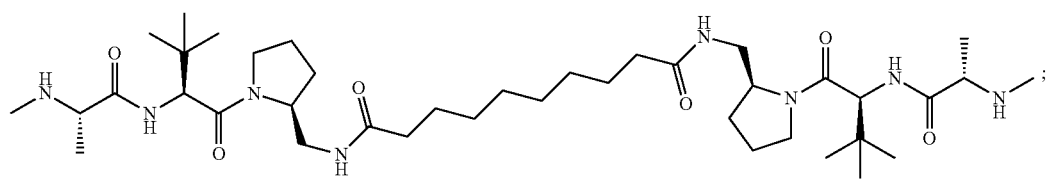 |

| Cmpd # | Structure |
|---|---|
| 15 | 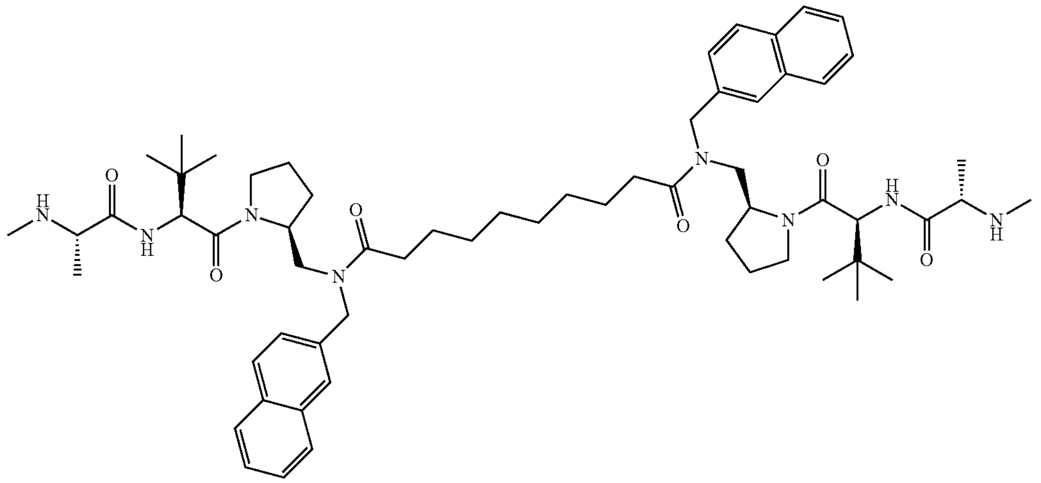 |
| 16 | 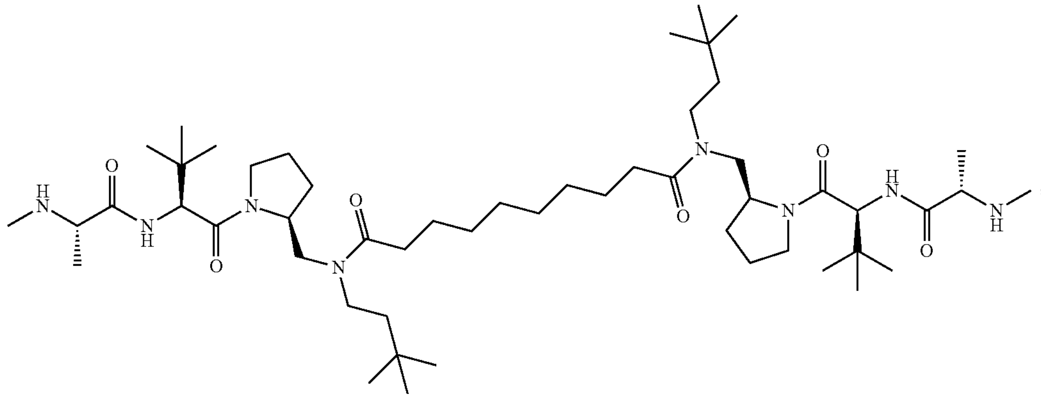 |
| 17 | 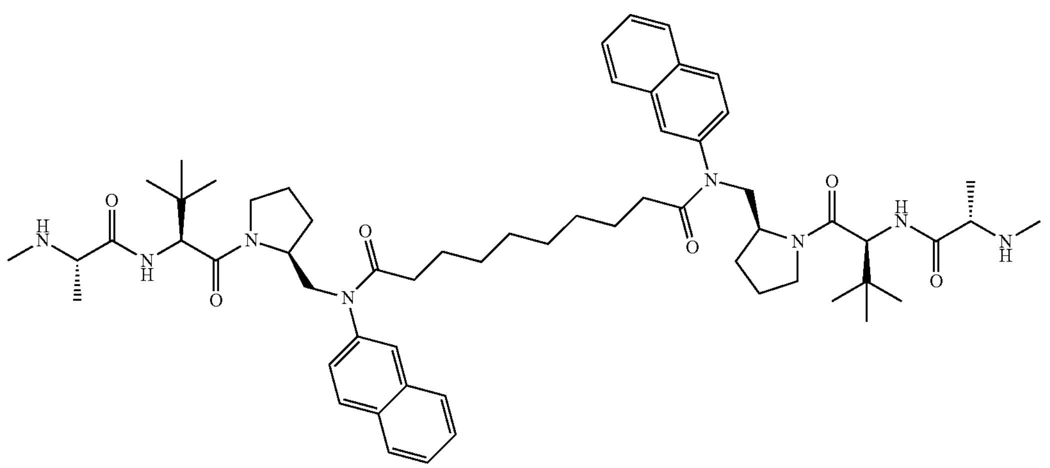 |

-continued
| Cmpd # | Structure |
|---|---|
| 18 | 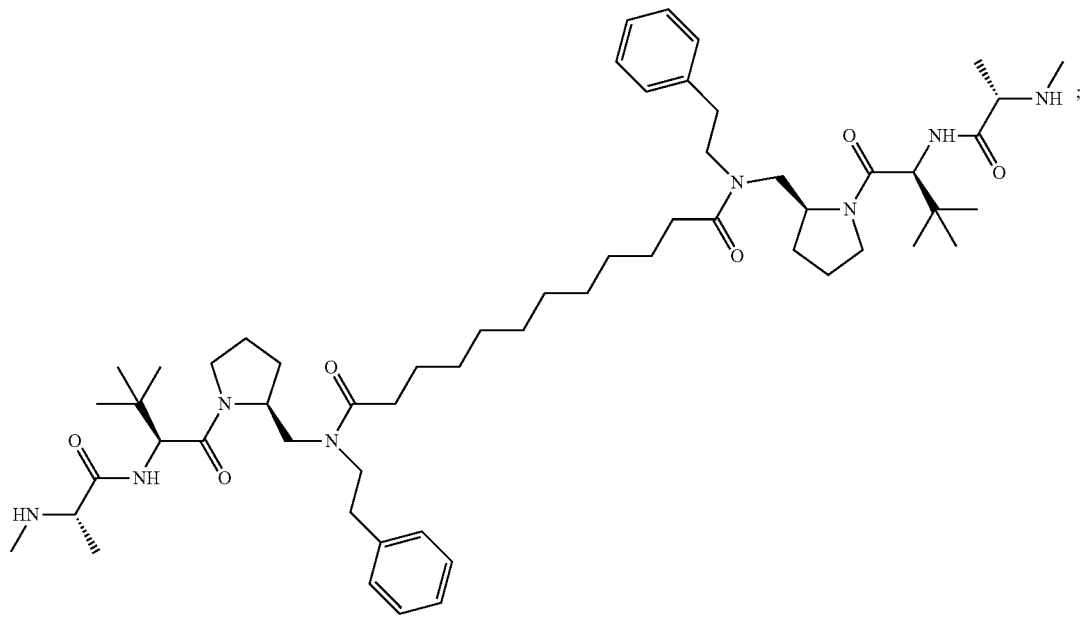 |
| 20 | 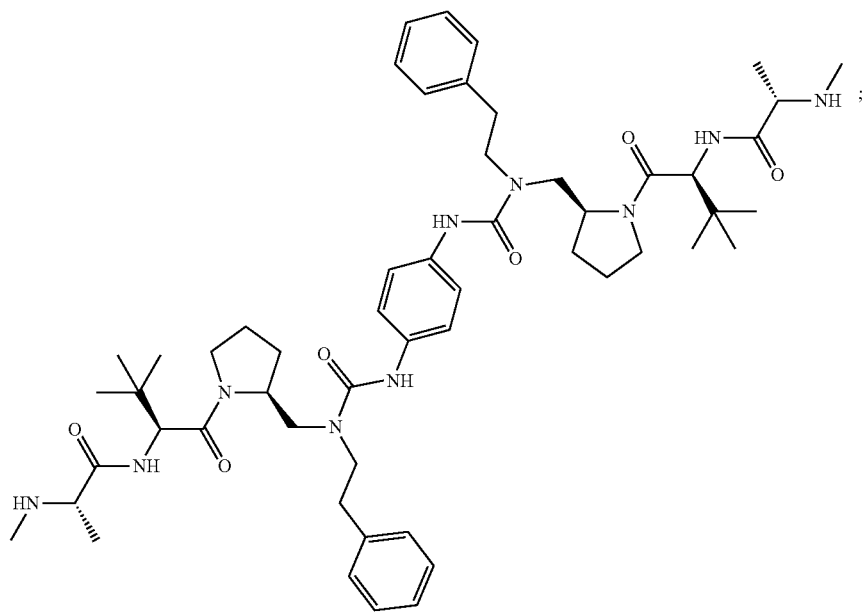 |

| Cmpd # | Structure |
|---|---|
| 21 | 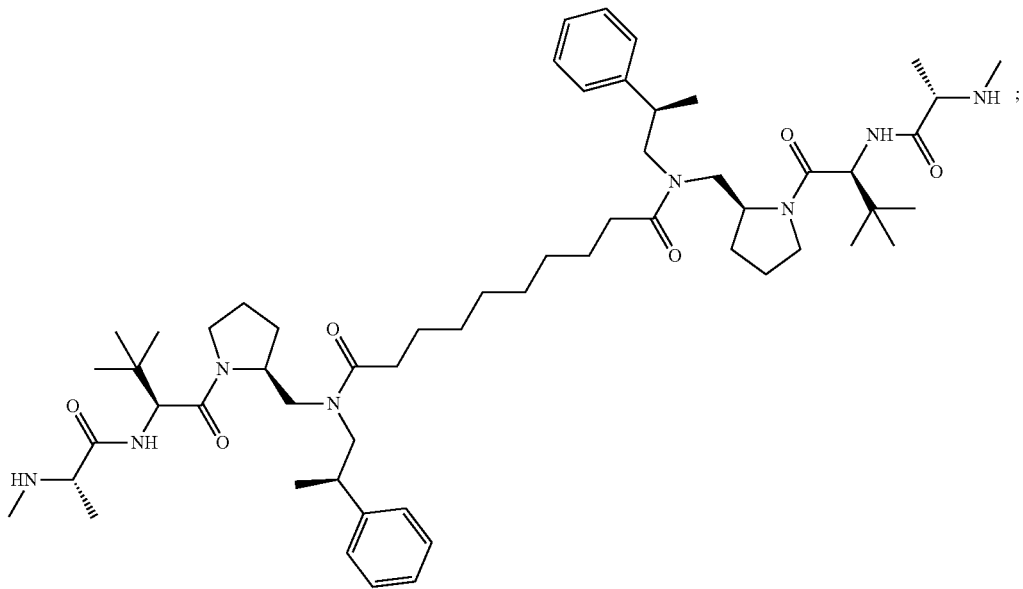 |
| 22 | 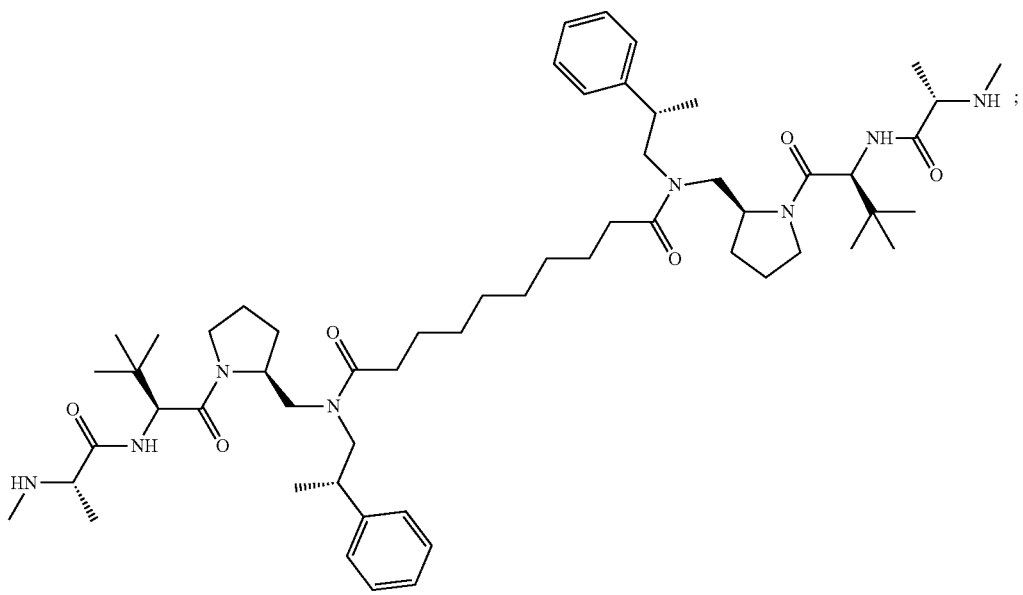 |

| Cmpd # | Structure |
|---|---|
| 23 | 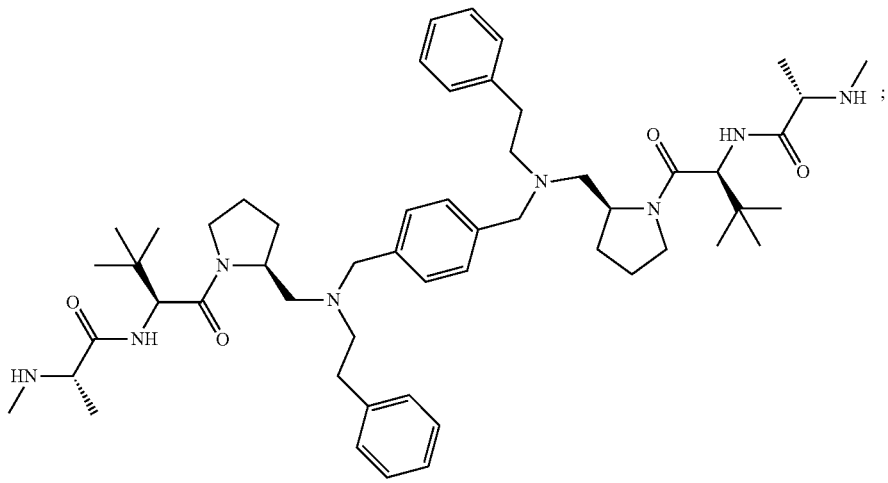 |
| 24 | 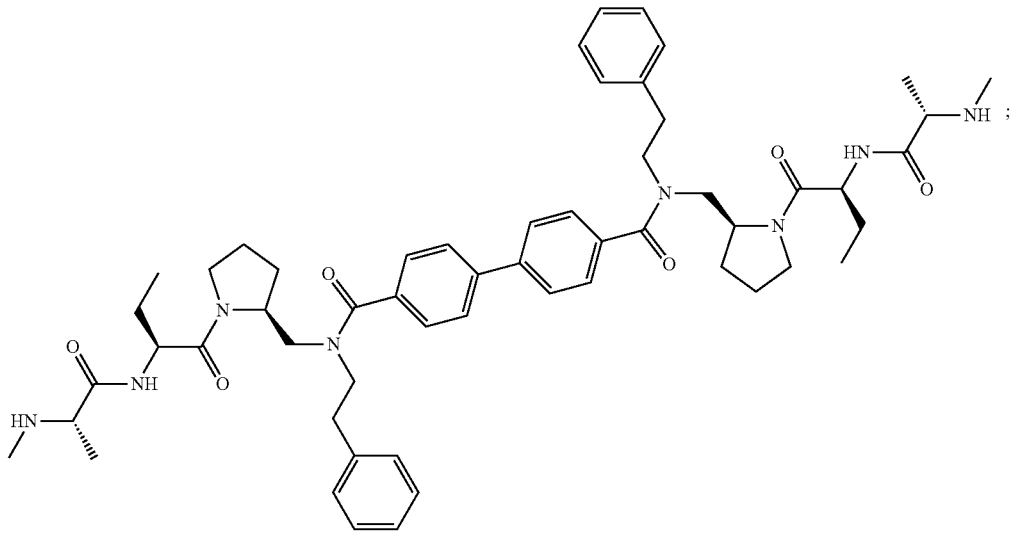 |

| Cmpd # | Structure |
|---|---|
| 25 | 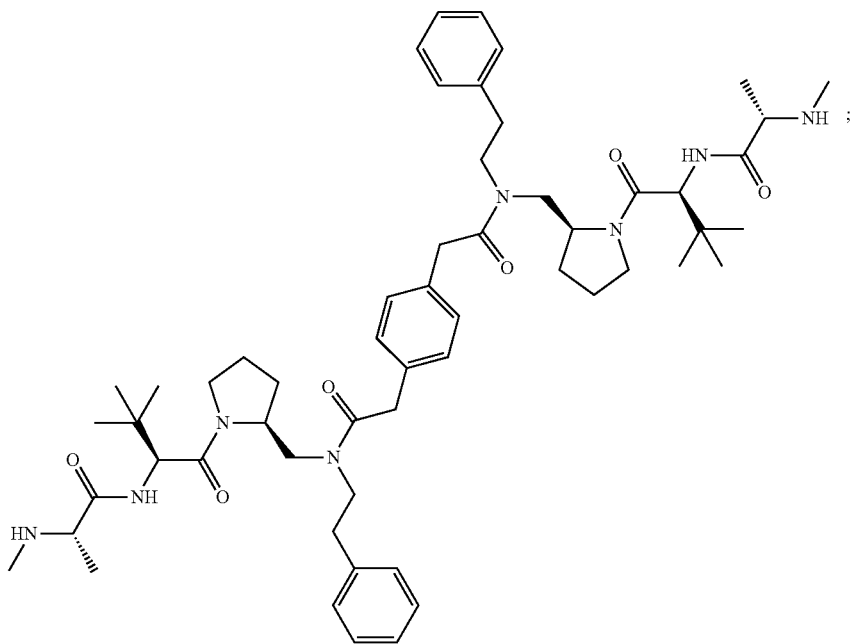 |
| 26 | 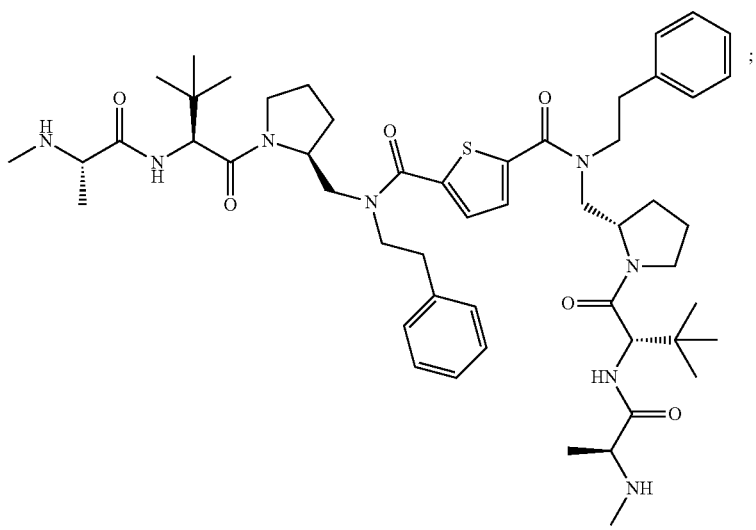 |

| Cmpd # | Structure |
|---|---|
| 28 | 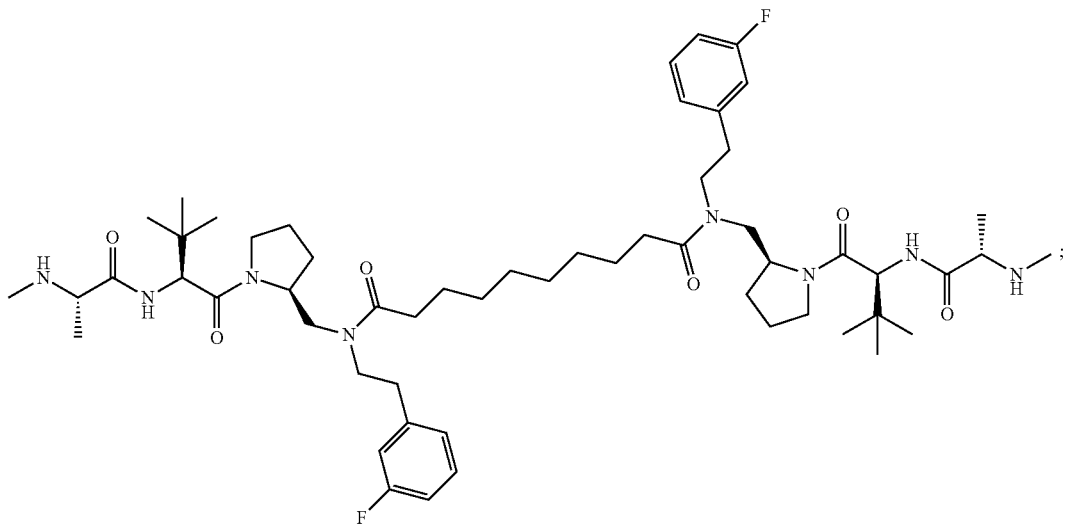 |
| 29 | 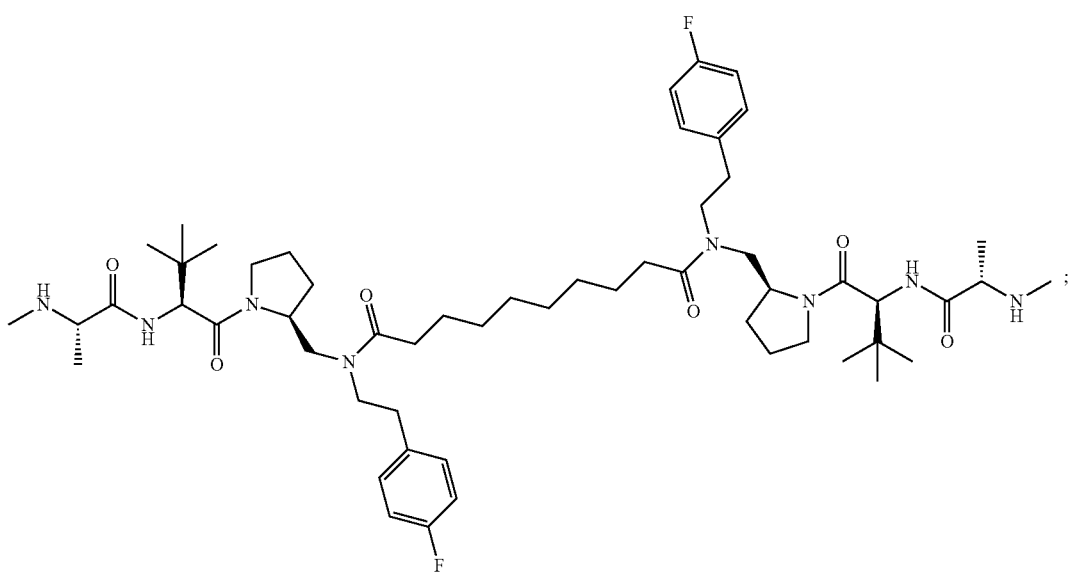 |
| 30 | 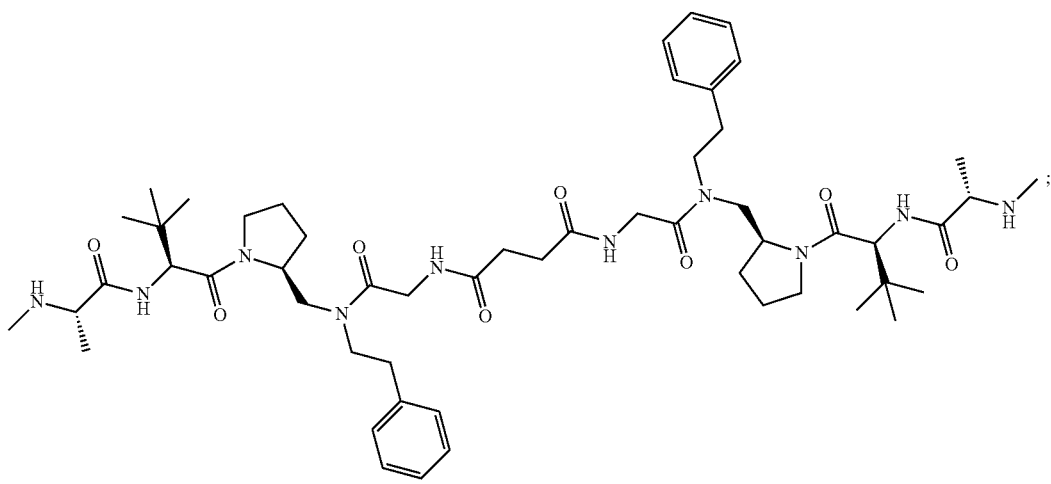 |

| Cmpd # | Structure |
|---|---|
| 31 | 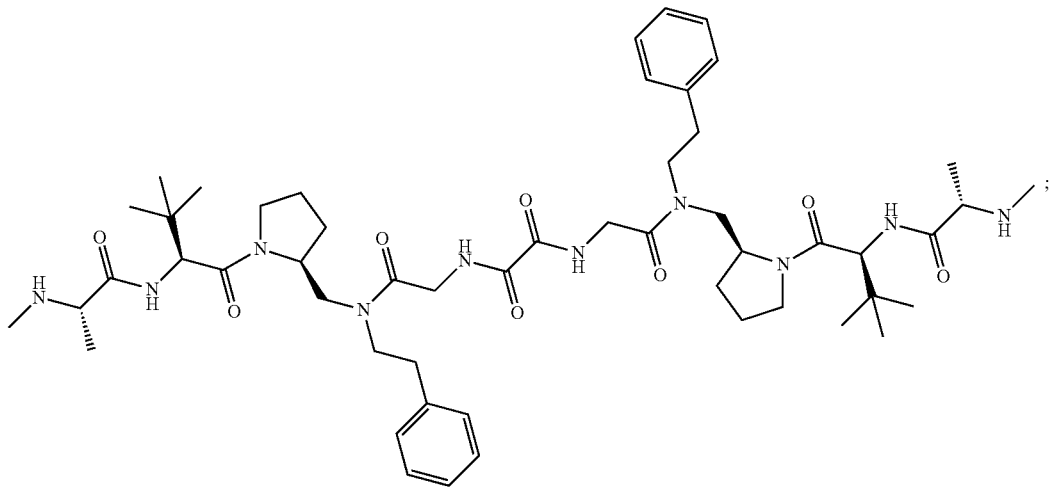 |
| 32 | 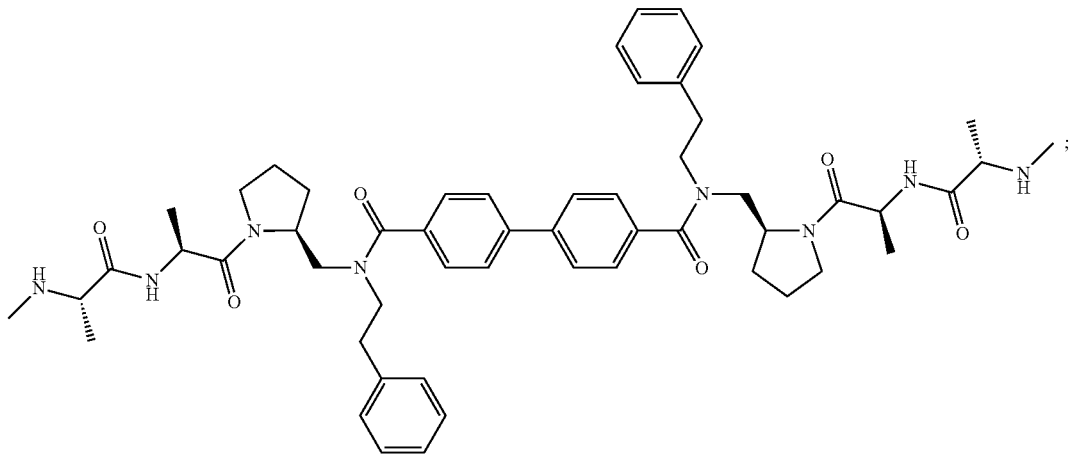 |
| 33 | 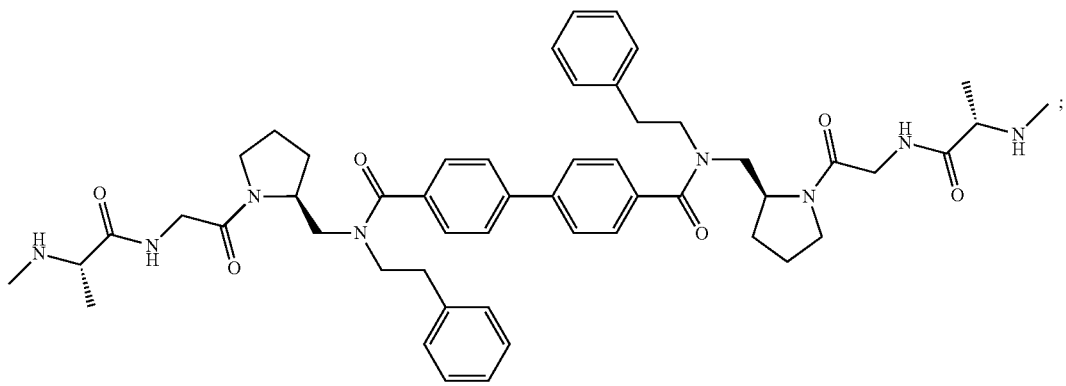 |

-continued
| Cmpd # | Structure |
|---|---|
| 34 | 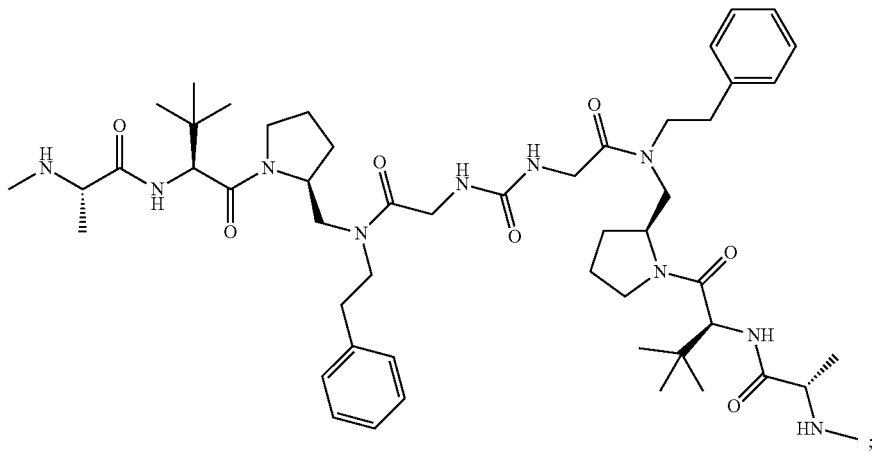 |
| 35 | 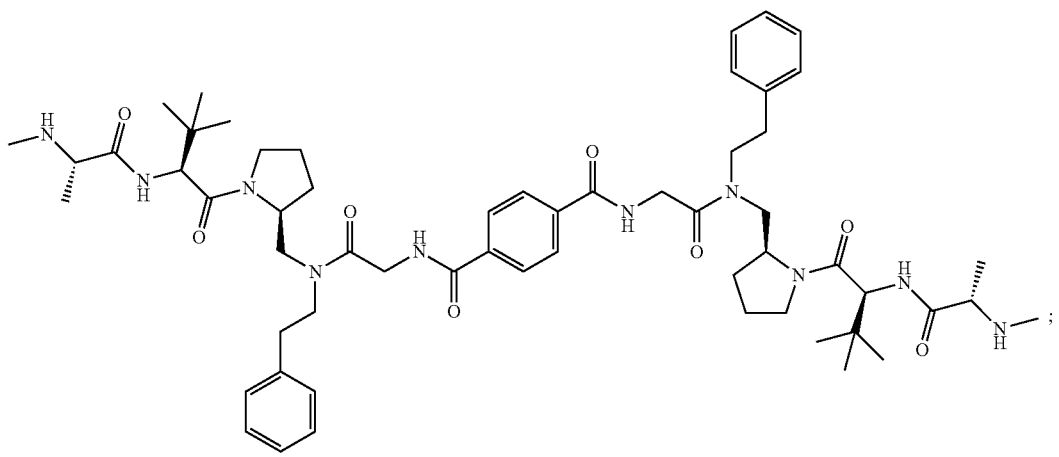 |
| 36 | 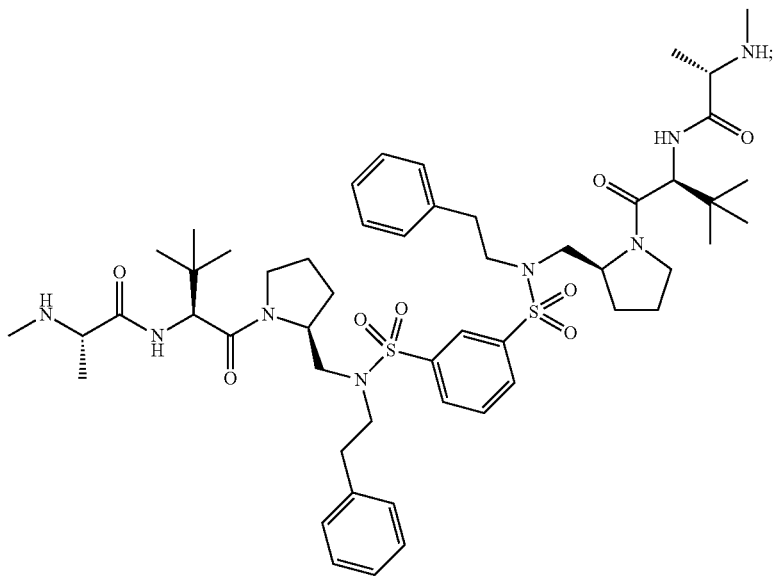 |

| Cmpd # | Structure |
|---|---|
| 37 | 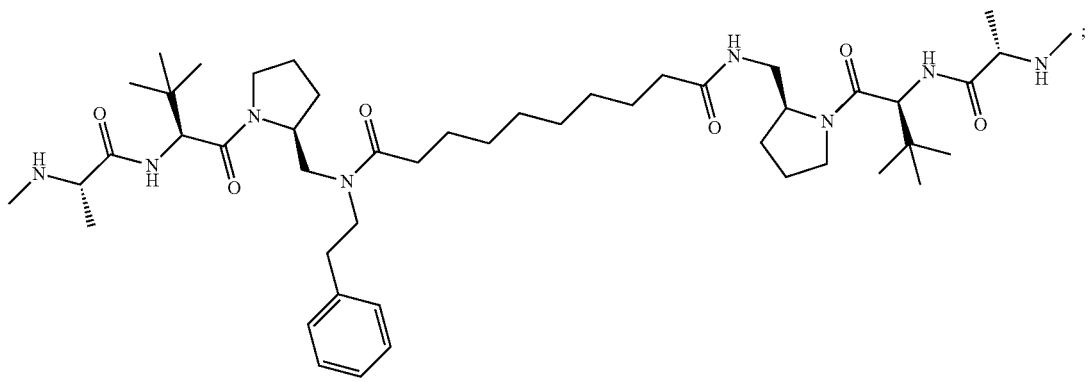 |
| 38 | 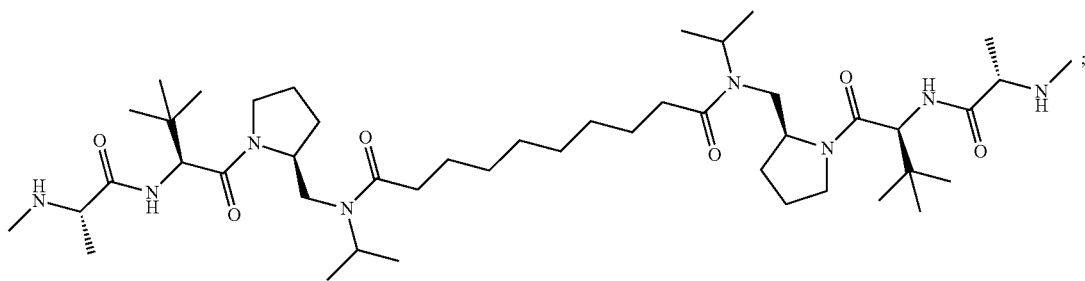 |
| 39 | 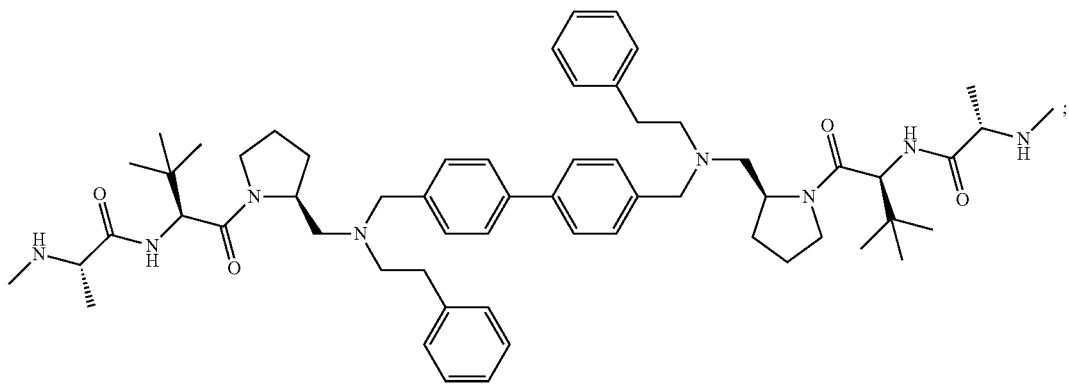 |

| Cmpd # | Structure |
|---|---|
| 40 | 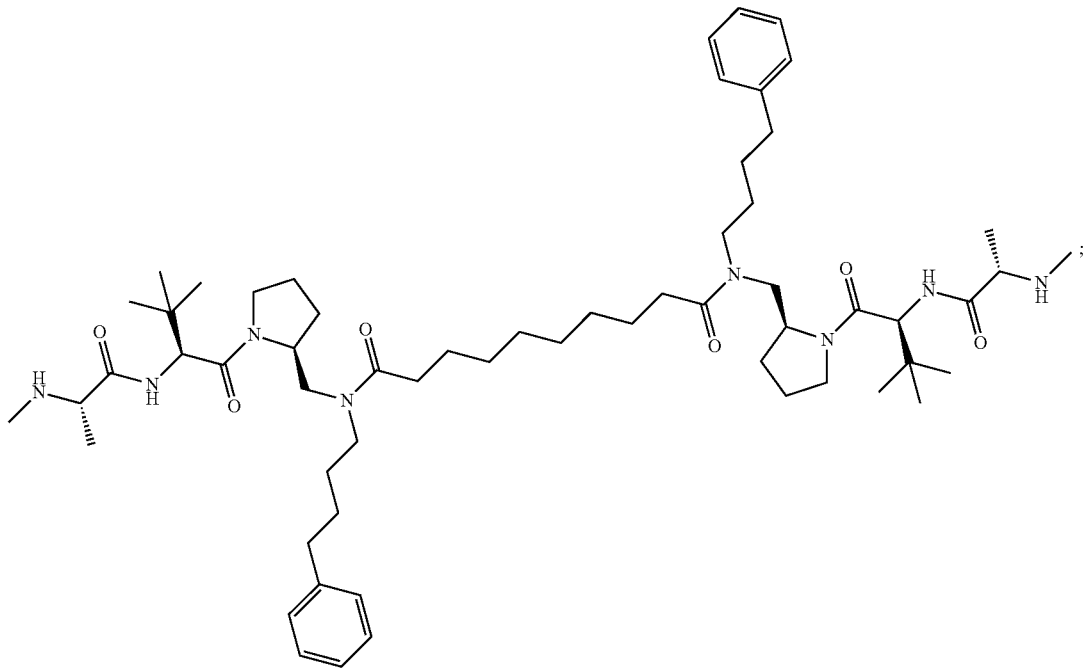 |
| 41 | 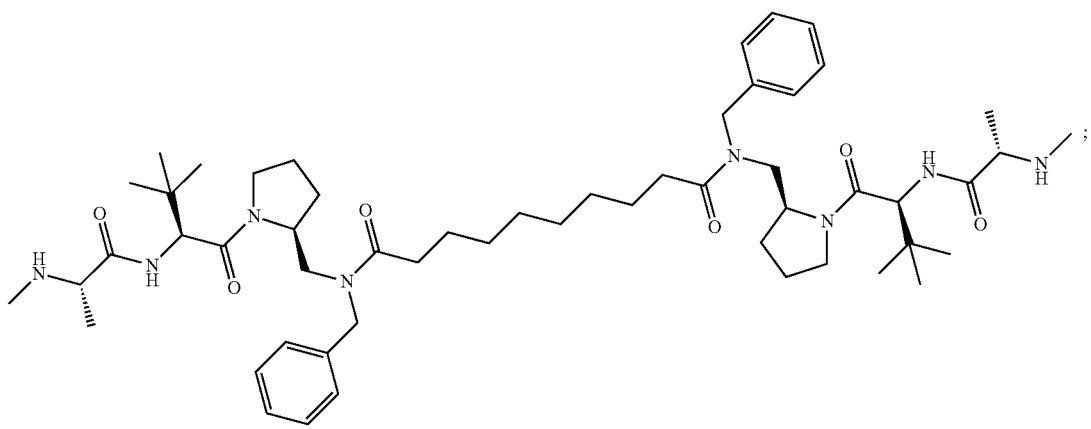 |

| Cmpd # | Structure |
|---|---|
| 42 | 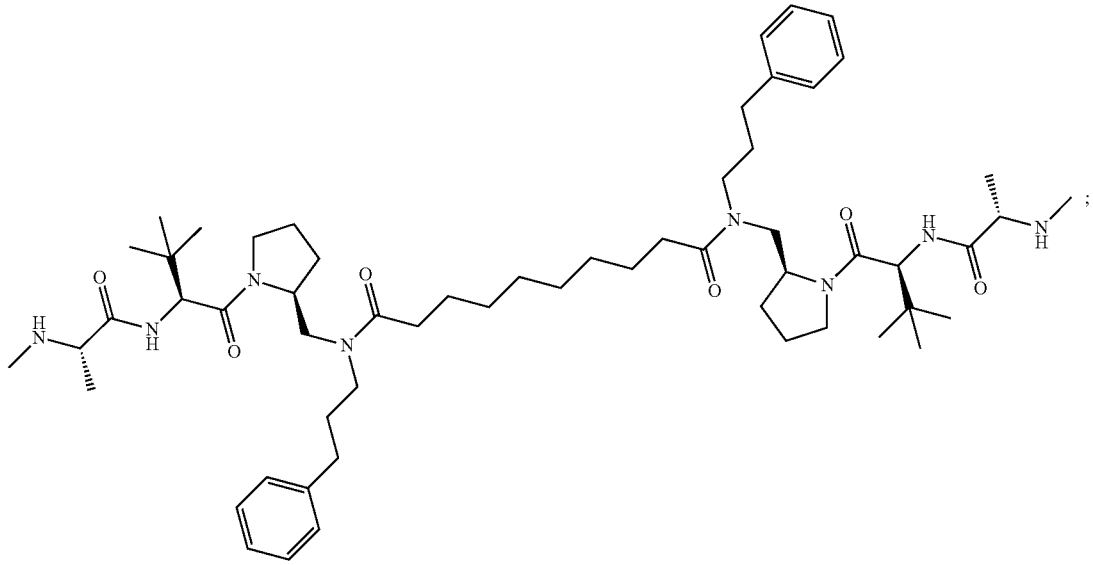 |
| 44 | 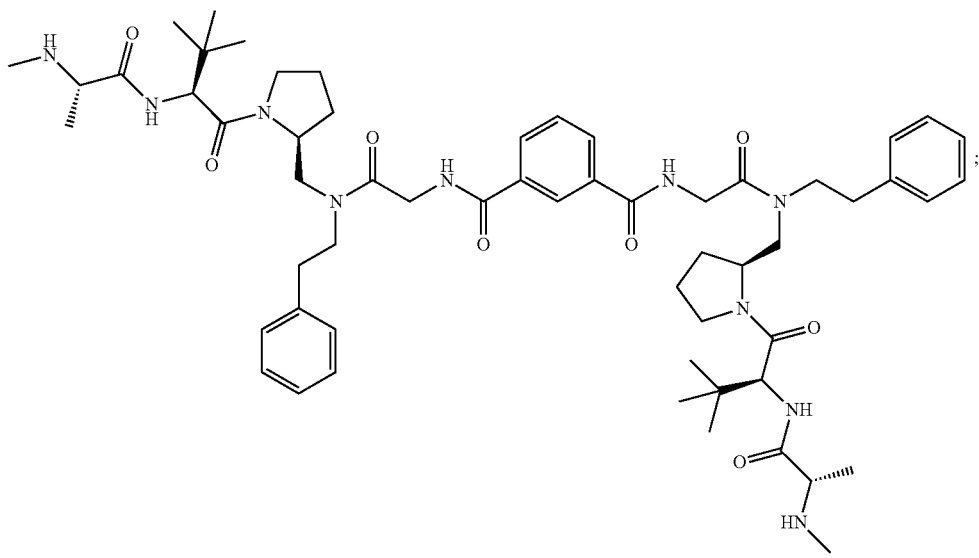 |

| Cmpd # | Structure |
|---|---|
| 46 | 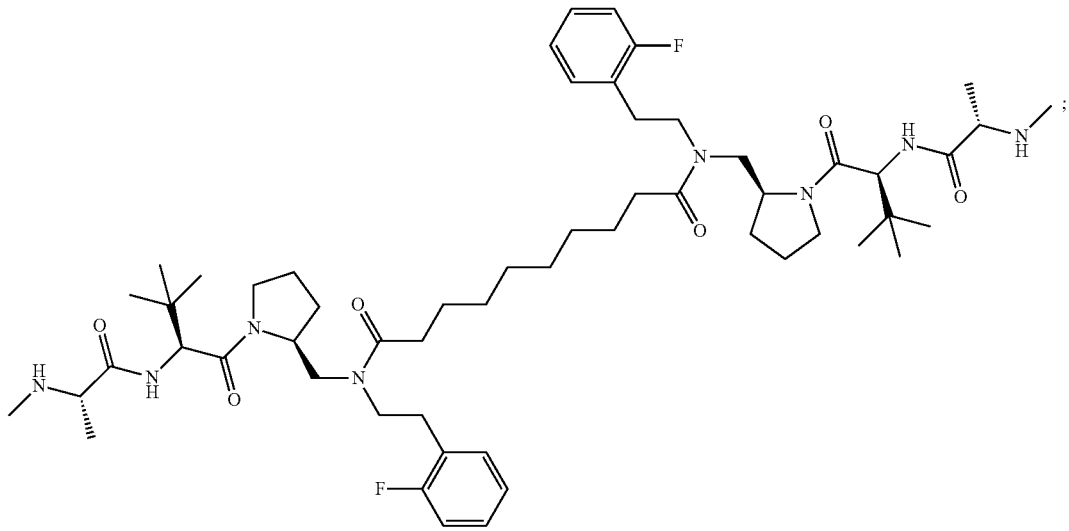 |
| 47 | 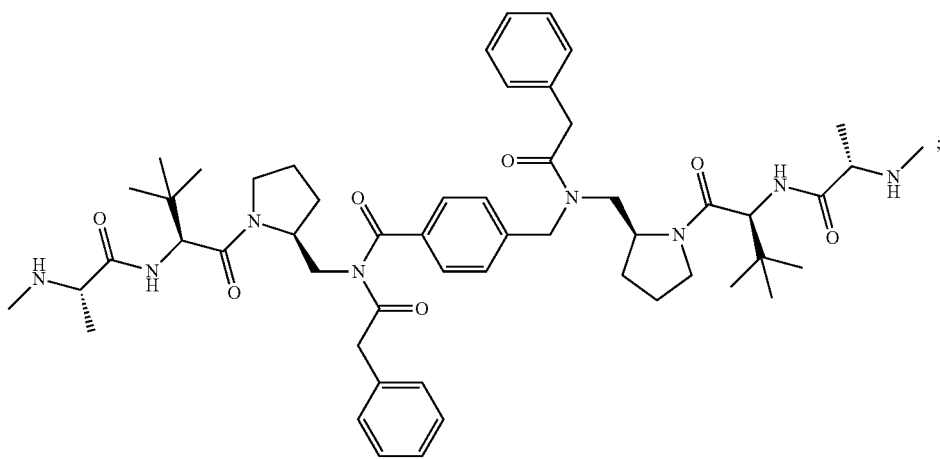 |
| 48 | 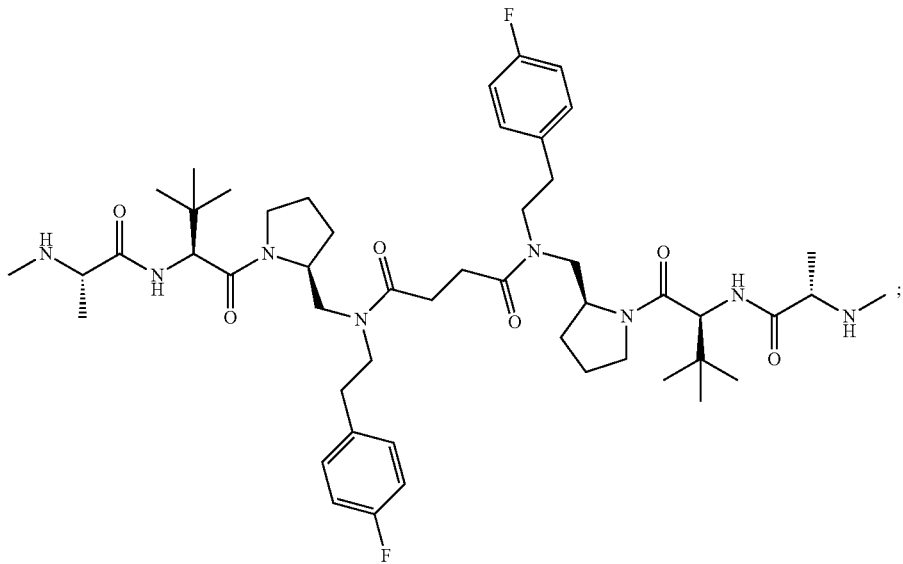 |

| Cmpd # | Structure |
|---|---|
| 49 | 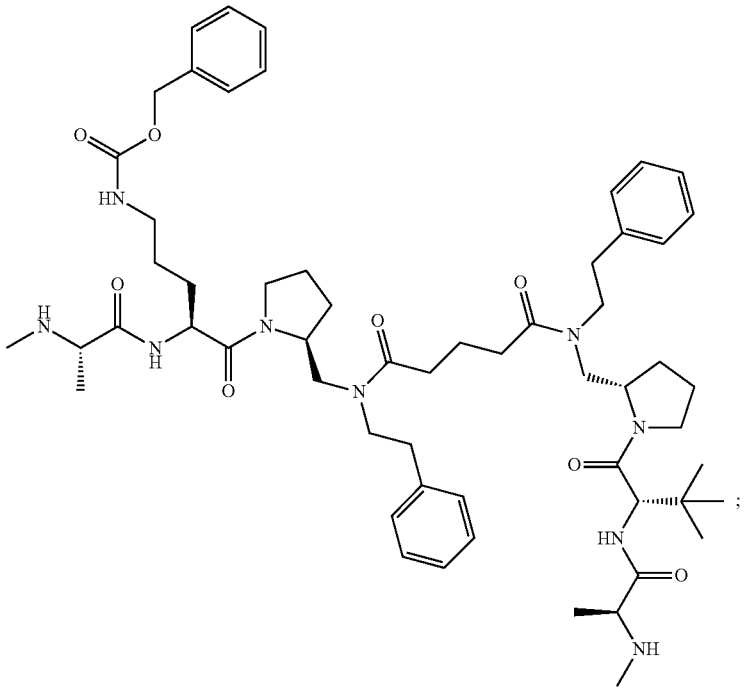 |
| 50 | 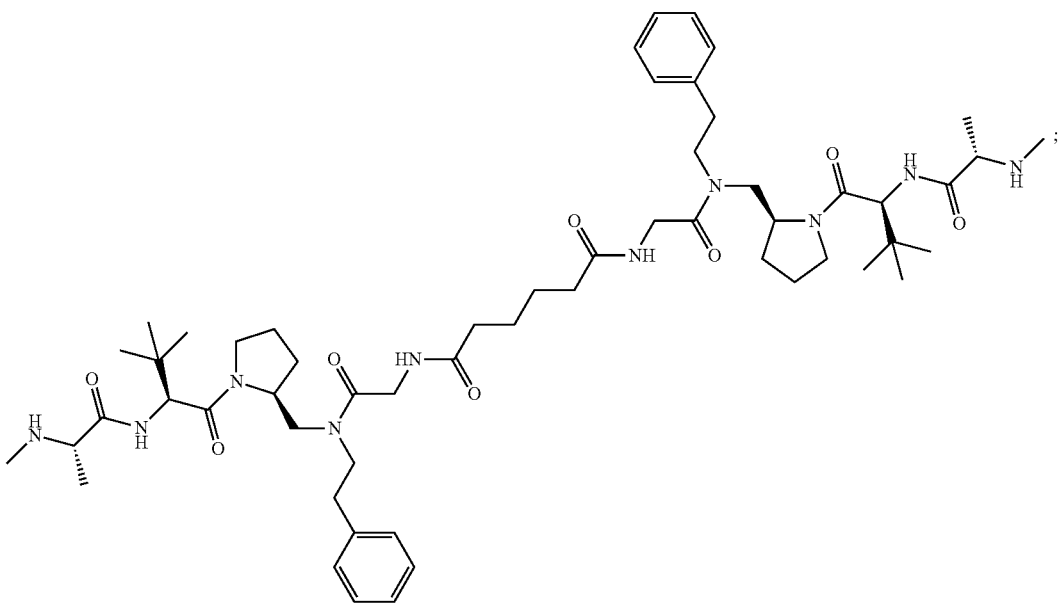 |

| Cmpd # | Structure |
|---|---|
| 52 | 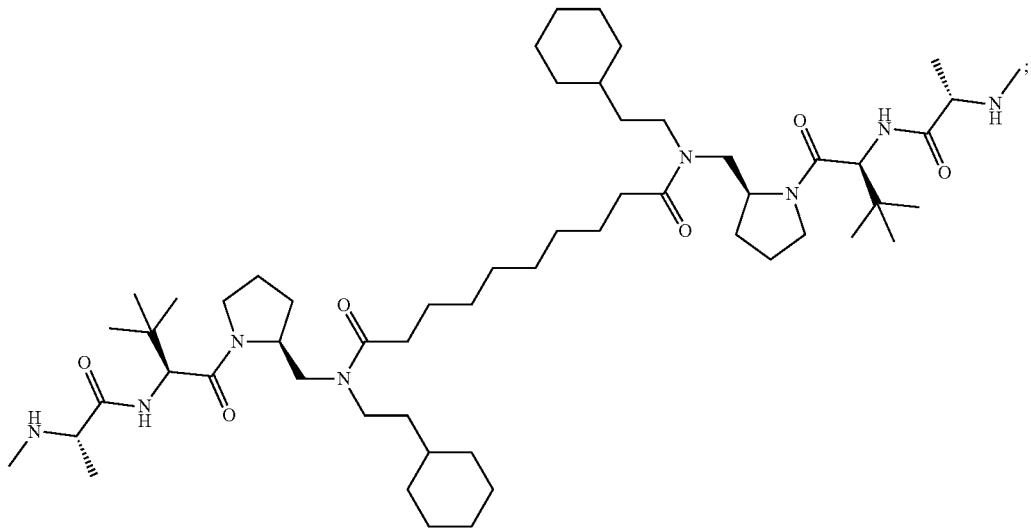 |
| 53 | 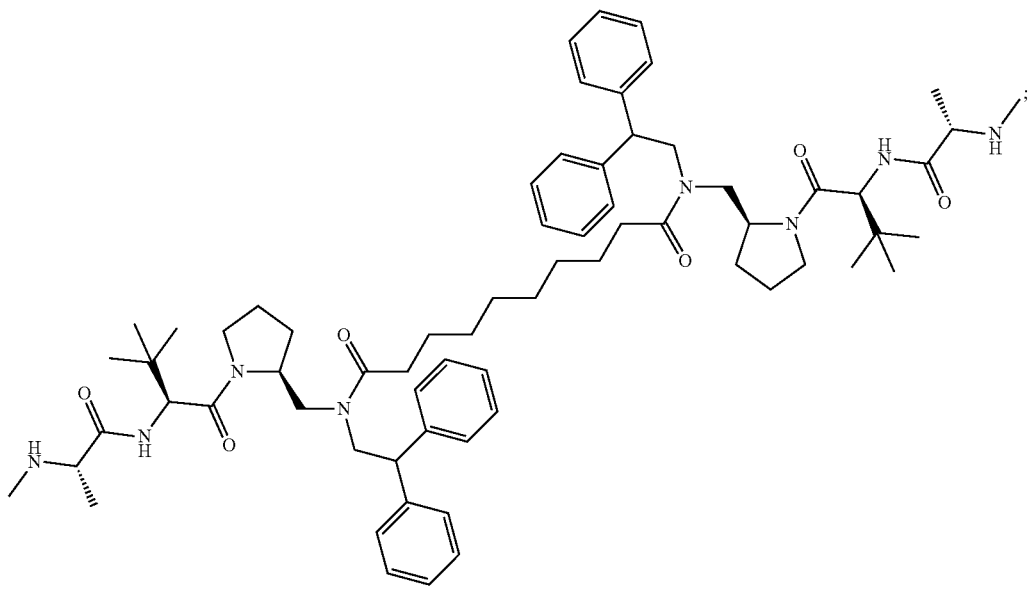 |

| Cmpd # | Structure |
|---|---|
| 54 | 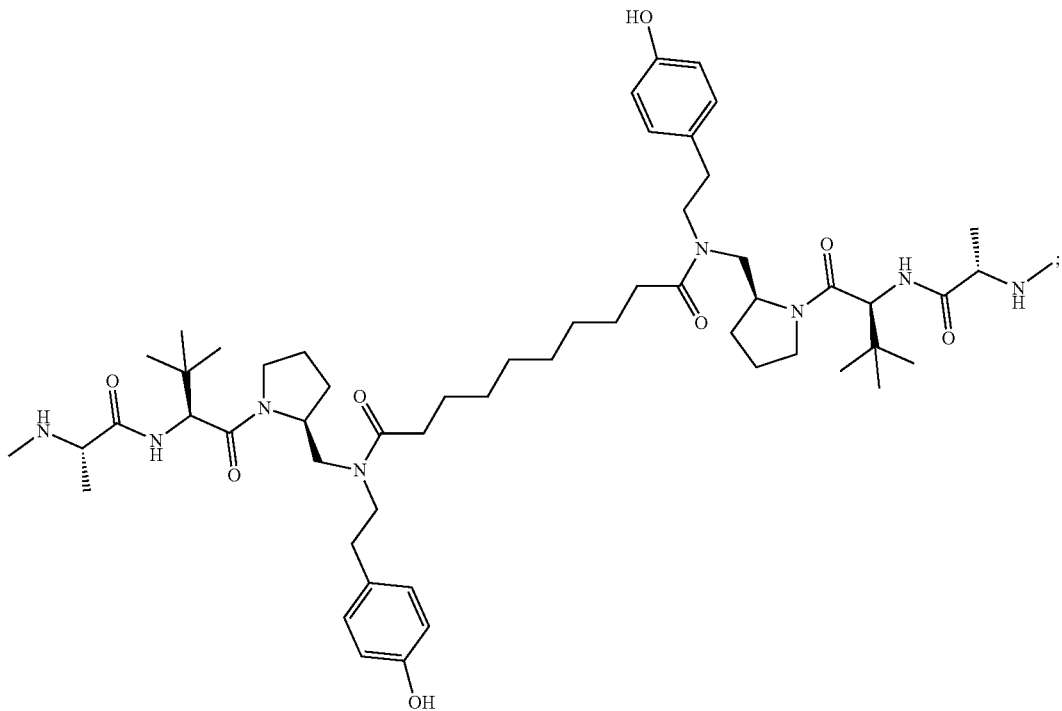 |
| 55 | 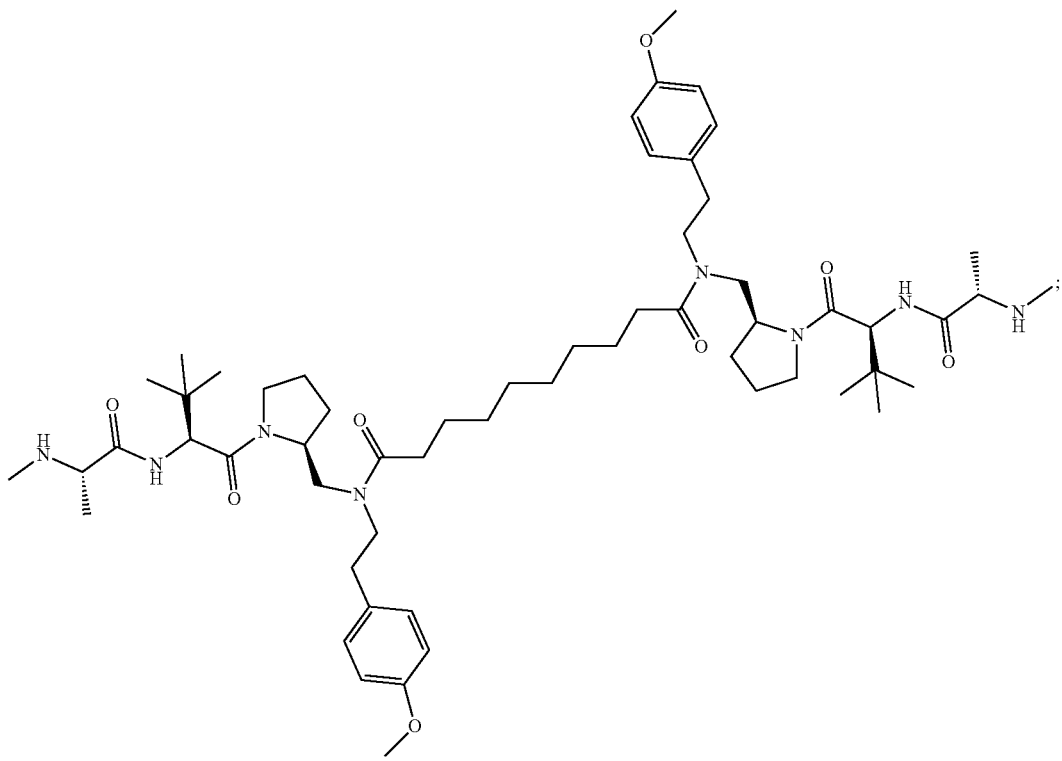 |

-continued
| Cmpd # | Structure |
|---|---|
| 57 | 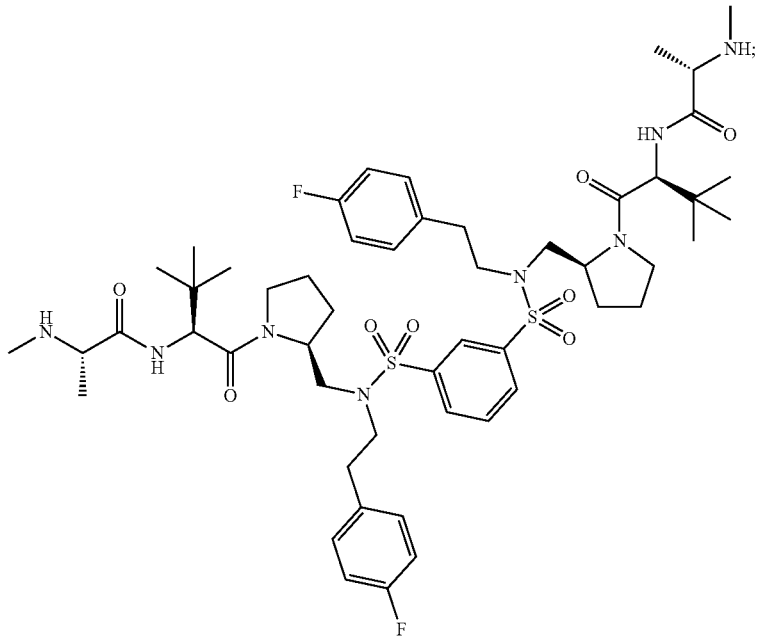 |
| 59 | 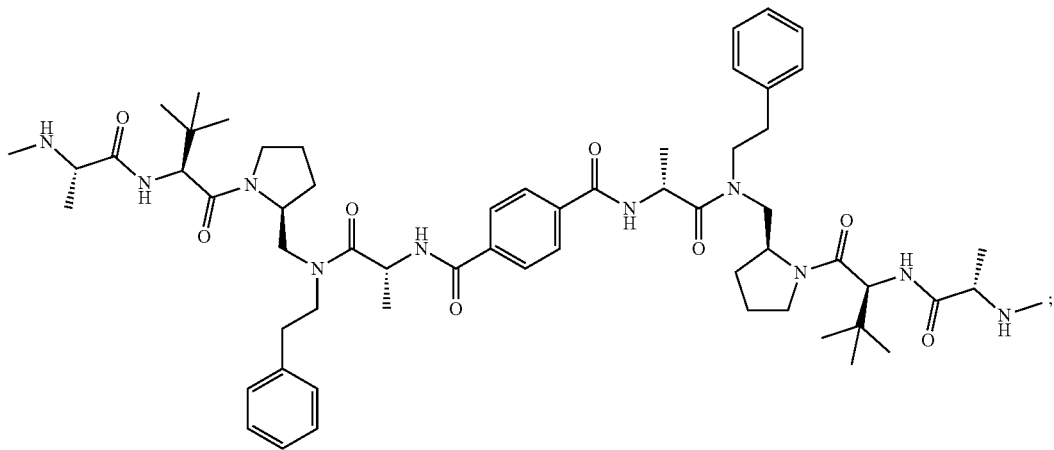 |
| 60 | 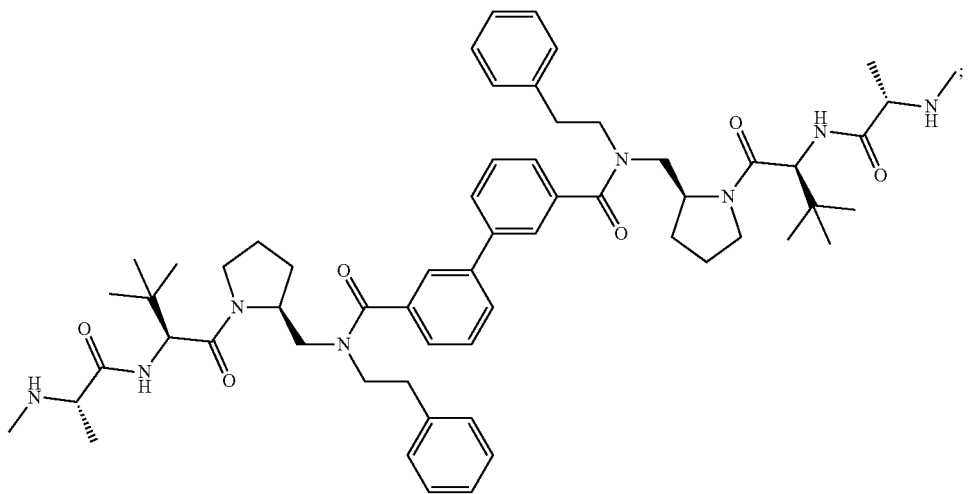 |

| Cmpd # | Structure |
|---|---|
| 61 | 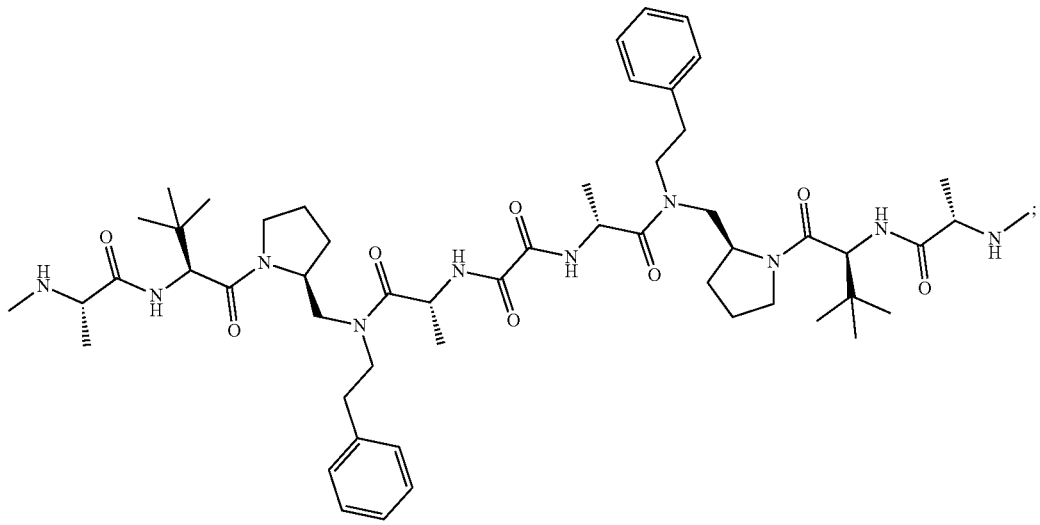 |
| 62 | 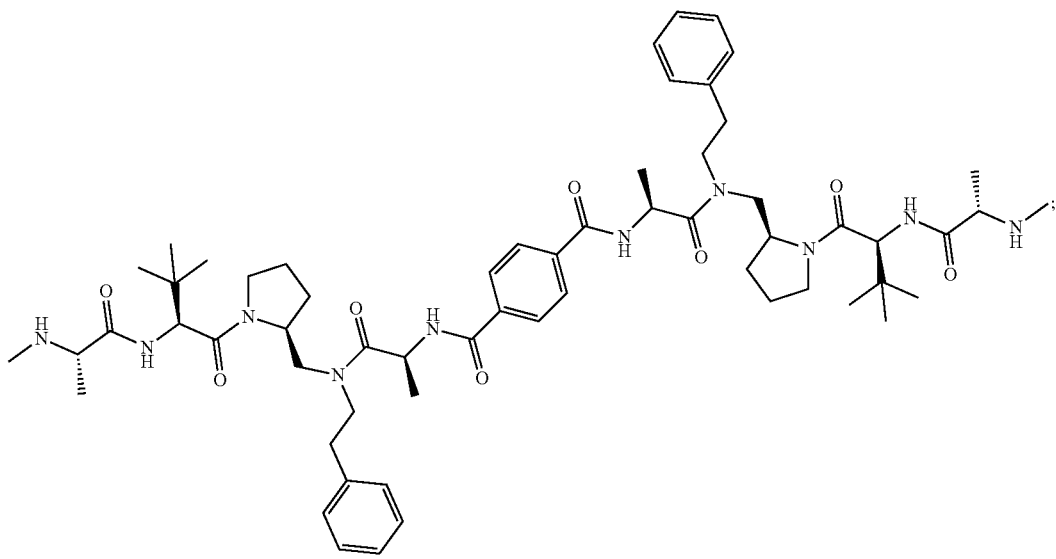 |

| Cmpd # | Structure |
|---|---|
| 63 | 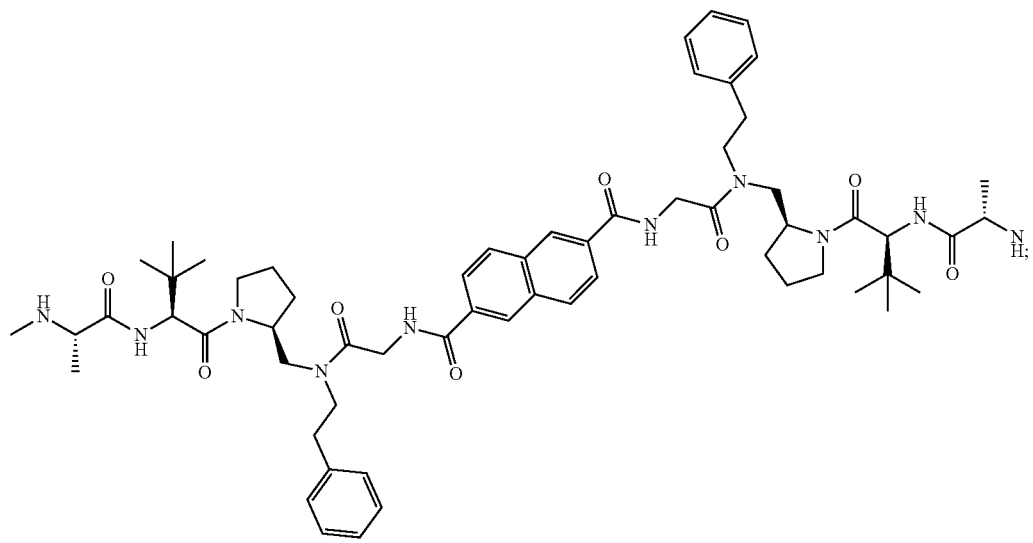 |
| 64 | 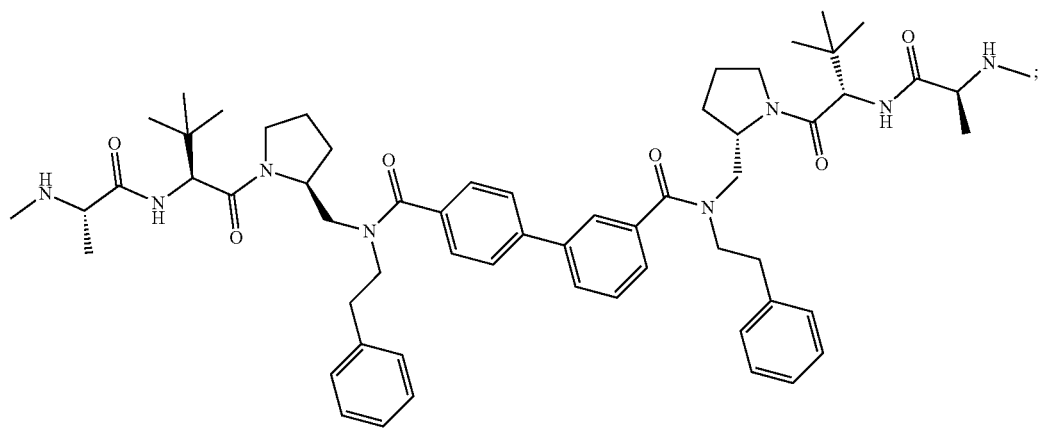 |
| 65 | 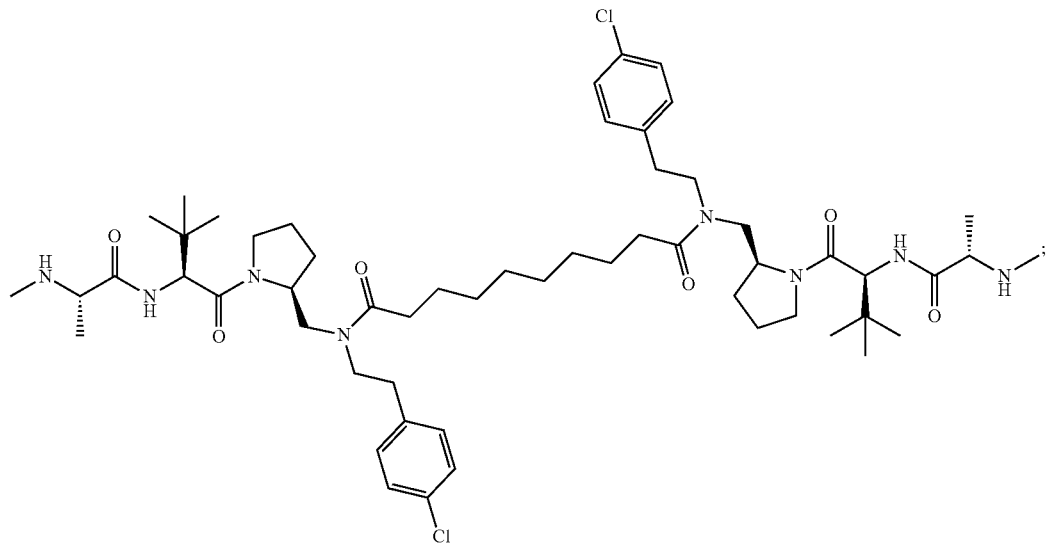 |

| Cmpd # | Structure |
|---|---|
| 66 | 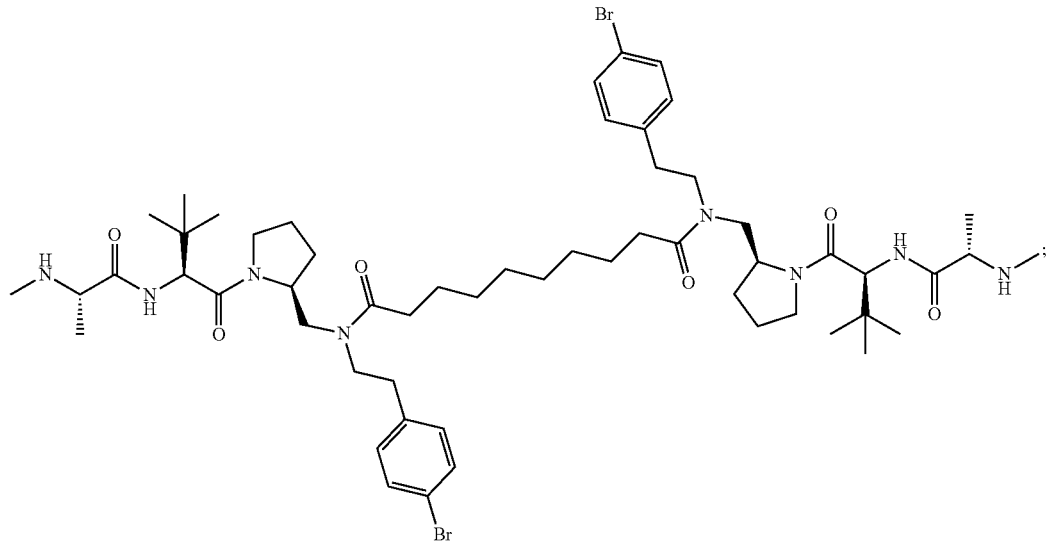 |
| 67 | 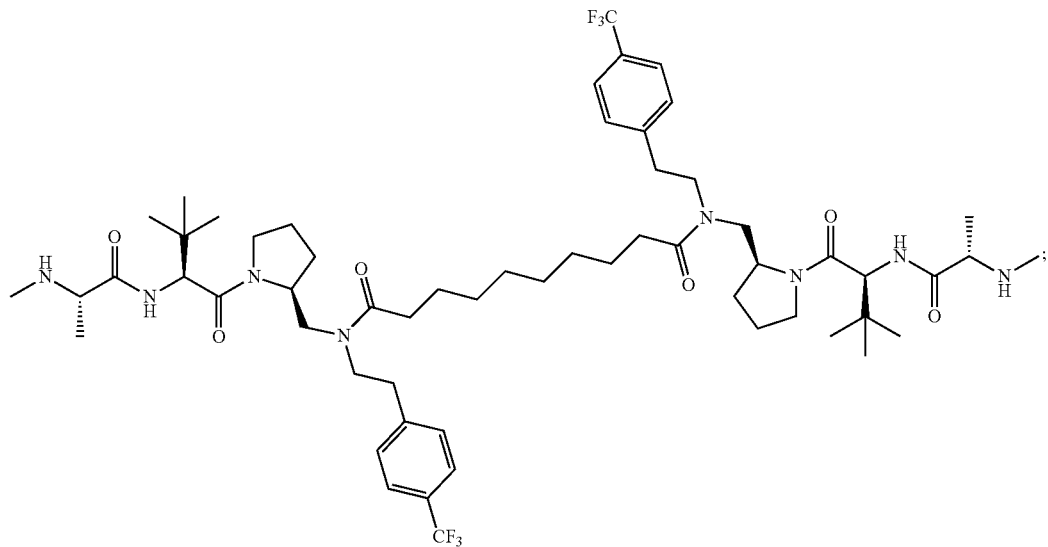 |
| 68 | 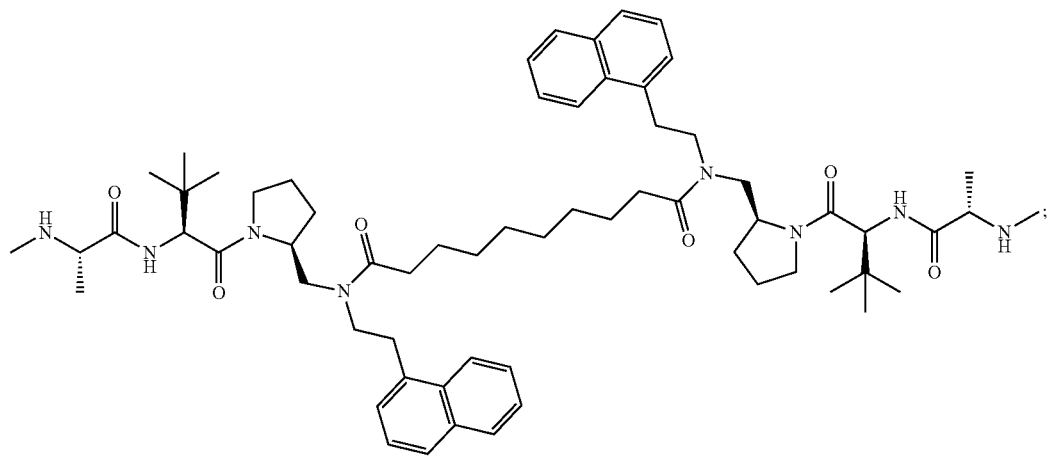 |

| Cmpd # | Structure |
|---|---|
| 69 | 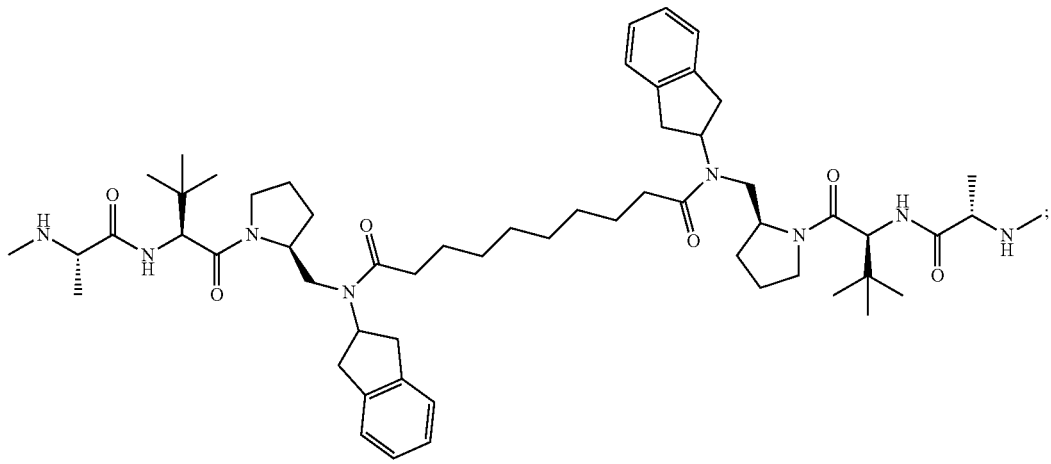 |
| 71 | 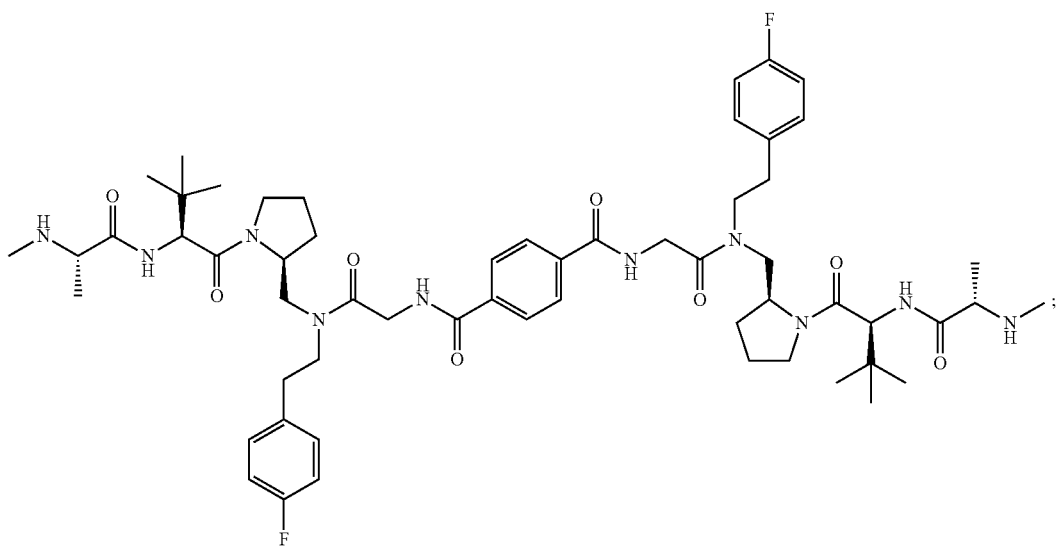 |
| 72 | 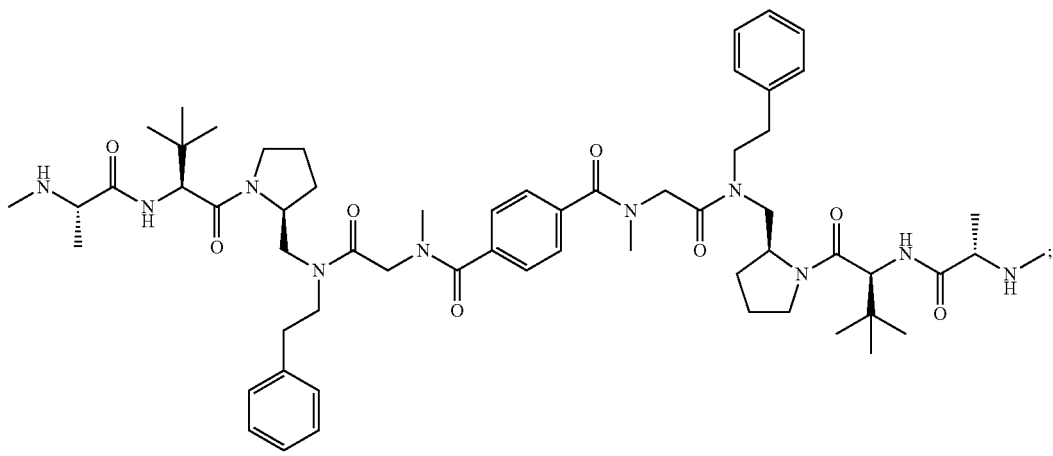 |

| Cmpd # | Structure |
|---|---|
| 73 | 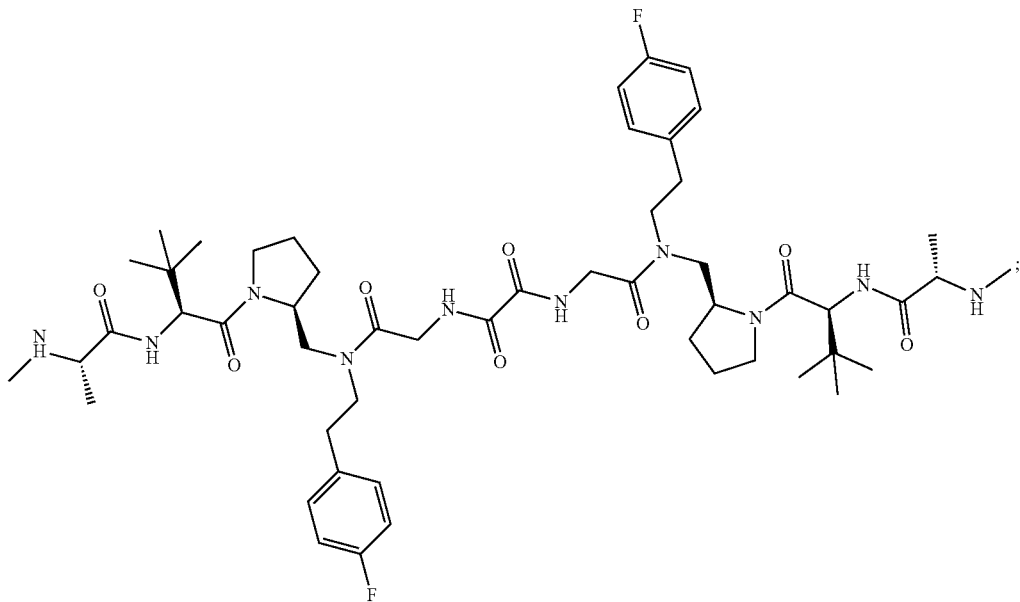 |
| 74 | 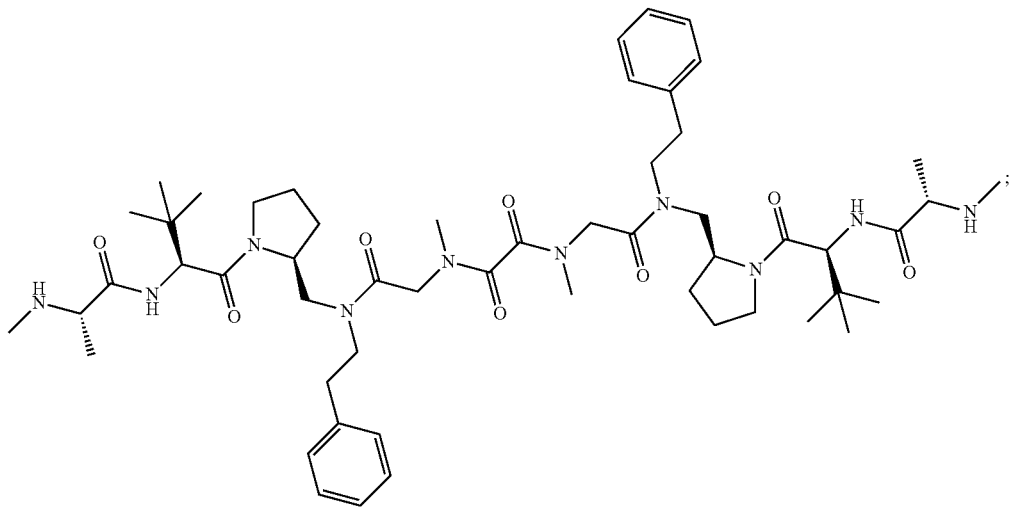 |

| Cmpd # | Structure |
|---|---|
| 75 | 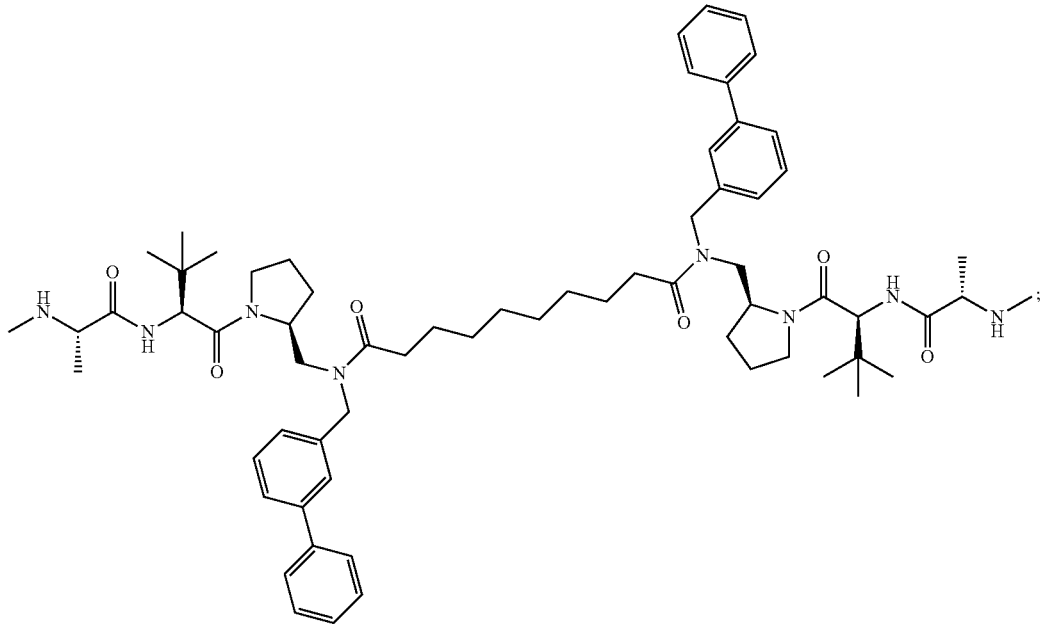 |
| 76 | 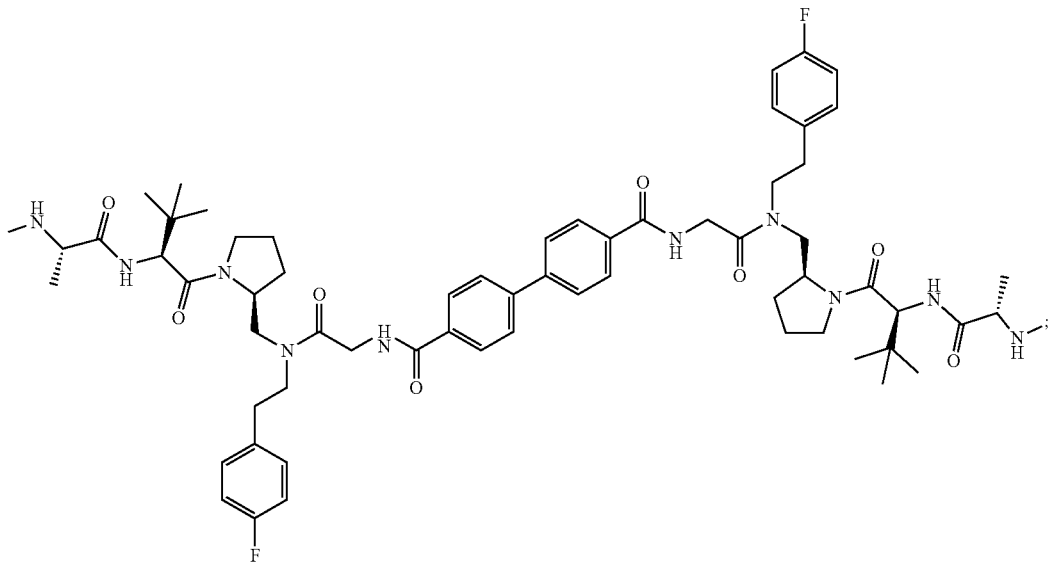 |

| Cmpd # | Structure |
|---|---|
| 77 | 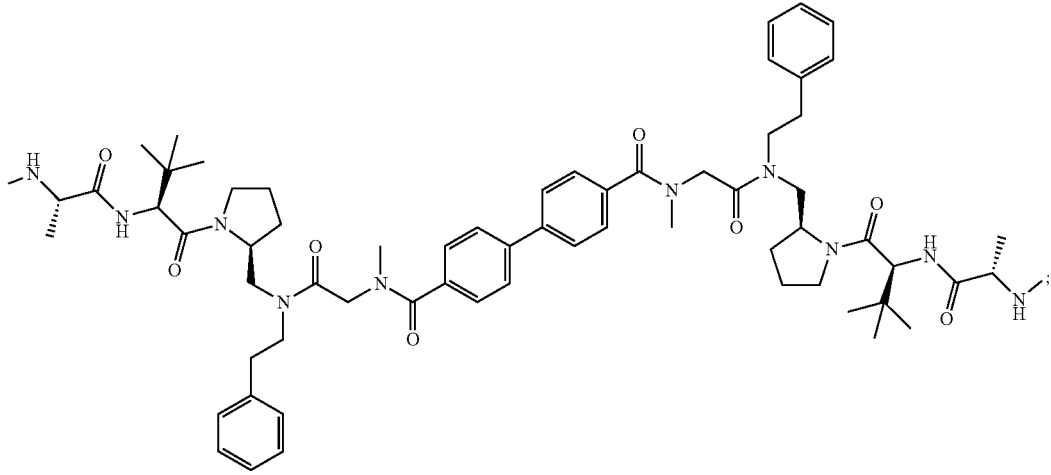 |
| 78 | 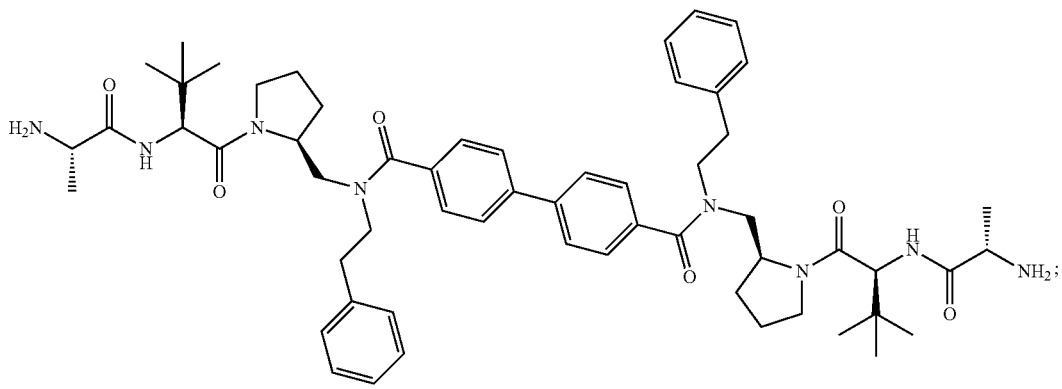 |
| 79 | 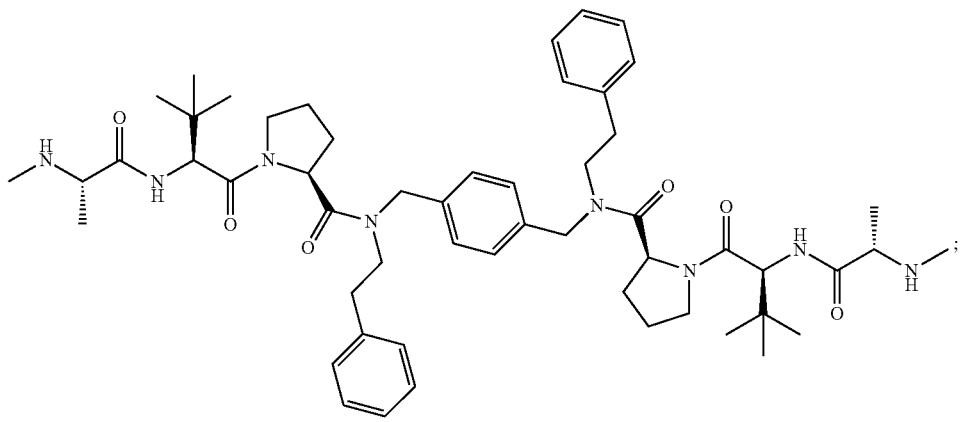 |

| Cmpd # | Structure |
|---|---|
| 82 | 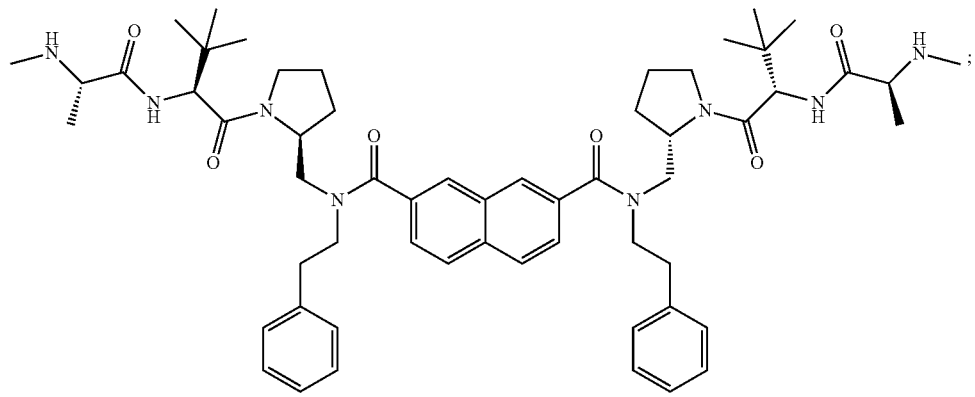 |
| 83 | 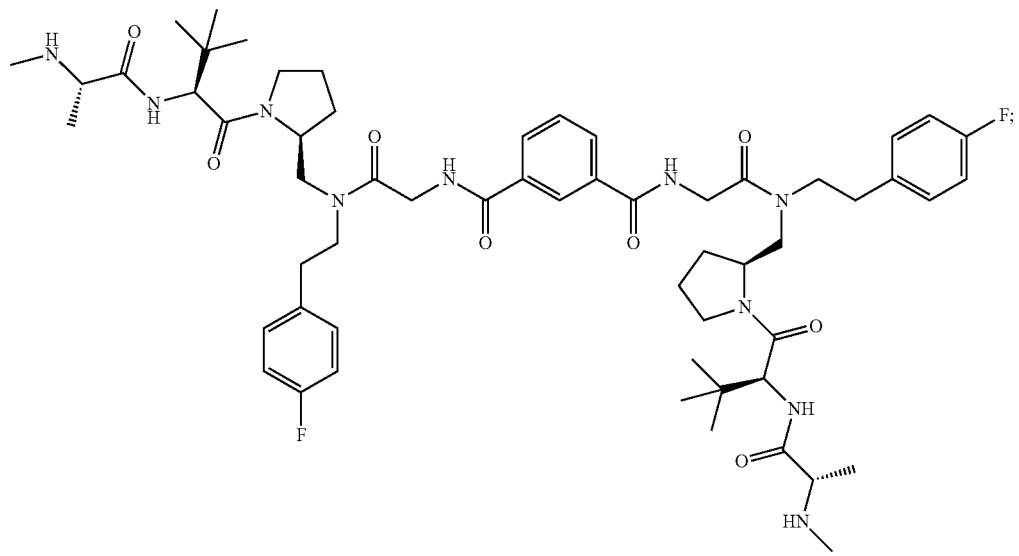 |
| 84 | 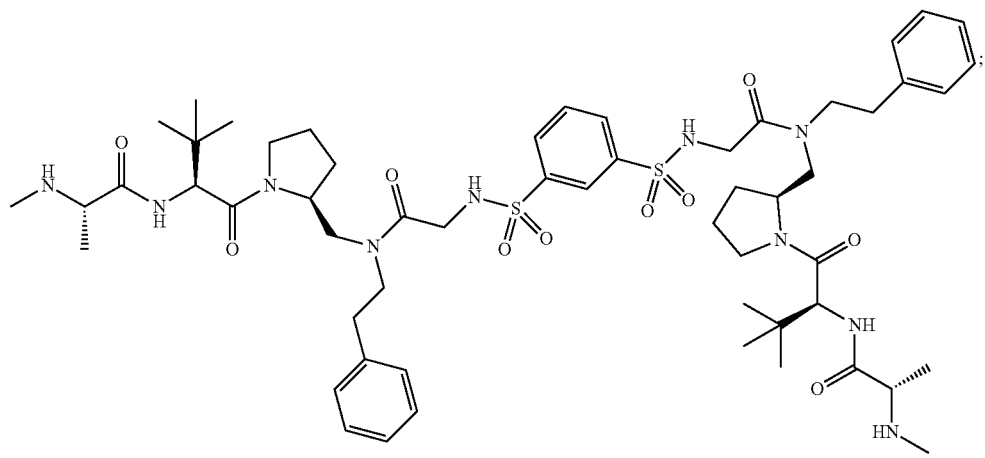 |

| Cmpd # | Structure |
|---|---|
| 85 | 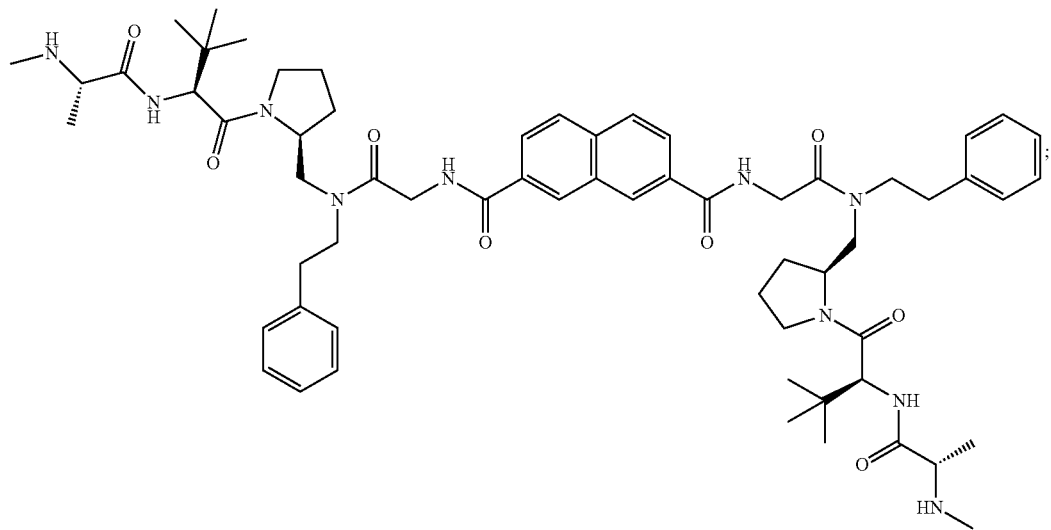 |
| 86 | 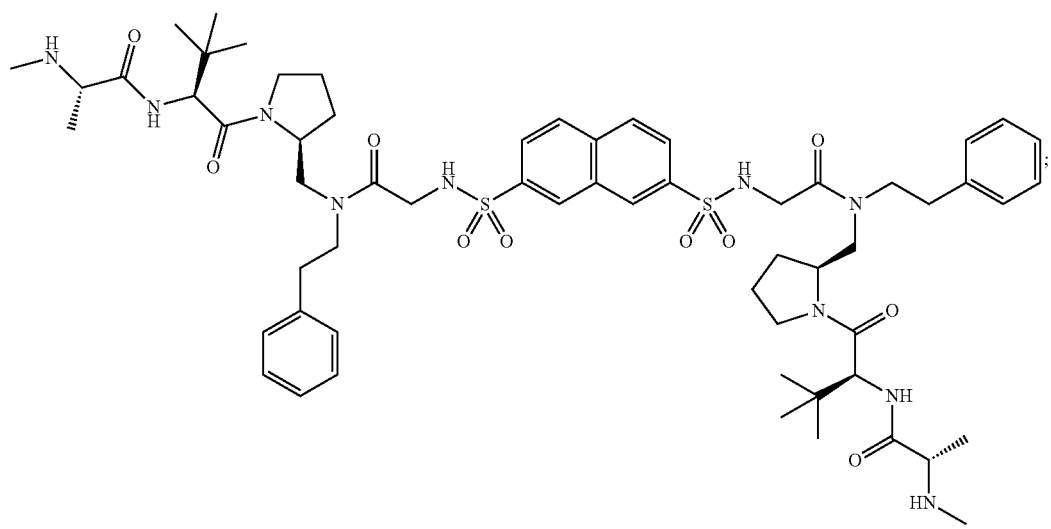 |
| 87 | 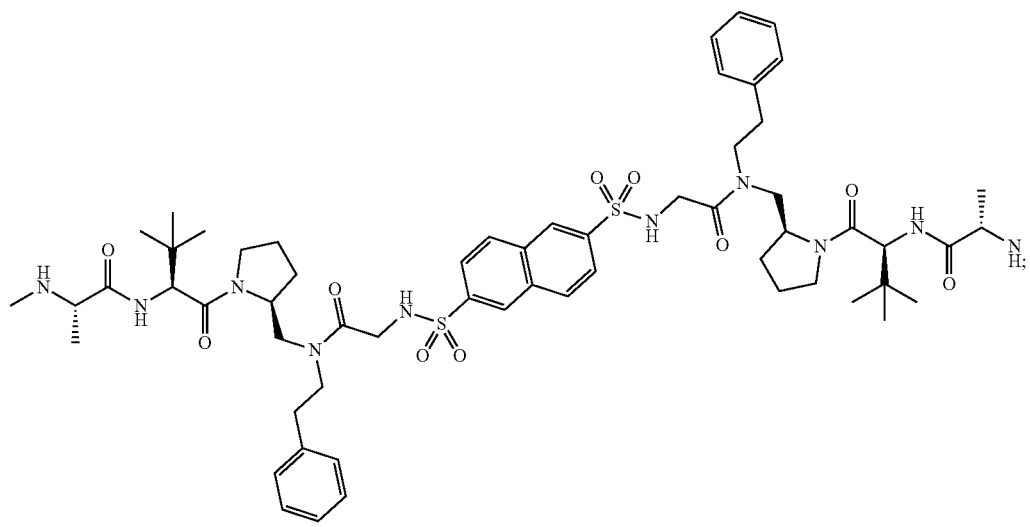 |

| Cmpd # | Structure |
|---|---|
| 89 | 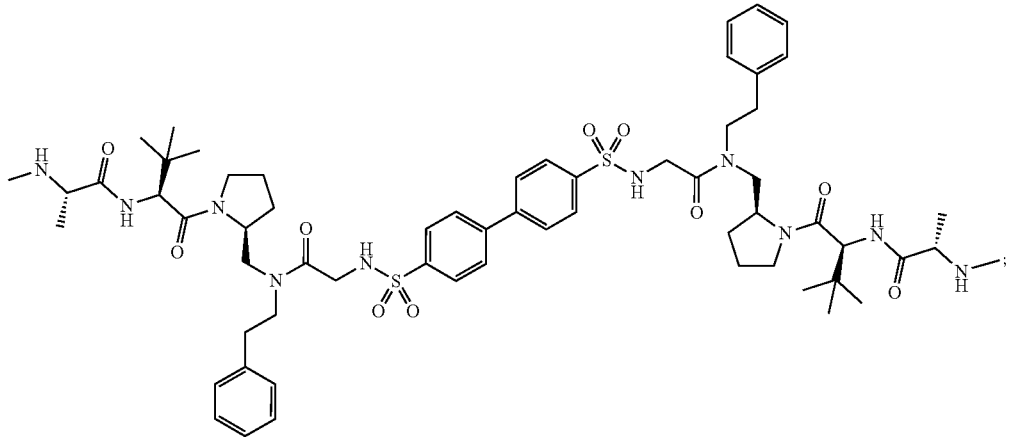 |
| 90 | 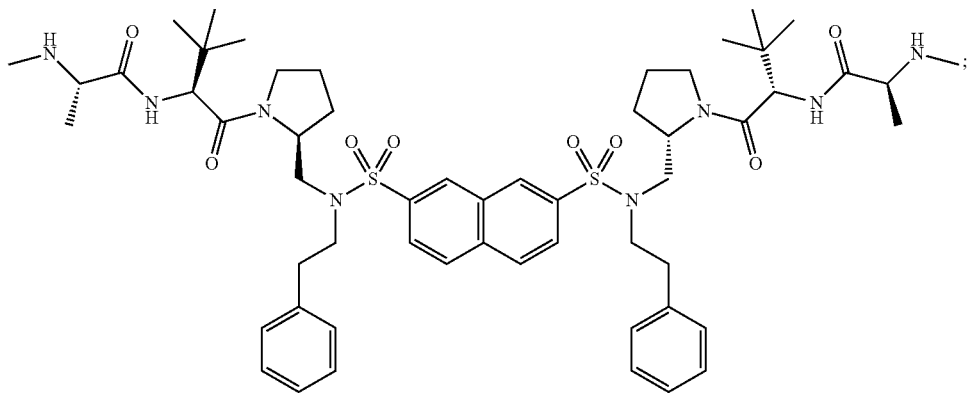 |
| 91 | 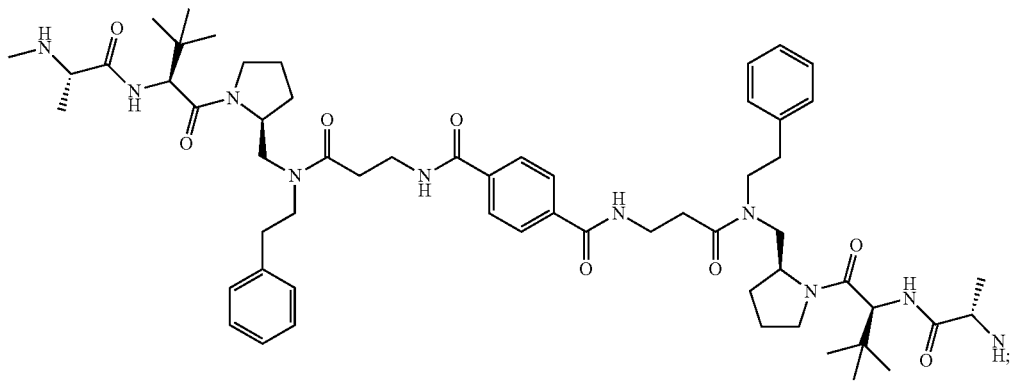 |

| Cmpd # | Structure |
|---|---|
| 93 | 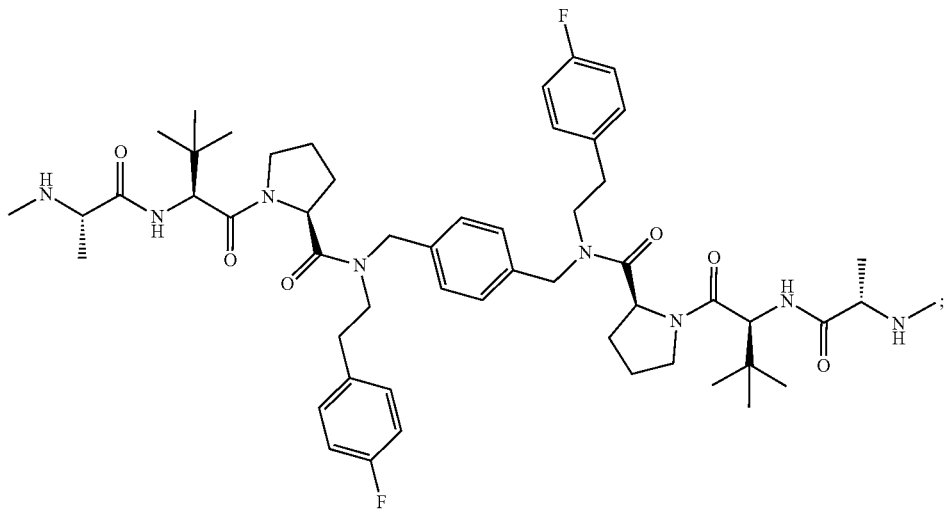 |
| 94 | 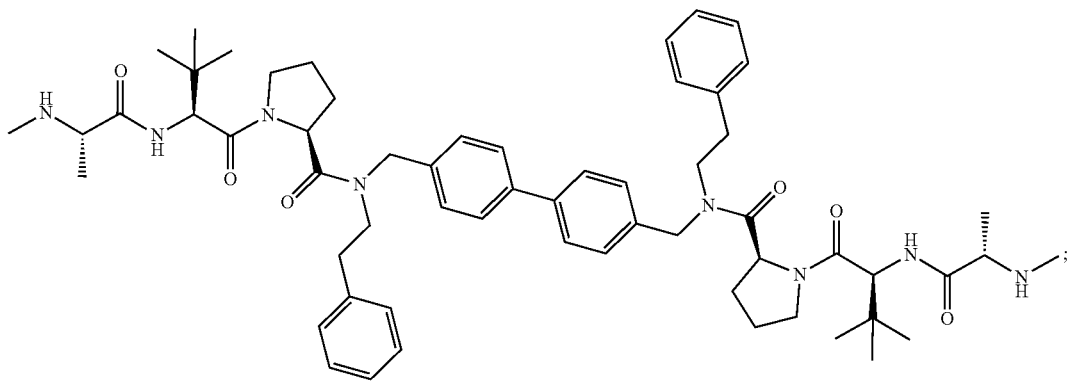 |
| 95 | 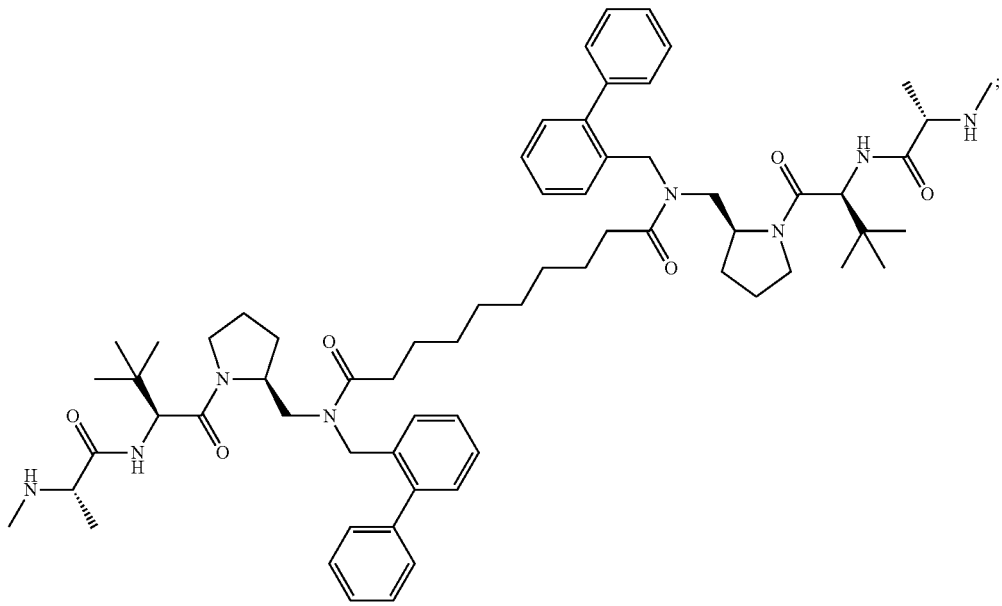 |

| Cmpd # | Structure |
|---|---|
| 96 | 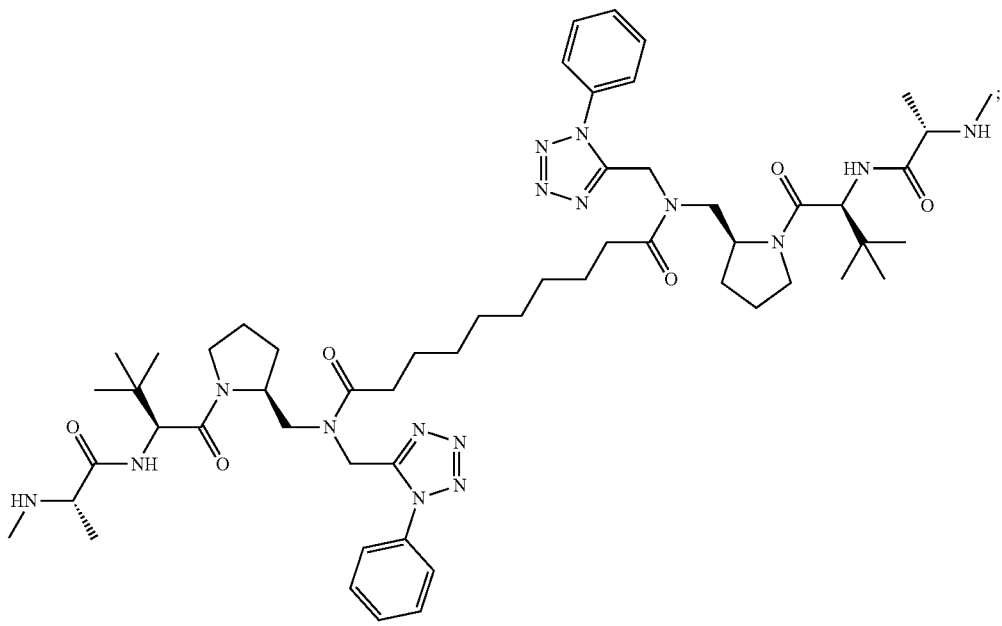 |
| 97 | 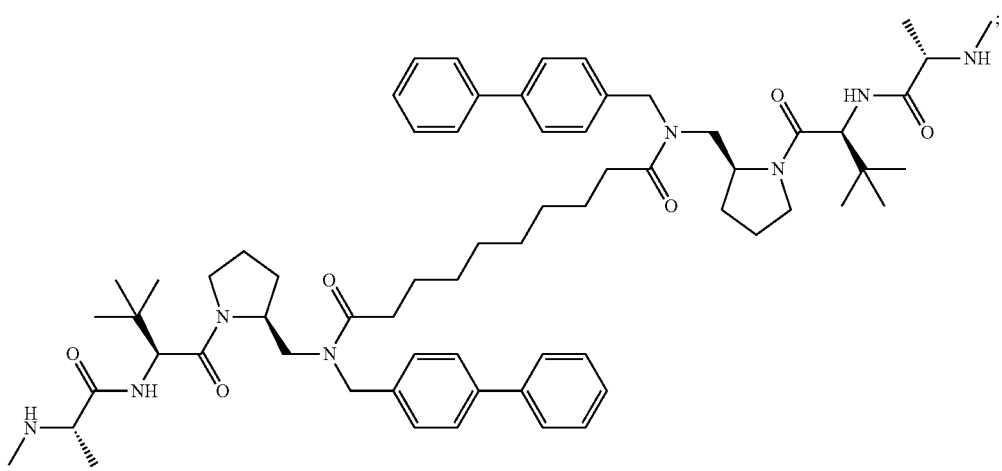 |

-continued
| Cmpd # | Structure |
|---|---|
| 98 | 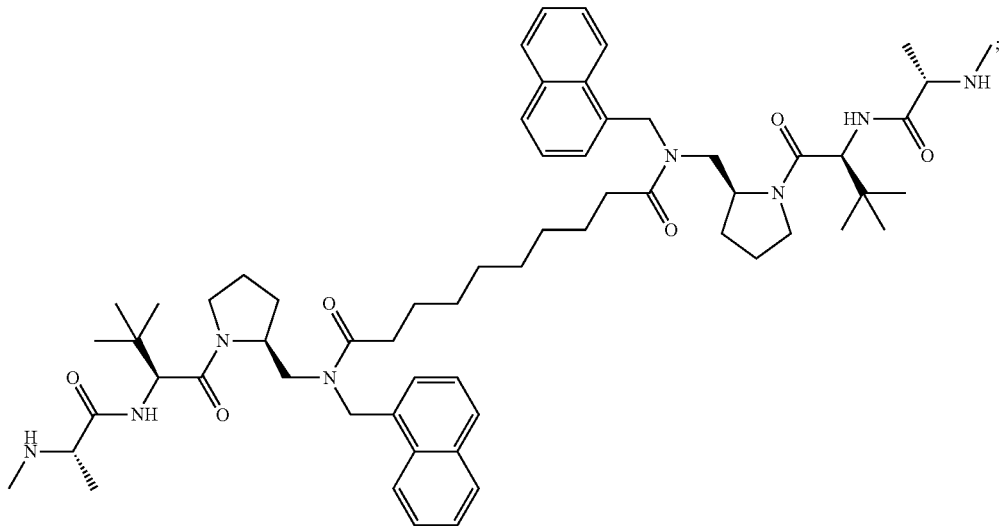 |
| 99 | 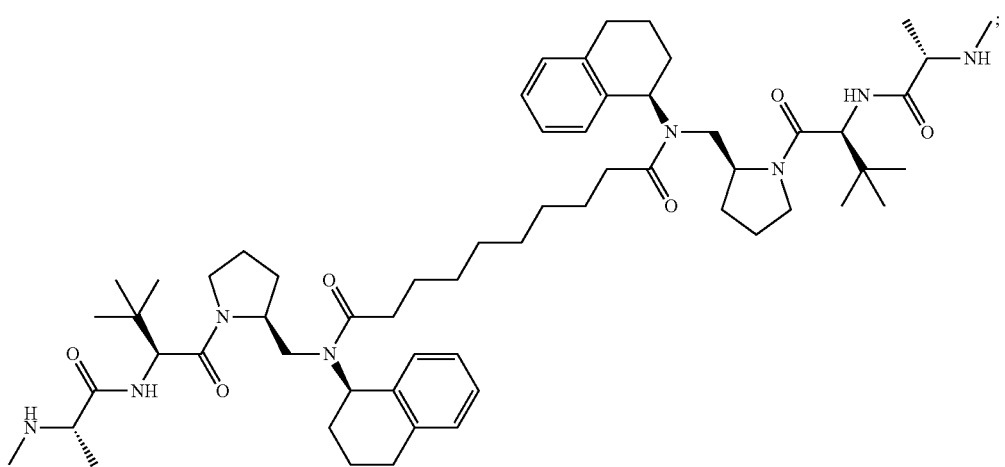 |
| 100 | 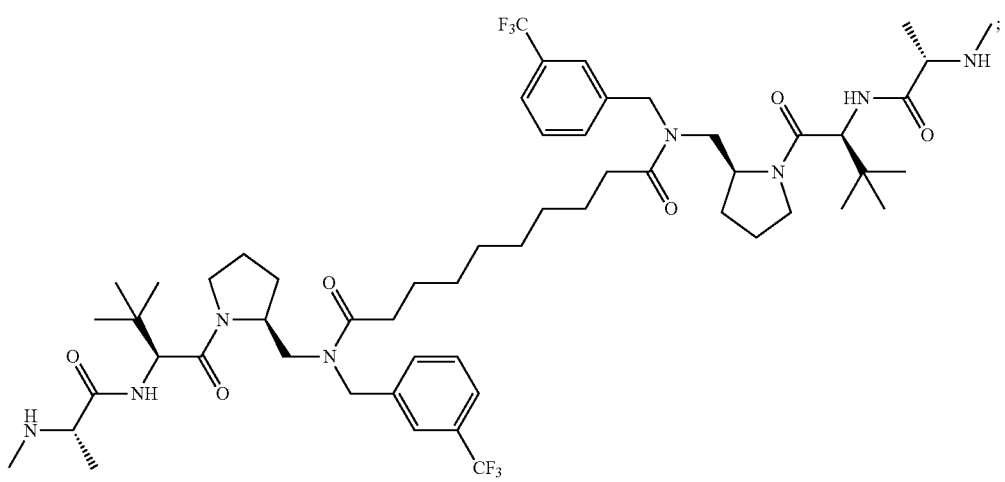 |

| Cmpd # | Structure |
|---|---|
| 101 | 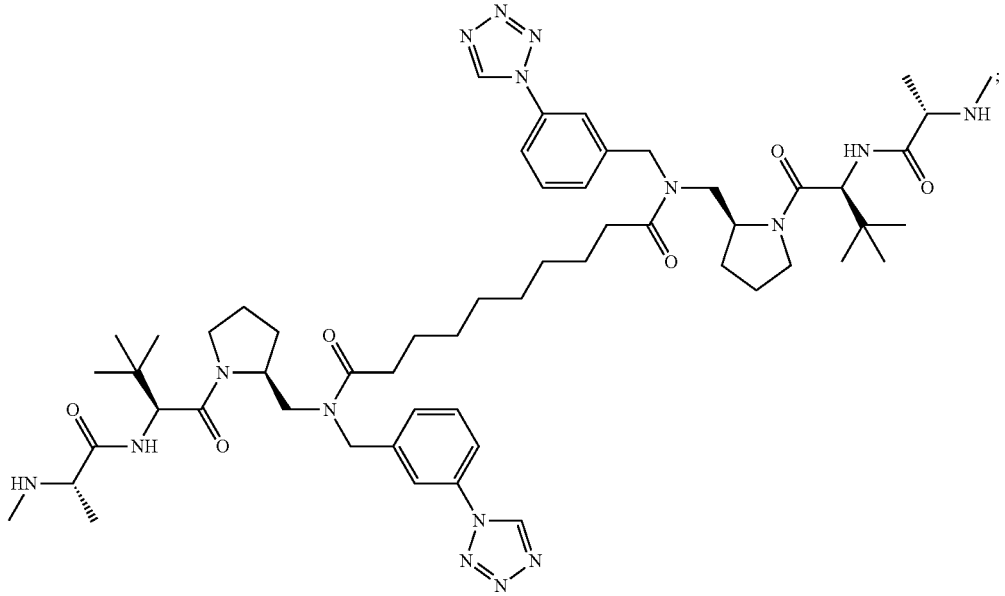 |
| 102 | 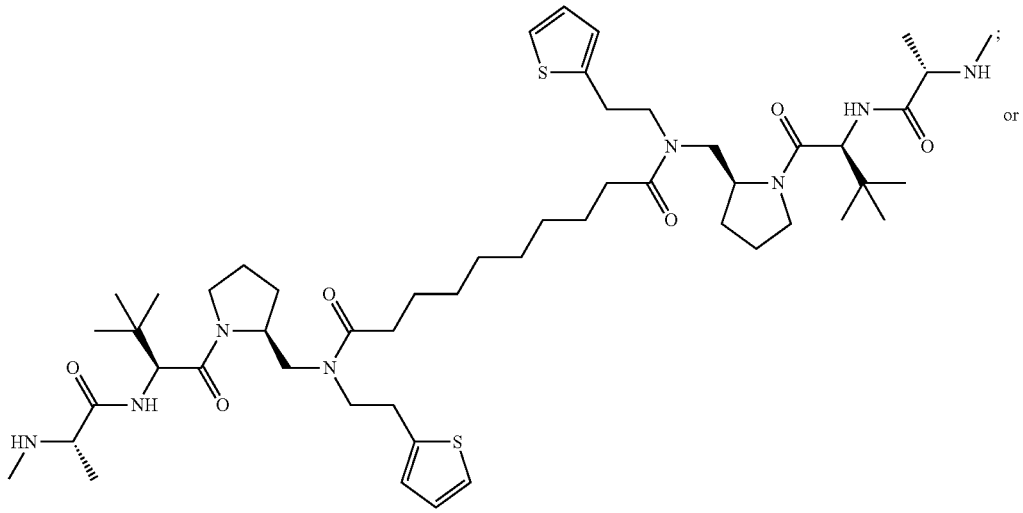 or |
| 103 | 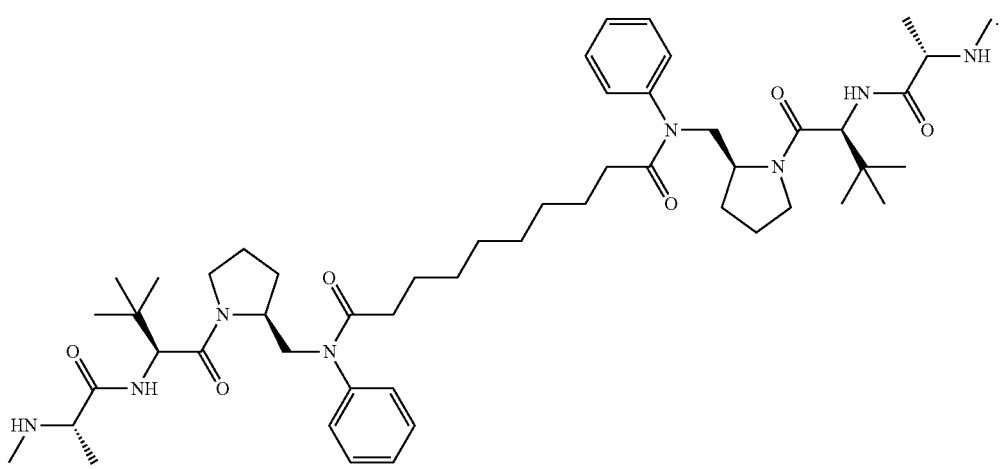 | or a san thereof.

16. A method for the preparation of a pharmaceutically acceptable salt of compound of Formula I, according to claim 1, by the treatment of a compound of Formula I with 1 to 2 equivalents of a pharmaceutically acceptable acid.

17. A pharmaceutical composition comprising a compound of Formula I, according to claim 1, and a pharmaceutically acceptable carrier, diluent or excipient.

18. A pharmaceutical composition according to claim 17 further comprising one or more death receptor agonists, a compound that increases the circulating level of one or more death receptor agonists, or a therapeutic agent that increases the response of one or more death receptor agonists.

19. A method of preparing a pharmaceutical composition, the method comprising: combining a compound, according to claim 1, with a pharmaceutically acceptable carrier, diluent or excipient.

20. The compound, according to claim 11, wherein
(a) $R^1$, $R^{1a}$, $R^{100}$ and $R^{100a}$ are independently H or $CH_3$;
(b) $R^2$ and $R^{200}$ display (S)-stereochemistry; and
(c) $R^3$ and $R^{300}$ are H, (S)-methyl, (S)-ethyl, (S)-tert-butyl, (S)-cyclohexylmethyl, (S)-2-phenylethyl or benzyl(S)-butylcarbamate.

21. The compound, according to claim 20, in which Z is:
1) —N($R^8$)CON($R^8$)—,
2) —N($R^8$)C(O)-aryl-C(O)N($R^8$)—,
3) —N($R^8$)C(O)-heteroaryl-C(O)N($R^8$)—,
4) —C(O)—,
5) —N($R^8$)—$C_1$-$C_{12}$-alkyl-N($R^8$)—,
6) —N($R^8$)—C(O)C(O)—N($R^8$)—,
7) —N($R^8$)—C(O)—$C_1$-$C_{12}$-alkyl-C(O)—N($R^8$)—,
8) —N($R^8$)—C(O)-aryl-O-aryl-C(O)—N($R^8$)—,
9) —N($R^8$)—C(O)-heteroaryl-C(O)—N($R^8$)—,
10) —N($R^8$)—C(O)-biphenyl-C(O)—N($R^8$)—,
11) —N($R^8$)—S(O)$_2$—$C_1$-$C_{12}$-alkyl-S(O)$_2$—N($R^8$)—,
12) —N($R^8$)—S(O)$_2$-aryl-S(O)$_2$—N($R^8$)—,
13) —N($R^8$)—S(O)$_2$-heteroaryl-S(O)$_2$—N($R^8$)—, or
14) —N($R^8$)—S(O)$_2$-biphenyl-S(O)$_2$—N($R^8$)—, wherein the alkyl and the cycloalkyl are optionally substituted with one or more $R^7$ substituents, and the aryl, the heteroaryl and the heterocyclyl are optionally substituted with one or more $R^{11}$ substituents.

22. The compound, according to claim 1, wherein the compound is:

1

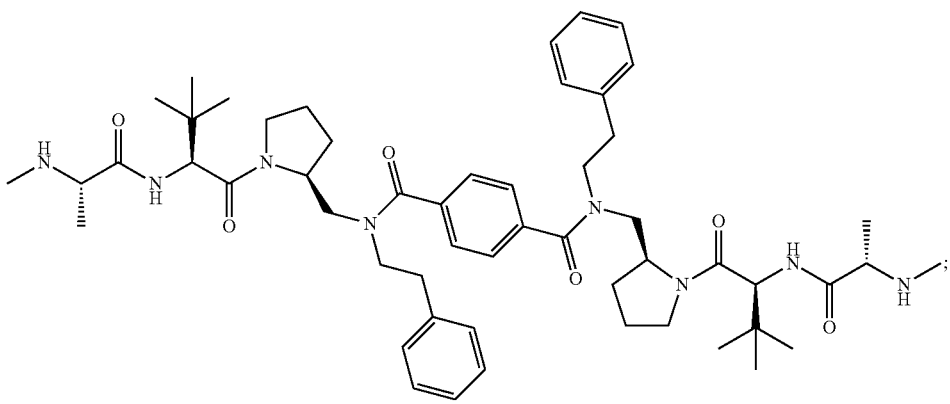

2

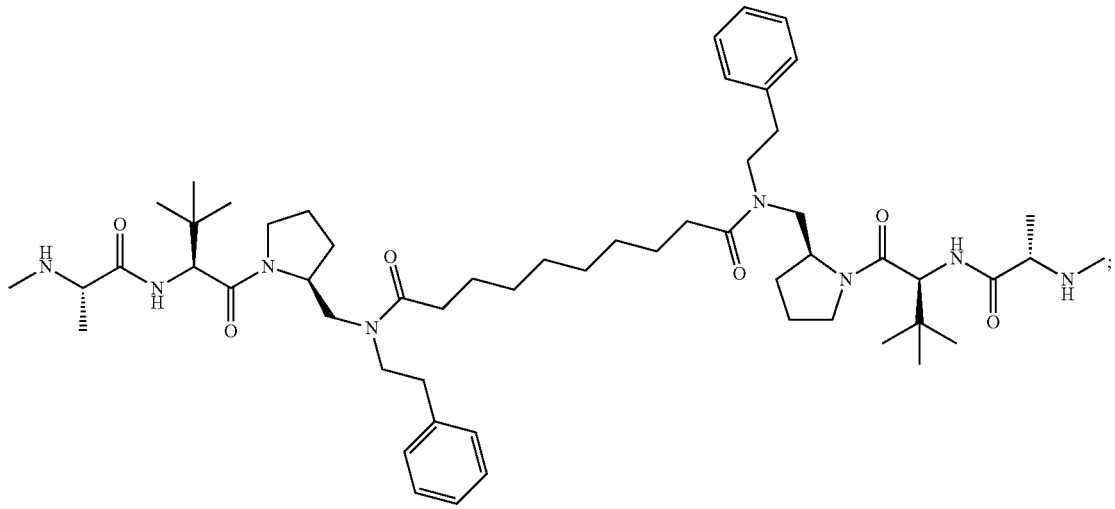

3
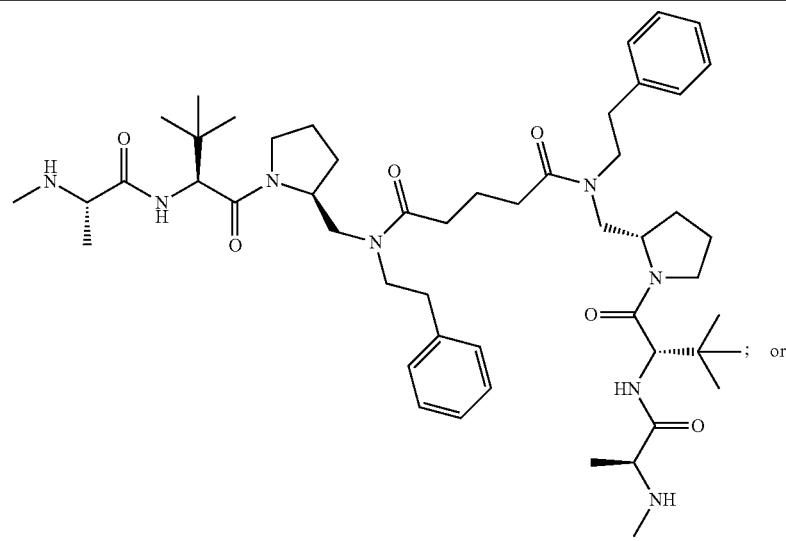
4
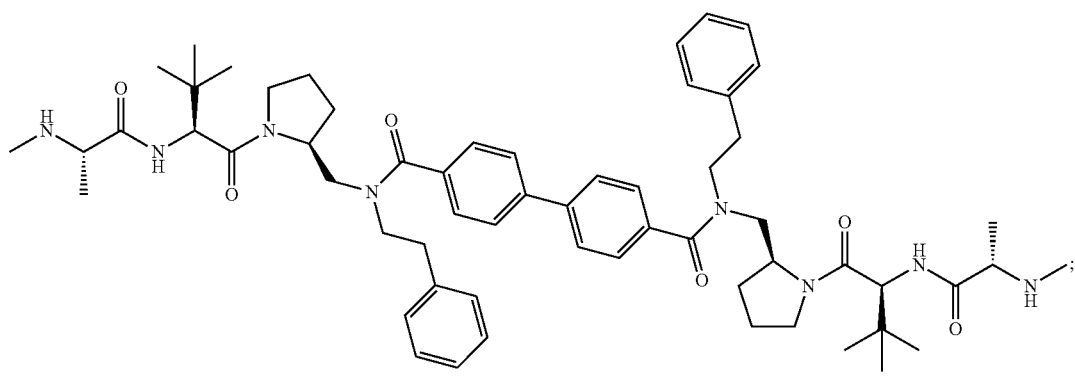
or a salt thereof.
23. The compound, according to claim 1, wherein the compound is:
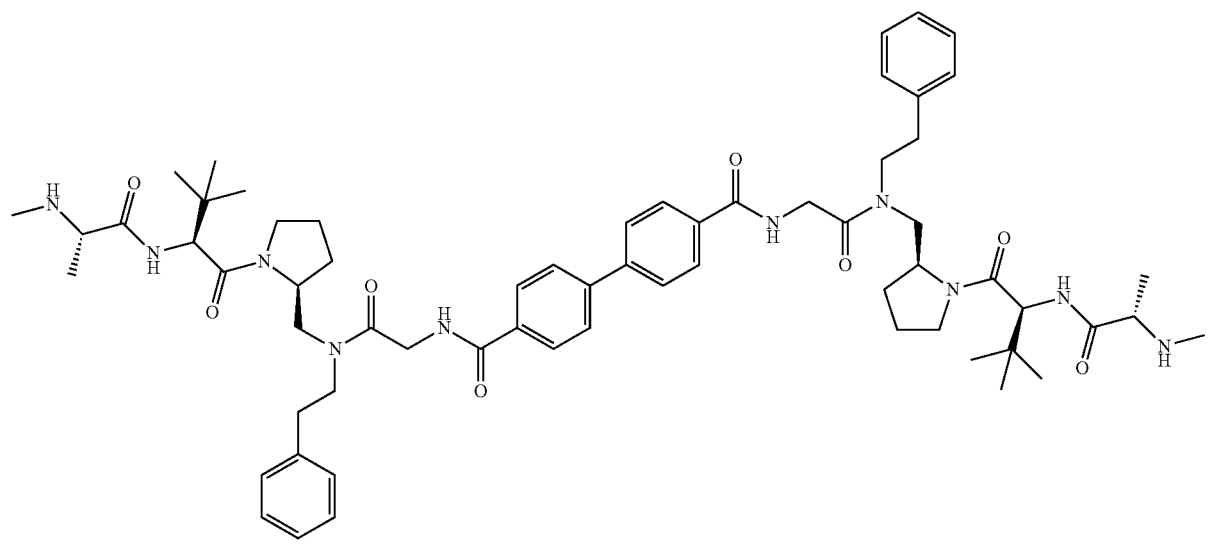
or a salt thereof.

24. The compound, according to claim 1, wherein the compound is:
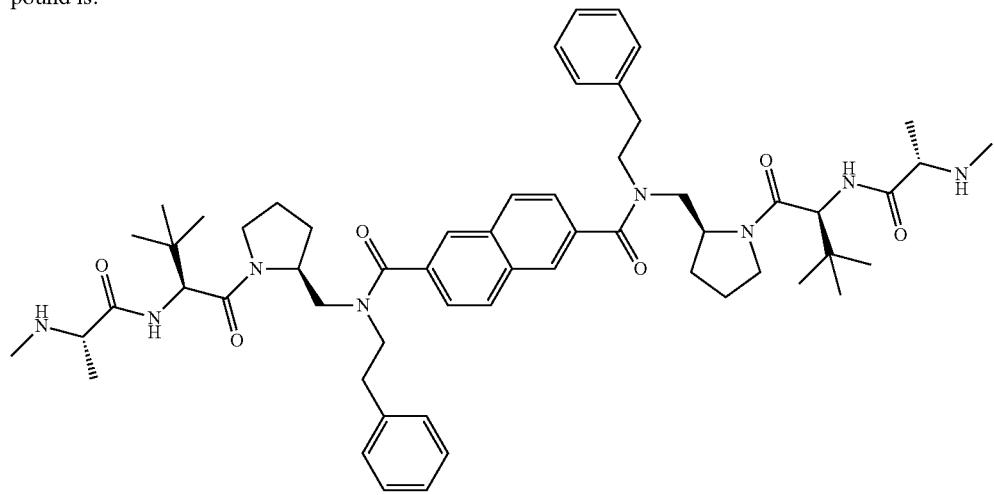
or a salt thereof.
25. The compound, according to claim 1, wherein the compound is:
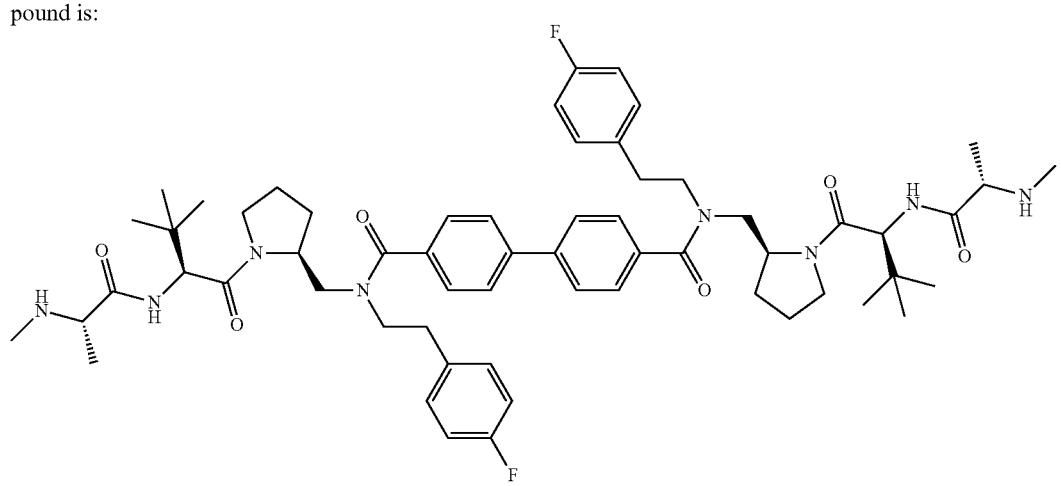
or a salt thereof.
26. The compound, according to claim 1, wherein the compound is:
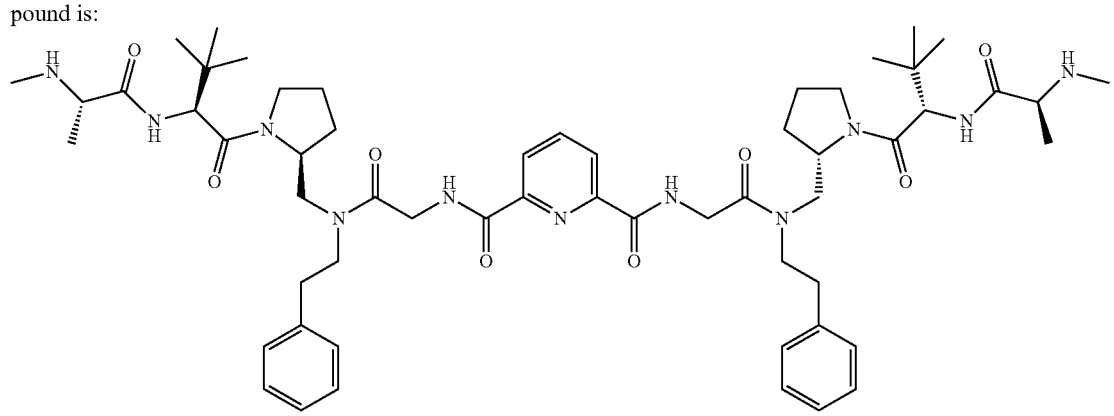
or a salt thereof.

27. The compound, according to claim 1, wherein the compound is:
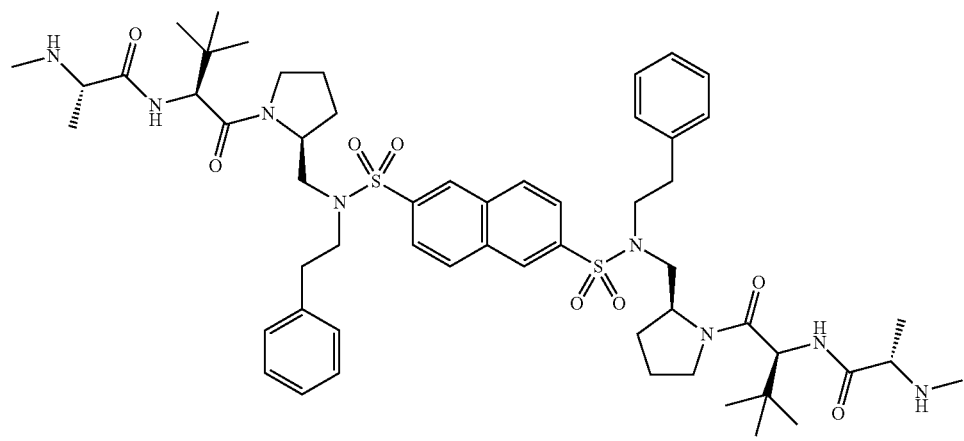
or a salt thereof.
28. A compound having the structure:
19
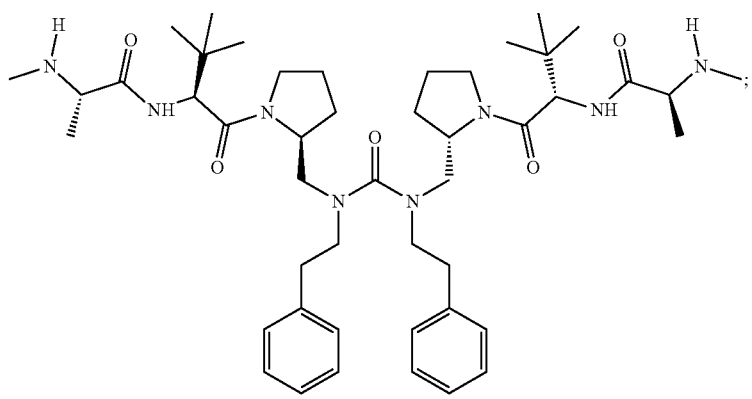
27
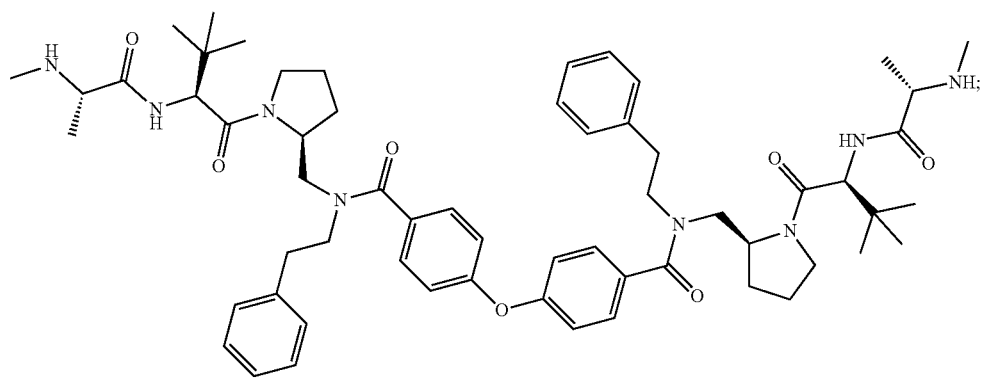

43
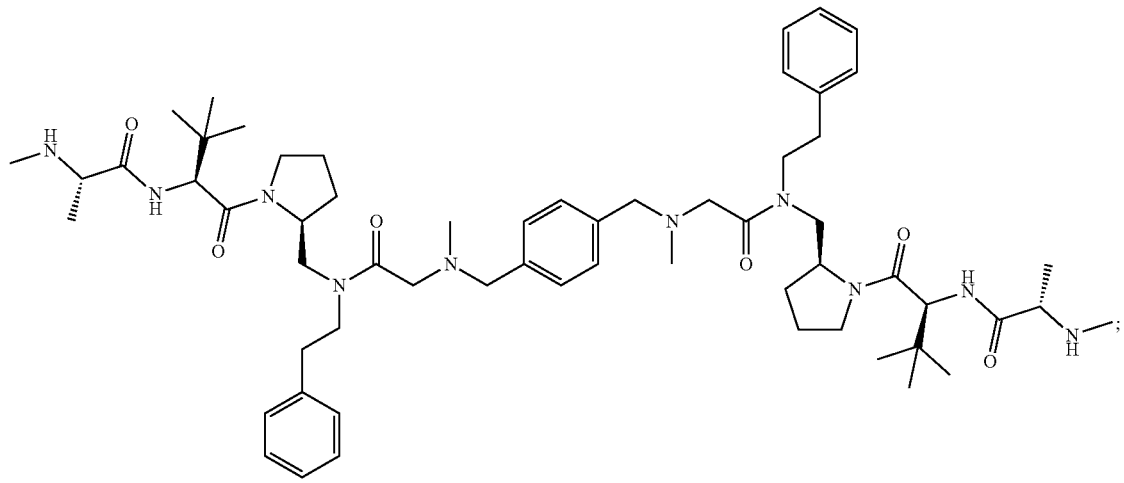
51
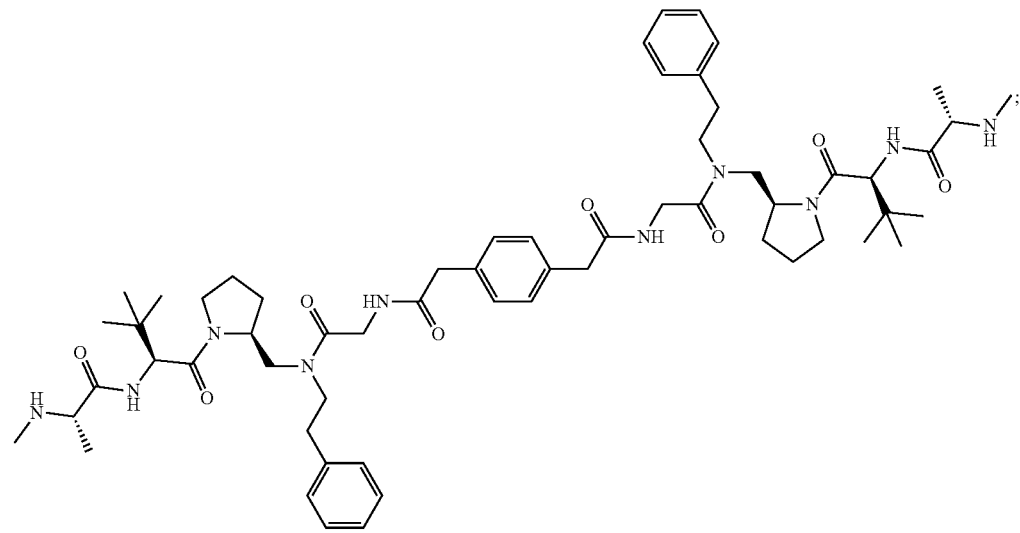
80
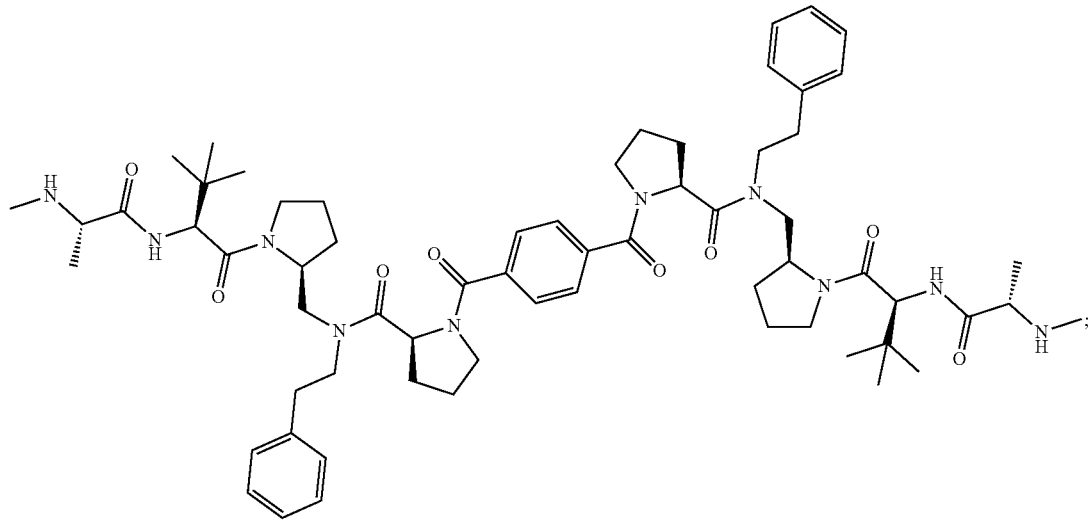

81
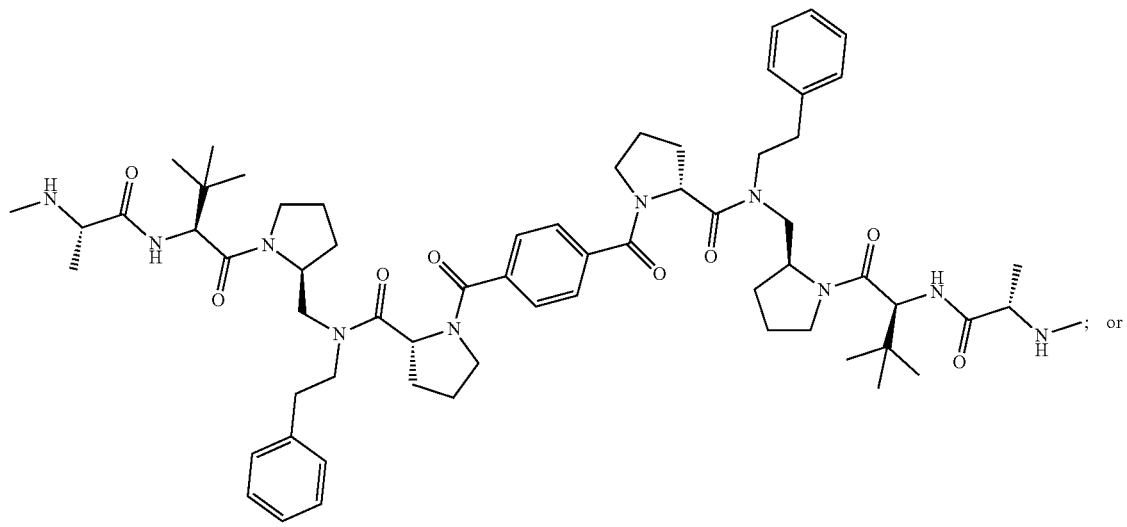
104
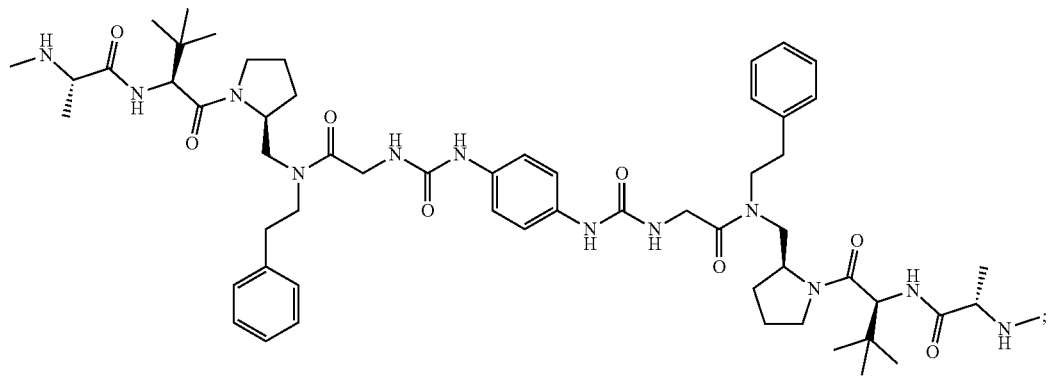
or salt thereof.
* * * * *